(12) United States Patent  
Aehle et al.

(10) Patent No.: US 7,985,569 B2  
(45) Date of Patent: Jul. 26, 2011

(54) CELLULOMONAS 69B4 SERINE PROTEASE VARIANTS

(75) Inventors: Wolfgang Aehle, Leiden (NL); David A. Estell, San Francisco, CA (US); Ronaldus W. J. Hommes, Leiden (NL); Brian E. Jones, Leiden (NL); Marc Kolkman, Leiden (NL); Chris Leeflang, Leiden (NL); Hiroshi Oh, Cincinnati, OH (US); Ayrookaran J. Poulose, Belmont, CA (US); Andrew Shaw, San Francisco, CA (US); Wilhelmus A. H. van der Kley, Leiden (NL); Leonardus P. M. van Marrewijk, Leiden (NL)

(73) Assignee: Danisco US Inc., Palo Alto, CA (US)

( * ) Notice: Subject to any disclaimer, the term of this patent is extended or adjusted under 35 U.S.C. 154(b) by 630 days.

(21) Appl. No.: 11/809,104

(22) Filed: May 31, 2007

(65) Prior Publication Data

US 2008/0063774 A1    Mar. 13, 2008

Related U.S. Application Data

(63) Continuation of application No. 11/583,334, filed on Oct. 19, 2006, now abandoned, which is a continuation-in-part of application No. 10/576,331, filed as application No. PCT/US2004/039066 on Nov. 19, 2004.

(60) Provisional application No. 60/523,609, filed on Nov. 19, 2003, now abandoned.

(51) Int. Cl.  
*C12N 9/48* (2006.01)

(52) U.S. Cl. ........................................................ 435/212

(58) Field of Classification Search ........................ None  
See application file for complete search history.

(56) References Cited

U.S. PATENT DOCUMENTS

| | | |
|---|---|---|
| 3,840,433 A | 10/1974 | Aunstrup et al. |
| 3,986,926 A | 10/1976 | Monsheimer et al. |
| 4,435,307 A | 3/1984 | Barbesgaard et al. |
| 4,533,359 A | 8/1985 | Kondo et al. |
| 5,147,642 A | 9/1992 | Lotz et al. |
| RE34,606 E | 5/1994 | Estell et al. |
| 5,314,692 A | 5/1994 | Haarasilta et al. |
| 5,340,735 A | 8/1994 | Christianson et al. |
| 5,500,364 A | 3/1996 | Christianson et al. |
| 5,612,055 A | 3/1997 | Bedford et al. |
| 5,646,101 A | 7/1997 | MacBeath |
| 5,686,014 A | 11/1997 | Baillely et al. |
| 5,695,679 A | 12/1997 | Christie et al. |
| 5,698,504 A | 12/1997 | Christie et al. |
| 5,700,676 A | 12/1997 | Bott et al. |
| 5,705,464 A | 1/1998 | Scheper et al. |
| 5,710,115 A | 1/1998 | Patel et al. |
| 5,801,039 A | 9/1998 | Maurer et al. |
| 5,855,625 A | 1/1999 | Maurer et al. |
| 5,874,276 A | 2/1999 | Fowler et al. |
| 5,955,340 A | 9/1999 | Bott et al. |
| 6,312,936 B1 | 11/2001 | Poulose et al. |
| 6,376,450 B1 | 4/2002 | Ghosh et al. |
| 6,440,991 B1 | 8/2002 | Zhu et al. |
| 6,482,628 B1 | 11/2002 | Poulose et al. |
| 6,566,114 B1 | 5/2003 | Kauppinen et al. |
| 6,602,842 B2 | 8/2003 | Cuperus et al. |
| 6,605,458 B1 | 8/2003 | Hansen et al. |
| 6,610,642 B2 | 8/2003 | Ghosh et al. |

FOREIGN PATENT DOCUMENTS

| | | |
|---|---|---|
| DE | 43 32 692 | 7/1994 |
| EP | 0 134 267 A1 | 3/1985 |
| EP | 0 214 761 A2 | 3/1987 |
| EP | 0 218 272 A1 | 4/1987 |
| EP | 0 238 023 A2 | 9/1987 |
| EP | 0 258 068 A2 | 3/1988 |
| EP | 0 305 216 A1 | 3/1989 |
| EP | 0 331 376 A2 | 9/1989 |
| EP | 0 495 257 A1 | 7/1992 |
| EP | 0 505 920 A1 | 9/1992 |
| GB | 1372034 | 10/1974 |
| GB | 2233665 A | 1/1991 |
| GB | A2250289 A | 6/1992 |
| JP | 4327274 A | 11/1992 |
| WO | WO 88/09367 | 12/1988 |
| WO | WO 89/04552 | 5/1989 |
| WO | WO 89/06270 | 7/1989 |
| WO | WO 90/09446 | 8/1990 |
| WO | WO 91/16422 | 10/1991 |
| WO | WO 92/21760 | 12/1992 |
| WO | WO 94/12621 | 6/1994 |

(Continued)

OTHER PUBLICATIONS

Galye et al, Identification of regions in interleukin-1 alpha important for activity. J Biol Chem. Oct. 15, 1993;268(29):22105-11.*  
Whisstock et al, Prediction of protein function from protein sequence and structure. Q Rev Biophys. Aug. 2003;36(3):307-40. Review.*  
Sigma, Inc. Catalogue 1997 p. 1159.*  
U.S. Appl. No. 10/576,331, filed Jul. 18, 2007, Jones, Brian.  
U.S. Appl. No. 11/583,334, filed Oct. 19, 2006, Aehle, Wolfgang.  
Beaucage, S.L. et al. "Deoxynucleoside phosphoramidites—A new class of key intermediates for deoxypolynucleotide synthesis." *Tetrahedron Lett.*, 22(20): 1859-1862, 1981.

(Continued)

*Primary Examiner* — Sheridan Swope

(57) ABSTRACT

The present invention provides novel *Micrococcineae* spp serine proteases having multiple substitutions. In particular, the present invention provides serine proteases having multiple substitutions, DNA encoding these proteases, vectors comprising the DNA encoding the proteases, host cells transformed with the vector DNA, and enzymes produced by the host cells. The present invention also provides cleaning compositions (e.g., detergent compositions), animal feed compositions, and textile and leather processing compositions comprising these serine protease variants. In particularly preferred embodiments, the present invention provides mutant (i.e., variant) proteases derived from the wild-type proteases described herein. These variant proteases also find use in numerous applications.

30 Claims, 7 Drawing Sheets

FOREIGN PATENT DOCUMENTS

| | | |
|---|---|---|
| WO | WO 95/01426 | 1/1995 |
| WO | WO 95/23221 | 8/1995 |
| WO | WO 96/10646 | 4/1996 |
| WO | WO 96/11285 | 4/1996 |
| WO | WO 96/34946 | 11/1996 |
| WO | WO 97/07770 | 3/1997 |
| WO | WO 99/34011 | 7/1999 |
| WO | WO 02/14490 A2 | 2/2002 |
| WO | WO 03/000865 A2 | 1/2003 |
| WO | WO 2005/052146 | 6/2005 |
| WO | WO 2005/052161 | 6/2005 |

OTHER PUBLICATIONS

Benton, W.D. et al. "Screening lambdagt recombinant clones by hybridization to single plaques in situ." *Science*, 196(4286): 180-182, Apr. 8, 1977.

Dartois, V. et al. "Cloning, nucleotide sequence and expression in *Escherichia coli* of a lipase gene from *Bacillus subtilis* 168." *Biochimica et Biophysica Acta*, 1131(3): 253-260, Jul. 15, 1992.

DelMar, E.G. et al. "A sensitive new substrate for chymotrypsin." *Analytical Biochemistry*, 99(2): 316-320, Nov. 1, 1979.

Devereaux, P. et al. "A comprehensive set of sequence analysis programs for the VAX." *Nucl. Acids Res*, 12: 387-395, 1984.

Dynan, W.S. et al. "Control of eukaryotic messenger RNA synthesis by sequence-specific DNA-binding proteins." *Nature*, 316(6031): 774-778, 1985.

Grünstein, M. et al. "Colony hybridization: A method for the isolation of cloned DNAs that contain a specific gene." *Proc. Natl. Acad. Sci. USA*, 72: 3961-3965, 1975.

Kalisz, H.M. "Microbial proteinases." *Advances in Biochemical Engineering/Biotechnology*, 36:1-65, 1988.

Kraut, J. "Serine Proteases: Structure and Mechanism of Catalysis." *Annual Review of Biochemistry*, 46(1): 331-358, 1977.

Kugimiya, W. et al. "Cloning and sequence analysis of cDNA encoding *Rhizopus niveus* lipase." *Bioscience, Biotechnology, and Biochemistry*, 56(5): 716-9, May 1992.

Needham-VanDevanter, D.R. et al. "Characterization of an adduct between CC-1065 and a defined oligodeoxynucleotide duplex." *Nucleic Acids Research* 12(15): 6159-6168, Aug. 10, 1984.

Needleman, S.B. et al. "A general method applicable to the search for similarities in the amino acid sequence of two proteins." *J. Mol. Biol*, 48(3): 443-53, Mar. 1970.

Pearson, W.R. et al. "Improved Tools for Biological Sequence Comparison." *Proc. Natl. Acad. Sci. USA*, 85(8): 2444-2448, Apr. 15, 1988.

Smith, T.F. et al. "Comparison of biosequences." *Adv. Appl. Math*, 2: 482-489, 1981.

Solingen, P. et al. "Cloning and expression of an endocellulase gene from a novel streptomycete isolated from an East African soda lake." *Extremophiles*, 5(5): 333-341, Oct. 1, 2001.

Stroud, R.M. "A family of protein-cutting proteins." *Scientific American*, 231(1): 74-88, Jul. 1974.

Yamaguchi, S. et al. "Cloning and structure of the mono- and diacylglycerol lipase-encoding gene from *Penicillium camembertii* U-150." *Gene*, 103(1): 61-7, Jul. 15, 1991.

* cited by examiner

Comments for pUC18
2686 nucleotides

LacZ alpha peptide: bases 149-469 (complementary strand)
lac promoter: bases 470-543 (complementary strand)
pUC origin: bases 808-1481 (complementary strand)
Ampicillin (bla) resistance gene: bases 1629-2486 (complementary strand)
bla promoter: bases 2487-2585 (complementary strand)

FIGURE 6. Tergotometer Tests Performed in the Absence of HEPES Buffer (Variant dosage was 0.55 ppm)

| Variants | EMPA 116 (BMI) Fixed Δ % SR | | | EMPA 116 (BMI) Unfixed Δ % SR | | | Equest Medium Grass Δ % SR | | |
|---|---|---|---|---|---|---|---|---|---|
| | Average | STD | (n) | Average | STD | (n) | Average | STD | (n) |
| G12D-R35E | 2.9 | 0.9 | 24 | 7.2 | 2.2 | 24 | 2.4 | 3.6 | 24 |
| R123L-R127Q-R179Q | | | | 6.0 | 1.5 | 6 | 1.7 | 3.7 | 6 |
| G12D-R35H | | | | 7.0 | 1.1 | 6 | -2.2 | 5.0 | 5 |
| G12D-R35E | | | | 8.2 | 1.2 | 6 | 1.3 | 5.4 | 6 |
| R35E-R123L-R127Q-R179Q | | | | 6.1 | 1.2 | 6 | 0.4 | 4.1 | 6 |
| R14I-R16Q-N24E-R35F-G49A-R61V-Q81P-R123F-R127A-R159F | -0.4 | 0.8 | 24 | 1.9 | 2.9 | 24 | 3.1 | 5.0 | 24 |
| N24E-G54D-R123S-R179N | 1.1 | 1.1 | 24 | 6.3 | 2.9 | 24 | 1.8 | 5.2 | 24 |
| G12D-R35H-R123F-R159E | 0.0 | 0.9 | 24 | 6.9 | 2.8 | 24 | -1.7 | 5.1 | 24 |
| G12D-R35E-R159E | 0.1 | 1.0 | 24 | 7.2 | 2.8 | 24 | -1.4 | 5.1 | 24 |
| R35E-R123L-R127Q-R179Q | 0.2 | 0.8 | 24 | 6.8 | 3.0 | 24 | -0.5 | 5.2 | 24 |
| R123L-R127Q-R179Q | 1.8 | 1.1 | 24 | 7.1 | 3.4 | 24 | 0.1 | 5.1 | 24 |
| G12D-R35H | 2.4 | 0.9 | 24 | 7.3 | 2.8 | 24 | 0.5 | 5.0 | 24 |
| R14S-R159L | 1.8 | 0.8 | 24 | 7.6 | 3.7 | 24 | -0.3 | 4.6 | 24 |
| R14N-R127K-R159L | 1.6 | 0.8 | 24 | 7.0 | 2.7 | 24 | 2.9 | 6.9 | 24 |
| R14I-R159G | 2.7 | 1.2 | 24 | 8.0 | 2.7 | 24 | 2.5 | 6.0 | 24 |
| N24T-R159Q | 3.3 | 1.0 | 24 | 6.0 | 3.0 | 24 | -0.6 | 6.8 | 24 |
| N24M-S76V-A93H-R127K-R159K | 3.2 | 1.3 | 24 | 6.0 | 2.5 | 24 | 2.6 | 4.4 | 24 |
| N24H-G54L-S76V-A93H-R127K-R159K | 2.7 | 1.0 | 24 | 5.0 | 2.6 | 24 | 2.3 | 4.1 | 24 |
| N24W-S76Y-A93G-R127K-R159K | 2.7 | 1.1 | 24 | 5.4 | 2.2 | 24 | 4.8 | 6.3 | 24 |
| N24W-G54D-A93H-R127K-R159K | 3.2 | 1.1 | 24 | 7.0 | 2.4 | 24 | 3.3 | 5.5 | 24 |
| R14I-S76A-A93H-R127K-R159K-I181Q | 3.6 | 1.2 | 24 | 6.0 | 2.5 | 24 | -2.0 | 6.7 | 24 |
| R14M-S76T-A93H-R127K-R159K-I181K | 3.3 | 1.1 | 24 | 5.5 | 2.1 | 24 | 5.9 | 6.7 | 24 |
| R14M-S76N-A93H-R127K-R159K-I181Q | 3.3 | 2.2 | 12 | 5.5 | 2.3 | 12 | 0.4 | 7.0 | 12 |
| R14M-S76A-A93S-R127K-R159K-I181K | 2.7 | 1.3 | 24 | 5.5 | 2.6 | 24 | -0.3 | 7.5 | 24 |
| R14I-S76V-A93S-R127K-R159K-I181K | 4.2 | 1.2 | 24 | 5.9 | 2.4 | 24 | 6.9 | 6.8 | 24 |
| R14L-S76A-A93H-R127K-R159K | 3.5 | 1.2 | 24 | 6.7 | 2.5 | 24 | 5.5 | 7.0 | 24 |
| R14I-S76N-A93H-R127K-R159K-I181Q | 2.6 | 1.6 | 24 | 5.5 | 2.9 | 24 | -0.5 | 7.0 | 24 |
| R14M-S76N-A93G-R127K-R159K-I181K | 3.9 | 1.7 | 24 | 5.4 | 2.5 | 24 | -0.6 | 7.2 | 24 |
| R14M-S76N-A93G-R127K-R159K-I181T | 3.5 | 1.7 | 24 | 6.7 | 2.6 | 24 | 0.6 | 6.1 | 24 |
| R14M-S76A-A93G-R127K-R159K-I181T | 3.6 | 1.4 | 24 | 6.4 | 2.8 | 24 | 4.5 | 6.2 | 24 |
| R14M-S76N-A93S-R127K-R159K-I181T | 3.8 | 1.5 | 24 | 5.90 | 2.50 | 24 | 7.0 | 7.1 | 24 |
| R14M-S76Y-A93H-R127K-R159K-I181K | 2.2 | 1.1 | 24 | 4.70 | 2.30 | 24 | 5.2 | 6.7 | 24 |

FIGURE 7. Tergotometer Tests Performed in the Presence of HEPES Buffer (Variant dosage was 0.55 ppm)

| Variants | EMPA 116 (BMI) Unfixed Δ % SR Average | STD | (n) | Equest Medium Grass Δ % SR Average | STD | (n) |
|---|---|---|---|---|---|---|
| N024T-G049A-Q071F | 7.20 | 2.90 | 24 | 5.10 | 5.70 | 24 |
| A093S-S099A-S187Q | 6.6 | 2.7 | 24 | 3.60 | 7.80 | 24 |
| N024T-G049A-Q071F-A093S-S099A-S187Q | 6.5 | 2.7 | 24 | 5.50 | 4.50 | 24 |
| N024T-G049A-Q071F-A093S-S099A-R127K-R159K-S187Q | 8.3 | 3 | 24 | 5 | 5 | 24 |
| R016Q-N024T-G049A-Q071F-A093S-S099A-R127K-R159K-I181Q-S187Q | 9.7 | 2.7 | 24 | 3.9 | 7.4 | 24 |
| R016Q-N024T-G049A-Q071F-A093S-S099A-R127K-R159K-I181Q-S187Q | 9 | 2.3 | 24 | 7.2 | 3.9 | 24 |
| R014I-R016Q-N024T-G049A-Q071F-S076T-A093S-S099A-R127K-I181Q-S187Q | 8.4 | 2.7 | 24 | 4.9 | 4.8 | 24 |
| R014I-R016Q-N024T-G049A-Q071F-S076T-A093S-S099A-R127K-I181Q-S187Q | 9.8 | 2.3 | 24 | 6.8 | 4.6 | 24 |
| R14M-S76A-A93G-R127K-R159K-I181K | 9.2 | 2.3 | 24 | 8.4 | 3.9 | 24 |
| R14I-S76N-A93H-R127K-R159K-I181Q | 9.7 | 2.4 | 24 | 8.2 | 4 | 24 |
| G12D-R35E-D184N | 10.2 | 3.3 | 24 | 6.2 | 6.6 | 24 |
| R14M-S76N-A93G-R127K-R159K-I181T | 7.8 | 3 | 24 | 8.1 | 6.2 | 24 |
| R14M-S76T-A93S-R127K-R159K-I181K | 10.2 | 2.8 | 24 | 8.4 | 6.9 | 24 |
| R14M-S76T-A93H-R127K-R159K-I181Q | 11.2 | 3 | 24 | 9.7 | 5.1 | 24 |
| R14I-A64K-T86K-T116E-R123F-R159F-D184T | 9.6 | 2.6 | 24 | 3.5 | 5.8 | 24 |
| R14I-A64K-T86K-T116E-R123F-R159F-D184T | 10.9 | 3 | 24 | 5.8 | 6 | 24 |
| R14I-Q81K-T116E-R123F-R159F-D184T | 10.6 | 3 | 24 | 5 | 6 | 24 |
| R14I-A64K-T86K-N112E-R123F-R159F-D184T | 12.5 | 3 | 24 | 8.6 | 5.7 | 24 |
| R14I-A64K-Q81K-T86K-T116E-R123F | 11.7 | 3.2 | 24 | 6.1 | 4.8 | 24 |
| R14I-Q81K-T86K-N112E-R123F-R159F-D184T | 11.4 | 3 | 24 | 6.8 | 6.2 | 24 |
| R14I-A64K-T86K-N112E-R123F-D184T | 8.7 | 3.2 | 24 | 3.2 | 5.2 | 24 |
| R14I-A64K-Q81K-T86K-N112E-R123F-R159F-D184T | 10.7 | 2.3 | 24 | 3.3 | 4.8 | 24 |
| R14I-A64K-T86K-R123F-R159F | 10.8 | 2.3 | 24 | 4.6 | 4.7 | 24 |
| R14I-A64K-T86K-N112E-R123F-R159F | 11 | 2.5 | 24 | 4.6 | 4.8 | 24 |
| R14I-A64K-Q81K-T116E-R123F-R159F | 10.9 | 2.1 | 24 | 5.3 | 4.6 | 24 |
| R14I-A64K-N112E-R123F-D184T | 12.3 | 2.5 | 24 | 8 | 4.2 | 24 |
| R14I-Q81K-T86K-T116E-R123F-D184T | 9 | 3.7 | 24 | 7.9 | 6.7 | 24 |
| R14I-T86K-T116E-R123F-R159F-D184T | 10.4 | 2.2 | 24 | 6 | 5 | 24 |
| R14I-Q81K-T116E-D184T | 12.3 | 3.1 | 24 | 6.7 | 4.3 | 24 |
| R14I-A64K-T116E | 11.3 | 2.4 | 24 | 5.5 | 5.2 | 24 |
| R14I-Q81K-R123F-D184T | 11.2 | 2.7 | 24 | 6.1 | 4.2 | 24 |
| R14I-T86K-N112E-R123F-D184T | 9.8 | 2.6 | 24 | 5.2 | 5.4 | 24 |
| R14I-A64K-T86K-R123F-R159F-D184T | 9.9 | 2.8 | 24 | 4.9 | 4.5 | 24 |
| R14I-T86K-R123F-R159F-D184T | 11 | 2.3 | 24 | 3.4 | 5.5 | 24 |
| G12D-R35E-G63R-R79K-T109M | 10.7 | 3.4 | 24 | 6.1 | 4.9 | 24 |

US 7,985,569 B2

CELLULOMONAS 69B4 SERINE PROTEASE VARIANTS

The present application is a Continuation of U.S. patent application Ser. No. 11/583,334, filed Oct. 19, 2006, now abandoned, which is a Continuation-in-Part of pending U.S. patent application Ser. No. 10/576,331 filed Jul. 18, 2007, which claims priority to PCT/US2004/039066, filed Nov. 19, 2004, which claims priority to U.S. Provisional Patent Application Ser. No. 60/523,609, filed Nov. 19, 2003.

FIELD OF THE INVENTION

The present invention provides novel *Micrococcineae* spp serine proteases having multiple substitutions. In particular, the present invention provides serine proteases having multiple substitutions, DNA encoding these proteases, vectors comprising the DNA encoding the proteases, host cells transformed with the vector DNA, and enzymes produced by the host cells. The present invention also provides cleaning compositions (e.g., detergent compositions), animal feed compositions, and textile and leather processing compositions comprising these serine protease variants. In particularly preferred embodiments, the present invention provides mutant (i.e., variant) proteases derived from the wild-type proteases described herein. These variant proteases also find use in numerous applications.

BACKGROUND OF THE INVENTION

Serine proteases are a subgroup of a diverse class of enzymes having a wide range of specificities and biological functions (See e.g., Stroud, Sci. Amer., 131:74-88 [1974]). Despite their functional diversity, the catalytic machinery of serine proteases is represented by at least two genetically distinct families of enzymes: 1) the subtilisins; and 2) the mammalian chymotrypsin-related and homologous bacterial serine proteases (e.g., trypsins). These two families of serine proteases show remarkably similar mechanisms of catalysis (See e.g., Kraut, Ann. Rev. Biochem., 46:331-358 [1977]). Furthermore, although the primary structure is unrelated, the tertiary structure of these two enzyme families brings together a conserved catalytic triad of amino acids consisting of serine, histidine and aspartate.

In contrast, the subtilisins and chymotrypsin-related serine proteases both have a catalytic triad comprising aspartate, histidine and serine. In the subtilisin-related proteases the relative order of these amino acids, reading from the amino to carboxy terminus, is aspartate-histidine-serine. However, in the chymotrypsin-related proteases, the relative order is histidine-aspartate-serine. Much research has been conducted on the subtilisins, due largely to their usefulness in cleaning and feed applications. Additional work has been focused on the adverse environmental conditions (e.g., exposure to oxidative agents, chelating agents, extremes of temperature and/or pH) which can adversely impact the functionality of these enzymes in various applications. Nonetheless, there remains a need in the art for enzyme systems that are able to resist these adverse conditions and retain or have improved activity over those currently known in the art.

SUMMARY OF THE INVENTION

The present invention provides novel *Micrococcineae* spp serine proteases having multiple substitutions. In particular, the present invention provides serine proteases having multiple substitutions, DNA encoding these proteases, vectors comprising the DNA encoding the proteases, host cells transformed with the vector DNA, and enzymes produced by the host cells. The present invention also provides cleaning compositions (e.g., detergent compositions), animal feed compositions, and textile and leather processing compositions comprising these serine protease variants. In particularly preferred embodiments, the present invention provides mutant (i.e., variant) proteases derived from the wild-type proteases described herein. These variant proteases also find use in numerous applications.

The present invention provides isolated serine protease variants having an amino acid sequence comprising at least two amino acid substitutions, wherein the substitutions are made at positions equivalent to the positions in a *Cellulomonas* 69B4 protease comprising the amino acid sequence set forth in SEQ ID NO:8. The present invention further provides compositions comprising the isolated serine protease variant(s) having at least two amino acid substitutions, wherein the substitutions are made at positions equivalent to positions in a *Cellulomonas* 69B4 protease comprising the amino acid sequence set forth in SEQ ID NO:8. In some preferred embodiments, the compositions comprise at least one variant serine protease, wherein the variant serine protease has immunological cross-reactivity with the serine protease set forth in SEQ ID NO:8. In some additional preferred embodiments, the sequence of a serine protease variant comprises substitutions at least two amino acid positions selected from positions 1, 2, 3, 4, 7, 8, 9, 10, 11, 12, 13, 14, 15, 16, 18, 19, 22, 24, 25, 26, 27, 28, 29, 30, 31, 32, 33, 34, 35, 36, 38, 39, 40, 41, 42, 43, 44, 45, 46, 47, 48, 49, 51, 52, 54, 55, 56, 57, 59, 61, 62, 63, 64, 65, 66, 67, 68, 69, 70, 71, 72, 73, 74, 75, 76, 77, 78, 79, 80, 81, 83, 84, 85, 86, 87, 88, 89, 90, 91, 92, 93, 96, 99, 100, 101, 103, 104, 105, 107, 109, 110, 111, 112, 113, 114, 115, 116, 117, 118, 119, 121, 123, 124, 125, 126, 127, 128, 129, 130, 132, 133, 134, 135, 136, 137, 140, 141, 142, 143, 144, 145, 146, 147, 150, 151, 152, 153, 154, 155, 156, 157, 158, 159, 160, 161, 162, 163, 164, 165, 166, 167, 168, 170, 171, 172, 175, 176, 177, 179, 180, 181, 182, 183, 184, 185, 186, 187, 188, and 189, wherein the substitutions are made at positions equivalent to the positions in a *Cellulomonas* 69B4 protease comprising the amino acid sequence set forth in SEQ ID NO:8.

In some preferred embodiments, the serine protease variant comprises at least two substitutions selected from G12D, R14I, R14L, R14M, R14S, R16I, R16L, R16Q, N24E, N24H, N24M, N24T, N24W, R35E, R35F, R35H, T36S, G49A, G54D, G54L, R61V, A64K, G65Q, Q71F, Y75G, S76A, S76L, S76N, S76T, S76V, R79K, R79T, Q81K, Q81P, T86K, A93G, A93H, A93S, S99A, T109M, N112E, T116E, R123F, R123L, R123Q, R123S, R127A, R127K, R127Q, R159E, R159F, R159G, R159K, R159L, R159Q, R179N, R179Q, I181K, I181Q, I181T, D184N, D184T, and S187Q, wherein the substitutions are made at positions equivalent to the positions in a *Cellulomonas* 69B4 protease comprising the amino acid sequence set forth in SEQ ID NO:8. In some yet additional preferred embodiments, the serine protease variant comprises multiple substitutions selected from R16Q/R35F/R159Q, R16Q/R123L, R14L/R127Q/R159Q, R14L/R179Q, R123L/R127Q/R179Q, R16Q/R79T/R127Q, R16Q/R79T, R35E/R123L/R127Q/R179Q, and G12D/R35E/G63R/R79K/T109M, wherein the substitutions are made at positions equivalent to the positions in a *Cellulomonas* 69B4 protease comprising the amino acid sequence set forth in SEQ ID NO:8. In some still further embodiments, the serine protease variant comprises the following substitutions R123L, R127Q, and R179Q, wherein the substitutions are made at positions equivalent to the positions in a *Cellulomonas* 69B4 protease comprising the amino acid sequence set forth in SEQ ID NO:8.

In some further preferred embodiments, the serine protease variant comprises at least two substitutions selected from D2G, D2Q, V3I, V3L, N7A, N7L, N7S, I11A, I11Q, R14E, N24A, N24E, N24H, N24L, N24M, N24Q, N24T, N24V, T36D, T36F, T36G, T36H, T36I, T36L, T36N, T36P, T36R, T36S, T36V, T36W, T36Y, A38D, A38F, A38H, A38L, A38N, A38R, A38S, G49F, S51A, G54A, G54D, G54H, G54K, G54L, G54M, G54R, N55F, A64H, A64N, A64R, A64W, A64Y, G65L, G65P, G65Q, G65R, G65S, G65T, G65Y, G65V, V66A, V66D, V66E, V66H, V66I, V66L, N67A, N67G, N67L, N67K, L69H, L69S, L69V, A70D, A70H, A70S, Q71A, Q71G, Q71H, Q71I, Q71K, Q71M, Q71N, N73S, N73T, N74G, Y75F, Y75G, Y75I, S76L, S76Y, S76V, S76W, G77S, G77T, G78A, G78D, G78H, G78N, G78S, G78T, R79P, V80H, V80L, Q81H, Q81K, Q81V, H85Q, H85T, V90I, V90P, V90S, S92G, W103I, W103M, H104K, T109A, T109H, T109I, S114G, T116F, P118A, P118F, P118H, P118R, E119K, E119R, N145E, N145I, N145Q, V150L, R159F, N170Y, G177M, R179A, R179D, R179E, R179I, R179K, R179L, R179M, R179N, R179T, R179Y, R179V, I181H, T183I, G186E, G186I, G186V, S187P, S187T, and S188M, wherein the substitutions are made at positions equivalent to the positions in a *Cellulomonas* 69B4 protease comprising the amino acid sequence set forth in SEQ ID NO:8.

In some additional embodiments, the serine protease variant comprises at least two substitutions selected from F1A, F1T, D2A, D2H, D2N, V3T, N7H, N7I, A8G, A8K, T10G, T10K, I11S, I11T, G12W, G13M, S15F, N24F, N24S, A30S, R35F, T36C, A38G, A38I, A38K, A38V, A38Y, T40S, T40V, A41N, N42H, F47I, F47M, G49A, G49K, G49L, S51F, S51Q, G54I, G54Q, N55K, N55Q, R61M, T62I, G63Q, G63V, G63W, A64F, A64I, A64K, A64L, A64M, A64Q, A64S, A64T, A64V, G65A, G65H, V66M, V66N, N67D, N67F, N67H, N67Q, N67R, N67S, N67T, N67V, N67Y, L68W, L69W, A70G, Q71D, Q71F, Q71L, Q71R, V72I, N73H, S76E, S76I, S76K, S76A, S76N, S76Q, S76R, S76T, G77N, G77Y, G78I, S78R, G78V, R79G, V80F, Q81D, Q81I, A83N, H85R, H85K, H85L, T86A, P89N, V90A, V90L, V90T, T107H, T107M, T107S, T107V, T109G, T109L, T109P, T109R, A110S, A110T, N112I, P118E, P118I, P118K, P118Q, R123E, R123I, I126L, R127F, I28L, T129S, E133Q, L142V, A143N, A143S, N145G, N145L, N145T, V150M, T151F, R159E, T163L, Q167N, N170A, N170D, N170L, 171S, G177S, I181G, I181N, T182V, T183K, T183M, D184F, D184H, D184Q, D184R, S185I, S185V, S187E, and S187L, wherein the substitutions are made at positions equivalent to the positions in a *Cellulomonas* 69B4 protease comprising the amino acid sequence set forth in SEQ ID NO:8.

In yet additional embodiments, the serine protease variant comprises at least two substitutions selected from D2P, A8G, T10C, T10L, I11E, I11Q, I11T, I11W, G12D, G12I, G12N, G12Q, G12S, G12V, R14A, R14C, R14E, R14D, R14G, R14I, R14N, R14Q, R14S, R14T, S15C, S15E, S15H, S15R, S15Y, R16C, R16D, R16E, R16T, R16V, A22C, A22S, N24E, R35A, R35C, R35D, R35E, R35H, R35M, R35N, R35P, R35Q, R35S, R35T, R35V, T36C, A38C, A38D, A41C, A41D, T44E, T46C, T46E, T46F, T46V, T46Y, F47R, A48E, G49A, G49C, G49E, G49H, G49L, G49N, G49Q, G49V, G54C, N55G, D56L, Y57G, F59W, R61E, R61M, R61T, R61V, G91Q, S99A, T100A, T100R, T107R, T109E, N112P, S113C, S114C, P118K, P118R, E119G, E119R, E119T, E119V, E119Y, T121E, T121F, T121L, R123C, R123D, R123E, R123F, R123H, R123N, R123Q, R123S, R123T, R123V, R123W, R123Y, G124D, L125Q, R127D, R127E, R127F, R127Q, R127S, P134R, T151C, T151L, S155C, S155I, S155W, S155Y, R159D, R159E, R159Q, R159S, R159T, R159V, T163D, F165E, F165W, Q167E, N170C, N170D, G177D, R179D, R179E, and M180L, wherein the substitutions are made at positions equivalent to the positions in a *Cellulomonas* 69B4 protease comprising the amino acid sequence set forth in SEQ ID NO:8. In still further additional embodiments, the serine protease variant comprises at least two substitutions selected from F1N, F1P, D2I, D2M, D2T, D2V, A8R, A8T, T10D, T10E, T10F, T10M, T10Q, T10Y, G12H, G12P, G12Y, G13D, G13E, R14H, R14L, R14M, S15F, S15G, S15N, R16I, R116Q, N24G, N24T, I28V, R35K, T36V, A41S, A41T, N42D, T44C, F47V, G49F, G49K, G49S, S511A, S511C, S511L, S115M, G54E, N55A, D56F, R61K, R61Q, A64C, G65D, V66N, A70G, A70M, A70P, R79T, R79V, Q811A, Q81G, Q811P, A83E, A83D, A83H, T86E, A87C, A87E, A88F, S92T, S99G, S99H, S99K, S99Q, T100K, T100Q, W103L, T109K, N112D, N112E, S113A, S113D, S114E, T115C, T116G, T116N, P118A, P118C, P118G, P118W, E119A, E119L, E119N, E119Q, E119S, T121A, T121D, R123A, R123G, R123I, R123K, R123M, A132S, L125M, R127A, R127C, T128A, S140P, L141M, T151V, S155E, S155F, S155T, S155V, N157D, R159A, R159C, R159K, R159M, R159N, T160D, T163C, F165H, N170L, I172A, Q174C, Q174S, Q174T, A175T, G177E, R179C, R179F, R179I, R179L, R179M, R179N, R179S, R179T, R179V, R179W, R179Y, S187E, and S188E, wherein the substitutions are made at positions equivalent to the positions in a *Cellulomonas* 69B4 protease comprising the amino acid sequence set forth in SEQ ID NO:8.

In some further embodiments, the present invention provides a serine protease variant, wherein the amino acid sequence of the protease comprises at least two substitutions selected from V3R, I4D, I4G, I4P, Y9E, Y9P, T10F, T10W, T10Y, G12D, S18E, A22C, A22S, A22T, N24T, G26E, G26I, G26K, G26Q, G26V, G26W, F27V, F27W, I28P, I28T, T29E, A30M, A30N, A30P, A30Y, G31H, G31M, G31N, G31V, G31Y, C33E, C33L, C33M, C33N, A38D, A38G, T39R, T40D, T40H, T40N, T40P, T40Q, R43D, P43G, P43H, P43K, P43L, P43N, G45A, G45V, T46V, T46Y, T46W, A48P, Y57M, Y57N, F59K, T62G, T62R, A70G, A70P, N73P, R79T, Q81A, Q81D, Q81F, Q81G, Q81H, Q811P, Q81S, A83H, G84C, G84P, P89W, G91L, A93S, R96C, R96E, R96F, S99A, T100A, C105E, C105G, C105K, C105M, C105N, C105P, C105S, C105W, T121E, R123F, R123N, R123W, R123Y, L125A, T128A, T128C, T128G, T128S, T128V, I28W, T129W, S137R, S140P, Q146P, A147E, S155F, S155K, S155P, S155R, S155W, S155Y, G156I, G156L, G156P, C158G, C158H, C158M, R159K, T160I, G161I, G161L, G161V, T164G, T164L, F166S, Q167L, P168Y, Y176P, G186S, and S188A, wherein the substitutions are made at positions equivalent to the positions in a *Cellulomonas* 69B4 protease comprising the amino acid sequence set forth in SEQ ID NO:8. In some embodiments, the amino acid sequence of the serine protease variant comprises at least two substitutions selected from A8G, T10C, T10L, G12A, G12H, S15C, S15N, S15Q, S15R, S15T, N24E, N24S, G25S, F27I, G31A, H32A, C33D, T36V, T39V, A41S, T46F, G49A, S51V, F59W, Q71A, Q71Y, N74F, R79V, Q80C, Q81E, A83E, A83F, A83M, A83R, G84M, G84V, T86I, T86M, T86S, A87E, A87S, P89A, V90A, V90M, S92T, A93D, S99G, T100Q, T101S, W103N, C105A, C105L, C105T, C105Y, T107A, T107F, T107L, T107Q, T107S, T110D, A110G, L111K, V115I, V115L, T116Q, Y117K, Y117Q, Y117R, Y117V, P118T, E119L, T121A, T121D, R123I, R123K, R123L, R123Q, R123T, L125M, R127F, R127K, R127Q, T129Y, V130T, A132C, P134W, L141C, A143H, G144A, V150N, T151C, G153K, G153V, G154L, G154R, S155T, R159Q, R159T, R159V, T160E, T160Q, G161K, G162P, T163I, F166A, F166C, P168I, N170D, N170E, G177N, R179K, M180L, T182L, T183A, T183I, T183P, S185R, G186P, S188C, S188E, S188G, S188M, S188T, S188V, and P189S, wherein the substitutions are made at positions equivalent to the positions in a *Cellulomonas* 69B4 protease comprising the amino acid sequence set forth in SEQ ID NO:8.

The present invention further provides a serine protease variant, wherein the amino acid sequence of the protease comprises at least two substitutions selected from F1T, T10N, R14D, R14G, R14I, R14L, R14N, R14Q, R14T, N24A, N24E, N24H, N24L, N24Q, N24T, N24V, R35A, R35E, R35F, R35L, R35Q, R35T, T36G, T36I, T36N, T36S, A38D, A38F, A38H, A38N, A38R, G49A, G49S, S51I, G54D, G54E, N55E, N55F, A64I, G65D, G65P, G65Q, G65S, G65T, G65V, N67D, L69S, N73T, N74G, Y75F, Y75G, S76D, S76E, S76I, S76L, S76N, S76T, S76V, S76Y, G77T, G78A, G78D, R79A, R79D, R79E, R79G, R79L, R79M, R79P, R79S, R79T, R79V, Q81E, A83E, H85Q, H85T, T86D, T86E, V90I, V90P, V90S, V90T, S99N, S99V, T107E, T107H, T107S, T107V, T109E, N112D, N112E, N112L, N112Q, N112V, T116E, T116Q, T121E, R123A, R123D, R123E, R123F, R123H, R123I, R123L, R123N, R123Q, R127A, R127Q, T129S, L142V, N145E, R159D, R159E, R159F, R159N, R159Q, N170D, N170Y, I172T, R179A, R179D, R179E, R179I, R179K, R179M, R179N, R179T, R179V, R179Y, I181L, and G186N, wherein the substitutions are made at positions equivalent to the positions in a *Cellulomonas* 69B4 protease comprising the amino acid sequence set forth in SEQ ID NO:8. In some alternative embodiments, the amino acid sequence of the protease comprises at least two substitutions selected from F1D, V3L, N7L, A8E, A8G, T10D, T10E, G12D, G13S, R14A, R14K, R14S, R14M, S15W, I19V, N24M, R35H, R35M, R35S, R35W, R35Y, T36D, T36H, A38L, A38S, A38T, A38Y, T40V, A41D, A41N, A48E, G49F, G49H, S51H, S51Q, S51T, S51V, R61E, R61H, R61M, R61S, R61T, G63D, A64F, A64H, A64L, A64M, A64N, A64P, A64Q, A64S, A64T, A64V, A64W, A64Y, G65L, G65Y, N67E, N67G, N67H, N67S, N67T, A70D, A70G, A70H, Q71D, Q71G, Q71H, Q71S, V72I, S76Q, S76W, G77S, Q81D, Q81H, Q81V, H85L, H85M, V90N, S92A, S92G, A93D, A93E, A93S, S99D, S99T, T101S, W103M, T107A, T107I, T107M, T107N, T109A, T109G, T109I, A110S, N112Y, S113T, S114A, V115A, T116F, T121D, N121I, R123G, R123S, R123T, R123V, R123Y, R127H, R127K, R127E, R127S, R127Y, N145D, N145T, R159A, R159C, R159K, R159L, R159S, R159Y, T160E, T163D, N170L, R179L, T182V, T183E, T183I, and S185N, wherein the substitutions are made at positions equivalent to the positions in a *Cellulomonas* 69B4 protease comprising the amino acid sequence set forth in SEQ ID NO:8. In some yet additional embodiments, the serine protease variant comprises at least two substitutions selected from D2Q, V3L, N7L, I11A, I11Q, R14I, R14M, R16L, R16Q, N24A, N24E, N24H, N24M, N24Q, N24T, N24V, R35F, R35L, T36D, T36G, T36H, T36I, T36L, T36N, T36P, T36S, T36W, T36Y, A38L, A38R, A38S, A48Q, G49A, G54D, G54I, G54Q, G54N, R61V, A64F, A64H, A64Y, G65L, G65P, G65Q, G65S, G65T, G65Y, V66H, N67A, N67G, N67L, N67S, N67V, N67Y, L69H, L69S, Q71I, N73T, N74G, Y75F, Y75G, Y75I, S76A, S76D, S76E, S76I, S76L, S76N, S76T, S76V, S76W, S76Y, G77T, G78D, R79G, R79P, Q81P, H85F, H85K, H85L, H85Q, H85R, P89D, S92A, A93T, A93S, S99A, S99D, S99N, S99T, S99W, T109E, N112E, S113A, S114G, T116F, T121D, R123F, R123I, R123L, R127A, R127F, R127G, R127H, R127K, R127L, R127Q, R127S, R127T, R127Y, A132V, P134E, A143N, N157D, R159D, R159E, R159F, R159K, R159N, R159V, G161K, N170Y, R179V, I181Q, D184F, D184H, G186E, G186I, G186V, and S187P, wherein the substitutions are made at positions equivalent to the positions in a *Cellulomonas* 69B4 protease comprising the amino acid sequence set forth in SEQ ID NO:8.

In some additional embodiments, the amino acid sequence of the serine protease variant comprises at least two substitutions selected from F1T, A8D, A8G, T10E, T10L, T10Q, I11L, I11S, I11T, G12D, G12Y, R14E, R14L, R14N, R14P, S15E, R16A, R16G, R16I, R16N, N24L, N24S, V31F, R35A, A38D, A38F, A38N, A38V, A38Y, T40V, A41N, N42H, G49F, G49H, G49S, S51Q, S51T, G54A, G54L, G54M, N55F, R61H, R61K, R61M, R61S, R61T, A64N, A64S, A64T, A64V, A64W, G65R, G65V, V66D, N67F, N67K, N67M, N67Q, N67T, L69W, A70G, A70P, Q71D, Q71F, Q71H, Q71L, Q71T, G77N, G77S, G78A, G78N, R79D, V80H, V80L, H85T, H85Y, T86N, A88F, P89N, P89V, V90I, V90P, V90T S92G, A93D, A93E, S99G, L111D, L111E, N112D, N112G, N112L, N112Q, S113G, T121E, R123E, R123K, R123Q, L125V, P134G, S140A, L142V, A143S, N145D, V150L, R159A, R159C, R159D, R159V, T160E, G161E, T163D, T163I, N170D, N170L, R179D, R179E, R179K, R179N, R179T, I181H, T183I, D184R, D184L, D184Q, D184T, S185W, S185I, G186L, S187E, S187Q, and S188Q, wherein the substitutions are made at positions equivalent to the positions in a *Cellulomonas* 69B4 protease comprising the amino acid sequence set forth in SEQ ID NO:8. In some still further embodiments, the amino acid sequence of the serine protease variant comprises at least two substitutions selected from A8R, A8S, A8T, A8V, R14E, R14L, R14M, R16Q, N24A, N24E, N24Q, N24T, R35F, R35L, T36D, T36G, T36I, T36N, T36P, T36S, A38D, A38F, A38L, A38R, A38S, S51A, S51D, G54D, G54I, N55E, N55F, N55S, R61M, R61T, G63V, A64H, A64N, A64S, G65Q, G65P, G65R, G65S, G65T, G65Y, V66D, N67D, S76E, N67F, N67G, N67L, N67M, N67S, N67T, N67V, N67Y, L69H, L69S, L69V, L69W, N73T, N74G, Y75F, Y75G, S76C, S76D, S76I, S76L, S76N, S76W, S76Y, S76V, G77T, G78D, R79C, R79D, R79E, R79G, R79P, Q81V, A83N, T85A, H85Q, T86F, T86I, T86L, V90I, V90N, V90P, V90S, V90T, A93D, A93E, T107M, T107N, T107S, T109A, T109E, T109I, N112E, T121D, T121E, R123D, R123E, R123F, R123I, I126L, R127A, R127H, R127K, R127L, R127Q, R127S, R127Y, P134A, P134E, L142V, A143N, N145E, N145S, R150Y, R159C, R159D, R159E, R159F, R159K, R159Q, G161E, T163D, N170Y, I172V, G177M, R179A, R179D, R179E, R179I, R179K, R179L, R179M, R179N, R179T, R179V, R179Y, M180D, T182V, T183I, G186E, G186V, and S187P, wherein the substitutions are made at positions equivalent to the positions in a *Cellulomonas* 69B4 protease comprising the amino acid sequence set forth in SEQ ID NO:8. In some yet additional embodiments, the amino acid sequence of the serine protease variant comprises at least two substitutions selected from V3L, I4M, A8E, A8H, A8L, A8N, A8P, I11T, R14I, R14Q, R16L, N24H, N24L, N24M, N24V, R35A, R35E, T36V, T36Y, A38H, A38I, A38N, T40V, A41N, G49A, G49L, S51F, S51Q, G54A, G54E, G54M, G54Q, N55Q, N55V, R61V, T62I, G63D, G63L, G63P, G63Q, A64F, A64I, A64L, A64M, A64Q, A64R, A64T, A64V, A64W, G65A, G65Q, V66E, N67A, N67C, N67Q, N67R, L69Q, A70G, A70P, A70S, Q71D, Q71M, S76A, S76Q, S76T, G77N, G77Q, R79L, Q81E, Q81H, Q81I, A83D, A83I, H85L, H85R, T86E, T86M, A88F, V90L, S92C, S92G, A93Q, R96K, T101S, W103M, W103Y, T107A, T107E, T107H, T107Q, T107V, T109G, T109H, T109L, T109N, A110S, A110T, N112D, S114G, T116F, T121L, R123A, R123H, R123K, R123L, R123P, R123Q, L125V, R127F, R127T, T129G, T129S, A132V, P134D, P134G, S140A, N145G, N145P, N145Q, N145T, Q146D, T151V, R159A, R159H, R159L, R159N, R159V, S161K, F166Y, N170C, N170D, P171M, A175T, A175V, Y176L, R179W, T182W, T183E, T183K, T183L, T183Q, G186I, G186L, G186P, G186T, S187E, S187T, and S188E, wherein the substitutions are made at positions equivalent to the positions in a *Cellulomonas* 69B4 protease comprising the amino acid sequence set forth in SEQ ID NO:8. In some additional embodiments, the amino acid sequence of the serine protease variant comprises at least two substitutions selected from: T10A, T10G, T10L, I11A, I11S, I11T, G12I, R14G, R14M, S15E, S15F, S15G, R16K, R16N, A22V, N24A, N24E, N24L, N24Q, N24T, N24V, G34A, T36G, T36I, T36N, T36S, A38F, A38T, G49A, G49F, S51A, G65V, L69H, L69S, Q71I, N73T, N74G, S76D, S76L, S76V, S76W, S76Y, G77T, V80A, V90I, V90P, S99N, S99T, T107K, T107R, N112S, S118A, E119R, R127F, P134D, P134E, P134H, P134L, P134R, P134V, S140A, L142V, V110L, I59F, R159K, T163I, F166Y, Q167N, N170Y, R179V, T182V, G186E, G186S, and G186V, wherein the substitutions are made at positions equivalent to the positions in a *Cellulomonas* 69B4 protease comprising the amino acid sequence set forth in SEQ ID NO:8.

The present invention also provides serine protease variants that have improved stability as compared to wild-type *Cellulomonas* 69B4 protease comprising the amino acid sequence set forth in SEQ ID NO:8. In some embodiments, the variants have improved thermostability as compared to wild-type *Cellulomonas* 69B4 protease comprising the amino acid sequence set forth in SEQ ID NO:8. In some particularly preferred embodiments, the variants comprise multiple substitutions selected from T121E/R123F/R159E, R79T/R127Q/R179Q, R16Q/R79T/R127Q, R16Q/R79T/R123L/R159Q/R179Q, R16Q/R79T/R123L, R16Q/R79T, R16Q/R123L/R159Q, R14Q/T121E, R14L/R79T, R123L/R159Q, R123L/R127Q/R159Q, G12D/S15E/R35D/R123F/R159E, G12D/S15E/R159E, G12D/S15E, G12D/R35H/T121E/R123Q, G12D/R35H/R123Q, G12D/R35H/R123F/R159E, G12D/R35H, G12D/R35E/R123Q, G12D/R35E, G12D/R159E, G12D/R14Q/S15E/R35D, G12D/R14Q/R35H, G12D/R14Q/R159E, G12D/R14E, G12D/R127Q/R159E, G12D/R123E/R159E, and R35E/R123L/R127Q/R175Q, wherein the substitutions are made at positions equivalent to the positions in a *Cellulomonas* 69B4 protease comprising the amino acid sequence set forth in SEQ ID NO:8. In some alternative embodiments, the variants have improved LAS stability as compared to wild-type *Cellulomonas* 69B4 protease comprising the amino acid sequence set forth in SEQ ID NO:8. In some particularly preferred embodiments, the variants comprise multiple substitutions selected from T121E/R123F/R159E, S15E/T121E/R123Q, S15E/R35H/R159E, S15E/R35E/R159E, S15E/R35E/R127Q/R159E, S15E/R35E, S15E/R35D/T121E/R123Q, S15E/R35D/R123Q, S15E/R35D/R123F/R159E, S15E/R35D, S15E/R159E, S15E/R127Q, S15E/R123Q, S15E/R123E, R79T/R127Q/R179Q, R35H/R159E, R35H/R127Q/R159E, R35H/R123D/R159E, R35F/R61S/R159Q, R35F/R159Q, R35F/F121E/R123E, R35E/R159E, R35E/R127Q, R35D/R159E, R35D/R127Q/R159E, R35D/R127Q, R35D/R123Q/R159E, R16Q/R79T/R159Q/R179Q, R16Q/R79T/R127Q, R16Q/R79T/R123L/R159Q/R179Q, R16Q/R79T/R123L/R159Q, R16Q/R79T/R123L, R16Q/R79T, R16Q/R61S/R159Q/R179Q, R16Q/R61S/R123L/R159Q, R16Q/R35F/R61S/R159Q, R16Q/R35F/R159Q, R16Q/R35F/R123L/R159Q, R16Q/R35F, R16Q/R159Q/R179Q, R16Q/R159Q, R16Q/R127Q/R179Q, R16Q/R127Q/R159Q, R16Q/R123L/R159Q, R14Q/T121E, R14Q/R35E/T121E, R14Q/R35E/R159E, R14Q/R35E, R14Q/R35D/R127Q, R14Q/R35D/R123E/R159E, R14Q/R35D/R123D/R159E, R14Q/R35D, R14Q/R123Q, R14L/R79T/R127Q/R159Q, R14L/R79T, R14L/R61S/R79T/R123L, R14L/R61S/R123L, R14L/R35F/R79T/R123L/R159Q, R14L/R35F/R61S, R14L/R127Q/R159Q/R179Q, R14L/R123L/R159Q, R14I/R35E/T121E/R159E, R14I/R35E/R127Q, R14I/R35E/R123E, R14I/R35D/R159E, R14I/R35D/R127Q/R159E, R14E/S15E/R35H, R14E/R35H/R127Q, R14D/S15E/R35E/R159E, R14D/R35H/R123Q/R159E, R127Q/R159E, R127Q/R159Q, R123Q/R159E, R123Q/R127Q/R159E, R123L/R159Q, R123L/R127Q/R159Q, R123F/R159E, R123E/R127Q/R159E, R123E/R127Q, G12D/S15E/R35H/R159E, G12D/S15E/R35H/R123F/R127Q/R159E, G12D/S15E/R35E/R159E, G12D/S15E/R35D/R127Q, G12D/S15E/R35D/R123F/R159E, G12D/S15E/R35D/R123E, G12D/S15E/R35D, G12D/S15E/R159E, G12D/S15E, G12D/R35H/T121E/R123Q, G12D/R35H/R159E, G12D/R35H/R123Q/R159E, G12D/R35H/R123Q, G12D/R35H/R123F/R159E, G12D/R35E/R159E, G12D/R35E, G12D/R35E/R123Q/R159E, G12D/R35E/R123Q, G12D/R35E/R123E, G12D/R35D/R159E, G12D/R35D/R127Q, G12D/R35D/R123Q/R159E, G12D/R35D, G12D/R159E, G12D/R14Q/S15E/R35D, G12D/R14Q/R35H, G12D/R14Q/R35E/R127Q/R159E, G12D/R14Q/R35D/R123H, G12D/R14Q/R159E, G12D/R14I/R35H, G12D/R14E, G12D/R14D/R35H/R123D/R127Q, G12D/R127Q/R159E, G12D/R123E/R159E, R127A/R159K, R14I/G65Q, R14I/G65Q/N67L/R159K, R14I/G65Q/N67L/Y75G/R127A/R159K, R14I/G65Q/R159K, R14I/G65Q/S76V/R127A/R159K, R14I/R127A, R14I/R127A/R159K, R14I/R159K, R14I/R35F, R14I/R35F/G65Q, R14I/R35F/G65Q/R127A/R159K, R14I/R35F/N67L/R127A/R159K, R14I/R35F/R127A/R159K, R14I/R35F/R159K, R14I/S76V, R14I/T36S/G65Q/R127A/R159K, R35F/R127A/R159K, R35F/S76A/R127A; 024A/G049A/A093H/S099N/R127K/A143N/R159K/I181Q, N024A/S076A/A093H/S099G/R127K/R159K, N024A/S076T/A093S/S099G/R127K/R159K, N024E/G049A/A093G/S099G/R127K/A143N/R159K/I181T, N024E/G049A/A093H/R127K/A143N/R159K/I181Q, N024E/G049A/A093H/S099A/R127K/A143N/R159K/I181T/V190I, N024E/G049A/A093S/S099D/R127K/A143N/R159K/I181Q, N024H/G049A/A093T/S099A/R127K/A143N/R159K/I181Q, N024H/S076A/A093G/S099G/R127K/R159K, N024H/S076A/A093H/S099G/R127K/R159K, N024H/S076A/A093S/S099A/R127K/R159K/G054H/L069H, N024H/S076A/A093T/S099G/R127K/R159K, N024H/S076N/A093Q/S099W/R127K/R159K, N024H/S076V/A093Q/S099G/R127K/R159K, N024L/G049A/A093H/S099A/R127K/A143N/R159K/I181Q, N024L/G049A/A093S/S099A/R127K/A143N/R159K/I181Q, N024L/S076V/A093H/S099G/R127K, N024L/S076V/A093S/S099A/R127K/R159K, N024M/G049A/A093G/S099A/R127K/A143N/R159K/I181Q, N024M/G049A/A093H/S099D/R127K/A143N/R59K/I181Q, N024M/G049A/A093S/S099A/R127K/A143N/R159K/I181Q, N024M/G049A/A093S/S099W/R127K/A143N/R159K/I181Q, N024Q/G049A/A093H/S099A/R127K/A143N/R159K/I181T, N024Q/G049A/A093S/S099A/R127K/A143N/R159K/I181Q, N024Q/G049A/A093S/S099A/R127K/A143N/R159K/I181Q, N024Q/S076A/A093H/S099A/R127K/R159K/F039N, N024Q/S076A/A093H/S099W/R127K/R159K, N024Q/S076I/A093T/

S099G/R159K, N024Q/S076T/A093S/R127K/R159K, N024S/S076A/A093G/S099G/R127K/R159K/G054A, N024S/S076A/A093H/S099T/R127K/R159K, N024S/S076A/A093S/S099W/R127K/R159K, N024S/S076A/A093T/S099W/R127K, N024S/S076T/A093Q/S099W/R127K/R159K, N024S/S076Y/A093T/S099A/R127K/R159K, N024T/G049A/A093G/S099A/R127K/A143N/R159K/I181Q, N024T/G049A/A093H/S099A/R127K/A143N/R159K/I181Q, N024T/G049A/A093H/S099A/R127K/A143N/R159K/I181T, N024T/G049A/A093H/S099D/R127K/A143N/R159K/I181Q, N024T/G049A/A093S/S099A/R127K/A143N/R159K/I181T, N024T/G049A/A093T/S099A/R127K/A143N/R159K/I181T, N024T/S076N/A093Q/S099T/R127K/R159K, N024T/S076T/A093T/S099A/R127K/R159K, N024V/S076A/R127K/R159K, N024V/S076V/A093Q/S099G/R127K/R159K, N024W/A093G/S099W/R127K/R159K, N024W/G049A/A093H/S099A/R127K/A143N/R159K/I181Q, N024W/G049A/A093S/S099A/R127K/A143N/R159K/I181K, N024W/G049A/A093S/S099A/R127K/A143N/R159K/I181Q, N024W/S076A/A093T/S099A/R127K/R159K, N024W/S076I/A093Q/S099G/R127K/R159K, N024W/S076N/A093T/S099G/R159K, N024W/S076T/A093H/S099A/R127K/R159K, N024W/S076T/A093H/S099W/R127K/R159K, N024W/S076V/A093H/S099A/R127K/R159K, N024W/S099W/R127K/R159K, N24A/G54E/S76D/A93G/R127K/R159K, N24E/A93G/R127K/R159K, N24E/G54L/S76E/A93G/R127K/R159K, N24E/G54Q/A93G/R127K/R159K, N24E/S76D/A93T/R127K/R159K, N24H/A93R/R127K/R159K, N24H/G54E/A93G/R127K/R159K, N24H/S76D/A93H/R127K/R159K, N24L/A93G/R127K/R159K, N24L/G54E/A93G/R127K/R159K, N24L/G54L/A93G/R127K/R159K, N24L/G54Q/S76A/A93H/R127K/R159K, N24L/S76T/A93G/R127K/R159K, N24L/S76T/A93H/R127K/R159K, N24M/A93G/R127K/R159K, N24M/A93H/R127K/R159K, N24M/A93S/R127K/R159K, N24M/A93T/R127K/R159K, N24M/G54E/A93H/R127K/R159K, N24M/G54E/S76N/A93S/R127K/R159K, N24M/G54I/A93H/R127K/R159K/S187I, N24Q/A93G/R127K/R159K, N24Q/G54D/A93H/R127K/R159K, N24Q/G54I/A93G/R127K/R159K, N24Q/G54I/S76E/A93H/R127K/R59K, N24Q/G54Q/A93G/R127K/R159K, N24Q/G54Q/S76T/A93H/R127K/R159K, N24Q/S76A/A93G/R127K/R159K, N24T/G54D/S76V/A93G/R127K/R159K, N24T/G54E/S76V/A93H/R127K/R159K, N24T/G54I/A93G/R127K/R159K, N24T/G54N/A93H/R127K/R159K, N24T/G54Q/S76N/A93G/R127K/R159K, N24T/G54Q/S76V/R127K/R159K, N24T/S76I/R127K/R159K, N24T/S76L/A93G/R127K/R159K, N24W/A93G/R127K/R159K, N24W/G54D/A93H/R127K/R159K, N24W/G54I/S76A/A93H/R127K/R159K, N24W/S76A/A93H/R127K/R159K, N24W/S76E/A93G/R127K/R159K, R014I/S076A/A093G/R127K/R159K/I181T, R014I/S076A/A093H/R127K/R159K/I181K, R014I/S076A/A093H/R127K/R159K/I181Q, R014I/S076A/A093H/R127K/R159K/I181T, R014I/S076D/A093H/R127K/R159K/I181Q, R014I/S076D/A093S/R127K/R159K/I181T, R014I/S076E/A093S/R127K/R159K/I181Q, R014I/S076E/A093T/R127K/R159K/I181K, R014I/S076I/A093S/R127K/R159K/I181Q, R014I/S076N/A093H/R127K/R159K/I181Q, R014I/S076T/A093G/R127K/R159K/I181Q, R014K/S076A/A093G/R127K/R159K/I181K, R014K/S076E/A093H/R127K/R159K/I181K, R014K/S076T/A093H/R127K/R159K/I181Q, R014L/S076A/A093H/R127K/R159K, R014L/S076A/A093H/R127K/R159K/I181Q, R014L/S076D/A093H/R127K/R159K/I181T, R014L/S076E/A093H/R127K/R159K/I181K, R014M/S076A/A093G/

R127K/R159K/I181K, R014M/S076A/A093G/R127K/R159K/I181T, R014M/S076A/A093H/R127K/R159K/I181T, R014M/S076A/A093S/R127K/R159K/I181K, R014M/S076A/A093S/R127K/R159K/I181T, R014M/S076A/A093T/R127K/R159K/I181Q, R014M/S076D/A093S/R127K/R159K/I181T, R014M/S076E/A093G/R127K/R159K/I181T R014M/S076E/A093H/R127K/R159K/I181T, R014M/S076E/A093S/R127K/R159K/I181T, R014M/S076N/A093G/R127K/R159K/I181K, R014M/S076N/A093G/R127K/R159K/I181T, R014M/S076N/A093H/R127K/R159K/I181Q, R014M/S076N/A093H/R127K/R159K/I181T, R014M/S076N/A093S/R127K/R159K/I181T, R014M/S076N/A093T/R127K/R159K/I181T, R014M/S076T/A093E/R127K/R159K/I181K, R014M/S076V/A093G/R127K/R159K/I181Q, R014M/S076V/A093H/R127K/R159K/I181Q, G54E/R14L, G54L/R127S, N24D/G54F/R127C, N24E/R127S, N24E/R159C, N24G/G54I/R127S, N24H/R159Y/T46I, N24I/R127V/R14V, N24T/R127Q/R179F, R127A/R159V/R179F, R127C/R14W, R127S/R159N/R123L, R14A/N24F/R159L, R14A/R127L, R14A/R127Y/R159W, R14A/R159W, R14C/S114F/R159G, R14F/R127L/R159F, R14F/R127Q/R159W, R14F/R127S/R159V, R14F/R127V/R159F, R14G/N24L/R159G, R14G/N24S/R127C, R14G/R127C/G63E, R14G/R127G, R14G/R127P, R14L/N24S/R159F, R14L/N24V/R127S/R159I, R14L/R123L, R14L/R127C/R159G, R14L/R127S, R14L/R127S/R159G, R14L/R127V, R14L/R127V/R159F, R14I/R127W/R123Y, R14L/R127Y, R14L/R127Y/R159F, R14L/R159G, R14I/R159L, R14L/R159S, R14L/R159V, R14L/R159W, R14M/N24L/R159S/R123V, R14M/R159F, R14Q/R123F, R14S/N24E/R127W, R14S/N24L/R159G, R14S/R127L/R159F, R14S/R127V, R14T/R14P/R159F, R14T/N24A, R14T/N24T/R127Q, R14T/N24T/R127Y/R159W, R14T/R127Y, R14V/N24A/R127I/R159A, R14V/N24D/R127C, R14V/N24G/P189S, R14V/N24S, R14V/N24Y/R127S/R159G, R14V/R127A, R14V/R127C/R159S, R14V/R127M/R159V, R14V/R127S/R159G, R14V/R127T/R159Y, R14V/R127V, R14V/R159F, R14V/R159V, R14V/R159W, R14W/N24T/R123E, R14W/R123L, R14W/R123V, R14W/R127Q/R159W, R14W/R159V, R159V/G49D, G012D/R035E/G065E, G012D/R035E/G065E, G012D/R035E/Q081P, G012D/R035E/R016S/A064T, G012D/R035E/R159W, G012D/R035E/R179I, G012D/R035E/S092T/I181V, R14I/N24A/A64K/R123F/R159E/D184T, R14I/A64K/R123F/R159F/D184T, R14I/A64K/R123F/R159E/D184T, R14I/N24Q/R35E/A64K/R123F/D184T, R14I/N24Q/A64K/N67S/R123F/R159F/D184T, R14I/N24A/R35E/A64K/N67S/R123F/R159E/D184T, R14I/N24A/R35E/A64K/N67S/G78D/R123F/D184T, R14I/N24A/R35D/A64K/G78D/R123F/R127K/R159E/D184T, R14I/N24A/R35D/A64K/R123F/R127K/R159F/D184T, R14I/N24T/R35D/A64K/G78D/R123F/R127Q/R159F/D184T, R14I/A64K/R123F/D184T, R14I/N24A/A64K/R123F/R159N/D184T, R14I/N24Q/R35D/A64K/N67S/R123F/R159K/D184T, R14I/N24E/R35E/A64K/G78D/R123F/R127Q/R159F/D184T, R14I/N24E/A64K/R123F/R127K/R159K/D184T, R14I/N24A/A64K/R123F/D184T, R14I/A64K/R123F/R127K/R159F/D184T, R14I/A64K/R123F/R159E/D184T, R14I/A64K/R123F/R159N/D184T, R14I/A64K/R123F/R159K/D184T, R14I/A64K/R123F/R127Y/R159E/D184T, R14I/N24A/R35E/A64K/N67A/G78D/R123F/D184T, R14I/A64K/R123F/R127Y/R159K/D184T, R14I/N24Q/A64K/R123F/R127Q/R159K/D184T, R14I/A64K/R123F/R159K/D184T, R14I/N24Q/A64K/G78D/R123F/R127Q/R159N/D184T, R14I/N24E/A64K/N67I/G78D/R123F/R159K/D184T, R14I/N24A/R35E/A64K/G78D/R123F/R127K/R159E/D184T, R14I/N24Q/R35D/A64K/N67S/R123F/R159K/

D184T, R14I/N24A/R35D/A64K/N67A/R123F/R159F/ D184T, R14I/N24E/R35E/G54D/A64K/N67L/G78D/ R123F/R127K/D184T, R14I/A64K/G78D/R123F/R127Q/ R159N/D184T, R14I/N24A/R35E/A64K/G78D/R123F/ R159N/D184T, R14I/A64K/R123F/R127K/R159E/D184T, R14I/N24A/R35E/A64K/N67S/G78D/R123F/R127K/ R159F/D184T, R14I/A64K/G78D/R123F/R159E/D184T, R14I/N24E/R35D/A64K/N67A/G78D/R123F/R159K/ D184T, N24T/R35D/G78D/R159K, N24T/R35E/N67A/ G78D/R127Q, N24Q/R35E, R127K/R159N, R35D/R159E, R35E/G54D/N67S/G78D/R159K, N24Q/G54D/G78D/ R159N, R127K/R159E, R127Q/R159K, N24E/R35E/G54D/ N67S/R127K/R159N, R35D/G78D/R159K, N67S/R159E, G54D/R127K/R159K, G78D/R127K/R159K, G78D/ R127K/R159E, N24E/R35D/G78D/R127K/R159N, R35D/ G78D/R127K/R159N, N24A/R35E/G78D/R159N, N24Q/ R35D/N67S/R127K/R159E, N24T/R35D/G78D/R159K, N67S/G78D/R127K/R159K, N24Q/R35D/R127K/R159K, N24E/G54D/G78D/R159K, R35D/R159K, R35E/R159K, R127K/R159K, R35E/N67S/G78D/R127Q, N24E/R35D/ G78D, R35D/G78D/R127K/R159E, N24E/R35E/G54D/ N67S/G78D/R127K/R159K, N24T/N67S/R159E, N24D/ R35D/G78D/R159F, N24Q/R35D/N67S/G78D/R127K/ R159F, R35D/G78D/R127Q/R159K, G78D/R159F, N24A/ N67S/R159K, G78D/R127Q/R159K, N24T/G54D/N67S/ G78D/R127Y/R159E, R14I/A63K/G78D/R123F/D184T, R14I/A63K/R123F/R159E/D184T, R14I/A63K/R123F/ R159F/D184T, R14I/A63K/R123F/R159K/D184T, R14I/ A63K/R123F/R159N/D184T, R14I/A63K/R123K/D184T, R14I/A63K/R123Q/D184T, R14I/A63K/R123Y/D184T, R14I/A64K/G78D/T86K/T116E/R123F, R14I/A64K/T86K/ T116E/R123F/R159E, R14I/A64K/T86K/T116E/R123F/ R159K, R14I/A64K/T86K/T116E/R123K, R14I/A64K/ T86K/T116E/R123Q, R14I/A64K/T86K/T116E/R123Y, R14I/G54D/A63K/R123F/D184T, R14I/G54D/A64K/ T86K/T116E/R123F, R14I/G54D/S76N/A93I/R127K/ R159K/I181Q, R14I/G54D/S76V/A93S/R127K/R159K/ I181K, R14I/N24A/A63K/R123F/D184T, R14I/N24A/ A64K/T86K/T116E/R123F, R14I/N24E/A63K/R123F/ D184T, R14I/N24E/A64K/T86K/T116E/R123F, R14I/ N24Q/A63K/R123F/D184T, R14I/N24Q/A64K/T86K/ Y116E/R123F, R14I/N24T/A63K/R123F/D184T, R14I/ N24T/A64K/T86K/T116E/R123F, R14I/N24TS76N/A93H/ R127K/R159K/I181Q, R14I/N24TS76V/A93S/R127K/ R159K/I181K, R14I/N67AS76N/A93H/R127K/R159K/ I181Q, R14I/N67LS76N/A93H/R127K/R159K/I181Q, R14I/N67SS76N/A93H/R127K/R159K/I181Q, R14I/ R35D/A64K/T86K/T116E/R123F, R14I/R35D/S76N/ A93H/R127K/R159K/I181Q, R14I/R35E/A63K/R123F/ D184T, R14I/R35E/A64K/T86K/T116E/R123F, R14I/ R35E/S76N/A93H/R127K/R159K/I181Q, R14I/R35E/ S76V/A93S/R127K/R159K/I181K, R14I/R35K/A63K/ R123F/D184T, R14I/S76N/A93H/R127K/R159E/I181Q, R14I/S76N/A93H/R127K/R159F/I181Q, R14I/S76N/ A93H/R127K/R159N/I181Q, R14I/S76N/A93H/R127Q/ R159K/I181Q, R14I/S76N/A93H/R127Y/R159K/I181Q, R14I/S76N/G78D/A93H/R127K/R159K/I181Q, R14I/ S76V/A93S/R127K/R159F/I181K, R14I/S76V/A93S/ R127K/R159N/I181K, R14I/S76V/A93S/R127Q/R159K/ I181K, R14I/S76V/A93S/R127Y/R159K/I181K, R14M/ G54D/S76N/A93G/R127K/R159K/I181K, R14M/N24A/ S76N/A93G/R127K/R159K/I181K, R14M/N24E/S76N/ A93G/R127K/R159K/I181K, R14M/N24Q/S76N/A93G/ R127K/R159K/I181K, R14M/N24T/S76N/A93G/R127K/ R159K/I181K, R14M/N67S/S76N/A93G/R127K/R159K/ I181K, R14M/R35D/S76N/A93G/R127K/R159K/I181K, R14M/R35E/S76N/A93G/R127K/R159K/I181K, R14M/ S76N/A93G/R127K/R159E/I181K, R14M/S76N/A93G/ R127K/R159F/I181K, R14M/S76N/A93G/R127K/R159N/ I181K, R14M/S76N/A93G/R127Q/R159K/I181K, R14M/ S76N/A93G/R127Y/R159K/I181K, and R14M/S76N/ G78D/A93G/R127K/R159K/I181K, wherein the substitutions are made at positions equivalent to the positions in a *Cellulomonas* 69B4 protease comprising the amino acid sequence set forth in SEQ ID NO:8.

The present invention also provides serine protease variants that have improved activity, as compared to wild-type *Cellulomonas* 69B4 protease comprising the amino acid sequence set forth in SEQ ID NO:8. In some preferred embodiments, the variants have improved caseinolytic activity as compared to wild-type *Cellulomonas* 69B4 protease comprising the amino acid sequence set forth in SEQ ID NO:8. In some particularly preferred embodiments, the variants comprise multiple substitutions selected from R14L/ R79T, G12D/R35H/R159E, G12D/R35H/R123Q, G12D/ R35H/R123F/R159E, G12D/R35H, G12D/R35E/R159E, G12D/R35E/R123Q/R159E, G12D/R35E/R123Q, G12D/ R35E, G12D/R35D/R159E, G12D/R35D/R123Q/R159E, G12D/R35D, G12D/R35E, G12D/R14Q/R35H, G12D/ R14I/R35H, 024E/G049A/A093H/R127K/A143N/R159K/ I181Q, N24M/S76V/A93H/R127K/R159K, R14I/N24E/ R35D/A64K/N67A/G78D/R123F/R159K/D184T R127A/ R159K, R14I/G65Q, and R14V/G65Q/R159K R14I/S76V, wherein the substitutions are made at positions equivalent to the positions in a *Cellulomonas* 69B4 protease comprising the amino acid sequence set forth in SEQ ID NO:8. In some alternative embodiments, the variants have improved keratinolytic activity as compared to wild-type *Cellulomonas* 69B4 protease comprising the amino acid sequence set forth in SEQ ID NO:8. In some particularly preferred embodiments, the variants comprise multiple substitutions selected from N024E/G049A/A093H/R127K/A143N/R159K/I181Q, N024E/G049A/A093H/S099A/R127K/A143N/R159K/ I181T/V090I, N024E/G049A/A093S/S099D/R127K/ A143N/R159K/I181Q, N024Q/G049A/A093S/S099A/ R127K/A143N/R159K/I181Q, N024Q/G049A/A093S/ S099A/R127K/A143N/R159K/I181T, N024Q/G049A/ A093S/S099N/R127K/A143N/R159K/I181Q, N024T/ G049A/A093S/S099A/R127K/A143N/R159K/I181T, N024W/G049A/A093S/S099A/R127K/A143N/R159K/ I181Q, N24A/G54E/S76D/A93G/R127K/R159K, N24E/ A93G/R127K/R159K, N24E/G54L/S76E/A93G/R127K/ R159K, N24E/G54Q/A93S/R127K/R159K, N24E/S76D/ A93T/R127K/R159K, N24M/G54E/A93H/R127K/R159K, N24M/G54E/S76N/A93S/R127K/R159K, N24Q/A93G/ R127K/R159K, N24Q/G54D/S76L/A93G/R127K/R159K, N24Q/G54I/S76E/A93H/R127K/R159K, N24T/G54D/ S76V/A93G/R127K/R159K, N24T/G54E/S76V/A93H/ R127K/R159K, N24W/G54D/A93H/R127K/R159K, N24W/S76E/A93G/R127K/R159K, R014I/S076A/A093G/ R127K/R159K/I181T, R014I/S076A/A093H/R127K/ R159K/I181Q, R014I/S076D/A093H/R127K/R159K/ I181Q, R014I/S076D/A093H/R127K/R159K/I181T, R014I/ S076D/A093S/R127K/R159K/I181T, R014I/S076E/A093S/ R127K/R159K/I181Q, R014I/S076E/A093T/R127K/ R159K/I181K, R014I/S076I/A093S/R127K/R159K/I181Q, R014I/S076N/A093H/R127K/R159K/I181Q, R014I/ S076T/A093G/R127K/R159K/I181Q, R014I/S076V/ A093H/R127K/R159K/I181Q, R014K/S076A/A093S/ R127K/R159K/I181T, R014K/S076E/A093H/R127K/ R159K/I181T, R014K/S076E/A093S/R127K/R159K/ I181T, R014K/S076T/A093H/R127K/R159K/I181Q, R014I/S076A/A093H/R127K/R159K, R014L/S076A/

A093H/R127K/R159K/I181Q, R014L/S076D/A093H/ R127K/R159K/I181T, R014L/S076E/A093H/R127K/ R159K/I181K, R014M/S076A/A093G/R127K/R159K/ I181T, R014M/S076A/A093H/R127K/R159K/I181T, R014M/S076A/A093S/R127K/R159K/I181K, R014M/ S076A/A093S/R127K/R159K/I181T, R014M/S076A/ A093T/R127K/R159K/I181Q, R614M/S076D/A093S/ R127K/R159K/I181T, R014M/S076E/A093G/R127K/ R159K/I181T, R014M/S076E/A093H/R127K/R159K/ I181T, R014M/S076E/A093S/R127K/R159K/I181T, R014M/S076N/A093G/R127K/R159K/I181K, R014M/ S076N/A093G/R127K/R159K/I181T, R014M/S076N/ A093H/R127K/R159K/I181T, R014M/S076N/A093S/ R127K/R159K/I181T, R014N/S076V/A093G/R127K/ R159K/I181Q, R14I/N24Q/A64K/G78D/R123F/R159K/ D184T, R14I/N24A/A64K/N67S/G78D/R123F/R159K/ D184T, R14I/N24Q/R35D/A64K/N67S/R123F/R159K/ D184T, R14I/N24E/A64K/R123F/R127K/R159K/D184T, R14I/N24Q/A64K/R123F/R127Q/R159K/D184T, R14I/ N24Q/A64K/G78D/R123F/R127Q/R159N/D184T, R14I/ N24E/A64K/N67L/G78D/R123F/R159K/D184T, R14I/ N24Q/R35D/A64K/N67S/R123F/R159K/D184T, R127Q/ R159K, G78D/R127K/R159K, N67S/G78D/R127K/ R159K, R35D/R159K, G78D/R127Q/R159K, N24A/N67A/ R159K, T36S/R127Q/R159E, S15E/T121E/R123Q, S15E/ R35H/R159E, S15E/R35E, S15E/R159E, S15E/R123Q, S15E/R123E, R79T/R127Q/R179Q, R35H/R159E, R35H/ R127Q/R159E, R35F/R61S/R159Q, R35F/R159Q, R35E/ R159E, R35E/R127Q, R35D/R159E, R35D/R127Q, R16Q/ R79T/R159Q/R179Q, R16Q/R79T/R127Q, R16Q/R79T/ R123L, R16Q/R79T, R16Q/R35F/R123L/R159Q, R16Q/ R159Q/R179Q, R16Q/R127Q/R159Q, R16Q/R123L/ R159Q, R14Q/T121E, R14Q/R35E/T121E, R14Q/R35E/ R159E, R14Q/R35E, R14Q/R35D/R127Q, R14Q/R35D, R14L/R79T/R127Q/R159Q, R14L/R61S/R79T/R123L, R14L/R35F/R61S, R14L/R127Q/R159Q/R179Q, R14L/ R123L/R159Q, R14I/R35E/R127Q, R14I/R35E/R123E, R14I/R35D/R159E, R14E/R35H/R127Q, R127Q/R159E, R127Q/R159Q, R123Q/R159E, R123Q/R127Q/R159E, R123L/R159Q, R123L/R127Q/R159Q, R123F/R159E, R123E/R127Q/R159E, R123E/R127Q, G12D/S15E/R35H/ R159E, G12D/S15E/R35D, G12D/S15E/R159E, G12D/ S15E, G12D/R35H/T121E/R123Q, G12D/R35H/R159E, G12D/R35H/R127Q/R159E, G12D/R35H/R123Q, G12D/ R35H/R127Q/R123F/R159E, G12D/R35H, G12D/R35E/R159E, G12D/R35E/R123Q/R159E, G12D/R35E/R123Q, G12D/ R35E, G12D/R35D/R159E, G12D/R35D/R127Q, G12D/ R35D, G12D/R159E, G12D/R14Q/R35H, G12D/R14Q/ R35D/R123H, G12D/R14Q/R159E, G12D/R14I/R35H, G12D/R14E, G12D/R127Q/R159E, G12D/R123E/R159E, R127A/R159K, R14I/G65Q, R14I/G65Q/R127A/R159K, R14I/G65Q/R159K, R14I/R127A, R14I/R127A/R159K, R14I/R159K, R14I/R35F, R14I/R35F/G65Q, R14I/R35F/ G65Q/R127A/R159K, R14I/R35F/R159K, R14I/S76V, R14I/T36S/G65Q/R127A/R159K, and R35F/R127A/ R159K, wherein the substitutions are made at positions equivalent to the positions in a *Cellulomonas* 69B4 protease comprising the amino acid sequence set forth in SEQ ID NO:8.

The present invention also provides serine protease variants that have improved wash performance activity as compared to wild-type *Cellulomonas* 69B4 protease comprising the amino acid sequence set forth in SEQ ID NO:8. In some preferred embodiments, the variants comprise multiple substitutions selected from N24F/R159G, /N24F/R159L/ R123V, N24I/R127S, /N24L/R159S, N24S/R159A, N24V/ R159L, N24Y/R159F, R14A/N24K/R127S, R14A/R159W, R14L/N24Y, R14L/R159G, R14L/R159S, R14L/T109M, R14L/T39P, R14M/R159W, R14S/N24V, R14S/N24Y, R14T/N24A, R14V/N24G/P189S, R14V/R159W, R127A/ R159K, R14I/G65Q, R14I/S76V, R14I/G65Q/N67L/R159K, R14I/G65Q/R159K, R14I/S76V, R35F/R159Q, R16Q/ R79T, R16Q/R35F, R16Q/R159Q, R14L/R79T, R123L/ R159Q, G12D/S15E, G12D/R35H, G12D/R35D, N024E/ G049A/A093H/R127K/A143N/R159K/I181Q, N024H/ S076A/A093S/S099A/R127K/R159K/G054H/L069H, N024H/S076A/A093T/S099G/R127K/R159K, N024L/ S076V/A093S/S099A/R127K/R159K, N024Q/G049A/ A093S/S099A/R127K/A143N/R159K/I181T, N024T/ G049A/A093S/S099A/R127K/A143N/R159K/I181T, N24E/G54Q/A93S/R127K/R159K, N24H/A93H/R127K/ R159K, N24H/G54L/S76V/A93H/R127K/R159K, N24L/ G54Q/S76A/A93H/R127K/R159K, N24M/A93G/R127K/ R159K, N24M/G54E/A93H/R127K/R159K, N24M/S76V/ A93H/R127K/R159K, N24Q/G54Q/S76T/A93H/R127K/ R159K, N24Q/S76A/A93G/R127K/R159K, N24T/G54Q/ S76N/A93G/R127K/R159K, N24T/S76I/R127K/R159K, N24W/G54D/A93G/R127K/R159K, N24W/S76A/A93H/ R127K/R159K, N24W/S76T/A93G/R127K/R159K, N24W/ S76V/A93G/R127K/R159K, N24W/S76Y/A93G/R127K/ R159K, R014I/S076A/A093G/R127K/R159K/I181T, R014I/S076A/A093H/R127K/R159K/I181K, R014I/ S076A/A093H/R127K/R159K/I181Q, R014I/S076A/ A093H/R127K/R159K/I181T, R014I/S076D/A093S/ R127K/R159K/I181T, R014I/S076E/A093T/R127K/ R159K/I181K, R014I/S076N/A093H/R127K/R159K/ I181Q, R014I/S076V/A093H/R127K/R159K/I181Q, R014I/S076V/A093S/R127K/R159K/I181K, R014K/ S076A/A093S/R127K/R159K/I181T, R014K/S076E/ A093E/R127K/R159K/I181K, R014K/S076I/A093S/ R127K/R159K/I181T, R014K/S076T/A093H/R127K/ R159K/I181K, R014K/S076T/A093H/R127K/R159K/ I181T, R014K/S076V/A093H/R127K/R159K/I181K, R014L/S076A/A093H/R127K/R159K, R014L/S076A/ A093H/R127K/R159K/I181Q, R014L/S076D/A093H/ R127K/R159K/I181T, R014L/S076E/A093H/R127K/ R159K/I181K, R014M/S076A/A093G/R127K/R159K/ I181K, R014M/S076A/A093G/R127K/R159K/I181T, R014M/S076A/A093H/R127K/R159K/I181T, R014M/ S076A/A093S/R127K/R159K/I181K, R014M/S076A/A093T/ R127K/R159K/I181Q, R014M/S076I/A093H/R127K/ R159K/I181T, R014N/S076I/A093S/R127K/R159K/I181T, R014M/S076N/A093G/R127K/R159K/I181K, R014N/ S076N/A093G/R127K/R159K/I181T, R014M/S076N/ A093H/R127K/R159K/I181T, R014N/S076N/A093S/ R127K/R159K/I181T, R014N/S076T/A093H/R127K/ R159K/I181K, R014M/S076V/A093G/R127K/R159K/ I181Q, R014M/S076W/A093H/R127K/R159K/I181K, R014M/S076Y/A093H/R127K/R159K/I181K, R014M/ S076Y/A093H/R127K/R159K/I181T, G012D/R035E/ D184N, G012D/R035E/N067K, R14I/A64K/R123F/R159F/ D184T, R14I/A64K/R123F/R159F/D184T, R14I/N24Q/ A64K/G78D/R123F/R159K/D184T, R14I/N24Q/A64K/ N67S/R123F/R159F/D184T, R14I/N24Q/A64K/N67A/ R123F/R159K/D184T, R14I/N24A/A64K/N67S/G78D/ R123F/R159K/D184T, R14I/A64K/R123F/D184T, R14I/ N24A/A64K/R123F/R159N/D184T, R14I/N24Q/R35D/ A64K/N67S/R123F/R159K/D184T, R14I/N24Q/A64K/ N67A/R123F/R159F/D184T, R14I/N24E/A64K/R123F/ R127K/R159K/D184T, R14I/N24A/A64K/R123F/D184T, R14I/A64K/R123F/R127K/R159F/D184T, R14I/A64K/ R123F/R159N/D184T, R14I/A64K/R123F/R159K/D184T, R14I/A64K/R123F/R127Y/R159K/D184T, R14I/N24Q/

A64K/R123F/R127Q/R159K/D184T, R14I/A64K/R123F/
R159K/D184T, R14I/N24Q/R35D/A64K/N67S/R123F/
R159K/D184T, R14I/A64K/N67S/G78D/R123F/R127K/
R159K/D184T, R14I/N24Q/A64K/N67A/R123F/R127K/
R159K/D184T, R127K/R159K, N24A/N67S/R159K,
N24A/N67A/R159K, R14I/A63K/G78D/R123F/D184T,
R14I/A63K/N67A/R123F/D184T, R14I/A63K/N67L/
R123F/D184T, R14I/A63K/N67S/R123F/D184T, R14I/
A63K/R123F/R159F/D184T, R14I/A63K/R123F/R159K/
D184T, R14I/A63K/R123F/R159N/D184T, R14I/A63K/
R123K/D184T, R14I/A63K/R123Q/D184T, R14I/A63K/
R123Y/D184T, R14I/A64K/G78D/T86K/T116E/R123F,
R14I/A64K/N67A/T86K/T116E/R123F, R14I/A64K/N67L/
T86K/T116E/R123F, R14I/A64K/T86K/T116E/R123F/
R159K, R14I/A64K/T86K/T116E/R123K, R14I/G54D/
A63K/R123F/D184T, R14I/G54D/A64K/T86K/T116E/
R123F, R14I/N24A/A63K/R123F/D184T, R14I/N24A/
A64K/T86K/T116E/R123F, R14I/N24A/S76V/A93S/
R127K/R159K/I181K, R14I/N24E/A63K/R123F/D184T,
R14I/N24E/A64K/T86K/T116E/R123F, R14I/N24Q/A63K/
R123F/D184T, R14I/N24Q/A64K/T86K/T116E/R123F,
R14I/N24Q/S76V/A93S/R127K/R159K/I181K, R14I/
N24T/A63K/R123F/D184T, R14I/N24T/A64K/T86K/
T116E/R123F, R14I/N24TS76V/A93S/R127K/R159K/
I181K, R14I/N67SS76N/A93H/R127K/R159K/I181Q,
R14I/R35E/A63K/R123F/D184T, R14I/R35K/A63K/
R123F/D184T, R14I/S76V/A93S/R127K/R159F/I181K,
R14I/S76V/A93S/R127K/R159N/I181K, R14I/S76V/
A93S/R127Y/R159K/I181K, R14M/N24T/S76N/A93G/
R127K/R159K/I181K, R14M/N67S/S76N/A93G/R127K/
R159K/I181K, R14M/S76N/A93G/R127K/R159F/I181K,
and R14M/S76N/G78D/A93G/R127K/R159K/I181K,
wherein the substitutions are made at positions equivalent to
the positions in a *Cellulomonas* 69B4 protease comprising
the amino acid sequence set forth in SEQ ID NO:8. In some
embodiments, the variants have improved dishwashing performance activity as compared to wild-type *Cellulomonas* 69B4 protease comprising the amino acid sequence set forth in SEQ ID NO:8. In some preferred embodiments, the variants comprise multiple substitutions selected from R14N/
R127K/R159L, R14I/A64K/T86K/N112E/R123F/D184T,
G12D/R35E/G63R/R79K/T109M, R14L, G12D/R35E, and
R14M/S76D/A93H/R127K/R159K/I181K, wherein the substitutions are made at positions equivalent to the positions in a *Cellulomonas* 69B4 protease comprising the amino acid sequence set forth in SEQ ID NO:8. In some still further embodiments, the variants have improved stain removal activity as compared to wild-type *Cellulomonas* 69B4 protease comprising the amino acid sequence set forth in SEQ ID NO:8. In some preferred embodiments, the variants comprise multiple substitutions selected from: G54E/R14L, N24D/
R127Y/R159V, N24E/R127S, N24E/R159C, N24F/R159G,
N24F/R159G/G54E, N24F/R159L/R123V, N24G/R127Y,
N24H/R159Y/T46I, N24I/R127S, N24I/R127V/R14/N24L/
R159S, N24S/R159A, N24V/R127M/R159V, N24V/R127S/
R159H, N24V/R159L, N24Y/G54A/N24Y/R127L, N24Y/
R127S, N24Y/R127V, N24Y/R159F, R127A/R159F,
R127H/R159Q, R127H/R159T/S185F, R127M/R159V,
R127S/R159G, R127S/R159L, R127T/R159F, R127V/
R159G, R127Y/R159L, R14A/N24K/R127S, R14A/R127Y/
R159W, R14G/N24S/R127C, R14G/R127G, R14L/N24D,
R14I/N24Y, R14L/R123L, R14L/R127S, R14I/R127V,
R14L/R127Y, R14L/R159G, R14L/R159S, R14L/T39P,
R14M/N24L/R159S/R123V, R14M/R159F, R14M/R159W,
R14Q/R123F, R14S/N24E/R127W, R14S/N24V, R14S/
N24Y, R14T/N24T/R127Q, R14T/R127Y, R14V/N24D/
R127C, R14V/N24G/P189S, R14V/N24L/R127F, R14V/
R127A, R14V/R159F, R14V/R159W, R14W/N24A, R14W/
R123L, R14W/R123V, R14W/R159V, R159V/G49D,
R159V/R123G, N024E/G049A/A093H/R127K/A143N/
R159K/I181Q, N024E/G049A/A093S/S099D/R127K/
A143N/R159K/I181Q, N024Q/G049A/A093S/S099A/
R127K/A143N/R159K/I181T, N24A/G54E/S76D/A93G/
R127K/R159K, N24E/A93G/R127K/R159K, N24E/G54L/
S76E/A93G/R127K/R159K, N24E/G54Q/A93S/R127K/
R159K, N24E/S76D/A93T/R127K/R159K, N24H/G54E/
A93G/R127K/R159K, N24L/S76T/A93G/R127K/R159K,
N24M/A93S/R127K/R159K, N24M/A93T/R127K/R159K,
N24M/G54E/A93H/R127K/R159K, N24M/G54E/S76N/
A93S/R127K/R159K, N24M/S76V/A93H/R127K/R159K,
N24Q/A93G/R127K/R159K, N24Q/G54D/S76L/A93G/
R127K/R159K, N24Q/G54I/S76T/A93G/R127K/R159K,
N24Q/G54Q/A93G/R127K/R159K, N24Q/S76A/A93G/
R127K/R159K, N24T/G54Q/S76N/A93G/R127K/R159K,
N24T/G54Q/S76V/R127K/R159K, N24T/S76I/R127K/
R159K, N24W/A93G/R127K/R159K, N24W/G54D/A93H/
R127K/R159K, R014I/S076A/A093G/R127K/R159K/
I181T, R014I/S076A/A093H/R127K/R159K/I181Q, R014I/
S076D/A093H/R127K/R159K/I181Q, R014I/S076D/
A093H/R127K/R159K/I181T, R014I/S076D/A093S/
R127K/R159K/I181T, R014I/S076E/A093S/R127K/
R159K/I181Q, R014I/S076E/A093T/R127K/R159K/
I181K, R014I/S076N/A093H/R127K/R159K/I181Q,
R014L/S076A/A093H/R127K/R159K, R014L/S076A/
A093H/R127K/R159K/I181Q, R014L/S076D/A093H/
R127K/R159K/I181T, R014M/S076A/A093G/R127K/
R159K/I181T, R014M/S076A/A093S/R127K/R159K/
I181K, R014M/S076A/A093S/R127K/R159K/I181T,
R014M/S076A/A093T/R127K/R159K/I181Q, R014M/
S076D/A093S/R127K/R159K/I181T, R014M/S076E/
A093E/R127K/R159K/I181T, R014M/S076E/A093S/
R127K/R159K/I181T, R014I/S076N/A093G/R127K/
R159K/I181K, R014M/S076N/A093G/R127K/R159K/
I181T, R014M/S076N/A093H/R127K/R159K/I181T,
R014M/S076N/A093S/R127K/R159K/I181T, T36S/
R127Q/R159E, S15E/R35E, S15E/R35D, S15E/R159E,
S15E/R127Q, S15E/R123Q, S15E/R123E, R79T/R127Q/
R179Q, R35H/R159E, R35F/R61S/R159Q, R35F/R159Q,
R35D/R127Q, R16Q/R79T/R159Q/R179Q, R16Q/R79T/
R123L, R16Q/R79T, R16Q/R35F, R16Q/R159Q/R179Q,
R16Q/R159Q, R14Q/T121E, R14Q/R35E, R14Q/R35D,
R14Q/R123Q, R14L/R79T, R127Q/R159E, R127Q/R159Q,
R123Q/R159E, R123L/R159Q, R123F/R159E, G12D/
S15E, G12D/R35H/R159E, G12D/R35H/R123Q, G12D/
R35H, G12D/R35E, G12D/R35D, G12D/R159E, G12D/
R14Q/R35H, G12D/R14I/R35H, G65Q/R127A/R159K,
R127A/R159K, R14I/G65Q, R14I/G65Q/N67L/R159K,
R14I/G65Q/R127A, R14I/G65Q/R127A/R159K, R14I/
G65Q/R159K, R14I/R127A, R14I/R127A/R159K, R14I/
R159K, R14I/R35F, R14I/R35F/G65Q, R14I/R35F/R159K,
R14I/S76V, and R35F/R127A/R159K, wherein the substitutions are made at positions equivalent to the positions in a *Cellulomonas* 69B4 protease comprising the amino acid sequence set forth in SEQ ID NO:8.

The present invention also provides serine protease variants that have at least one altered surface property, as compared to wild-type *Cellulomonas* 69B4 protease comprising the amino acid sequence set forth in SEQ ID NO:8. In some preferred embodiments, the variants comprise at least two substitutions at sites selected from the group consisting of 1, 2, 4, 7, 8, 10, 11, 12, 13, 14, 15, 16, 22, 24, 25, 32, 34, 35, 36, 37, 38, 39, 40, 41, 42, 43, 44, 45, 46, 47, 48, 49, 50, 51, 52, 53, 54, 55, 57, 59, 61, 62, 63, 64, 65, 66, 67, 68, 69, 71, 73, 74, 75, 76, 77, 78, 79, 80, 81, 83, 84, 85, 86, 87, 88, 89, 90, 91, 92, 93, 95, 99, 100, 101, 102, 103, 104, 105, 106, 107, 108, 109, 110, 111, 112, 113, 114, 115, 116, 117, 118, 119, 120, 121, 123, 124, 126, 127, 128, 130, 131, 132, 133, 134, 135, 137, 143, 144, 145, 146, 147, 148, 152, 153, 154, 155, 156, 157, 158, 159, 160, 161, 162, 163, 164, 165, 166, 167, 168, 170, 111, 173, 174, 175, 176, 177, 178, 179, 180, 181, 182, 183, and 184, wherein the substitutions are made at positions equivalent to the positions in a *Cellulomonas* 69B4 protease comprising the amino acid sequence set forth in SEQ ID NO:8

In some particularly preferred embodiments, the variant proteases have at least one improved property as compared to the wild-type *Cellulomonas* 69B4 protease comprising the amino acid sequence set forth in SEQ ID NO:8. In some particularly preferred embodiments, the at least one improved property is selected from the group consisting of acid stability, thermostability, casein hydrolysis, keratin hydrolysis, cleaning performance, and LAS stability.

The present invention also provides expression vectors comprising a polynucleotide sequence encoding the serine protease variants having an amino acid sequence comprising at least two amino acid substitutions, wherein the substitutions are made at positions equivalent to positions in a *Cellulomonas* 69B4 protease comprising the amino acid sequence set forth in SEQ ID NO:8. The present invention also provides host cells comprising at least one expression vector. In some preferred embodiments, the host cell is a *Bacillus* sp., while in some other embodiments, the host cell is a *Streptomyces* sp., in yet some other embodiments, the host cell is an *Aspergillus* sp., and in some still further embodiments, the host cell is a *Trichoderma* sp. The present invention also provides serine protease variants produced the host cells.

The present invention also provides compositions comprising at least a portion of the serine protease variants having an amino acid sequence comprising at least two amino acid substitutions, wherein the substitutions are made at positions equivalent to the positions in a *Cellulomonas* 69B4 protease comprising the amino acid sequence set forth in SEQ ID NO:8, provided herein.

The present invention also further provides polynucleotide sequences encoding the serine protease variants having amino acid sequences comprising at least two amino acid substitutions, wherein the substitutions are made at positions equivalent to positions in a *Cellulomonas* 69B4 protease comprising the amino acid sequence set forth in SEQ ID NO:8. The present invention further provides expression vectors comprising a polynucleotide sequence encoding the serine protease variants having an amino acid sequence comprising at least two amino acid substitutions, wherein the substitutions are made at positions equivalent to positions in a *Cellulomonas* 69B4 protease comprising the amino acid sequence set forth in SEQ ID NO:8. The present invention also provides host cells comprising at least one expression vector. In some preferred embodiments, the host cell is a *Bacillus* sp., while in some other embodiments, the host cell is a *Streptomyces* sp., in yet some other embodiments, the host cell is an *Aspergillus* sp., and in some still further embodiments, the host cell is a *Trichoderma* sp. The present invention also provides serine protease variants produced the host cells.

The present invention further provides cleaning compositions comprising serine protease variants having amino acid sequences comprising at least two amino acid substitutions, wherein the substitutions are made at positions equivalent to the positions in a *Cellulomonas* 69B4 protease comprising the amino acid sequence set forth in SEQ ID NO:8. In some preferred embodiments, the cleaning compositions comprise at least one variant serine protease, wherein the serine protease has immunological cross-reactivity with the serine protease set forth in SEQ ID NO:8. In some preferred embodiments, the substitutions are made at positions equivalent to positions 1, 2, 3, 4, 7, 8, 9, 10, 11, 12, 13, 14, 15, 16, 18, 19, 22, 24, 25, 26, 27, 28, 29, 30, 31, 32, 33, 34, 35, 36, 38, 39, 40, 41, 42, 43, 44, 45, 46, 47, 48, 49, 51, 52, 54, 55, 56, 57, 59, 61, 62, 63, 64, 65, 66, 67, 68, 69, 70, 71, 72, 73, 74, 75, 76, 77, 78, 79, 80, 81, 83, 84, 85, 86, 87, 88, 89, 90, 91, 92, 93, 96, 99, 100, 101, 103, 104, 105, 107, 109, 110, 111, 112, 113, 114, 115, 116, 117, 118, 119, 121, 123, 124, 125, 126, 127, 128, 129, 130, 132, 133, 134, 135, 136, 131, 140, 141, 142, 143, 144, 145, 146, 147, 150, 151, 152, 153, 154, 155, 156, 157, 158, 159, 160, 161, 162, 163, 164, 165, 166, 167, 168, 170, 171, 172, 175, 176, 177, 179, 180, 181, 182, 183, 184, 185, 186, 187, 188, and 189, in a *Cellulomonas* 69B4 protease comprising the amino acid sequence set forth in SEQ ID NO:8. In some preferred embodiments, the cleaning compositions further comprise one or more additional enzymes or enzyme derivatives selected from the group consisting of proteases, amylases, lipases, mannanases, pectinases, cutinases, oxidoreductases, hemicellulases, and cellulases.

The present invention also provides compositions comprising the serine protease variants having amino acid sequences comprising at least two amino acid substitutions, wherein the substitutions are made at positions equivalent to the positions in a *Cellulomonas* 69B4 protease comprising the amino acid sequence set forth in SEQ ID NO:8, and at least one stabilizing agent. In some preferred embodiments, the compositions are cleaning compositions. In some particularly preferred embodiments, the stabilizing agent is selected from borax, glycerol, and competitive inhibitors. In some further particularly preferred embodiments, the competitive inhibitors stabilize the serine protease variants to anionic surfactants. In some still further embodiments, the serine protease variant is an autolytically stable variant.

The present invention also provides cleaning compositions comprising at least 0.0001 weight percent of the serine protease variants having amino acid sequences comprising at least two amino acid substitutions, wherein the substitutions are made at positions equivalent to the positions in a *Cellulomonas* 69B4 protease comprising the amino acid sequence set forth in SEQ ID NO:8, and optionally, an adjunct ingredient. In some preferred embodiments, the compositions comprise from about 0.001 to about 0.5 weight percent of at least one serine protease variant. In some preferred embodiments, the compositions comprise from about 0.01 to about 0.1 weight percent of the serine protease. In some additional preferred embodiments, the cleaning compositions comprise an adjunct ingredient. In some still further preferred embodiments, the cleaning compositions comprise a sufficient amount of a pH modifier to provide the composition with a neat pH of from about 3 to about 5, wherein the compositions are essentially free of materials that hydrolyze at a pH of from about 3 to about 5. In some alternative preferred embodiments, the cleaning compositions comprise materials that hydrolyze comprise a surfactant material. In some particularly preferred embodiments, the surfactant material comprises a sodium alkyl sulfate surfactant that comprises an ethylene oxide moiety.

The present invention further provides cleaning compositions comprising the serine protease variants having amino acid sequences comprising at least two amino acid substitutions, wherein the substitutions are made at positions equivalent to the positions in a *Cellulomonas* 69B4 protease comprising the amino acid sequence set forth in SEQ ID NO:8, wherein the cleaning composition is a liquid. In some alternative embodiments, the cleaning composition is a powder, granular or tablet composition.

The present invention further provides cleaning compositions comprising the serine protease variants having amino acid sequences comprising at least two amino acid substitutions, wherein the substitutions are made at positions equivalent to the positions in a *Cellulomonas* 69B4 protease comprising the amino acid sequence set forth in SEQ ID NO:8, wherein the cleaning compositions further comprise a hydrogen peroxide source. In some preferred embodiments, the hydrogen peroxide source comprises at least one persalt, wherein the persalt is alkalimetal perborate, alkalimetal percarbonate, alkalimetal perphosphate, alkalimetal persulfate, or a mixture thereof. In some particularly preferred embodiments, the cleaning compositions further comprise a bleach catalyst, bleach activator and/or mixtures thereof.

The present invention also provides methods of cleaning, comprising the steps of: a) contacting a surface and/or an article comprising a fabric with at least one cleaning composition of the present invention; and b) optionally washing and/or rinsing the surface or material.

The present invention also provides animal feeds comprising serine protease variants having amino acid sequences comprising at least two amino acid substitutions, wherein the substitutions are made at positions equivalent to the positions in a *Cellulomonas* 69B4 protease comprising the amino acid sequence set forth in SEQ ID NO:8.

The present invention also provides textile and/or leather processing compositions comprising serine protease variants having amino acid sequences comprising at least two amino acid substitutions, wherein the substitutions are made at positions equivalent to the positions in a *Cellulomonas* 69B4 protease comprising the amino acid sequence set forth in SEQ ID NO:8.

The present invention also provides personal care compositions comprising serine protease variants having amino acid sequences comprising at least two amino acid substitutions, wherein the substitutions are made at positions equivalent to the positions in a *Cellulomonas* 69B4 protease comprising the amino acid sequence set forth in SEQ ID NO:8.

DESCRIPTION OF THE FIGURES

FIG. 7 provides a table showing the results from tergotometer tests performed in the presence of HEPES buffer (enzyme dosage was 0.55 ppm).

DESCRIPTION OF THE INVENTION

Figure 1:
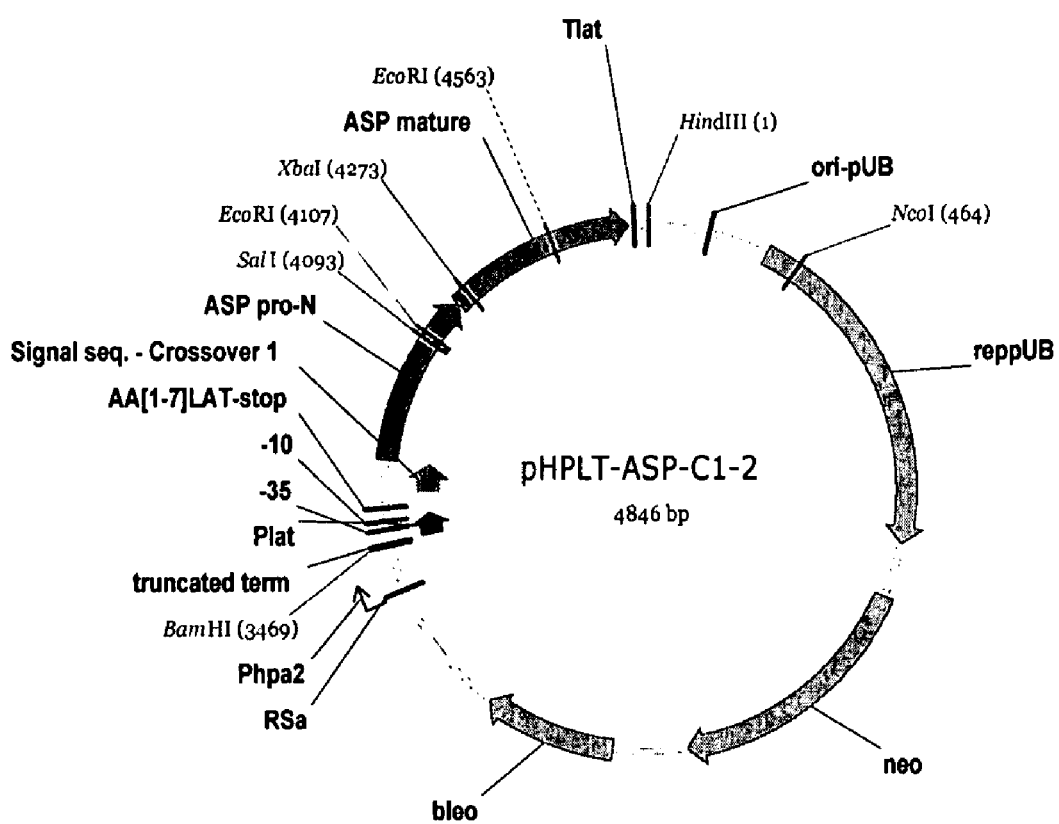
FIG. 1 provides a map of the plasmid pHPLT-ASP-C1-2.

The present invention provides novel-*Micrococcineae* spp serine proteases having multiple substitutions. In particular, the present invention provides serine proteases having multiple substitutions, DNA encoding these proteases, vectors comprising the DNA encoding the proteases, host cells transformed with the vector DNA, and enzymes produced by the host cells. The present invention also provides cleaning compositions (e.g., detergent compositions), animal feed compositions, and textile and leather processing compositions comprising these serine protease variants. In particularly preferred embodiments, the present invention provides mutant (i.e., variant) proteases derived from the wild-type proteases described herein. These variant proteases also find use in numerous applications.

The present invention provides variant protease enzymes having multiple substitutions. Importantly, these variant enzymes have good stability and proteolytic activity. These variant enzymes find use in various applications including but not limited to cleaning compositions, animal feed, textile processing and etc. The present invention also provides means to produce these enzymes. In some preferred embodiments, the variant proteases of the present invention are in pure or relatively pure form.

The present invention also provides nucleotide sequences which are suitable to produce the variant proteases of the present invention in recombinant organisms. In some embodiments, recombinant production provides means to produce the variant proteases in quantities that are commercially viable.

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology*, 2d Ed., John Wiley and Sons, NY (1994); and Hale and Marham, *The Harper Collins Dictionary of Biology*, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a", "an" and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

The practice of the present invention employs, unless otherwise indicated, conventional techniques of protein purification, molecular biology, microbiology, recombinant DNA techniques and protein sequencing, all of which are within the skill of those in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below. Additional definitions are provided in U.S. patent application Ser. No. 10/576, 331, which is incorporated by reference in its entirety.

I. Definitions

As used herein, the terms "protease," and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), *Advances in Biochemical Engineering/Biotechnology*, [1988]). For example, proteolytic activity may be ascertained by comparative assays which analyze the respective protease's ability to hydrolyze a commercial substrate. Exemplary substrates useful in the analysis of protease or protelytic activity, include, but are not limited to di-methyl casein (Sigma C-9801), bovine collagen (Sigma C-9879), bovine-elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference). The pNA assay (See e.g., Del Mar et al., Anal. Biochem., 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration. In addition, absorbance measurements at 280 nm can be used to determine the total protein concentration. The active enzyme/total-protein ratio gives the enzyme purity.

As used herein, the terms "ASP protease," "Asp protease," and "Asp," refer to the serine proteases described herein. In some preferred embodiments, the Asp protease is the protease designed herein as 69B4 protease obtained from *Cellulomonas* strain 69B4. Thus, in preferred embodiments, the term "69B4 protease" refers to a naturally occurring mature protease derived from *Cellulomonas* strain 69B4 (DSM 16035) having substantially identical amino acid sequences as provided in SEQ ID NO:8. In alternative embodiments, the present invention provides portions of the ASP protease.

The term "*Cellulomonas* protease homologues" refers to naturally occurring proteases having substantially identical amino acid sequences to the mature protease derived from *Cellulomonas* strain 69B4 or polynucleotide sequences which encode for such naturally occurring proteases, and which proteases retain the functional characteristics of a serine protease encoded by such nucleic acids. In some embodiments, these protease homologues are referred to as "cellulomonadins."

As used herein, the terms "protease variant," "ASP variant," "ASP protease variant," and "69B protease variant" are used in reference to proteases that are similar to the wild-type ASP, particularly in their function, but have mutations (e.g., substitutions) in their amino acid sequence that make them different in sequence from the wild-type protease. Some of the amino acid residues identified for substitution are conserved residues whereas others are not. In some embodiments, the protease variants of the present invention include the mature forms of protease variants, while in other embodiments, the present invention provides the pro- and prepro-forms of such protease variants.

As used herein, "*Cellulomonas* ssp." refers to all of the species within the genus "*Cellulomonas*," which are Gram-positive bacteria classified as members of the Family Cellulomon adaceae, Suborder Micrococcineae, Order Actinomycetales, Class Actinobacteria. It is recognized that the genus *Cellulomonas* continues to undergo taxonomical reorganization. Thus, it is intended that the genus include species that have been reclassified.

As used herein, "*Streptomyces* ssp." refers to all of the species within the genus "*Streptomyces*," which are Gram-positive bacteria classified as members of the Family Streptomycetaceae, Suborder Streptomycineae, Order Actinomycetales, class Actinobacteria. It is recognized that the genus *Streptomyces* continues to undergo taxonomical reorganization. Thus, it is intended that the genus include species that have been reclassified.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus*, *Amphibacillus*, *Aneurinibacillus*, *Anoxybacillus*, *Brevibacillus*, *Filobacillus*, *Gracilibacillus*, *Halobacillus*, *Paenibacillus*, *Salibacillus*, *Thermobacillus*, *Ureibacillus*, and *Virgibacillus*.

The terms "polynucleotide" and "nucleic acid," used interchangeably herein, refer to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracyl, other sugars and linking groups such as fluororibose and thioate, and nucleotide branches. In alternative embodiments, the sequence of nucleotides is interrupted by non-nucleotide components.

As used herein the term "gene" refers to a polynucleotide (e.g., a DNA segment), that encodes a polypeptide and includes regions preceding and following the coding regions as well as intervening sequences (introns) between individual coding segments (exons).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

As used herein, an "analogous sequence" is one wherein the function of the gene is essentially the same as the gene based on the *Cellulomonas* strain 69B4 protease. Additionally, analogous genes include at least 45%, 50%, 55%, 60%, 65%, 70%, 75%, 80%, 85%, 90%, 95%, 97%, 98%, 99% or 100% sequence identity with the sequence of the *Cellulomonas* strain 69B4 protease. Alternately, analogous sequences have an alignment of between 70 to 100% of the genes found in the *Cellulomonas* strain 69B4 protease region and/or have at least between 5-10 genes found in the region aligned with the genes in the *Cellulomonas* strain 69B4 chromosome. In additional embodiments more than one of the above properties applies to the sequence. Analogous sequences are determined by known methods of sequence alignment. A commonly used alignment method is BLAST, although as indicated above and below, there are other methods that also find use in aligning sequences.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination," "recombining," and generating a "recombined" nucleic acid are generally the assembly of two or more nucleic acid fragments wherein the assembly gives rise to a chimeric gene.

In a preferred embodiment, mutant DNA sequences are generated with site saturation mutagenesis in at least one codon. In another preferred embodiment, site saturation mutagenesis is performed for two or more codons. In a further embodiment, mutant DNA sequences have more than 50%, more than 55%, more than 60%, more than 65%, more than 70%, more than 75%, more than 80%, more than 85%, more than 90%, more than 95%, or more than 98% homology with the wild-type sequence. In alternative embodiments, mutant DNA is generated in vivo using any known mutagenic procedure such as, for example, radiation, nitrosoguanidine and the like. The desired DNA sequence is then isolated and used in the methods provided herein.

As used herein "amino acid" refers to peptide or protein sequences or portions thereof.

As used herein, "protein of interest" and "polypeptide of interest" refer to a protein/polypeptide that is desired and/or being assessed. In some embodiments, the protein of interest is expressed intracellularly, while in other embodiments, it is a secreted polypeptide. In particularly preferred embodiments, these enzyme include the serine proteases of the present invention. In some embodiments, the protein of interest is a secreted polypeptide which is fused to a signal peptide (i.e., an amino-terminal extension on a protein to be secreted). Nearly all secreted proteins use an amino-terminal protein extension which plays a crucial role in the targeting to and translocation of precursor proteins across the membrane. This extension is proteolytically removed by a signal peptidase during or immediately following membrane transfer.

As used herein, the term "heterologous protein" refers to a protein or polypeptide that does not naturally occur in the host cell. Examples of heterologous proteins include enzymes such as hydrolases including proteases. In some embodiments, the gene encoding the proteins are naturally occurring genes, while in other embodiments, mutated and/or synthetic genes are used.

As used herein, "homologous protein" refers to a protein or polypeptide native or naturally occurring in a cell. In preferred embodiments, the cell is a Gram-positive cell, while in particularly preferred embodiments, the cell is a *Bacillus* host cell. In alternative embodiments, the homologous protein is a native protein produced by other organisms, including but not limited to *E. coli, Streptomyces, Trichoderma,* and *Aspergillus*. The invention encompasses host cells producing the homologous protein via recombinant DNA technology.

The terms "protein" and "polypeptide" are used interchangeability herein. The 3-letter code for amino acids as defined in conformity with the IUPAC-IUB Joint Commission on Biochemical Nomenclature (JCBN) is used through out this disclosure. It is also understood that a polypeptide may be coded for by more than one nucleotide sequence due to the degeneracy of the genetic code.

"Naturally occurring enzyme" refers to an enzyme having the unmodified amino acid sequence identical to that found in nature. Naturally occurring enzymes include native enzymes, those enzymes naturally expressed or found in the particular microorganism.

The terms "derived from" and "obtained from" refer to not only a protease produced or producible by a strain of the organism in question, but also a protease encoded by a DNA sequence isolated from such strain and produced in a host organism containing such DNA sequence. Additionally, the term refers to a protease which is encoded by a DNA sequence of synthetic and/or cDNA origin and which has the identifying characteristics of the protease in question To exemplify, "proteases derived from *Cellulomonas*" refers to those enzymes having proteolytic activity which are naturally-produced by *Cellulomonas*, as well as to serine proteases like those produced by *Cellulomonas* sources but which through the use of genetic engineering techniques are produced by non-*Cellulomonas* organisms transformed with a nucleic acid encoding the serine proteases.

A "derivative" within the scope of this definition generally retains the characteristic proteolytic activity observed in the wild-type, native or parent form to the extent that the derivative is useful for similar purposes as the wild-type, native or parent form. Functional derivatives of serine protease encompass naturally occurring, synthetically or recombinantly produced peptides or peptide fragments which have the general characteristics of the serine protease of the present invention.

The term "functional derivative" refers to a derivative of a nucleic acid which has the functional characteristics of a nucleic acid which encodes serine protease. Functional derivatives of a nucleic acid which encode serine protease of the present invention encompass naturally occurring, synthetically or recombinantly produced nucleic acids or fragments and encode serine protease characteristic of the present invention. Wild type nucleic acid encoding serine proteases according to the invention include naturally occurring alleles and homologues based on the degeneracy of the genetic code known in the art.

The term "identical" in the context of two nucleic acids or polypeptide sequences refers to the residues in the two sequences that are the same when aligned for maximum correspondence, as measured using one of the following sequence comparison or analysis algorithms.

The term "optimal alignment" refers to the alignment giving the highest percent identity score.

"Percent sequence identity," "percent amino acid sequence identity," "percent gene sequence identity," and/or "percent nucleic acid/polynucleotide sequence identity," with respect to two amino acid, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least 70% sequence identity, preferably at least 75%, preferably at least 80%, preferably at least 85%, preferably at least 90%, preferably at least 95%, preferably at least 97%, preferably at least 98% and preferably at least 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

The phrase "equivalent," in this context, refers to serine proteases enzymes that are encoded by a polynucleotide capable of hybridizing to the polynucleotide having the sequence as shown in SEQ ID NO:1, under conditions of medium to maximal stringency. For example, being equivalent means that an equivalent mature serine protease comprises at least 70%, at least 75%, at least 80%, at least 85%, at least 90%, at least 91%, at least 92%, at least 93%, at least 94%, at least 95%, at least 96%, at least 97%, at least 98% and/or at least 99% sequence identity to the mature *Cellulomonas* serine protease having the amino acid sequence of SEQ ID NO:8.

The term "isolated" or "purified" refers to a material that is removed from its original environment (e.g., the natural environment, if it is naturally occurring). For example, the material is said to be "purified" when it is present in a particular composition in a higher concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector, and/or such polynucleotides or polypeptides could be part of a composition, and still be isolated in that such vector or composition is not part of its natural environment. In preferred embodiments, a nucleic acid or protein is said to be purified, for example, if it gives rise to essentially one band in an electrophoretic gel or blot.

The term "isolated," when used in reference to a DNA sequence, refers to a DNA sequence that has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (See e.g., Dynan and Tijan, Nature 316:774-78 [1985]). The term "an isolated DNA sequence" is alternatively referred to as "a cloned DNA sequence".

The term "isolated," when used in reference to a protein, refers to a protein that is found in a condition other than its native environment. In a preferred form, the isolated protein is substantially free of other proteins, particularly other homologous proteins. An isolated protein is more than 10% pure, preferably more than 20% pure, and even more preferably more than 30% pure, as determined by SDS-PAGE. Further aspects of the invention encompass the protein in a highly purified form (i.e., more than 40% pure, more than 60% pure, more than 80% pure, more than 90% pure, more than 95% pure, more than 97% pure, and even more than 99% pure), as determined by SDS-PAGE.

As used herein, the term "combinatorial mutagenesis" refers to methods in which libraries of variants of a starting sequence are generated. In these libraries, the variants contain one or several mutations (e.g., substitutions) chosen from a predefined set of mutations. In addition, the methods provide means to introduce random mutations which were not members of the predefined set of mutations (e.g., substitutions). In some embodiments, the methods include those set forth in U.S. patent application Ser. No. 09/699,250, filed Oct. 26, 2000, hereby incorporated by reference. In alternative embodiments, combinatorial mutagenesis methods encompass commercially available kits (e.g., QuikChange® Multi-site, Stratagene, San Diego, Calif.).

As used herein, the term "library of mutants" refers to a population of cells which are identical in most of their genome but include different homologues of one or more genes. Such libraries can be used, for example, to identify genes or operons with improved traits.

As used herein, the term "starting gene" refers to a gene of interest that encodes a protein of interest that is to be improved and/or changed using the present invention.

As used herein, the term "multiple sequence alignment" ("MSA") refers to the sequences of multiple homologs of a starting gene that are aligned using an algorithm (e.g., Clustal W).

As used herein, the terms "consensus sequence" and "canonical sequence" refer to an archetypical amino acid sequence against which all variants of a particular protein or sequence of interest are compared. The terms also refer to a sequence that sets forth the nucleotides that are most often present in a DNA sequence of interest. For each position of a gene, the consensus sequence gives the amino acid that is most abundant in that position in the MSA.

As used herein, the term "consensus mutation" refers to a difference in the sequence of a starting gene and a consensus sequence. Consensus mutations are identified by comparing the sequences of the starting gene and the consensus sequence resulting from an MSA. In some embodiments, consensus mutations are introduced into the starting gene such that it becomes more similar to the consensus sequence. Consensus mutations also include amino acid changes that change an amino acid in a starting gene to an amino-acid that is more frequently found in an MSA at that position relative to the frequency of that amino acid in the starting gene. Thus, the term consensus mutation comprises all single amino acid changes that replace an amino acid of the starting gene with an amino acid that is more abundant than the amino acid in the MSA.

As used herein, the term "initial hit" refers to a variant that was identified by screening a combinatorial consensus mutagenesis library. In preferred embodiments, initial hits have improved performance characteristics, as compared to the starting gene.

As used herein, the term "improved hit" refers to a variant that was identified by screening an enhanced combinatorial consensus mutagenesis library.

As used herein, the terms "improving mutation" and "performance-enhancing mutation" ("improving substitution" and "performance-enhancing substitution") refer to a mutation (e.g., substitution) that leads to improved performance when it is introduced into the starting gene. In some preferred embodiments, these mutations (e.g., substitutions) are identified by sequencing hits that were identified during the screening step of the method. In most embodiments, mutations (e.g., substitutions) that are more frequently found in hits are likely to be improving mutations (e.g., substitutions) as compared to an unscreened combinatorial consensus mutagenesis library.

As used herein, the term "enhanced combinatorial consensus mutagenesis library" refers to a CCM library that is designed and constructed based on screening and/or sequencing results from an earlier round of CCM mutagenesis and screening. In some embodiments, the enhanced CCM library is based on the sequence of an initial hit resulting from an earlier round of CCM. In additional embodiments, the enhanced CCM is designed such that mutations that were frequently observed in initial hits from earlier rounds of mutagenesis and screening are favored. In some preferred embodiments, this is accomplished by omitting primers that encode performance-reducing mutations or by increasing the concentration of primers that encode performance-enhancing mutations relative to other primers that were used in earlier CCM libraries.

As used herein, the term "performance-reducing mutations" refer to mutations in the combinatorial consensus mutagenesis library that are less frequently found in hits resulting from screening as compared to an unscreened combinatorial consensus mutagenesis library. In preferred embodiments, the screening process removes and/or reduces the abundance of variants that contain "performance-reducing mutations."

As used herein, the term "functional assay" refers to an assay that provides an indication of a protein's activity. In particularly preferred embodiments, the term refers to assay systems in which a protein is analyzed for its ability to function in its usual capacity. For example, in the case of enzymes, a functional assay involves determining the effectiveness of the enzyme in catalyzing a reaction.

As used herein, the term "target property" refers to the property of the starting gene that is to be altered. It is not intended that the present invention be limited to any particular target property. However, in some preferred embodiments, the target property is the stability of a gene product (e.g., resistance to denaturation, proteolysis or other degradative factors), while in other embodiments, the level of production in a production host is altered. Indeed, it is contemplated that any property of a starting gene will find use in the present invention.

The term "property" or grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, enhancer function), a property affecting RNA processing (e.g., RNA splicing, RNA stability, RNA conformation, and post-transcriptional modification), a property affecting translation (e.g., level, regulation, binding of mRNA to ribosomal proteins, post-translational modification). For example, a binding site for a transcription factor, polymerase, regulatory factor, etc., of a nucleic acid may be altered to produce desired characteristics or to identify undesirable characteristics.

The term "property" or grammatical equivalents thereof in the context of a polypeptide, as used herein, refer to any characteristic or attribute of a polypeptide that can be selected or detected. These properties include, but are not limited to oxidative stability, substrate specificity, catalytic activity, thermal stability, alkaline stability, pH activity profile, resistance to proteolytic degradation, $K_M$, $k_{cat}$, $k_{cat}/K_M$ ratio, protein folding, inducing an immune response, ability to bind to a ligand; ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, ability to treat disease.

As used herein, the term "screening" has its usual meaning in the art and is, in general a multi-step process. In the first step, a mutant nucleic acid or variant polypeptide therefrom is provided. In the second step, a property of the mutant nucleic acid or variant polypeptide is determined. In the third step, the determined property is compared to a property of the corresponding precursor nucleic acid, to the property of the corresponding naturally occurring polypeptide or to the property of the starting material (e.g., the initial sequence) for the generation of the mutant nucleic acid.

It will be apparent to the skilled artisan that the screening procedure for obtaining a nucleic acid or protein with an altered property depends upon the property of the starting material the modification of which the generation of the mutant nucleic acid is intended to facilitate. The skilled artisan will therefore appreciate that the invention is not limited to any specific property to be screened for and that the following description of properties lists illustrative examples only. Methods for screening for any particular property are generally described in the art. For example, one can measure binding, pH, specificity, etc., before and after mutation, wherein a change indicates an alteration. Preferably, the screens are performed in a high-throughput manner, including multiple samples being screened simultaneously, including, but not limited to assays utilizing chips, phage display, and multiple substrates and/or indicators.

As used herein, in some embodiments, screens encompass selection steps in which variants of interest are enriched from a population of variants. Examples of these embodiments include the selection of variants that confer a growth advantage to the host organism, as well as phage display or any other method of display, where variants can be captured from a population of variants based on their binding or catalytic properties. In a preferred embodiment, a library of variants is exposed to stress (e.g., heat, protease, denaturation, etc.) and subsequently variants that are still intact are identified in a screen or enriched by selection. It is intended that the term encompass any suitable means for selection. Indeed, it is not intended that the present invention be limited to any particular method of screening.

As used herein, the term "targeted randomization" refers to a process that produces a plurality of sequences where one or several positions have been randomized. In some embodiments, randomization is complete (i.e., all four nucleotides, A, T, G, and C can occur at a randomized position). In alternative embodiments, randomization of a nucleotide is limited to a subset of the four nucleotides. Targeted randomization can be applied to one or several codons of a sequence, coding for one or several proteins of interest. When expressed, the resulting libraries produce protein populations in which one or more amino acid positions can contain a mixture of all 20 amino acids or a subset of amino acids, as determined by the randomization scheme of the randomized codon. In some embodiments, the individual members of a population resulting from targeted randomization differ in the number of amino acids, due to targeted or random insertion or deletion of codons. In further embodiments, synthetic amino acids are included in the protein populations produced. In some preferred embodiments, the majority of members of a population resulting from targeted randomization show greater sequence homology to the consensus sequence than the starting gene. In some embodiments, the sequence encodes one or more proteins of interest. In alternative embodiments, the proteins have differing biological functions. In some preferred embodiments, the incoming sequence comprises at least one selectable marker.

The terms "modified sequence" and "modified genes" are used interchangeably herein to refer to a sequence that includes a deletion, insertion or interruption of naturally occurring nucleic acid sequence. In some preferred embodiments, the expression product of the modified sequence is a truncated protein (e.g., if the modification is a deletion or interruption of the sequence). In some particularly preferred embodiments, the truncated protein retains biological activity. In alternative embodiments, the expression product of the modified sequence is an elongated protein (e.g., modifications comprising an insertion into the nucleic acid sequence). In some embodiments, an insertion leads to a truncated protein (e.g., when the insertion results in the formation of a stop codon). Thus, an insertion may result in either a truncated protein or an elongated protein as an expression product.

As used herein, the term "substutition" encompasses the replacement of one amino acid in an amino acid sequence with another amino acid at that position in the amino acid sequence. Thus, the term encompasses situations in which insertion and/or deletion of another amino acid in an amino acid sequence changes the relative positions of the amino acids in the sequence. Thus, while an amino acid may not be specifically targeted for substitution (e.g., using the methods described herein), that amino acid may be "substituted" by another amino acid in the sequence due to a change in its relative position in the sequence. For example, by inserting an amino acid between the amino acids at positions 1 and 2 of SEQ ID NO:8, the resulting sequence will be shifted by one amino acid (i.e., the amino acid originally in position 2 is now in position 3, etc.). It is intended that the term encompass multiple, as well as single changes in the amino acid sequence (i.e., single or multiple substitutions). It is also noted that as used herein, amino acid substitutions are indicated by the naturally occurring amino acid, followed by the position, followed by the substituted amino acid. Thus, N024E (also indicated as N24E) indicates that the asparagine at position 24 of SEQ ID NO:8 has been substituted with glutamic acid. As indicated herein, multiple substitutions are indicated by either "/" or "-". Thus, "R127A-G65Q" and "R127A/G65Q" both indicate that the amino acids at positions 127 and 65 have been substituted (i.e., the arginine at position 127 has been substituted with an alanine and the glycine at position 65 has been substituted with a glutamine).

As used herein, the terms "mutant sequence" and "mutant gene" are used interchangeably and refer to a sequence that has an alteration in at least one codon occurring in a host cell's wild-type sequence. The expression product of the mutant sequence is a protein with an altered amino acid sequence relative to the wild-type. The expression product may have an altered functional capacity (e.g., enhanced enzymatic activity).

As used herein, the term "up mutation" refers to mutations for which $\Delta\Delta G$ values for a property are better than the parent protein ($\Delta\Delta G$ values, <0).

As used herein, the term "down mutation" refers to mutations for which $\Delta\Delta G$ values for a property are worse than the parent protein ($\Delta\Delta G$ values, >0).

As used herein, the term "productive site" refers to positions which have at least one up mutation for a given property.

As used herein, the term "unproductive site" refers to positions which have no up mutations for a given property.

The terms "mutagenic primer" or "mutagenic oligonucleotide" (used interchangeably herein) are intended to refer to oligonucleotide compositions which correspond to a portion of the template sequence and which are capable of hybridizing thereto. With respect to mutagenic primers, the primer will not precisely match the template nucleic acid, the mismatch or mismatches in the primer being used to introduce the desired mutation into the nucleic acid library. As used herein, "non-mutagenic primer" or "non-mutagenic oligonucleotide" refers to oligonucleotide compositions which will match precisely to the template nucleic acid. In one embodiment of the invention, only mutagenic primers are used. In another preferred embodiment of the invention, the primers are designed so that for at least one region at which a mutagenic primer has been included, there is also non-mutagenic primer included in the oligonucleotide mixture. By adding a mixture of mutagenic primers and non-mutagenic primers corresponding to at least one of the mutagenic primers, it is possible to produce a resulting nucleic acid library in which a variety of combinatorial mutational patterns are presented. For example, if it is desired that some of the members of the mutant nucleic acid library retain their precursor sequence at certain positions while other members are mutant at such sites, the non-mutagenic primers provide the ability to obtain a specific level of non-mutant members within the nucleic acid library for a given residue. The methods of the invention employ mutagenic and non-mutagenic oligonucleotides which are generally between 10-50 bases in length, more preferably about 1545 bases in length. However, it may be necessary to use primers that are either shorter than 10 bases or longer than 50 bases to obtain the mutagenesis result desired. With respect to corresponding mutagenic and non-mutagenic primers, it is not necessary that the corresponding oligonucleotides be of identical length, but only that there is overlap in the region corresponding to the mutation to be added.

Primers may be added in a pre-defined ratio according to the present invention. For example, if it is desired that the resulting library have a significant level of a certain specific mutation and a lesser amount of a different mutation at the same or different site, by adjusting the amount of primer added, it is possible to produce the desired biased library. Alternatively, by adding lesser or greater amounts of non-mutagenic primers, it is possible to adjust the frequency with which the corresponding mutation(s) are produced in the mutant nucleic acid library.

As used herein, the phrase "contiguous mutations" refers to mutations which are presented within the same oligonucleotide primer. For example, contiguous mutations may be adjacent or nearby each other, however, they will be introduced into the resulting mutant template nucleic acids by the same primer.

As used herein, the phrase "discontiguous mutations" refers to mutations which are presented in separate oligonucleotide primers. For example, discontiguous mutations will be introduced into the resulting mutant template nucleic acids by separately prepared oligonucleotide primers.

The terms "wild-type sequence," or "wild-type gene" are used interchangeably herein, to refer to a sequence that is native or naturally occurring in a host cell. In some embodiments, the wild-type sequence refers to a sequence of interest that is the starting point of a protein engineering project. The wild-type sequence may encode either a homologous or heterologous protein. A homologous protein is one the host cell would produce without intervention. A heterologous protein is one that the host cell would not produce but for the intervention.

As used herein, the term "antibodies" refers to immunoglobulins. Antibodies include but are not limited to immunoglobulins obtained directly from any species from which it is desirable to produce antibodies. In addition, the present invention encompasses modified antibodies. The term also refers to antibody fragments that retain the ability to bind to the epitope that the intact antibody binds and include polyclonal antibodies, monoclonal antibodies, chimeric antibodies, anti-idiotype (anti-ID) antibodies. Antibody fragments include, but are not limited to the complementarity-determining regions (CDRs), single-chain fragment variable regions (scFv), heavy chain variable region (VH), light chain variable region (VL). Polyclonal and monoclonal antibodies are also encompassed by the present invention. Preferably, the antibodies are monoclonal antibodies.

The term "oxidation stable" refers to proteases of the present invention that retain a specified amount of enzymatic activity over a given period of time under conditions prevailing during the proteolytic, hydrolyzing, cleaning or other process of the invention, for example while exposed to or contacted with bleaching agents or oxidizing agents. In some embodiments, the proteases retain at least 50%, 60%, 70%, 75%, 80%, 85%, 90%, 92%, 95%, 96%, 97%, 98% or 99% proteolytic activity after contact with a bleaching or oxidizing agent over a given time period, for example, at least 1 minute, 3 minutes, 5 minutes, 8 minutes, 12 minutes, 16 minutes, 20 minutes, etc. In some embodiments, the stability is measured as described in the Examples.

The term "chelator stable" refers to proteases of the present invention that retain a specified amount of enzymatic activity over a given period of time under conditions prevailing during the proteolytic, hydrolyzing, cleaning or other process of the invention, for example while exposed to or contacted with chelating agents. In some embodiments, the proteases retain at least 50%, 60%, 70%, 75%, 80%, 85%, 90%, 92%, 95%, 96%, 97%, 98% or 99% proteolytic activity after contact with a chelating agent over a given time period, for example, at least 10 minutes, 20 minutes, 40 minutes, 60 minutes, 100 minutes, etc. In some embodiments, the chelator stability is measured as described in the Examples.

The terms "thermally stable" and "thermostable" refer to proteases of the present invention that retain a specified amount of enzymatic activity after exposure to identified temperatures over a given period of time under conditions prevailing during the proteolytic, hydrolyzing, cleaning or other process of the invention, for example while exposed altered temperatures. Altered temperatures includes increased or decreased temperatures. In some embodiments, the proteases retain at least 50%, 60%, 70%, 75%, 80%, 85%, 90%, 92%, 95%, 96%, 97%, 98% or 99% proteolytic activity after exposure to altered temperatures over a given time period, for example, at least 60 minutes, 120 minutes, 180 minutes, 240 minutes, 300 minutes, etc. In some embodiments, the thermostability is determined as described in the Examples.

The term "enhanced stability" in the context of an oxidation, chelator, thermal and/or pH stable protease refers to a higher retained proteolytic activity over time as compared to other serine proteases (e.g., subtilisin proteases) and/or wild-type enzymes.

The term "diminished stability" in the context of an oxidation, chelator, thermal and/or pH stable protease refers to a lower retained proteolytic activity over time as compared to other serine proteases (e.g., subtilisin proteases) and/or wild-type enzymes.

The term "cleaning activity" refers to the cleaning performance achieved by the protease under conditions prevailing during the proteolytic, hydrolyzing, cleaning or other process of the invention. In some embodiments, cleaning performance is determined by the application of various cleaning assays concerning enzyme sensitive stains, for example grass, blood, milk, or egg protein as determined by various chromatographic, spectrophotometric or other quantitative methodologies after subjection of the stains to standard wash conditions. Exemplary assays include, but are not limited to those described in WO 99/34011, and U.S. Pat. No. 6,605,458 (both of which are herein incorporated by reference), as well as those methods included in the Examples.

The term "cleaning effective amount" of a protease refers to the quantity of protease described hereinbefore that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, bar) composition is required, etc.

The term "cleaning adjunct materials," as used herein, means any liquid, solid or gaseous material selected for the particular type of cleaning composition desired and the form of the product (e.g., liquid, granule, powder, bar, paste, spray, tablet, gel; or foam composition), which materials are also preferably compatible with the protease enzyme used in the composition. In some embodiments, granular compositions are in "compact" form, while in other embodiments, the liquid compositions are in a "concentrated" form.

The term "enhanced performance" in the context of cleaning activity refers to an increased or greater cleaning activity of certain enzyme sensitive stains such as egg, milk, grass or blood, as determined by usual evaluation after a standard wash cycle and/or multiple wash cycles.

The term "diminished performance" in the context of cleaning activity refers to an decreased or lesser cleaning activity of certain enzyme sensitive stains such as egg, milk, grass or blood, as determined by usual evaluation after a standard wash cycle.

The term "comparative performance" in the context of cleaning activity refers to at least 60%, at least 70%, at least 80% at least 90% at least 95% of the cleaning activity of a comparative subtilisin protease (e.g., commercially available proteases), including but not limited to OPTIMASE™ protease (Genencor), PURAFECT™ protease products (Genencor), SAVINASE™ protease (Novozymes), BPN'-variants (See e.g., U.S. Pat. No. Re 34, 606), RELASE™, DURAZYME™, EVERLASE™, KANNASE™ protease (Novozymes), MAXACAL™, MAXAPEM™, PROPERASE™ proteases (Genencor; See also, U.S. Pat. No. Re 34, 606, and U.S. Pat. Nos. 5,700,676; 5,955,340; 6,312,936; and 6,482, 628), and B. lentus variant protease products (e.g., those described in WO 92/21760, WO 95/23221 and/or WO 97/07770). Exemplary subtilisin protease variants include, but are not limited to those having substitutions or deletions at residue positions equivalent to positions 76, 101, 103, 104, 120, 159, 167, 170, 194, 195, 217, 232, 235, 236, 245, 248, and/or 252 of BPN'. Cleaning performance can be determined by comparing the proteases of the present invention with those subtilisin proteases in various cleaning assays concerning enzyme sensitive stains such as grass, blood or milk as determined by usual spectrophotometric or analytical methodologies after standard wash cycle conditions.

As used herein, a "low detergent concentration" system includes detergents where less than about 800 ppm of detergent components are present in the wash water. Japanese detergents are typically considered low detergent concentration systems, as they have usually have approximately 667 ppm of detergent components present in the wash water.

As used herein, a "medium detergent concentration" systems includes detergents wherein between about 800 ppm and about 2000 ppm of detergent components are present in the wash water. North American detergents are generally considered to be medium detergent concentration systems as they have usually approximately 975 ppm of detergent components present in the wash water. Brazilian detergents typically have approximately 1500 ppm of detergent components present in the wash water.

As used herein, "high detergent concentration" systems includes detergents wherein greater than about 2000 ppm of detergent components are present in the wash water. European detergents are generally considered to be high detergent concentration systems as they have approximately 3000-8000 ppm of detergent components in the wash water.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., fabric) surface cleaning compositions, including but not limited to dishwashing detergent compositions, oral cleaning compositions, denture cleaning compositions, and personal cleansing compositions.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically 17-35% by weight of the total composition. In contrast, in compact compositions, the filler salt is present in amounts not exceeding 15% of the total composition. In some embodiments, the filler salt is present in amounts that do not exceed 10%, or more preferably, 5%, by weight of the composition. In some embodiments, the inorganic filler salts are selected from the alkali and alkaline-earth-metal salts of sulfates and chlorides. A preferred filler salt is sodium sulfate.

II. Serine Protease Enzymes of the Present Invention and Sequences Therefor

The present invention provides isolated polynucleotides encoding amino acid sequences which encode variant proteases. U.S. patent application Ser. No. 10/576,331, incorporated by reference in its entirety provides various proteases, including the wild-type *Cellulomonas* serine protease, as well as numerous variant proteases, signal peptide coding sequences, and amino acid sequences. In some preferred embodiments of the present invention, the *Cellulomonas* spp. is *Cellulomonas* strain 69B4 (DSM16035), as described in U.S. patent application Ser. No. 10/576,331.

A. Serine Proteases

Although there may be variations in the sequence of a naturally occurring enzyme within a given species of organism, enzymes of a specific type produced by organisms of the same species generally are substantially identical with respect to substrate specificity and/or proteolytic activity levels under given conditions (e.g., temperature, pH, water hardness, oxidative conditions, chelating conditions, and concentration), etc. Thus, for the purposes of the present invention, it is contemplated that other strains and species of *Cellulomonas* also produce the *Cellulomonas* protease of the present invention and thus provide useful sources for the proteases of the present invention. Indeed, as presented herein, it is contemplated that other members of the Micrococcineae will find use in the present invention.

In some embodiments, the proteolytic polypeptides of this invention are characterized physicochemically, while in other embodiments, they are characterized based on their functionally, while in further embodiments, they are characterized using both sets of properties. Physicochemical characterization takes advantages of well-known techniques such as SDS-electrophoresis, gel filtration, amino acid composition, mass spectrometry (e.g., MALDI-TOF-MS, LC-ES-MS/MS, etc.), and sedimentation to determine the molecular weight of proteins, isoelectric focusing to determine the pI of proteins, amino acid sequencing to determine the amino acid sequences of protein, crystallography studies to determine the tertiary structures of proteins, and antibody binding to determine antigenic epitopes present in proteins.

In some embodiments, functional characteristics are determined by techniques well known to the practitioner in the protease field and include, but are not limited to, hydrolysis of various commercial substrates, such as di-methyl casein ("DMC") and/or AAPF-pNA. This preferred technique for functional characterization is described in greater detail in the Examples provided herein.

The mature protease also displays proteolytic activity (e.g., hydrolytic activity on a substrate having peptide linkages) such as DMC. In further embodiments, proteases of the present invention provide enhanced wash performance under identified conditions. Although the present invention encompasses the protease 69B as described herein, in some embodiments, the proteases of the present invention exhibit at least 50%, 60%, 70%, 75%, 80%, 85%, 90%, 92%, 95%, 96%, 97%, 98% or 99% proteolytic activity as compared to the proteolytic activity of 69B4. In some embodiments, the proteases display at least 50%, 60%, 70%, 75%, 80%, 85%, 90%, 92%, 95%, 96%, 97%, 98% or 99% proteolytic activity as compared to the proteolytic activity of proteases sold under the tradenames SAVINASE® (Novzymes) or PURAFECT® (Genencor) under the same conditions. In some embodiments, the proteases of the present invention display comparative or enhanced wash performance under identified conditions as compared to 69B4 under the same conditions. In some preferred embodiments, the proteases of the present invention display comparative or enhanced wash performance under identified conditions, as compared to proteases sold under the tradenames SAVINASE® (Novzymes) or PURAFECT® (Genencor) under the same conditions.

In yet further embodiments, the proteases and/or polynucleotides encoding the proteases of the present invention are provided in purified form (i.e., present in a particular composition in a higher or lower concentration than exists in a naturally occurring or wild type organism), or in combination with components not normally present upon expression from a naturally occurring or wild-type organism. However, it is not intended that the present invention be limited to proteases of any specific purity level, as ranges of protease purity find use in various applications in which the proteases of the present invention are suitable.

B. Nucleic and Amino Acid Sequences of Serine Proteases

The DNA sequence of the asp gene (SEQ ID NO: 1) derived from *Cellulomonas* strain 69B4 (DSM 16035) is provided below. The initiating polynucleotide encoding the signal peptide of the *Cellulomonas* strain 69B4 protease is in bold (ATG). This sequence also includes the signal peptide and precursor serine protease.

The following DNA sequence (SEQ ID NO:2) encodes the signal peptide (SEQ ID NO:9) that is operatively linked to the precursor protease (SEQ ID NO:7) derived from *Cellulomonas* strain 69B4 (DSM 16035). The initiating polynucleotide encoding the signal peptide of the *Cellulomonas* strain 69B4 protease is in bold (ATG). The termination codon (TGA) begins with residue 1486. Residues 85, 595, and 1162, relate to the initial residues of the N terminal prosequence, mature sequence and Carboxyl terminal prosequence, respectively, are bolded and underlined.

(SEQ ID NO: 2)

```
ATGACACCAC GCACAGTCAC GCGGGCCCTG GCCGTGGCCA CCGCAGCCGC CACACTCCTG      60
GCAGGCGGCA TGGCCGCCCA GGCCAACGAG CCCGCACCAC CCGGGAGCGC GAGCGCACCG     120
CCACGCCTGG CCGAGAAGCT CGACCCCGAC CTCCTCGAGG CCATGGAGCG CGACCTGGGC     180
CTCGACGCGG AGGAAGCCGC CGCCACCCTG GCGTTCCAGC ACGACGCAGC CGAGACCGGC     240
GAGGCCCTCG CCGAAGAGCT CGACGAGGAC TTCGCCGGCA CCTGGGTCGA GGACGACGTC     300
CTGTACGTCG CCACCACCGA CGAGGACGCC GTCGAGGAGG TCGAGGGCGA AGGCGCCACG     360
GCCGTCACCG TCGAGCACTC CCTGGCCGAC CTCGAGGCCT GGAAGACCGT CCTCGACGCC     420
GCCCTCGAGG GCCACGACGA CGTGCCCACC TGGTACGTCG ACGTCCCGAC CAACAGCGTC     480
GTCGTCGCCG TCAAGGCCGG AGCCCAGGAC GTCGCCGCCG GCCTCGTCGA AGGTGCCGAC     540
GTCCCGTCCG ACGCCGTGAC CTTCGTCGAG ACCGACGAGA CCCCGCGGAC CATGTTCGAC     600
GTGATCGGCG GCAACGCCTA CACCATCGGG GGCGCAGCC GCTGCTCGAT CGGGTTCGCG     660
GTCAACGGCG GGTTCATCAC CGCCGGCCAC TGCGGCCGCA CCGGCGCCAC CACCGCCAAC     720
CCCACCGGGA CCTTCGCCGG GTCCAGCTTC CCGGGCAACG ACTACGCGTT CGTCCGTACC     780
GGGGCCGGCG TGAACCTGCT GGCCCAGGTC AACAACTACT CCGGTGGCCG CGTCCAGGTC     840
GCCGGGCACA CCGCGGCCCC CGTCGGCTCG GCCGTGTGCC GGTCCGGGTC GACCACCGGG     900
TGGCACTGCG GCACCATCAC TGCGCTCAAC TCCTCGGTCA CCTACCCCGA GGGCACCGTC     960
CGCGGCCTGA TCCGCACCAC CGTCTGCGCC GAGCCCGGCG ACTCCGGTGG CTCGCTGCTC    1020
GCCGGCAACC AGGCCCAGGG CGTCACGTCC GGCGGCTCCG GCAACTGCCG CACCGGTGGC    1080
ACCACGTTCT TCCAGCCGGT CAACCCCATC CTCCAGGCGT ACGGCCTGAG GATGATCACC    1140
ACGGACTCGG GCAGCAGCCC GGCCCCTGCA CCGACCTCCT GCACCGGCTA CGCCCGCACC    1200
TTCACCGGGA CCCTCGCGGC CGGCCGGGCC GCCGCCCAGC CAACGGGTC CTACGTGCAG    1260
GTCAACCGGT CCGGGACCCA CAGCGTGTGC CTCAACGGGC CCTCCGGTGC GGACTTCGAC    1320
CTCTACGTGC AGCGCTGGAA CGGCAGCTCC TGGGTGACCG TCGCCCAGAG CACCTCCCCC    1380
GGCTCCAACG AGACCATCAC CTACCGCGGC AACGCCGGCT ACTACCGCTA CGTGGTCAAC    1440
GCCGCGTCCG GCTCCGGTGC CTACACCATG GGGCTCACCC TCCCCTGA                1488
```

The following DNA sequence (SEQ ID NO:3) encodes the precursor protease derived from *Cellulomonas* strain 69B4 (DSM 16035).

(SEQ ID NO: 3)

```
  1  AACGAGCCCG CACCACCCGG GAGCGCGAGC GCACCGCCAC GCCTGGCCGA GAAGCTCGAC
     TTGCTCGGGC GTGGTGGGCC CTCGCGCTCG CGTGGCGGTG CGGACCGGCT CTTCGAGCTG
 61  CCCGACCTCC TCGAGGCCAT GGAGCGCGAC CTGGGCCTCG ACGCGGAGGA AGCCGCCGCC
     GGGCTGGAGG AGCTCCGGTA CCTCGCGCTG GACCCGGAGC TGCGCCTCCT TCGGCGGCGG
121  ACCCTGGCGT TCCAGCACGA CGCAGCCGAG ACCGGCGAGG CCCTCGCCGA AGAGCTCGAC
     TGGGACCGCA AGGTCGTGCT GCGTCGGCTC TGGCCGCTCC GGGAGCGGCT TCTCGAGCTG
181  GAGGACTTCG CCGGCACCTG GGTCGAGGAC GACGTCCTGT ACGTCGCCAC CACCGACGAG
     CTCCTGAAGC GGCCGTGGAC CCAGCTCCTG CTGCAGGACA TGCAGCGGTG GTGGCTGCTC
241  GACGCCGTCG AGGAGGTCGA GGGCGAAGGC GCCACGGCCG TCACCGTCGA GCACTCCCTG
     CTGCGGCAGC TCCTCCAGCT CCCGCTTCCG CGGTGCCGGC AGTGGCAGCT CGTGAGGGAC
301  GCCGACCTCG AGGCCTGGAA GACCGTCCTC GACGCCGCCC TCGAGGGCCA CGACGACGTG
     CGGCTGGAGC TCCGGACCTT CTGGCAGGAG CTGCGGCGGG AGCTCCCGGT GCTGCTGCAC
361  CCCACCTGGT ACGTCGACGT CCCGACCAAC AGCGTCGTCG TCGCCGTCAA GGCCGGAGCC
     GGGTGGACCA TGCAGCTGCA GGGCTGGTTG TCGCAGCAGC AGCGGCAGTT CCGGCCTCGG
421  CAGGACGTCG CCGCCGGCCT CGTCGAAGGT GCCGACGTCC CGTCCGACGC CGTGACCTTC
     GTCCTGCAGC GCCGGCCGGA GCAGCTTCCA CGGCTGCAGG GCAGGCTGCG GCACTGGAAG
```

-continued

```
 481 GTCGAGACCG ACGAGACCCC GCGGACCATG TTCGACGTGA TCGGCGGCAA CGCCTACACC
     CAGCTCTGGC TGCTCTGGGG CGCCTGGTAC AAGCTGCACT AGCCGCCGTT GCGGATGTGG

541 ATCGGGGGGC GCAGCCGCTG CTCGATCGGG TTCGCGGTCA ACGGCGGGTT CATCACCGCC
     TAGCCCCCCG CGTCGGCGAC GAGCTAGCCC AAGCGCCAGT TGCCGCCCAA GTAGTGGCGG

601 GGCCACTGCG GCCGCACCGG CGCCACCACC GCCAACCCCA CCGGGACCTT CGCCGGGTCC
     CCGGTGACGC CGGCGTGGCC GCGGTGGTGG CGGTTGGGGT GGCCCTGGAA GCGGCCCAGG

661 AGCTTCCCGG GCAACGACTA CGCGTTCGTC CGTACCGGGG CCGGCGTGAA CCTGCTGGCC
     TCGAAGGGCC CGTTGCTGAT GCGCAAGCAG GCATGGCCCC GGCCGCACTT GGACGACCGG

721 CAGGTCAACA ACTACTCCGG TGGCCGCGTC CAGGTCGCCG GCACACCGC GGCCCCCGTC
     GTCCAGTTGT TGATGAGGCC ACCGGCGCAG GTCCAGCGGC CCGTGTGGCG CCGGGGGCAG

781 GGCTCGGCCG TGTGCCGGTC CGGGTCGACC ACCGGGTGGC ACTGCGGCAC CATCACTGCG
     CCGAGCCGGC ACACGGCCAG GCCCAGCTGG TGGCCCACCG TGACGCCGTG GTAGTGACGC

841 CTCAACTCCT CGGTCACCTA CCCCGAGGGC ACCGTCCGCG GCCTGATCCG CACCACCGTC
     GAGTTGAGGA GCCAGTGGAT GGGGCTCCCG TGGCAGGCGC CGGACTAGGC GTGGTGGCAG

901 TGCGCCGAGC CCGGCGACTC CGGTGGCTCG CTGCTCGCCG GCAACCAGGC CCAGGGCGTC
     ACGCGGCTCG GGCCGCTGAG GCCACCGAGC GACGAGCGGC CGTTGGTCCG GGTCCCGCAG

961 ACGTCCGGCG GCTCCGGCAA CTGCCGCACC GGTGGCACCA CGTTCTTCCA GCCGGTCAAC
     TGCAGGCCGC CGAGGCCGTT GACGGCGTGG CCACCGTGGT GCAAGAAGGT CGGCCAGTTG

1021 CCCATCCTCC AGGCGTACGG CCTGAGGATG ATCACCACGG ACTCGGGCAG CAGCCCGGCC
     GGGTAGGAGG TCCGCATGCC GGACTCCTAC TAGTGGTGCC TGAGCCCGTC GTCGGGCCGG

1081 CCTGCACCGA CCTCCTGCAC CGGCTACGCC CGCACCTTCA CCGGGACCCT CGCGGCCGGC
     GGACGTGGCT GGAGGACGTG GCCGATGCGG GCGTGGAAGT GGCCCTGGGA GCGCCGGCCG

1141 CGGGCCGCCG CCCAGCCCAA CGGGTCCTAC GTGCAGGTCA ACCGGTCCGG GACCCACAGC
     GCCCGGCGGC GGGTCGGGTT GCCCAGGATG CACGTCCAGT TGGCCAGGCC CTGGGTGTCG

1201 GTGTGCCTCA ACGGGCCCTC CGGTGCGGAC TTCGACCTCT ACGTGCAGCG CTGGAACGGC
     CACACGGAGT TGCCCGGGAG GCCACGCCTG AAGCTGGAGA TGCACGTCGC GACCTTGCCG

1261 AGCTCCTGGG TGACCGTCGC CCAGAGCACC TCCCCCGGCT CCAACGAGAC CATCACCTAC
     TCGAGGACCC ACTGGCAGCG GGTCTCGTGG AGGGGGCCGA GGTTGCTCTG GTAGTGGATG

1321 CGCGGCAACG CCGGCTACTA CCGCTACGTG GTCAACGCCG CGTCCGGCTC CGGTGCCTAC
     GCGCCGTTGC GGCCGATGAT GGCGATGCAC CAGTTGCGGC GCAGGCCGAG GCCACGGATG

1381 ACCATGGGGC TCACCCTCCC CTGA
     TGGTACCCCG AGTGGGAGGG GACT
```

The following DNA sequence (SEQ ID NO:4) encodes the mature protease derived from *Cellulomonas* strain 69B4 (DSM 16035).

```
                                                              (SEQ ID NO: 4)
  1 TTCGACGTGA TCGGCGGCAA CGCCTACACC ATCGGGGGC GCAGCCGCTG CTCGATCGGG
    AAGCTGCACT AGCCGCCGTT GCGGATGTGG TAGCCCCCCG CGTCGGCGAC GAGCTAGCCC

61 TTCGCGGTCA ACGGCGGGTT CATCACCGCC GGCCACTGCG GCCGCACCGG CGCCACCACC
    AAGCGCCAGT TGCCGCCCAA GTAGTGGCGG CCGGTGACGC CGGCGTGGCC GCGGTGGTGG

121 GCCAACCCCA CCGGGACCTT CGCCGGGTCC AGCTTCCCGG GCAACGACTA CGCGTTCGTC
    CGGTTGGGGT GGCCCTGGAA GCGGCCCAGG TCGAAGGGCC CGTTGCTGAT GCGCAAGCAG
181 CGTACCGGGG CCGGCGTGAA CCTGCTGGCC CAGGTCAACA ACTACTCCGG TGGCCGCGTC
    GCATGGCCCC GGCCGCACTT GGACGACCGG GTCCAGTTGT TGATGAGGCC ACCGGCGCAG

241 CAGGTCGCCG GCACACCGC GGCCCCCGTC GGCTCGGCCG TGTGCCGGTC CGGGTCGACC
    GTCCAGCGGC CCGTGTGGCG CCGGGGGCAG CCGAGCCGGC ACACGGCCAG GCCCAGCTGG

301 ACCGGGTGGC ACTGCGGCAC CATCACTGCG CTCAACTCCT CGGTCACCTA CCCCGAGGGC
    TGGCCCACCG TGACGCCGTG GTAGTGACGC GAGTTGAGGA GCCAGTGGAT GGGGCTCCCG

361 ACCGTCCGCG GCCTGATCCG CACCACCGTC TGCGCCGAGC CCGGCGACTC CGGTGGCTCG
    TGGCAGGCGC CGGACTAGGC GTGGTGGCAG ACGCGGCTCG GGCCGCTGAG GCCACCGAGC

421 CTGCTCGCCG GCAACCAGGC CCAGGGCGTC ACGTCCGGCG GCTCCGGCAA CTGCCGCACC
    GACGAGCGGC CGTTGGTCCG GGTCCCGCAG TGCAGGCCGC CGAGGCCGTT GACGGCGTGG
```

```
481 GGTGGCACCA CGTTCTTCCA GCCGGTCAAC CCCATCCTCC AGGCGTACGG CCTGAGGATG
    CCACCGTGGT GCAAGAAGGT CGGCCAGTTG GGGTAGGAGG TCCGCATGCC GGACTCCTAC

561 ATCACCACGG ACTCGGGCAG CAGCCCG
    TAGTGGTGCC TGAGCCCGTC GTCGGGC
```

The following DNA sequence (SEQ ID NO:5) encodes the signal peptide derived from *Cellulomonas* strain 69B4 (DSM 16035).

```
                                                     (SEQ ID NO: 5)
  1 ATGACACCAC CACAGTCAC GCGGGCCCTG GCCGTGGCCA CCGCAGCCGC CACACTCCTG
    TACTGTGGTG CGTGTCAGTG CGCCCGGGAC CGGCACCGGT GGCGTCGGCG GTGTGAGGAC

61 GCAGGCGGCA TGGCCGCCCA GGCC
    CGTCCGCCGT ACCGGCGGGT CCGG
```

The following sequence is the amino acid sequence (SEQ ID NO:6) of the signal sequence and precursor protease derived from *Cellulomonas* strain 69B4 (DSM 16035), including the signal sequence [segments 1a-c] (residues 1-28 [−198 to −171]), an N-terminal prosequence [segments 2a-r] (residues 29-198 [−170 to −1]), a mature protease [segments 3a-t] (residues 199-387 [1-189]), and a C-terminal prosequence [segments 4a-l] (residues 388-495 [190-398]) encoded by the DNA sequences set forth in SEQ ID NOS:1, 2, 3 and 4. The N-terminal sequence of the mature protease amino acid sequence is in bold.

```
                                                             (SEQ ID NO: 6)
  1 MTPRTVTRAL AVATAAATLL AGGMAAQA NE PAPPGSASAP PRLAEKLDPD
       1a         1b         1c    2a 2b        2c

51 LLEAMERDLG LDAEEAAATL AFQHDAAETG EALAEELDED FAGTWVEDDV
       2d         2e         2f         2g         2h

101 LYVATTDEDA VEEVEGEGAT AVTVEHSLAD LEAWKTVLDA ALEGHDDVPT
       2i         2j         2k         2l         2m

151 WYVDVPTNSV WAVKAGAQD VAAGLVEGAD VPSDAVTFVE TDETPRTM FD
       2n         2o         2p         2q         2r    3a

201 VIGGNAYTIG GRSRCSIGFA VNGGFITAGH CGRTGATTAN PTGTFAGSSF
       3b         3c         3d         3e         3f

251 PGNDYAFVRT GAGVNLLAQV NNYSGGRVQV AGHTAAPVGS AVCRSGSTTG
       3g         3h         3i         3j         3k

301 WHCGTITALN SSVTYPEGTV RGLIRTTVCA EPGDSGGSLL AGNQAQGVTS
       3l         3m         3n         3o         3p

351 GGSGNCRTGG TTFFQPVNPI LQAYGLRMIT TDSGSSP APA PTSCTGYART
       3q         3r         3s         3t     4a 4b

401 FTGTLAAGRA AAQPNGSYVQ VNRSGTHSVC LNGPSGADFD LYVQRWNGSS
       4c         4d         4e         4f         4g

451 WVTVAQSTSP GSNETITYRG NAGYYRYVVN AASGSGAYTM GLTLP
       4h         4i         4j         4k        4l
```

The following sequence (SEQ ID NO:7) is the amino acid sequence of the precursor protease derived from *Cellulomonas* strain 69B4 (DSM 16035) (SEQ ID NO:7).

```
                                                             (SEQ ID NO: 7)
  1 NEPAPPGSAS APPRLAEKLD PDLLEAMERD.LGLDAEEAAA.TLAFQHDAAE

51 TGEALAEELD EDFAGTWVED DVLYVATTDE DAVEEVEGEG ATAVTVEHSL

101 ADLEAWKTVL DAALEGHDDV PTWYVDVPTN SVVVAVKAGA QDVAAGLVEG

151 ADVPSDAVTF VETDETPRTM FDVIGGNAYT IGGRSRCSIG FAVNGGFITA

201 GHCGRTGATT ANPTGTFAGS SFPGNDYAFV RTGAGVNLLA QVNNYSGGRV

251 QVAGHTAAPV GSAVCRSGST TGWHCGTITA LNSSVTYPEG TVRGLIRTTV
```

```
                        -continued
301    CAEPGDSGGS LLAGNQAQGV TSGGSGNCRT GGTTFFQPVN PILQAYGLRM

351    ITTDSGSSPA PAPTSCTGYA RTFTGTLAAG RAAAQPNGSY VQVNRSGTHS

401    VCLNGPSGAD FDLYVQRWNG SSWVTVAQST SPGSNETITY RGNAGYYRYV

451    VNAASGSGAY TMGLTLP
```

The following sequence (SEQ ID NO:8) is the amino acid sequence of the mature protease derived from *Cellulomonas* strain 69B4 (DSM 16035). The catalytic triad residues H32, D56 and S132 are bolded and underlined.

```
                                                     (SEQ ID NO: 8)
  1    FDVIGGNAYT IGGRSRCSIG FAVNGGFITA GHCGRTGATT ANPTGTFAGS

51    SFPGNDYAFV RTGAGVNLLA QVNNYSGGRV QVAGHTAAPV GSAVCRSGST

101    TGWHCGTITA LNSSVTYPEG TVRGLIRTTV CAEPGDSGGS LLAGNQAQGV

151    TSGGSGNCRT GGTTFFQPVN PILQAYGLRM ITTDSGSSP
```

The following sequence (SEQ ID NO:9) is the amino acid sequence of the signal peptide of the protease derived from *Cellulomonas* strain 69B4 (DSM 16035).

```
  1    MTPRTVTRAL AVATAAATLL AGGMAAQA  (SEQ ID NO: 9)
```

In some embodiments, the present invention encompasses variants that comprise at least a portion of the approximately 1621 base pairs in length polynucleotide set forth in SEQ. ID NO:1. In some particularly preferred embodiments, the present invention provides variants that have multiple mutations as compared to the wild-type (e.g., "parent") serine protease. In some of these more particularly preferred embodiments, these multiply mutated variants exhibit improved performance, as compared to the wild-type (e.g., "parent") serine protease.

As will be understood by the skilled artisan, due to the degeneracy of the genetic code, a variety of polynucleotides can encode the signal peptide, precursor protease and/or mature protease provided herein and/or in U.S. patent application Ser. No. 10/576,331, incorporated by reference in its entirety (e.g., SEQ ID NOS:6, 7, and/or 8 of U.S. patent application Ser. No. 10/576,331) or a protease having the % sequence identity described above. Another embodiment of the present invention encompasses a polynucleotide comprising a nucleotide sequence having at least 70% sequence identity, at least 75% sequence identity, at least 80% sequence identity, at least 85% sequence identity, at least 90% sequence identity, at least 92% sequence identity, at least 95% sequence identity, at least 97% sequence identity, at least 98% sequence identity and at least 99% sequence identity to the polynucleotide sequence of SEQ ID NOS, 2, 3, and/or 4, respectively, encoding the signal peptide and precursor protease, the precursor protease and/or the mature protease, respectively.

In additional embodiments, the present invention provides fragments or portions of DNA that encodes proteases, so long as the encoded fragment retains proteolytic activity. Another embodiment of the present invention encompasses polynucleotides having at least 20% of the sequence length, at least 30% of the sequence length, at least 40% of the sequence length, at least 50% of the sequence length, at least 60% of the sequence length, 70% of the sequence length, at least 75% of the sequence length, at least 80% of the sequence length, at least 85% of the sequence length, at least 90% of the sequence length, at least 92% of the sequence length, at least 95% of the sequence length, at least 97% of the sequence length, at least 98% of the sequence length and at least 99% of the sequence of the polynucleotide sequence of SEQ ID NO:1, encoding the precursor protease. In alternative embodiments, these fragments or portions of the sequence length are contiguous portions of the sequence length, useful for shuffling of the DNA sequence in recombinant DNA sequences (See e.g., U.S. Pat. No. 6,132,970)

Another embodiment of the invention includes fragments of the DNA described herein that find use according to art recognized techniques in obtaining partial length DNA fragments capable of being used to isolate or identify polynucleotides encoding mature protease enzyme described herein from *Cellulomonas* 69B4, or a segment thereof having proteolytic activity. Moreover, the DNA provided in SEQ ID NO:1 finds use in identifying homologous fragments of DNA from other species, and particularly from *Cellulomonas* spp. which encode a protease or portion thereof having proteolytic activity.

In addition, the present invention encompasses using primer or probe sequences constructed from SEQ ID NO:1, or a suitable portion or fragment thereof (e.g., at least about 5-20 or 10-15 contiguous nucleotides), as a probe or primer for screening nucleic acid of either genomic or cDNA origin. In some embodiments, the present invention provides DNA probes of the desired length (i.e., generally between 100 and 1000 bases in length), based on the sequences in SEQ ID NO:1.

In some embodiments, the DNA fragments are electrophoretically isolated, cut from the gel, and recovered from the agar matrix of the gel. In preferred embodiments, this purified fragment of DNA is then labeled (using, for example, the Megaprime labeling system according to the instructions of the manufacturer) to incorporate $P^{32}$ in the DNA. The labeled probe is denatured by heating to 95° C. for a given period of time (e.g., 5 minutes), and immediately added to the membrane and prehybridization solution. The hybridization reaction proceeds for an appropriate time and under appropriate conditions (e.g., 18 hours at 37° C.), with gentle shaking or rotation. The membrane is rinsed (e.g., twice in SSC/0.3% SDS) and then washed in an appropriate wash solution with gentle agitation. The stringency desired is a reflection of the conditions under which the membrane (filter) is washed. In some embodiments herein, "low-stringency" conditions involve washing with a solution of 0.2×SSC/0.1% SDS at 20° C. for 15 minutes, while in other embodiments, "medium-stringency" conditions, involve a further washing step comprising washing with a solution of 0.2×SSC/0.1% SDS at 37°

C. for 30 minutes, while in other embodiments, "high-stringency" conditions involve a further washing step comprising washing with a solution of 0.2×SSC/0.1% SDS at 37° C. for 45 minutes, and in further embodiments, "maximum-stringency" conditions involve a further washing step comprising washing with a solution of 0.2×SSC/0.1% SDS at 37° C. for 60 minutes. Thus, various embodiments of the present invention provide polynucleotides capable of hybridizing to a probed derived from the nucleotide sequence provided in SEQ ID NOS:1 or 2, under conditions of medium, high and/or maximum stringency.

After washing, the membrane is dried and the bound probe detected. If $P^{32}$ or another radioisotope is used as the labeling agent, the bound probe is detected by autoradiography. Other techniques for the visualization of other probes are well-known to those of skill in the art. The detection of a bound probe indicates a nucleic acid sequence has the desired homology, and therefore identity, to any sequence of interest provided herein is encompassed by the present invention. Accordingly, the present invention provides methods for the detection of nucleic acid encoding a protease encompassed by the present invention which comprises hybridizing part or all of a nucleic acid sequence of SEQ ID NO:1 with other nucleic acid of either genomic or cDNA origin.

As indicated above, in other embodiments, hybridization conditions are based on the melting temperature (Tm) of the nucleic acid binding complex, to confer a defined "stringency" as explained below. "Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As known to those of skill in the art, medium, high and/or maximum stringency hybridization are chosen such that conditions are optimized to identify or detect polynucleotide sequence homologues or equivalent polynucleotide sequences.

In yet additional embodiments, the present invention provides nucleic acid constructs (i.e., expression vectors) comprising the polynucleotides encoding the proteases of the present invention. In further embodiments, the present invention provides host cells transformed with at least one of these vectors.

In further embodiments, the present invention provides polynucleotide sequences further encoding a signal sequence, as described in U.S. patent application Ser. No. 10/576,331, incorporated by reference in its entirety. In some of these embodiments, the present invention provides a sequence with a putative signal sequence, and polynucleotides being capable of hybridizing to a probe derived from the nucleotide sequence disclosed in SEQ ID NO:1 under conditions of medium, high and/or maximal stringency, wherein the signal sequences have substantially the same signal activity as the signal sequence encoded by the polynucleotide of the present invention.

In some embodiments, the signal activity is indicated by substantially the same level of secretion of the protease into the fermentation medium, as the starting material, as described in U.S. patent application Ser. No. 10/576,331. Additional means for determining the levels of secretion of a heterologous or homologous protein in a Gram-positive host cell and detecting secreted proteins include using either polyclonal or monoclonal antibodies specific for the protein. Examples include enzyme-linked immunosorbent assay (ELISA), radioimmunoassay (RIA) and fluorescent activated cell sorting (FACS), as well-known to those in the art.

Further aspects of the present invention encompass polypeptides having proteolytic activity comprising 65% amino acid sequence identity, at least 70% sequence identity, at least 75% amino acid sequence identity, at least 80% amino acid sequence identity, at least 85% amino acid sequence identity, at least 90% amino acid sequence identity, at least 92% amino acid sequence identity, at least 95% amino acid sequence identity, at least 97% amino acid sequence identity, at least 98% amino acid sequence identity and at least 99% amino acid sequence identity to the amino acid sequence of SEQ ID NOS:7 or 8, and as described herein and in U.S. patent application Ser. No. 10/576,331. The proteolytic activity of these polypeptides is determined using methods known in the art and include such methods as those used to assess detergent function. In further embodiments, the polypeptides are isolated.

III. Obtaining Polynucleotides Encoding Micrococcineae (e.g., *Cellulomonas*) Proteases of the Present Invention In some embodiments, nucleic acid encoding a protease of the present invention is obtained by standard procedures known in the art from, for example, cloned DNA (e.g., a DNA "library"), chemical synthesis, cDNA cloning, PCR, cloning of genomic DNA or fragments thereof, or purified from a desired cell, such as a bacterial or fungal species (See, for example, Sambrook et al., supra [1989]; and Glover and Hames (eds.), *DNA Cloning: A Practical Approach*, Vols. 1 and 2, Second Edition). Synthesis of polynucleotide sequences is well known in the art (See e.g., Beaucage and Caruthers, Tetrahedron Lett., 22:1859-1862 [1981]), including the use of automated synthesizers (See e.g., Needham-VanDevanter et al., Nucl. Acids Res., 12:6159-6168 [1984]). DNA sequences can also be custom made and ordered from a variety of commercial sources. As described in greater detail herein, in some embodiments, nucleic acid sequences derived from genomic DNA contain regulatory regions in addition to coding regions.

In some embodiments involving the molecular cloning of the gene from genomic DNA, DNA fragments are generated, some of which comprise at least a portion of the desired gene. In some embodiments, the DNA is cleaved at specific sites using various restriction enzymes. In some alternative embodiments, DNAse is used in the presence of manganese to fragment the DNA, or the DNA is physically sheared (e.g., by sonication). The linear DNA fragments created are then be separated according to size and amplified by standard techniques, including but not limited to, agarose and polyacrylamide gel electrophoresis, PCR and column chromatography.

Once nucleic acid fragments are generated, identification of the specific DNA fragment encoding a protease may be accomplished in a number of ways. For example, in some embodiments, a proteolytic hydrolyzing enzyme encoding the asp gene or its specific RNA, or a fragment thereof, such as a probe or primer, is isolated, labeled, and then used in hybridization assays well known to those in the art, to detect a generated gene (See e.g., Benton and Davis, Science 196: 180 [1977]; and Grunstein and Hogness, Proc. Natl. Acad. Sci. USA 72:3961 [1975]). In preferred embodiments, DNA fragments sharing substantial sequence similarity to the probe hybridize under medium to high stringency.

In some preferred embodiments, amplification is accomplished using PCR, as known in the art. In some preferred embodiments, a nucleic acid sequence of at least about 4 nucleotides and as many as about 60 nucleotides from SEQ ID NOS:1-5, (i.e., fragments), preferably about 12 to 30 nucleotides, and more preferably about 25 nucleotides are used in any suitable combinations as PCR primer. These same fragments also find use as probes in hybridization and product detection methods.

In some embodiments, isolation of nucleic acid constructs of the invention from a cDNA or genomic library utilizes PCR with using degenerate oligonucleotide primers prepared on the basis of the amino acid sequence of the protein., The primers can be of any segment length, for example at least 4, at least 5, at least 8, at least 15, at least 20, nucleotides in length.

In view of the above, it will be appreciated that the polynucleotide sequences provided herein and based on the polynucleotide sequences provided in SEQ ID NOS:1-5 are useful for obtaining identical or homologous fragments of polynucleotides from other species, and particularly from bacteria that encode enzymes having the serine protease activity expressed by protease 69B4. Additional sequences are provided in U.S. patent application Ser. No. 10/576,331.

IV. Multiple Mutation Variants of Serine Proteases of the Present Invention

As indicated herein, in particularly preferred embodiments, the present invention provides multiple mutation variants of serine protease. In some most particularly preferred embodiments, these variants exhibit improved performance as compared to the parent (e.g., wild-type) protease. In some of these most particularly preferred embodiments, the variants have improved wash performance, LAS stability, and/or proteolytic activity. Thus, these variants find use in numerous applications, including but not limited to dishwashing detergents, laundry detergents, and surface cleaning detergents.

V. Expression and Recovery of Serine Proteases of the Present Invention

Any suitable means for expression and recovery of the serine proteases of the present invention find use herein. Indeed, those of skill in the art know many methods suitable for cloning a *Cellulomonas*-derived polypeptide having proteolytic activity, as well as an additional enzyme (e.g., a second peptide having proteolytic activity, such as a protease, cellulase, mannanase, or amylase, etc.). Numerous methods are also known in the art for introducing at least one (e.g., multiple) copies of the polynucleotide(s) encoding the enzyme(s) of the present invention in conjunction with any additional sequences desired, into the genes or genome of host cells.

In general, standard procedures for cloning of genes and introducing exogenous proteases encoding regions (including multiple copies of the exogenous encoding regions) into said genes find use in obtaining a *Cellulomonas* 69B4 protease derivative or homologue thereof. Indeed, the present Specification, including the Examples provides such teaching. However, additional methods known in the art are also suitable (See e.g., Sambrook et al. supra (1989); Ausubel et al., supra [1995]; and Harwood and Cutting, (eds.) *Molecular Biological Methods for Bacillus*," John Wiley and Sons, [1990]; and WO 96/34946).

In some preferred embodiments, the polynucleotide sequences of the present invention are expressed by operatively linking them to an expression control sequence in an appropriate expression vector and employed by that expression vector to transform an appropriate host according to techniques well established in the art. In some embodiments, the polypeptides produced on expression of the DNA sequences of this invention are isolated from the fermentation of cell cultures and purified in a variety of ways according to well-established techniques in the art. Those of skill in the art are capable of selecting the most appropriate isolation and purification techniques.

More particularly, the present invention provides constructs, vectors comprising polynucleotides described herein, host cells transformed with such vectors, proteases expressed by such host cells, expression methods and systems for the production of serine protease enzymes derived from microorganisms, in particular, members of the Micrococcineae, including but not limited to *Cellulomonas* species. In some embodiments, the polynucleotide(s) encoding serine protease(s) are used to produce recombinant host cells suitable for the expression of the serine protease(s). In some preferred embodiments, the expression hosts are capable of producing the protease(s) in commercially viable quantities. Additional details are provided in U.S. patent application Ser. No. 10/576,331.

VI. Recombinant Vectors and Host Cells

As indicated above, in some embodiments, the present invention provides vectors comprising the aforementioned polynucleotides. In some embodiments, the vectors (i.e., constructs) of the invention encoding the protease are of genomic origin (e.g., prepared though use of a genomic library and screening for DNA sequences coding for all or part of the protease by hybridization using synthetic oligonucleotide probes in accordance with standard techniques). These vectors are described in greater detail in U.S. patent application Ser. No. 10/576,331.

As indicated above, in some embodiments, the present invention also provides host cells transformed with the vectors described above. Additional host cells are described in greater detail in U.S. patent application Ser. No. 10/576,331.

VII. Applications for Serine Protease Enzymes

As described in greater detail herein, the proteases of the present invention have important characteristics that make them very suitable for certain applications. For example, the proteases of the present invention have enhanced thermal stability. In some embodiments, the enzymes also exhibit enhanced oxidative stability, and enhanced chelator stability, as compared to some currently used proteases. Thus, these proteases find use in cleaning compositions. Indeed, under certain wash conditions, the present proteases exhibit comparative or enhanced wash performance as compared with currently used subtilisin proteases. Thus, it is contemplated that the cleaning and/or enzyme compositions of the present invention will be provided in a variety of cleaning compositions. In some embodiments, the proteases of the present invention are utilized in the same manner as subtilisin proteases (i.e., proteases currently in use). Thus, the present proteases find use in various cleaning compositions, as well as animal feed applications, leather processing (e.g., bating), protein hydrolysis, and in textile uses. The identified proteases also find use in personal care applications.

Thus, the proteases of the present invention find use in a number of industrial applications, in particular within the cleaning, disinfecting, animal feed, and textile/leather industries. In some embodiments, the protease(s) of the present invention are combined with detergents, builders, bleaching agents and other conventional ingredients to produce a variety of novel cleaning compositions useful in the laundry and other cleaning arts such as, for example, laundry detergents (both powdered and liquid), laundry pre-soaks, all fabric bleaches, automatic dishwashing detergents (both liquid and powdered), household cleaners, particularly bar and liquid soap applications, and drain openers. In addition, the proteases find use in the cleaning of contact lenses, as well as other items, by contacting such materials with an aqueous solution of the cleaning composition. In addition these naturally occurring proteases can be used, for example in peptide hydrolysis, waste treatment, textile applications, medical device cleaning, biofilm removal and as fusion-cleavage enzymes in protein production, etc. The composition of these products is not critical to the present invention, as long as the protease(s) maintain their function in the setting used. In some embodiments, the compositions are readily prepared by combining a cleaning effective amount of the protease or an enzyme composition comprising the protease enzyme preparation with the conventional components of such compositions in their art recognized amounts.

The proteases of the present invention find particular use in the cleaning industry, including, but not limited to laundry and dish detergents. These applications place enzymes under various environmental stresses. The proteases of the present invention provide advantages over many currently used enzymes, due to their stability under various conditions.

Indeed, there are a variety of wash conditions including varying detergent formulations, wash water volumes, wash water temperatures, and lengths of wash time, to which proteases involved in washing are exposed. In addition, detergent formulations used in different geographical areas have different concentrations of their relevant components present in the wash water. For example, a European detergent typically has about 4500-5000 ppm of detergent components in the wash water, while a Japanese detergent typically has approximately 667 ppm of detergent components in the wash water. In North America, particularly the United States, detergents typically have about 975 ppm of detergent components present in the wash water.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan can be between 10 and 30° C. (e.g., about 20° C.), whereas the temperature of wash water in Europe is typically between 30 and 60° C. (e.g., about 40° C.).

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals (See, Table 13-1).

European water hardness is typically greater than 10.5 (e.g., 10.5-20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between 3 to 10 grains, 3-8 grains or about 6 grains. Japanese water hardness is typically lower than North American water hardness, usually less than 4, for example 3 grains per gallon mixed $Ca^{2+}/Mg^{2+}$.

Accordingly, in some embodiments, the present invention provides proteases that show surprising wash performance in at least one set of wash conditions (e.g., water temperature, water hardness, and/or detergent concentration). In some embodiments, the proteases of the present invention are comparable in wash performance to subtilisin proteases. In some embodiments, the proteases of the present invention exhibit enhanced wash performance as compared to subtilisin proteases. Thus, in some preferred embodiments of the present invention, the proteases provided herein exhibit enhanced oxidative stability, enhanced thermal stability, and/or enhanced chelator stability.

In some preferred embodiments, the present invention provides the ASP protease, as well as homologues and variants of the protease. In particularly preferred embodiments, the ASP variants comprise multiple substitutions in the wild-type ASP protease sequence. These proteases find use in any applications in which it is desired to clean protein based stains from textiles or fabrics.

In some embodiments, the cleaning compositions of the present invention are formulated as hand and machine laundry detergent compositions including laundry additive compositions, and compositions suitable for use in the pretreatment of stained fabrics, rinse-added fabric softener compositions, and compositions for use in general household hard surface cleaning operations, as well as dishwashing operations. Those in the art are familiar with different formulations which can be used as cleaning compositions. In preferred embodiments, the proteases of the present invention comprise comparative or enhanced performance in detergent compositions (i.e., as compared to other proteases). In some embodiments, cleaning performance is evaluated by comparing the proteases of the present invention with subtilisin proteases in various cleaning assays that utilize enzyme-sensitive stains such as egg, grass, blood, milk, etc., in standard methods. Indeed, those in the art are familiar with the spectrophotometric and other analytical methodologies used to assess detergent performance under standard wash cycle conditions.

Assays that find use in the present invention include, but are not limited to those described in WO 99/34011, and U.S. Pat. No. 6,605,458 (See e.g., Example 3). In U.S. Pat. No. 6,605,458, at Example 3, a detergent dose of 3.0 g/l at pH 10.5, wash time 15 minutes, at 15 C, water hardness of 6° dH, 10 nM enzyme concentration in 150 ml glass beakers with stirring rod, 5 textile pieces (phi 2.5 cm) in 50 ml, EMPA 117 test material from Center for Test Materials Holland are used. The measurement of reflectance "R" on the test material was done at 460 nm using a Macbeth ColorEye 7000 photometer. Additional methods are provided in the Examples herein. Thus, these methods also find use in the present invention.

The addition of proteases of the invention to conventional cleaning compositions does not create any special use limitation. In other words, any temperature and pH suitable for the detergent is also suitable for the present compositions, as long as the pH is within the range set forth herein, and the temperature is below the described protease's denaturing temperature. In addition, proteases of the present invention find use in cleaning compositions that do not include detergents, again either alone or in combination with builders and stabilizers.

When used in cleaning compositions or detergents, oxidative stability is a further consideration. Thus, in some applications, the stability is enhanced, diminished, or comparable to subtilisin proteases as desired for various uses. In some preferred embodiments, enhanced oxidative stability is desired. Some of the proteases of the present invention find particular use in such applications.

When used in cleaning compositions or detergents, thermal stability is a further consideration. Thus, in some applications, the stability is enhanced, diminished, or comparable to subtilisin proteases as desired for various uses. In some preferred embodiments, enhanced thermostability is desired. Some of the proteases of the present invention find particular use in such applications.

When used in cleaning compositions or detergents, chelator stability is a further consideration. Thus, in some applications, the stability is enhanced, diminished, or comparable to subtilisin proteases as desired for various uses. In some preferred embodiments, enhanced chelator stability is desired. Some of the proteases of the present invention find particular use in such applications.

In some embodiments of the present invention, naturally occurring proteases are provided which exhibit modified enzymatic activity at different pHs when compared to subtilisin proteases. A pH-activity profile is a plot of pH against enzyme activity and may be constructed as described in the Examples and/or by methods known in the art. In some embodiments, it is desired to obtain naturally occurring proteases with broader profiles (i.e., those having greater activity at range of pHs than a comparable subtilisin protease). In other embodiments, the enzymes have no significantly greater activity at any pH, or naturally occurring homologues with sharper profiles (i.e., those having enhanced activity when compared to subtilisin proteases at a given pH, and lesser activity elsewhere). Thus, in various embodiments, the proteases of the present invention have differing pH optima and/or ranges. It is not intended that the present invention be limited to any specific pH or pH range.

In some embodiments of the present invention, the cleaning compositions comprise, proteases of the present invention at a level from 0.00001% to 10% of 69B4 and/or other proteases of the present invention by weight of the composition and the balance (e.g., 99.999% to 90.0%) comprising cleaning adjunct materials by weight of composition. In other aspects of the present invention, the cleaning compositions of the present invention comprise, the 69B4 and/or other proteases at a level of 0.0001% to 10%, 0.001% to 5%, 0.001% to 2%, 0.005% to 0.5% 69B4 or other protease of the present invention by weight of the composition and the balance of the cleaning composition (e.g., 99.9999% to 90.0%, 99.999% to 98%, 99.995% to 99.5% by weight) comprising cleaning adjunct materials.

In some embodiments, preferred cleaning compositions, in addition to the protease preparation of the invention, comprise one or more additional enzymes or enzyme derivatives which provide cleaning performance and/or fabric care benefits. Such enzymes include, but are not limited to other proteases, lipases, cutinases, amylases, cellulases, peroxidases, oxidases (e.g. laccases), and/or mannanases.

Any other protease suitable for use in alkaline solutions finds use in the compositions of the present invention. Suitable proteases include those of animal, vegetable or microbial origin. In particularly preferred embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, lentus, amyloliquefaciens, subtilisin Carlsberg, subtilisin 309, subtilisin 147 and subtilisin 168). Additional examples include those mutant proteases described in U.S. Pat. Nos. RE 34,606, 5,955,340, 5,700,676, 6,312,936, and 6,482,628, all of which are incorporated herein by reference. Additional protease examples include, but are not limited to trypsin (e.g., of porcine or bovine origin), and the hprotease described in WO 89/06270. Preferred commercially available protease enzymes include those sold under the trade names MAXATASE®, MAXACAL™, MAXAPEM™, OPTICLEAN®; OPTIMASE®, PROPERASE®, PURAFECT® and PURAFECT® OXP (Genencor), those sold under the trade names ALCALASE®, SAVINASE®, PRIMASE®, DURAZYM™, RELASE® and ESPERASE® (Novozymes); and those sold under the trade name BLAP™ (Henkel Kommanditgesellschaft auf Aktien, Duesseldorf, Germany. Various proteases are described in WO95/23221, WO 92/21760, and U.S. Pat. Nos. 5,801,039, 5,340,735, 5,500,364, 5,855,625. An additional BPN' variant ("BPN'-var I" and "BPN-variant I"; as referred to herein) is described in U.S. RE 34, 606. An additional GG36-variant ("GG36-var.1" and "GG36-variant 1"; as referred to herein) is described in U.S. Pat. Nos. 5,955,340 and 5,700,676. A further GG36-variant is described in U.S. Pat. Nos. 6,312,936 and 6,482,628. In one aspect of the present invention, the cleaning compositions of the present invention comprise additional protease enzymes at a level from 0.00001% to 10% of additional protease by weight of the composition and 99.999% to 90.0% of cleaning adjunct materials by weight of composition. In other embodiments of the present invention, the cleaning compositions of the present invention also comprise, proteases at a level of 0.0001% to 10%, 0.001% to 5%, 0.001% to 2%, 0.005% to 0.5% 69B4 protease (or its homologues or variants) by weight of the composition and the balance of the cleaning composition (e.g., 99.9999% to 90.0%, 99.999% to 98%, 99.995% to 99.5% by weight) comprising cleaning adjunct materials.

In addition, any lipase suitable for use in alkaline solutions finds use in the present invention. Suitable lipases include, but are not limited to those of bacterial or fungal origin. Chemically or genetically modified mutants are encompassed by the present invention. Examples of useful lipases include *Humicola lanuginosa* lipase (See e.g., EP 258 068, and EP 305 216), *Rhizomucor miehei* lipase (See e.g., EP 238 023), *Candida* lipase, such as *C. antarctica* lipase (e.g., the *C. antarctica* lipase A or B; See e.g., EP 214 761), a *Pseudomonas* lipase such as *P. alcaligenes* and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipolytic enzymes such as cutinases also find use in some embodiments of the present invention, including but not limited to the cutinase derived from *Pseudomionas mendocina* (See, WO 88/09367), or cutinase derived from *Fusarium solani pisi* (See, WO 90/09446).

Additional suitable lipases include commercially available lipases such as MI LIPASE™, LUMA FAST™, and LIPOMAX™ (Genencor); LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from 0.00001% to 10% of additional lipase by weight of the composition and the balance of cleaning adjunct materials by weight of composition. In other aspects of the present invention, the cleaning compositions of the present invention also comprise, lipases at a level of 0.0001% to 10%, 0.001% to 5%, 0.001% to 2%, 0.005% to 0.5% lipase by weight of the composition.

Any amylase (alpha and/or beta) suitable for use in alkaline solutions also find use in some embodiments of the present invention. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296,839). Commercially available amylases that find use in the present invention include, but are not limited to DURAMYL®, TERMAMYL®, FUNGAMYL®, STAINZYME®, and BAN™ (Novozymes) and RAPIDASE®, and MAXAMYL® P (Genencor International). In some embodiments of the present invention, the cleaning compositions of the present invention further comprise amylases at a level from 0.00001% to 10% of additional amylase by weight of the composition and the balance of cleaning adjunct materials by weight of composition. In other aspects of the present invention, the cleaning compositions of the present invention also comprise, amylases at a level of 0.0001% to 10%, 0.001% to 5%, 0.001% to 2%, 0.005% to 0.5% amylase by weight of the composition.

Any cellulase suitable for use in alkaline solutions find use in embodiments of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257).

Commercially available cellulases that find use in the present include, but are not limited to CELLUZYME® (Novozymes), and KAC-500(B)™ (Kao Corporation). In some embodiments, cellulases are incorporated as portions or fragments of mature wild-type or variant cellulases, wherein a portion of the N-terminus is deleted (See e.g., U.S. Pat. No. 5,874,276).

In some embodiments, the cleaning compositions of the present invention can further comprise cellulases at a level from 0.00001% to 10% of additional cellulase by weight of the composition and the balance of cleaning adjunct materials by weight of composition. In other aspects of the present invention, the cleaning compositions of the present invention also comprise cellulases at a level of 0.0001% to 10%, 0.001% to 5%, 0.001% to 2%, 0.005% to 0.5% cellulase by weight of the composition.

Any mannanases suitable for use in detergent compositions and or alkaline solutions find use in the present invention. Suitable mannanases include, but are not limited to those of bacterial or fungal origin. Chemically or genetically modified mutants are included in some embodiments. Various mannanases are known which find use in the present invention (See e.g., U.S. Pat. No. 6,566,114, U.S. Pat. No. 6,602,842, and U.S. Pat. No. 6,440,991, all of which are incorporated herein by reference).

In some embodiments, the cleaning compositions of the present invention can further comprise mannanases at a level from 0.00001% to 10% of additional mannanase by weight of the composition and the balance of cleaning adjunct materials by weight of composition. In other aspects of the present invention, the cleaning compositions of the present invention also comprise, mannanases at a level of 0.0001% to 10%, 0.001% to 5%, 0.001% to 2%, 0.005% to 0.5% mannanases by weight of the composition.

In some embodiments, peroxidases are used in combination with hydrogen peroxide or a source thereof (e.g., a percarbonate, perborate or persulfate). In alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments.

In some embodiments, the cleaning compositions of the present invention can further comprise peroxidase and/or oxidase enzymes at a level from 0.00001% to 10% of additional peroxidase and/or oxidase by weight of the composition and the balance of cleaning adjunct materials by weight of composition. In other aspects of the present invention, the cleaning compositions of the present invention also comprise, peroxidase and/or oxidase enzymes at a level of 0.0001% to 10%, 0.001% to 5%, 0.001% to 2%, 0.005% to 0.5% peroxidase and/or oxidase enzymes by weight of the composition.

Mixtures of the above mentioned enzymes are encompassed herein, in particular a mixture of a the 69B4 enzyme, one or more additional proteases, at least one amylase, at least one lipase, at least one mannanase, and/or at least one cellulase. Indeed, it is contemplated that various mixtures of these enzymes will find use in the present invention.

It is contemplated that the varying levels of the protease and one or more additional enzymes may both independently range to 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below.

If the cleaning adjunct materials are not compatible with the proteases of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapulation, tablets, physical separation, etc.).

Preferably an effective amount of one or more protease(s) provided herein are included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the protease of the present invention find use are described in greater detail below. In embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials).

The compositions of the present invention also find use detergent additive products in solid or liquid form. Such additive products are intended to supplement and/or boost the performance of conventional detergent compositions and can be added at any stage of the cleaning process.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, the density of the laundry detergent compositions herein ranges from 400 to 1200 g/liter, while in other embodiments, it ranges from 500 to 950 g/liter of composition measured at 20° C.

In some embodiments, various cleaning compositions such as those provided in U.S. Pat. No. 6,605,458 find use with the proteases of the present invention. Thus, in some embodiments, the compositions comprising at least one protease of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition.

In some embodiments, the compositions comprising at least one protease of the present invention are fabric cleaning compositions such as those described in U.S. Pat. No. 6,610, 642 and U.S. Pat. No. 6,376,450. In addition, the proteases of the present invention find use in granular laundry detergent compositions of particular utility under European or Japanese washing conditions (See e.g., U.S. Pat. No. 6,610,642).

In alternative embodiments, the present invention provides hard surface cleaning compositions comprising at least one protease provided herein. Thus, in some embodiments, the compositions comprising at least one protease of the present invention is a hard surface cleaning composition such as those described in U.S. Pat. Nos. 6,610,642, U.S. Pat. No. 6,376, 450, and U.S. Pat. No. 6,376,450.

In yet further embodiments, the present invention provides dishwashing compositions comprising at least one protease provided herein. Thus, in some embodiments, the compositions comprising at least one protease of the present invention is a hard surface cleaning composition such as those in U.S. Pat. No. 6,610,642, and U.S. Pat. No. 6,376,450.

In still further embodiments, the present invention provides dishwashing compositions comprising at least one protease provided herein. Thus, in some embodiments, the compositions comprising at least one protease of the present invention comprise oral care compositions such as those in U.S. Pat. No. 6,376,450, and U.S. Pat. No. 6,376,450.

The formulations and descriptions of the compounds and cleaning adjunct materials contained in the aforementioned U.S. Pat. Nos. 6,376,450; 6,605,458; 6,605,458; and 6,610, 642 are expressly incorporated by reference herein. Still further examples are set forth in the Examples below.

Still further, the present invention provides compositions and methods for the production of a food or animal feed, characterized in that protease according to the invention is mixed with food or animal feed. In some embodiments, the protease is added as a dry product before processing, while in other embodiments it is added as a liquid before or after processing. In some embodiments, in which a dry powder is used, the enzyme is diluted as a liquid onto a dry carrier such as milled grain. The proteases of the present invention find use as components of animal feeds and/or additives such as those described in, U.S. Pat. No. 5,612,055, U.S. Pat. No. 5,314, 692, and U.S. Pat. No. 5,147,642, all of which are hereby incorporated by reference.

The enzyme feed additive according to the present invention is suitable for preparation in a number of methods. For example, in some embodiments, it is prepared simply by mixing different enzymes having the appropriate activities to produce an enzyme mix. In some embodiments, this enzyme mix is mixed directly with a feed, while in other embodiments, it is impregnated onto a cereal-based carrier material such as milled wheat, maize or soya flour. The present invention also encompasses these impregnated carriers, as they find use as enzyme feed additives.

In some alternative embodiments, a cereal-based carrier (e.g., milled wheat or maize) is impregnated either simultaneously or sequentially with enzymes having the appropriate activities. For example, in some embodiments, a milled wheat carrier is first sprayed with a xylanase, secondly with a protease, and optionally with a O-glucanase. The present invention also encompasses these impregnated carriers, as they find use as enzyme feed additives. In preferred embodiments, these impregnated carriers comprise at least one protease of the present invention.

In some embodiments, the feed additive of the present invention is directly mixed with the animal feed, while in alternative embodiments, it is mixed with one or more other feed additives such as a vitamin feed additive, a mineral feed additive, and/or an amino acid feed additive. The resulting feed additive including several different types of components is then mixed in an appropriate amount with the feed.

In some preferred embodiments, the feed additive of the present invention, including cereal-based carriers is normally mixed in amounts of 0.01-50 g per kilogram of feed, more preferably 0.1-10 g/kilogram, and most preferably about 1 g/kilogram.

In alternative embodiments, the enzyme feed additive of the present invention involves construction of recombinant microorganisms that produces the desired enzyme(s) in the desired relative amounts. In some embodiments, this is accomplished by increasing the copy number of the gene encoding at least one protease of the present invention, and/or by using a suitably strong promoter operatively linked to the polynucleotide encoding the protease(s). In further embodiments, the recombinant microorganism strain has certain enzyme activities deleted (e.g., cellulases, endoglucanases, etc.), as desired.

In additional embodiments, the enzyme feed additives provided by the present invention also include other enzymes, including but not limited to at least one xylanase, α-amylase, glucoamylase, pectinase, mannanase, α-galactosidase, phytase, and/or lipase. In some embodiments, the enzymes having the desired activities are mixed with the xylanase and protease either before impregnating these on a cereal-based carrier or alternatively such enzymes are impregnated simultaneously or sequentially on such a cereal-based carrier. The carrier is then in turn mixed with a cereal-based feed to prepare the final feed. In alternative embodiments, the enzyme feed additive is formulated as a solution of the individual enzyme activities and then mixed with a feed material pre-formed as pellets or as a mash.

In still further embodiments, the enzyme feed additive is included in animals' diets by incorporating it into a second (i.e., different) feed or the animals' drinking water. Accordingly, it is not essential that the enzyme mix provided by the present invention be incorporated into the cereal-based feed itself, although such incorporation forms a particularly preferred embodiment of the present invention. The ratio of the units of xylanase activity per g of the feed additive to the units of protease activity per g of the feed additive is preferably 1:0.001-1,000, more preferably 1:0.01-100, and most preferably 1:0.1-10. As indicated above, the enzyme mix provided by the present invention preferably finds use as a feed additive in the preparation of a cereal-based feed.

In some embodiments, the cereal-based feed comprises at least 25% by weight, or more preferably at least 35% by weight, wheat or maize or a combination of both of these cereals. The feed further comprises a protease (i.e., at least one protease of the present invention) in such an amount that the feed includes a protease in such an amount that the feed includes 100-100,000 units of protease activity per kg.

Cereal-based feeds provided the present invention according to the present invention find use as feed for a variety of non-human animals, including poultry (e.g., turkeys, geese, ducks, chickens, etc.), livestock (e.g., pigs, sheep, cattle, goats, etc.), and companion animals (e.g., horses, dogs, cats, rabbits, mice, etc.). The feeds are particularly suitable for poultry and pigs, and in particular broiler chickens.

The present invention also provides compositions for the treatment of textiles that include at least one of the proteases of the present invention. In some embodiments, at least one protease of the present invention is a component of compositions suitable for the treatment of silk or wool (See e.g., U.S. RE Pat. No. 216,034, EP 134,267, U.S. Pat. No. 4,533,359, and EP 344,259).

In addition, the proteases of the present invention find use in a variety of applications where it is desirable to separate phosphorous from phytate. Accordingly, the present invention also provides methods producing wool or animal hair material with improved properties. In some preferred embodiments, these methods comprise the steps of pretreating wool, wool fibres or animal hair material in a process selected from the group consisting of plasma treatment processes and the Delhey process; and subjecting the pretreated wool or animal hair material to a treatment with a proteolytic enzyme (e.g., at least one protease of the present invention) in an amount effective for improving the properties. In some embodiments, the proteolytic enzyme treatment occurs prior to the plasma treatment, while in other embodiments, it occurs after the plasma treatment. In some further embodiments, it is conducted as a separate step, while in other embodiments, it is conducted in combination with the scouring or the dyeing of the wool or animal hair material. In additional embodiments, at least one surfactant and/or at least one softener is present during the enzyme treatment step, while in other embodiments, the surfactant(s) and/or softener(s) are incorporated in a separate step wherein the wool or animal hair material is subjected to a softening treatment.

In some embodiments, the compositions of the present invention find use in methods for shrink-proofing wool fibers (See e.g., JP 4-327274). In some embodiments, the compositions are used in methods for shrink-proofing treatment of wool fibers by subjecting the fibers to a low-temperature plasma treatment, followed by treatment with a shrink-proofing resin such as a block-urethane resin, polyamide epochlorohydrin resin, glyoxalic resin, ethylene-urea resin or acrylate resin, and then treatment with a weight reducing proteolytic enzyme for obtaining a softening effect). In some embodiments, the plasma treatment step is a low-temperature treatment, preferably a corona discharge treatment or a glow discharge treatment.

In some embodiments, the low-temperature plasma treatment is carried out by using a gas, preferably a gas selected from the group consisting of air, oxygen, nitrogen, ammonia, helium, or argon. Conventionally, air is used but it may be advantageous to use any of the other indicated gasses.

Preferably, the low-temperature plasma treatment is carried out at a pressure between about 0.1 torr and 5 torr for from about 2 seconds to about 300 seconds, preferably for about 5 seconds to about 100 seconds, more preferably from about 5 seconds to about 30 seconds.

As indicated above, the present invention finds use in conjunction with methods such as the Delhey process (See e.g., DE-A-43 32 692). In this process, the wool is treated in an aqueous solution of hydrogen peroxide in the presence of soluble wolframate, optionally followed by treatment in a solution or dispersion of synthetic polymers, for improving the anti-felting properties of the wool. In this method, the wool is treated in an aqueous solution of hydrogen peroxide (0.1-35% (w/w), preferably 2-10% (w/w)), in the presence of a 2-60% (w/w), preferably 8-20% (w/w) of a catalyst (preferably $Na_2WO_4$), and in the presence of a nonionic wetting agent. Preferably, the treatment is carried out at pH 8-11, and room temperature. The treatment time depends on the concentrations of hydrogen peroxide and catalyst, but is preferably 2 minutes or less. After the oxidative treatment, the wool is rinsed with water. For removal of residual hydrogen peroxide, and optionally for additional bleaching, the wool is further treated in acidic solutions of reducing agents (e.g., sulfites, phosphites etc.).

In some embodiments, the enzyme treatment step carried out for between about 1 minute and about 120 minutes. This step is preferably carried out at a temperature of between about 20° C. and about 60° C., more preferably between about 30° C. and about 50° C. Alternatively, the wool is soaked in or padded with an aqueous enzyme solution and then subjected to steaming at a conventional temperature and pressure, typically for about 30 seconds to about 3 minutes. In some preferred embodiments, the proteolytic enzyme treatment is carried out in an acidic or neutral or alkaline medium which may include a buffer.

In alternative embodiments, the enzyme treatment step is conducted in the presence of one or more conventional anionic, non-ionic (e.g., Dobanol; Henkel AG) or cationic surfactants. An example of a useful nonionic surfactant is Dobanol (from Henkel AG). In further embodiments, the wool or animal hair material is subjected to an ultrasound treatment, either prior to or simultaneous with the treatment with a proteolytic enzyme. In some preferred embodiments, the ultrasound treatment is carried out at a temperature of about 50° C. for about 5 minutes. In some preferred embodiments, the amount of proteolytic enzyme used in the enzyme treatment step is between about 0.2 w/w % and about 10 w/w %, based on the weight of the wool or animal hair material. In some embodiments, in order to the number of treatment steps, the enzyme treatment is carried out during dyeing and/or scouring of the wool or animal hair material, simply by adding the protease to the dyeing, rinsing and/or scouring bath. In some embodiments, enzyme treatment is carried out after the plasma treatment but in other embodiments, the two treatment steps are carried out in the opposite order.

Softeners conventionally used on wool are usually cationic softeners, either organic cationic softeners or silicone based products, but anionic or non-inoc softeners are also useful. Examples of useful softeners include, but are not limited to polyethylene softeners and silicone softeners (i.e., dimethyl polysiloxanes (silicone oils)), H-polysiloxanes, silicone elastomers, aminofunctional dimethyl polysiloxanes, aminofunctional silicone elastomers, and epoxyfunctional dimethyl polysiloxanes, and organic cationic softeners (e.g. alkyl quarternary ammonium derivatives).

In additional embodiments, the present invention provides compositions for the treatment of an animal hide that includes at least one protease of the present invention. In some embodiments, the proteases of the present invention find use in compositions for treatment of animal hide, such as those described in WO 03/00865 (Insect Biotech Co., Taejeon-Si, Korea). In additional embodiments, the present invention provides methods for processing hides and/or skins into leather comprising enzymatic treatment of the hide or skin with the protease of the present invention (See e.g., WO 96/11285). In additional embodiments, the present invention provides compositions for the treatment of an animal skin or hide into leather that includes at least one protease of the present invention.

Hides and skins are usually received in the tanneries in the form of salted or dried raw hides or skins. The processing of hides or skins into leather comprises several different process steps including the steps of soaking, unhairing and bating. These steps constitute the wet processing and are performed in the beamhouse. Enzymatic treatment utilizing the proteases of the present invention are applicable at any time during the process involved in the processing of leather. However, proteases are usually employed during the wet processing (i.e., during soaking, unhairing and/or bating). Thus, in some preferred embodiments, the enzymatic treatment with at least one of the proteases of the present invention occurs during the wet processing stage.

In some embodiments, the soaking processes of the present invention are performed under conventional soaking conditions (e.g., at a pH in the range pH 6.0-11). In some preferred embodiments, the range is pH 7.0-10.0. In alternative embodiments, the temperature is in the range of 20-30° C., while in other embodiments it is preferably in the range 24-28° C. In yet further embodiments, the reaction time is in the range 2-24 hours, while preferred range is 4-16 hours. In additional embodiments, tensides and/or preservatives are provided as desired.

The second phase of the bating step usually commences with the addition of the bate itself. In some embodiments, the enzymatic treatment takes place during bating. In some preferred embodiments, the enzymatic treatment takes place during bating, after the deliming phase. In some embodiments, the bating process of the presents invention is performed using conventional conditions (e.g., at a pH in the range pH 6.0-9.0). In some preferred embodiments, the pH range is 6.0 to 8.5. In further embodiments, the temperature is in the range of 20-30° C., while in preferred embodiments, the temperature is in the range of 25-28° C. In some embodiments, the reaction time is in the range of 20-90 minutes, while in other embodiments, it is in the range 40-80 minutes. Processes for the manufacture of leather are well-known to those skilled in the art (See e.g., WO 94/069429 WO 90/1121189, U.S. Pat. No. 3,840,433, EP 505920, GB 2233665, and U.S. Pat. No. 3,986,926, all of which are herein incorporated by reference).

In further embodiments, the present invention provides bates comprising at least one protease of the present invention. A bate is an agent or an enzyme-containing preparation comprising the chemically active ingredients for use in beamhouse processes, in particular in the bating step of a process for the manufacture of leather. In some embodiments, the present invention provides bates comprising protease and suitable excipients. In some embodiments, agents including, but not limited to chemicals known and used in the art, e.g. diluents, emulgators, delimers and carriers. In some embodiments, the bate comprising at least one protease of the present invention is formulated as known in the art (See e.g., GB-A2250289, WO 96/11285, and EP 0784703).

In some embodiments, the bate of the present invention contains from 0.00005 to 0.01 g of active protease per g of bate, while in other embodiments, the bate contains from 0.0002 to 0.004 g of active protease per g of bate.

Thus, the proteases of the present invention find use in numerous applications and settings.

Experimental

The present invention is described in further detail in the following Examples which are not in any way intended to limit the scope of the invention as claimed. The attached Figures are meant to be considered as integral parts of the specification and description of the invention. All references cited are herein specifically incorporated by reference for all that is described therein. The following Examples are offered to illustrate, but not to limit the claimed invention In the experimental disclosure which follows, the following abbreviations apply: PI (proteinase inhibitor), ppm (parts per million); M (molar); mM (millimolar); µM (micromolar); nM (nanomolar); mol (moles); mmol (millimoles); gmol (micromoles); nmol (nanomoles); gm (grams); mg (milligrams); µg (micrograms); pg (picograms); L (liters); ml and mL (milliliters); µl and µL (microliters); cm (centimeters); mm (millimeters); um (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); (HCl (hydrochloric acid); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto Tryptone, 24 g/l glycerol, 2.31 g/l $KH_2PO_4$, and 12.54 g/l $K_2HPO_4$); $OD_{280}$ (optical density at 280 nm); $OD_{600}$ (optical density at 600 nm); A405 (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN® 20); PEG-(polyethylene glycol); PCR (polymerase chain reaction); RT-PCR (reverse transcription PCR); SDS (sodium dodecyl sulfate); Tris (tris(hydroxymethyl)aminomethane); HEPES (N-[2-Hydroxyethyl]piperazine-N-[2-ethanesulfonic acid]); HBS (HEPES buffered saline); Tris-HCl (tris[Hydroxymethyl] aminomethane-hydrochloride); Tricine (N-[tris-(hydroxymethyl)-methyl]-glycine); CHES (2-(N-cyclo-hexylamino) ethane-sulfonic acid); TAPS (3-1 [tris-(hydroxymethyl)-methyl]-amino)-propanesulfonic acid); CAPS (3-(cyclo-hexylamino)-propane-sulfonic acid; DMSO (dimethyl sulfoxide); DTT (1,4-dithio-DL-threitol); SA (sinapinic acid (s, 5-dimethoxy-4-hydroxy cinnamic acid); TCA (trichloroacetic acid); Glut and GSH (reduced glutathione); GSSG (oxidized glutathione); TCEP (Tris[2-carboxyethyl]phosphine); Ci (Curies); mCi (milliCuries); µCi (microCuries); HPLC (high pressure liquid chromatography); RP-HPLC (reverse phase high pressure liquid chromatography); TLC (thin layer chromatography); MALDI-TOF (matrix-assisted laser desorption/ionization—time of flight); Ts (tosyl); Bn (benzyl); Ph (phenyl); Ms (mesyl); Et (ethyl), Me (methyl); Taq (*Thermus aquaticus* DNA polymerase); Klenow (DNA polymerase I large (Klenow) fragment); EGTA (ethylene glycol-bis(β-aminoethyl ether) N,N,N',N'-tetraacetic acid); EDTA (ethylenediaminetetracetic acid); bla (β-lactamase or ampicillin-resistance gene); HDL (high density liquid); MJ Research (MJ Research, Reno, Nev.); Baseclear (Baseclear BV, Inc., Leiden, the Netherlands); PerSeptive (PerSeptive Biosystems, Framingham, Mass.); ThermoFinnigan (ThermoFinnigan, San Jose, Calif.); Argo (Argo BioAnalytica, Morris Plains, N.J.); Seitz EKS (SeitzSchenk Filtersystems GmbH, Bad Kreuznach, Germany); Pall (Pall Corp., East Hills, N.Y.); EMPA Testmaterialien AG (EMPA Testmaterialien AG, St. Gallen-Winkeln, Switzerland); Warwick Equest (Warwick Equest Limited, Durham, UK); Minolta (Konica Minolta, Inc., Japan); United States Testing (United States Testing Co, Inc, Hoboken, N.J.); Spectrum (Spectrum Laboratories, Dominguez Rancho, Calif.); Molecular Structure (Molecular Structure Corp., Woodlands, Tex.); Accelrys (Accelrys, Inc., San Diego, Calif.); Chemical Computing (Chemical Computing Corp., Montreal, Canada); New Brunswick (New Brunswick Scientific, Co., Edison, N.J.); CFT (Center for Test Materials, Vlaardingen, the Netherlands); Procter & Gamble (Procter & Gamble, Inc., Cincinnati, Ohio); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Finnzymes (Finnzymes Oy, Espoo, Finland); Kelco (CP Kelco, Wilmington, Del.); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); NCBI (National Center for Biotechnology Information); Applied Biosystems (Applied Biosystems, Foster City, Calif.); BD Biosciences and/or Clontech (BD Biosciences CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc., King of Prussia, Pa.); Difco (Difco Laboratories, Detroit, Mich.); Mediatech (Mediatech, Herndon, Va.; Santa Cruz (Santa Cruz Biotechnology, Inc., Santa Cruz, Calif.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Sorvall (Sorvall brand, from Kendro Laboratory Products, Asheville, N.C.); Molecular Devices (Molecular Devices, Corp., Sunnyvale, Calif.); R&D Systems (R&D Systems, Minneapolis, Minn.); Stratagene (Stratagene Cloning Systems, La Jolla, Calif.); Marsh (Marsh Biosciences, Rochester, N.Y.); Geneart (Geneart GmbH, Regensburg, Germany); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); New Objective (New Objective brand; Scientific Instrument Services, Inc., Ringoes, N.J.); Waters (Waters, Inc., Milford, Mass.); Matrix Science (Matrix Science, Boston, Mass.); Dionex (Dionex, Corp., Sunnyvale, Calif.); Monsanto (Monsanto Co., St. Louis, Mo.); Wintershall (Wintershall AG, Kassel, Germany); BASF (BASF Co., Florham Park, N.J.); Huntsman (Huntsman Petrochemical Corp., Salt Lake City, Utah); Enichem (Enichem Iberica, Barcelona, Spain); Fluka Chemie AG (Fluka Chemie AG, Buchs, Switzerland); Gist-Brocades (Gist-Brocades, Nev., Delft, the Netherlands); Dow Corning (Dow Corning Corp., Midland, Mich.); and Microsoft (Microsoft, Inc., Redmond, Wash.).

The wild-type serine protease used in the following Examples is described in detail in US04/39006 and US04/39066, both of which are herein incorporated by reference in their entirety. In addition, Example 2 of U.S. patent application Ser. No. 10/576,331 provides details for the production of 69B4 protease from the Gram-positive alkaliphilic bacterium 69B4. As indicated throughout the present application, this priority application is incorporated by reference herein in its entirety.

Example 1

Assays

In the following Examples, various assays were used, such as protein determinations, application-based tests, and stability-based tests. For ease in reading, the following assays are set forth below and referred to in the respective Examples. Any deviations from the protocols provided below in any of the experiments performed during the development of the present invention are indicated in the Examples.

Some of the detergents used in the following Examples had the following compositions. In Compositions I and II, the balance (to 100%) is perfume/dye and/or water. The pH of these compositions was from about 5 to about 7 for Composition I, and about 7.5 to about 8.5 Composition II. In Composition III, the balance (to 100%) comprised of water and/or the minors perfume, dye, brightener/SRPI/sodium carboxymethylcellulose/photobleach/MgSo$_4$/PVPVI/suds suppressor/high molecular PEG/clay.

| DETERGENT COMPOSITIONS | | |
|---|---|---|
|  | Composition I | Composition II |
| LAS | 24.0 | 8.0 |
| $C_{12}$-$C_{15}$ $AE_{1.8}$S | — | 11.0 |
| $C_8$-$C_{10}$ propyl dimethyl amine | 2.0 | 2.0 |
| $C_{12}$-$C_{14}$ alkyl dimethyl amine oxide | — | — |
| $C_{12}$-$C_{15}$ AS | — | 7.0 |
| CFAA | — | 4.0 |
| $C_{12}$-$C_{14}$ Fatty alcohol ethoxylate | 12.0 | 1.0 |
| $C_{12}$-$C_{18}$ Fatty acid | 3.0 | 4.0 |
| Citric acid (anhydrous) | 6.0 | 3.0 |
| DETPMP | — | 1.0 |
| Monoethanolamine | 5.0 | 5.0 |
| Sodium hydroxide | — | 1.0 |
| 1 N HCl aqueous solution | #1 | — |

-continued

| DETERGENT COMPOSITIONS | | |
|---|---|---|
| Propanediol | 12.7 | 10. |
| Ethanol | 1.8 | 5.4 |
| DTPA | 0.5 | 0.4 |
| Pectin Lyase | — | 0.005 |
| Lipase | 0.1 | — |
| Amylase | 0.001 | — |
| Cellulase | — | 0.0002 |
| Protease A | — | — |
| Aldose Oxidase | — | — |
| DETBCHD | — | 0.01 |
| SRP1 | 0.5 | 0.3 |
| Boric acid | 2.4 | 2.8 |
| Sodium xylene sulfonate | — | — |
| DC 3225C | 1.0 | 1.0 |
| 2-butyl-octanol | 0.03 | 0.03 |
| Brightener 1 | 0.12 | 0.08 |

| Detergent Composition III | |
|---|---|
| $C_{14}$-$C_{15}$AS or sodium tallow alkyl sulfate | 3.0 |
| LAS | 8.0 |
| $C_{12}$-$C_{15}AE_3S$ | 1.0 |
| $C_{12}$-$C_{15}E_5$ or $E_3$ | 5.0 |
| QAS | — |
| Zeolite A | 11.0 |
| SKS-6 (dry add) | 9.0 |
| MA/AA | 2.0 |
| AA | — |
| 3Na Citrate 2H$_2$O | — |
| Citric Acid (Anhydrous) | 1.5 |
| DTPA | — |
| EDDS | 0.5 |
| HEDP | 0.2 |
| PB1 | — |
| Percarbonate | 3.8 |
| NOBS | — |
| NACA OBS | 2.0 |
| TAED | 2.0 |
| BB1 | 0.34 |
| BB2 | — |
| Anhydrous Na Carbonate | 8.0 |
| Sulfate | 2.0 |
| Silicate | — |
| Protease B | — |
| Protease C | — |
| Lipase | — |
| Amylase | — |
| Cellulase | — |
| Pectin Lyase | 0.001 |
| Aldose Oxidase | 0.05 |
| PAAC | — |

A. TCA Assay for Protein Content Determination in 96-Well Microtiter Plates

This assay was started using filtered culture supernatant from microtiter plates grown 4 days, at 33° C. with shaking at 230 RPM and humidified aeration. A fresh 96-well flat bottom plate was used for the assay. First, 100 µL/well of 0.25 N HCl were placed in the wells. Then, 50 µL filtered culture broth were added to the wells. The light scattering/absorbance at 405 nm (use 5 sec mixing mode in the plate reader) was then determined, in order to provide the "blank" reading.

For the test, 100 µL/well 15% (w/v) TCA was placed in the plates and incubated between 5 and 30 min at room temperature. The light scattering/absorbance at, 405 nm (use 5 sec mixing mode in the plate reader) was then determined.

The calculations were performed by subtracting the blank (i.e., no TCA) from the test reading with TCA. If desired, a standard curve can be created by calibrating the TCA readings with AAPF assays of clones with known conversion factors. However, the TCA results are linear with respect to protein concentration from 50 to 500 ppm and can thus be plotted directly against enzyme performance for the purpose of choosing good-performing variants.

B. suc-AAPF-pNA Assay of Proteases in 96-Well Microtiter Plates

In this assay system, the reagent solutions used were:
1. 100 mM Tris/HCl, pH 8.6, containing 0.005% TWEEN®-80 (Tris buffer)
2. 100 mM Tris buffer, pH 8.6, containing 10 mM $CaCl_2$ and 0.005% TWEEN®-80 (Tris buffer)
3. 160 mM suc-AAPF-pNA in DMSO (suc-AAPF-pNA stock solution) (Sigma: S-7388)

To prepare suc-AAPF-pNA working solution, 1 ml AAPF stock was added to 100 ml Tris buffer and mixed well for at least 10 seconds.

The assay was performed by adding 10 g of diluted protease solution to each well, followed by the addition (quickly) of 190 µl 1 mg/ml AAPF-working solution. The solutions were mixed for 5 sec., and the absorbance change was read at 410 nm in an MTP reader, at 25° C. The protease activity was expressed as AU (activity=$\Delta OD \cdot min^{-1} \cdot ml^{-1}$).

C. Keratin Hydrolysis Assay

In this assay system, the chemical and reagent solutions used were:

| | |
|---|---|
| Keratin | ICN 902111 |
| Detergent | 1.6 g. detergent was dissolved in 1000 ml water (pH = 8.2) 0.6 ml. $CaCl_2/MgCl_2$ of 10,000 gpg was also added, as well as 1190 mg HEPES, giving a hardness and buffer strength of 6 gpg and 5 mM respectively. The pH was adjusted to 8.2 with NaOH. |
| Picrylsulfonic acid (TNBS) | Sigma P-2297 (5% solution in water) |
| Reagent A | 45.4 g $Na_2B_4O_7 \cdot 10$ $H2O$ (Merck 6308) and 15 ml of 4N NaOH were dissolved together to a final volume of 1000 ml (by heating if needed) |
| Reagent B | 35.2 g $NaH_2PO_4 \cdot 1H_2O$ (Merck 6346) and 0.6 g $Na_2SO_3$ (Merck 6657) were dissolved together to a final volume of 1000 ml. |

Method:

Prior to the incubations, keratin was sieved on a 100 µm sieve in small portions at a time. Then, 10 g of the <100 µm keratin was stirred in detergent solution for at least 20 minutes at room temperature with regular adjustment of the pH to 8.2. Finally, the suspension was centrifuged for 20 minutes at room temperature (Sorvall, GSA rotor, 13,000 rpm). This procedure was then repeated. Finally, the wet sediment was suspended in detergent to a total volume of 200 ml., and the suspension was kept stirred during pipetting. Prior to incubation, microtiter plates (MTPs) were filled with 200 µl substrate per well with a Biohit multichannel pipette and 1200 µl tip (6 dispenses of 200 µl and dispensed as fast as possible to avoid settling of keratin in the tips). Then, 10 µl of the filtered culture was added to the substrate containing MTPs. The plates were covered with tape, placed in an incubator and incubated at 20° C. for 3 hours at 350 rpm (Innova 4330 [New Brunswick]). Following incubation, the plates were centrifuged for 3 minutes at 3000 rpm (iSigma 6K 15 centrifuge). About 15 minutes before removal of the $1^{st}$ plate from the incubator, the TNBS reagent was prepared by mixing 1 ml TNBS solution per 50 ml of reagent A.

MTPs were filled with 60 µl TNBS reagent A per well. From the incubated plates, 10 µl was transferred to the MTPs with TNBS reagent A. The plates were covered with tape and shaken for 20 minutes in a bench shaker (BMG Thermostar) at room temperature and 500 rpm. Finally, 200 µl of reagent B was added to the wells, mixed for 1 minute on a shaker, and the absorbance at 405 nm was measured with the MTP-reader.

Calculation of the Keratin Hydrolyzing Activity:

The obtained absorbance value was corrected for the blank value (substrate without enzyme). The resulting absorbance provides a measure for the hydrolytic activity. For each sample (variant) the performance index was calculated. The performance index compares the performance of the variant (actual value) and the standard enzyme (theoretical value) at the same protein concentration. In addition, the theoretical values can be calculated, using the parameters of the Langmuir equation of the standard enzyme. A performance index (PI) that is greater than 1 (PI>1) identifies a better variant (as compared to the standard [e.g., wild-type]), while a PI of 1 (PI=1) identifies a variant that performs the same as the standard, and a PI that is less than 1 (PI<1) identifies a variant that performs worse than the standard. Thus, the PI identifies winners, as well as variants that are less desirable for use under certain circumstances.

D. Microswatch Assay for Testing Protease Performance

All of the detergents used in these assays did not contain enzymes.

Detergent Preparations:

1. Cold Water Liquid Detergent (US Conditions):

Milli-Q water was adjusted to 6 gpg water hardness (Ca/Mg=3/1), 1.60 g/l detergent was added, and the detergent solution was stirred vigorously for at least 15 minutes. Then, 5 mM Hepes buffer was added and the pH adjusted to 8.2. The detergent was filtered before use in the assay through a 0.22 µm filter (e.g. Nalgene top bottle filter).

2. Low pH Liquid Detergent (US Conditions):

Milli-Q water was adjusted to 6 gpg water hardness (Ca/Mg=3/1), 1.60 g/l detergent TIDE®-LVJ-1 or TIDE® 2005) or 1.50 g/l detergent (TIDE®-SNOW) was added, and the detergent solution stirred vigorously for at least 15 minutes. The pH was adjusted to 6.0 using 1N NaOH.solution. The detergent was filtered before use in the assay through a 0.22 µm filter (e.g. Nalgene top bottle filter).

Microswatches:

Microswatches of ¼" circular diameter were ordered and delivered by CFT Vlaardingen. The microswatches were pretreated using the fixation method described below. Single microswatches were placed in each well of a 96-well microtiter plate vertically to expose the whole surface area (i.e., not flat on the bottom of the well).

"3K" Swatch Fixation:

This particular swatch fixation was done at room temperature. However the amount of 30% $H_2O_2$ added is 10× more than in the superfixed swatch fixation method i.e., conducted at 60° C., used with European conditions). Bubble formation (frothing) will be visible and therefore it is necessary to use a bigger beaker to account for this. First, 8 liters of distilled water were placed in a 10 L beaker, and 80 ml of 30% hydrogen peroxide added. The water and peroxide were mixed well with a ladle. Then, 40 pieces of EMPA 116 swatches were spread into a fan before adding into the solution to ensure uniform fixation. The swatches were swirled in the solution (using the ladle) for 30 minutes, continuously for the first five minutes and occasionally for the remaining 25 minutes. The solution was discarded and the swatches were rinsed 6 times with approximately 6 liters of distilled water each time. The swatches were placed on top of paper towels to dry. The air-dried swatches were punched using a ¼" circular die on an expulsion press. A single microswatch was placed vertically into each well of a 96-well microtiter plate to expose the whole surface area (i.e., not flat on the bottom of the well).

Enzyme Samples:

The enzyme samples were tested at appropriate concentrations for the respective geography, and diluted in 10 mM NaCl, 0.005% TWEEN®-80 solution.

Test Method:

The incubator was set at the desired temperature: 20° C. for cold water liquid conditions or 30° C. for low-pH liquid conditions. The pretreated and precut swatches were placed into the wells of a 96-well MTP, as described above. The enzyme samples were diluted, if needed, in 10 mM NaCl, 0.005% TWEEN®-80 to 20× the desired concentration. The desired detergent solutions were prepared as described above. Then, 190 μl of detergent solution were added to each well of the MTP. To this mixture, 10 μl of enzyme solution were added to each well (to provide a total volume to 200 μl/well). The MTP was sealed with a plate sealer and placed in an incubator for 60 minutes, with agitation at 350 rpm. Following incubation under the appropriate conditions, 100 gi of solution from each well were removed and placed into a fresh MTP. The new MTP containing 100 μl of solution/well was read at 405 nm in a MTP reader. Blank controls, as well as a control containing a microswatch and detergent but no enzyme were also included. The stock solution was used at a concentration of 15,000 gpg (Ca/Mg 3:1 (1.92 M $Ca^{2+}$=282.3 g/L $CaCl_2.2H_2O$; 0.64 M $Mg^{2+}$=30.1 g/L $MgCl_2.6H_2O$).

1 ml 5% TWEEN®-80 is added and the volume brought up to 1000 ml. The final concentration of PIPES and TWEEN®-80 is 50 mM and 0.005% respectively.

Picrylsulfonic acid (TNBS): Sigma P-2297 (5% solution in water)

Reagent A: 45.4 g $Na_2B_4O_7.10H_2O$ (Merck 6308) and 15 ml of 4N NaOH are dissolved together to a final volume of 1000 ml (by heating if needed)

Reagent B: 35.2 g $NaH_2PO_4.1H_2O$ (Merck 6346) and 0.6 g $Na_2SO_3$ (Merck 6657) are dissolved together to a final volume of 1000 ml.

Method:

To prepare the substrate, 4 g DMC were dissolved in 400 ml PIPES buffer. The filtered culture supernatants were diluted with PIPES buffer; the final concentration of the controls in the growth plate was 20 ppm. Then, 10 μl of each diluted supernatant were added to 200 μl substrate in the wells of a MTP. The MTP plate was covered with tape, shaken for a few seconds and placed in an oven at 37° C. for 2 hours without agitation.

About 15 minutes before removal of the 15' plate from the oven, the TNBS reagent was prepared by mixing 1 ml TNBS solution per 50 ml of reagent A. MTPs were filled with 60 μl TNBS reagent A per well. The incubated plates were shaken for a few seconds, after which 10 μl were transferred to the MTPs with TNBS reagent A. The plates were covered with tape and shaken for 20 minutes in a bench shaker (BMG Thermostar) at room temperature and 500 rpm. Finally, 200 μl

TABLE 1-1

Detergent Composition and Incubation Conditions in the μSwatch Assay.

| Detergent | Reference Enzyme | Detergent | Water Hardness | Enzyme Dosage [ppm] | Temp. (° C.) | Swatch |
|---|---|---|---|---|---|---|
| Cold Water Liquid | ASP | 1.5 or 1.6 g/l Detergent | 6 gpg - Ca/Mg:3/1 | 0.3-4 | 20° | 3K |
| Low pH Liquid Detergent | ASP | 1.6 g/l Detergent | 6 gpg - Ca/Mg:3/1 | 0.5-4 | 30° | 3K |

Calculation of the BMI Performance:

The obtained absorbance value was corrected for the blank value (obtained after incubation of microswatches in the absence of enzyme). The resulting absorbance was a measure for the hydrolytic activity. For each sample (variant) the performance index was calculated. The performance index compares the performance of the variant (actual value) and the standard enzyme (theoretical value) at the same protein concentration. In addition, the theoretical values can be calculated, using the parameters of the Langmuir equation of the standard enzyme. A performance index (PI) that is greater than 1 (PI>1) identifies a better variant (as compared to the standard [e.g., wild-type]), while a PI of 1 (PI=1) identifies a variant that performs the same as the standard, and a PI that is less than 1 (PI<1) identifies a variant that performs worse than the standard.

Thus, the PI identifies winners, as well as variants that are less desirable for use under certain circumstances.

D. Dimethylcasein Hydrolysis Assay (96 Wells)

In this assay system, the chemical and reagent solutions used were:

Dimethylcasein (DMC):Sigma C-9801
TWEEN®-80: Sigma P-8074
PIPES buffer (free acid): Sigma P-1851; 15.1 g is dissolved in about 960 ml water; pH is adjusted: to 7.0 with 4N NaOH, reagent B were added to the wells, mixed for 1 minute on a shaker, and the absorbance at 405 nm was determined using an MTP-reader.

Calculation of Dimethylcasein Hydrolyzing Activity:

The obtained absorbance value was corrected for the blank value (substrate without enzyme). The resulting absorbance is a measure for the hydrolytic activity. The (arbitrary) specific activity of a sample was calculated by dividing the absorbance and the determined protein concentration.

E. Thermostability Assay

This assay is based on the dimethylcasein hydrolysis, before and after heating of the buffered culture supernatant. The same chemical and reagent solutions were used as described in the dimethylcasein hydrolysis assay.

Method:

The filtered culture supernatants were diluted to 20 ppm in PIPES buffer (based on the concentration of the controls in the growth plates). First, 10 ul of each diluted enzyme sample was taken to determine the initial activity in the dimethylcasein assay and treated as described below. Then, 50 μl of each diluted supernatant were placed in the empty wells of a MTP. The MTP plate was incubated in an iEMS incubator/shaker HT (Thermo Labsystems) for 90 minutes at 60° C. and 400 rpm. The plates were cooled on ice for 5 minutes. Then, 10 μl of the solution was added to a fresh MTP containing 200

μl dimethylcasein substrate/well to determine the final activity after incubation. This MTP was covered with tape, shaken for a few seconds and placed in an oven at 37° C. for 2 hours without agitation. The same detection method as used for the DMC hydrolysis assay was used.

Calculation of Thermostability:

The residual activity of a sample was expressed as the ratio of the final absorbance and the initial absorbance, both corrected for blanks.

F. LAS Stability Assay

LAS stability was measured after incubation of the test protease in the presence of 0.06% LAS (dodecylbenzenesulfonate sodium), and the residual activity was determined using the AAPF assay.

Reagents:
  Dodecylbenzenesulfonate, Sodium salt (=LAS): Sigma D-2525
  TWEEN®-80: Sigma P-8074
  TRIS buffer (free acid): Sigma T-1378); 6.35 g is dissolved in about 960 ml water; pH is adjusted to 8.2 with 4N HCl. Final concentration of TRIS is 52.5 mM.
  LAS stock solution: Prepare a 10.5% LAS solution in MQ water (=10.5 g per 100 ml MQ)
  TRIS buffer-100 mM/pH 8.6 (100 mM Tris/0.005% Tween80)
  TRIS-Ca buffer, pH 8.6 (100 mM Tris/10 mM CaCl$_2$/0.005% Tween80)

Hardware:
  Flat bottom MTPs: Costar (#9017)
  Biomek FX
  ASYS Multipipettor
  Spectramax MTP Reader
  IEMS Incubator/Shaker
  Innova 4330 Incubator/Shaker
  Biohit multichannel pipette
  BMG Thermostar Shaker Method:

A 0.063% LAS solution was prepared in 52.5 mM Tris buffer pH 8.2. The AAPF working solution was prepared by adding 1 ml of 100 mg/ml AAPF stock solution (in DMSO) to 100 ml (100 mM) TRIS buffer, pH 8.6. To dilute the supernatants, flat-bottomed plates were filled with dilution buffer and an aliquot of the supernatant was added and mixed well. The dilution ratio depended on the concentration of the ASP-controls in the growth plates (AAPF activity). The desired protein concentration was 80 ppm.

Ten μl of the diluted supernatant were added to 190 μl 0.063% LAS buffer/well. The MTP was covered with tape, shaken for a few seconds and placed in an incubator (Innova 4230) at 25° or 35° C., for 60 minutes at 200 rpm agitation. The initial activity (t=10 minutes) was determined after 10 minutes of incubation by transferring 10 μl of the mixture in each well to a fresh MTP containing 190 μl AAPF work solution. These solutions were mixed well and the AAPF activity was measured using a MTP Reader (20 readings in 5 minutes and 25° C.).

The final activity (t=60 minutes) was determined by removing another 10 μl of solution from the incubating plate after 60 minutes of incubation. The AAPF activity was then determined as described above. The calculations were performed as follows: the % Residual Activity was [t−60 value]*100/[t−10 value].

Example 2

ASP Protease Production in *B. subtilis*

In this Example, experiments conducted to produce 69B4 protease (also referred to herein as "ASP," "Asp," and "ASP protease," and "Asp protease") in *B. subtilis* are described. In this Example, the transformation of plasmid pHPLT-ASP-C1-2 (See, FIG. 1) into *B. subtilis* is described. Transformation was performed as known in the art (See e.g., WO 02/14490, incorporated herein by reference). To optimize ASP expression in *B. subtilis*, a synthetic DNA sequence was produced by DNA2.0, and utilized in these expression experiments. The DNA sequence (synthetic ASP DNA sequence) provided below, with codon usage adapted for *Bacillus* species, encodes the wild type ASP precursor protein:

```
ATGACACCACGAACTGTCACAAGAGCTCTGGCTGTGGCAACAGCAGCTGCTACACTCTTGGC    (SEQ ID NO: 10)

TGGGGGTATGGCAGCACAAGCTAACGAACCGGCTCCTCCAGGATCTGCATCAGCCCCTCCAC

GATTAGCTGAAAAACTTGACCCTGACTTACTTGAAGCAATGGAACGCGATCTGGGGTTAGAT

GCAGAGGAAGCAGCTGCAACGTTAGCTTTTCAGCATGACGCAGCTGAAACGGGAGAGGCTC

TTGCTGAGGAACTCGACGAAGATTTCGCGGGCACGTGGGTTGAAGATGATGTGCTGTATGTT

GCAACCACTGATGAAGATGCTGTTGAAGAAGTCGAAGGCGAAGGAGCAACTGCTGTGACTG

TTGAGCATTCTCTTGCTGATTTAGAGGCGTGGAAGACGGTTTTGGATGCTGCGCTGGAGGGT

CATGATGATGTGCCTACGTGGTACGTCGACGTGCCTACGAATTCGGTAGTCGTTGCTGTAAA

GGCAGGAGCGCAGGATGTAGCTGCAGGACTTGTGGAAGGCGCTGATGTGCCATCAGATGCG

GTCACTTTTGTAGAAACGGACGAAACGCCTAGAACGATGTTCGACGTAATTGGAGGCAAC

GCATATACTATTGGCGGCCGGTCTAGATGTTCTATCGGATTCGCAGTAAACGGTGGCT

TCATTACTGCCGGTCACTGCGGAAGAACAGGAGCCACTACTGCCAATCCGACTGGCAC

ATTTGCAGGTAGCTCGTTTCCGGGAAATGATTATGCATTCGTCCGAACAGGGGCAGGA

GTAAATTTGCTTGCCCAAGTCAATAACTACTCGGGCGGCAGAGTCCAAGTAGCAGGAC

ATACGGCCGCACCAGTTGGATCTGCTGTATGCCGCTCAGGTAGCACTACAGGTTGGCA

TTGCGGAACTATCACGGCGCTGAATTCGTCTGTCACGTATCCAGAGGGAACAGTCCGA
```

-continued

```
GGACTTATCCGCACGACGGTTTGTGCCGAACCAGGTGATAGCGGAGGTAGCCTTTTAG

CGGGAAATCAAGCCCAAGGTGTCACGTCAGGTGGTTCTGGAAATTGTCGGACGGGGG

GAACAACATTCTTTCAACCAGTCAACCCGATTTTGCAGGCTTACGGCCTGAGAATGATT

ACGACTGACTCTGGAAGTTCCCCTGCTCCAGCACCTACATCATGTACAGGCTACGCAAGA

ACGTTCACAGGAACCCTCGCAGCAGGAAGAGCAGCAGCTCAACCGAACGGTAGCTATGTTC

AGGTCAACCGGAGCGGTACACATTCCGTCTGTCTCAATGGACCTAGCGGTGCGGACTTTGAT

TTGTATGTGCAGCGATGGAATGGCAGTAGCTGGGTAACCGTCGCTCAATCGACATCGCCGGG

AAGCAATGAAACCATTACGTACCGCGGAAATGCTGGATATTATCGCTACGTGGTTAACGCTG

CGTCAGGATCAGGAGCTTACACAATGGGACTCACCCTCCCCTGA
```

In the above sequence, bold indicates the DNA that encodes the mature protease, standard font indicates the leader sequence, and the underline indicates the N-terminal and C-terminal prosequences.

Expression of the Synthetic ASP Gene

Figure 2:
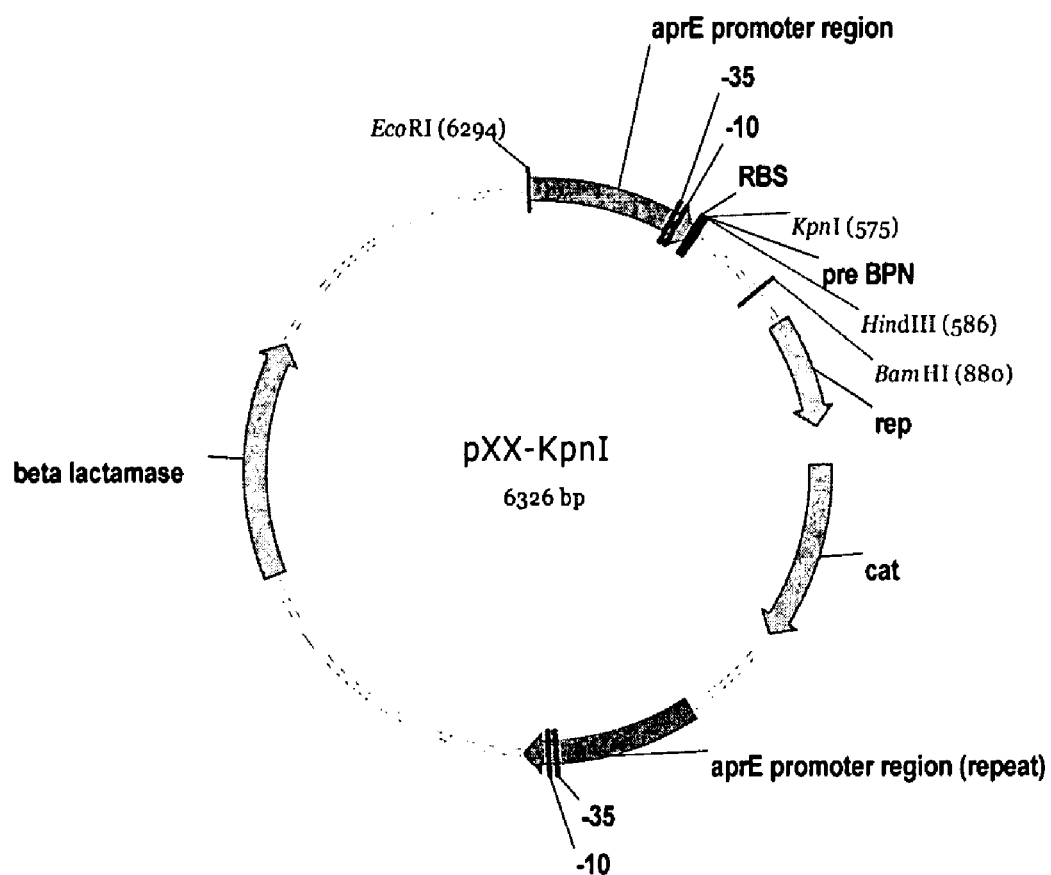
FIG. 2 provides a map of the plasmid pXX-KpnI.
Figure 3:
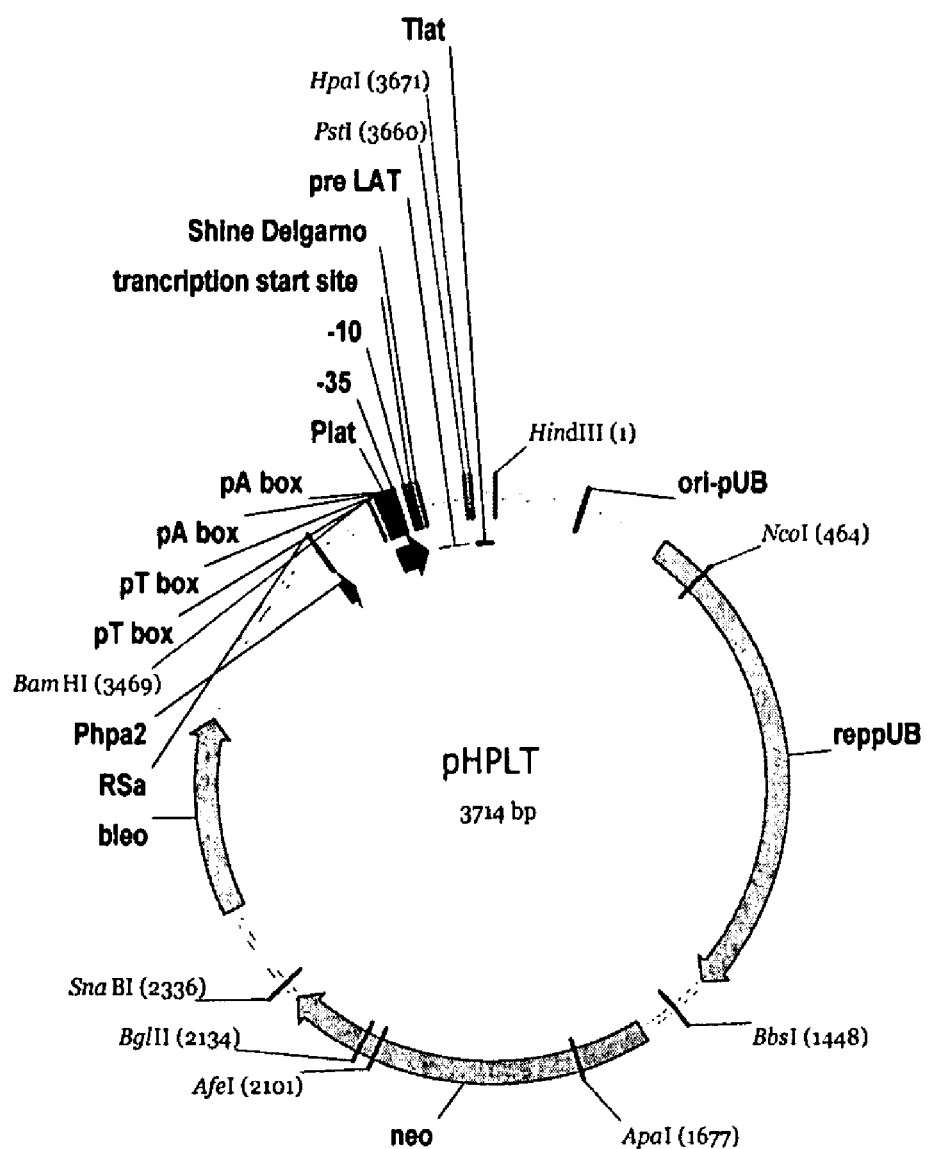
FIG. 3 provides a map of the plasmid pHPLT.
Figure 4:
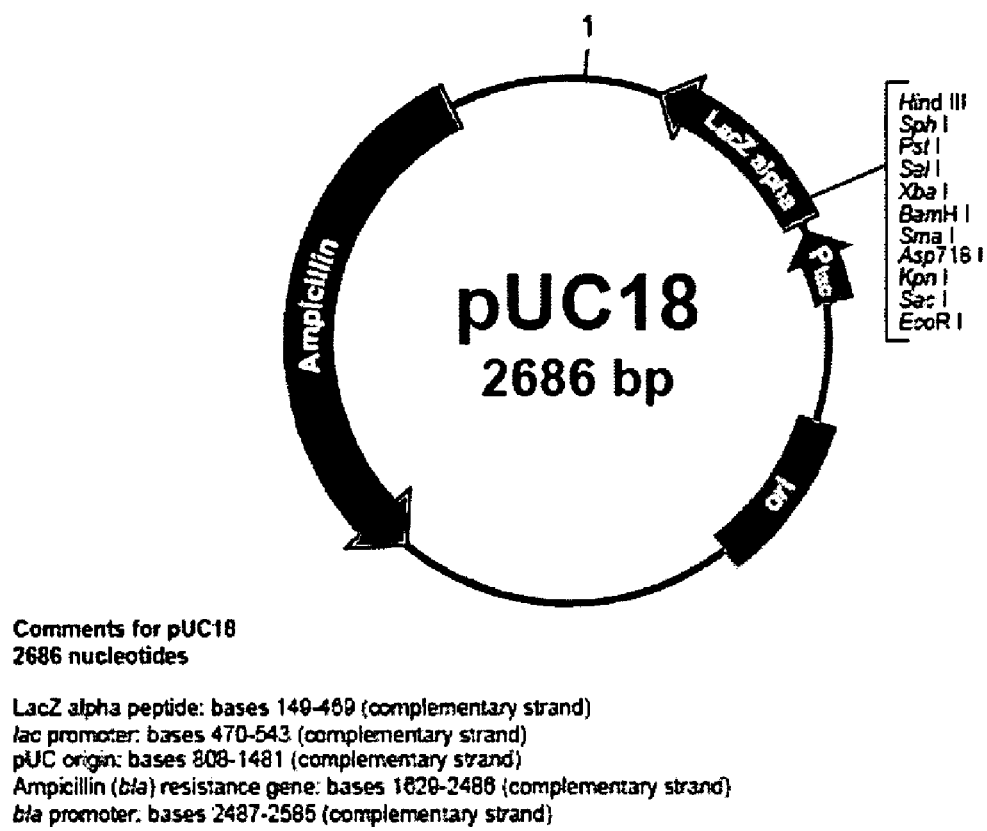
FIG. 4 provides a map of the plasmid pUC18.
Figure 5:
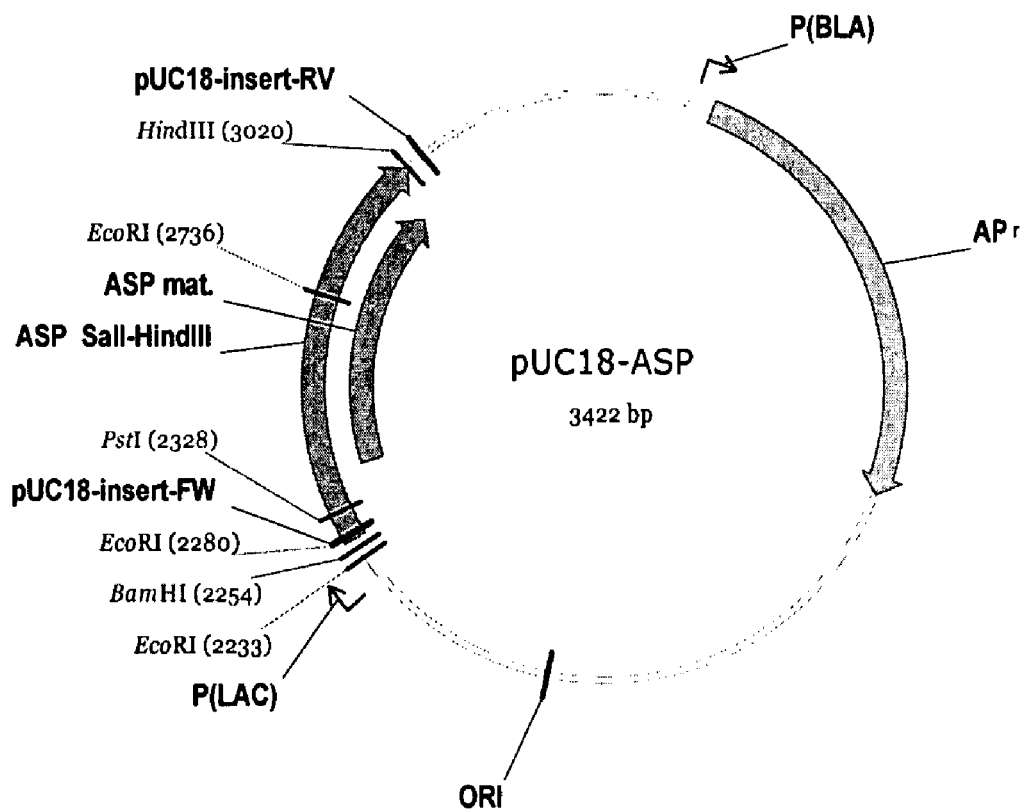
FIG. 5 provides a map of the plasmid pUC18-ASP
FIG. 6 provides a table showing the results from tergotometer tests performed in the absence of HEPES Buffer (enzyme dosage was 0.55 ppm).

Asp expression cassettes were constructed in the pXX-KpnI (See, FIG. 2) vector and subsequently cloned into the pHPLT vector (See, FIG. 3) for expression of ASP in *B. subtilis*. pXX-KpnI is a pUC based vector with the aprE promoter (*B. subtilis*) driving expression, a cat gene, and a duplicate aprE promoter for amplification of the copy number in *B. subtilis*. The bla gene allows selective growth in *E. coli*. The KpnI, introduced in the ribosomal binding site, downstream of the aprE promoter region, together with the HindIII site enables cloning of Asp expression cassettes in pXX-KpnI. pHPLT-EBS2c2, a derivative of pHPLT (Solingen et al., Extremophiles 5:333-341 [2001]), contains the thermostable amylase LAT promoter (PLAT) of *Bacillus licheniformis*, followed by XbaI and HpaI restriction sites for cloning ASP expression constructs.

The Asp expression cassette was cloned in the pXX-KpnI vector containing DNA encoding a hybrid signal peptide constructed of 5 subtilisin AprE N-terminal signal peptide amino acids fused to the Asp C-terminal signal peptide amino acids (MRSKKRTVTRALAVATAAATLLAGGMAAQA; SEQ ID NO:11). The Asp expression cassette cloned in the pXX-KpnI vector was transformed into *E. coli* (Electromax DH10B, Invitrogen, Cat. No. 12033-015). The primers and cloning strategy used are provided in Table 2-1. Subsequently, the expression cassettes were cloned from these vectors and introduced in the pHPLT expression vector for transformation into a *B. subtilis* (ΔaprE, ΔnprE, oppA, ΔspoIIE, degUHy32, ΔamyE::(xylR, pxylA-comK) strain. The primers and cloning strategy for ASP expression cassettes cloning in pHPLT are provided in Table 2-2. Transformation into *B. subtilis* was performed as described in WO 02/14490, incorporated herein by reference.

TABLE 2-1

ASP in pXX-KpnI and p2JM103-DNNDPI

| Vector Construct | Signal Peptide | ASP C-Terminal prosequence | Primers | DNA Template | Host Vector | Restriction Sites Used for Cloning |
|---|---|---|---|---|---|---|
| pXX-ASP-4 | MRSKKRTVTRALAVATAAATLLAGGMAAQA (SEQ ID NO:11) | Not incorporated | ASP-PreCross-I-FW TCATGCAGGGTACCATG AGAAGCAAGAAGCGAA CTGTCACAAGAGCTCTG GCT (SEQ ID NO:12) ASP-syntc-mature-RV GTGTGCAAGCTTTCAAG GGGAACTTCCAGAGTCA GTC (SEQ ID NO:13) | ASP synthetic DNA sequence | pXX-KpnI | KpnI and HindIII |

TABLE 2-2

ASP Expression Cassettes in pHPLT

| Vector Construct | Primers | DNA Template | Host Vector | Restriction Sites Used for Cloning |
|---|---|---|---|---|
| pHPLT-ASP-C1-2 | ASP-Cross-1 & 2-FW TGAGCTGCTAGCAAAAGGAGAGGG TAAAGAATGAGAAGCAAGAAG (SEQ ID NO: 14) | pXX-ASP-4 | PHPLT-EBS2c2 (XbaI x HpaI) | NheI x SmaI |

TABLE 2-2-continued

ASP Expression Cassettes in pHPLT

| Vector Construct | Primers | DNA Template | Host Vector | Restriction Sites Used for Cloning |
|---|---|---|---|---|
| | pHPLT-ASPmat-RV CATGCATCCCGGGTTAAGGGGAAC TTCCAGAGTCAGTC (SEQ ID NO: 15) | | | |

Primers were obtained from MWG and Invitrogen. Invitrogen Platinum Taq DNA polymerase High Fidelity (Cat. No. 11304-029) was used for PCR amplification (0.2 µM primers, up to 30 cycles) according to the Invitrogen's protocol. Ligase reactions of ASP expression cassettes and host vectors were completed by using Invitrogen T4 DNA Ligase (Cat. No. 15224-025), utilizing Invitrogen's protocol as recommended for general cloning of cohesive ends).

Expression of the asp gene was investigated in a B. subtilis strain (ΔaprE, ΔnprE, oppA, ΔspoIIE, degUHy32, ΔamyE::(xylR, pxylA-comK.) The plasmid pHPLT-ASP-C1-2 (See, Table 2-2, and FIG. 1), was transformed into B. subtilis (ΔaprE, ΔnprE, oppA, ΔspoIIE, degUHy32, ΔamyE::(xylR, pxylA-comK). Transformation was performed as known in the art (See e.g., WO 02/14490, incorporated herein by reference).

Selective growth of B. subtilis (ΔaprE, ΔnprE, oppA, ΔspoIIE, degUHy32, ΔamyE::(xylR, pxylA-comK) transformants harboring the pBPLT-ASP-C1-2 vector was performed in shake flasks containing 25 ml Synthetic Maxatase Medium (SMM), with 0.97 g/l $CaCl_2.6H_2O$ instead of 0.5 g/l $CaCl_2$ (See, U.S. Pat. No. 5,324,653, herein incorporated by reference) with 20 mg/L neomycin. This growth resulted in the production of secreted ASP protease with proteolytic activity. Gel analysis was performed using NuPage Novex 10% Bis-Tris gels (Invitrogen, Cat. No. NP0301 BOX). To prepare samples for analysis, 2 volumes of supernatant were mixed with 1 volume 1M HCl, 1 volume 4×LDS sample buffer (Invitrogen, Cat. No. NP0007), and 1% PMSF (20 mg/ml) and subsequently heated for 10 minutes at 70° C. Then, 25 µL of each sample was loaded onto the gel, together with 10 µL of SeeBlue plus 2 pre-stained protein standards (Invitrogen, Cat. No. LC5925). The results clearly demonstrated that the asp cloning strategy described in this Example yield active Asp produced by B. subtilis.

In addition, samples of the same fermentation broths were assayed as follows: 101 of the diluted supernataent was taken and added to 190 µl AAPF substrate solution (conc. 1 mg/ml, in 0.1 M Tris/0.005% TWEEN®, pH 8.6). The rate of increase in absorbance at 410 nm due to release of p-nitroaniline was monitored (25° C.), as it provides a measure of the ASP concentration produced. These results indicated that the B. subtilis pHPLT-ASP-C1-2 transformants resulted in the production of measurable ASP protease.

Example 3

Construction of Combinatorial Mutants

In this Example, the construction of a multiple mutation library of a ASP variant is described. The ASP variant that served as the backbone for the multiple mutation library contains the substitutions R014I-A064K-T086K-T116E-R123F. This variant was cloned in the pHPLT vector. The QuikChange® multi site-directed mutagenesis (QCMS) kit (Stratagene) was used to construct the library. The 5' phosphorylated primers used to create the library are shown in Table 3-1. It was noted that HPLC, PAGE or any other type of purified primers gave far better results in terms of incorporation of full length primers as well as significant reduction in primer-containing errors. However, in these experiments, purified primers were not used.

TABLE 3-1

Primers and Sequences

| Primer name | Primer sequences |
|---|---|
| ASP-N24E-FW | TATCGGATTCGCAGTAGAGGGTGGCTTCATTA CTGCCGG (SEQ ID NO: 16) |
| ASP-N24A-FW | TATCGGATTCGCAGTAGCCGGTGGCTTCATTA CTGCCGG (SEQ ID NO: 17) |
| ASP-N24T-FW | TATCGGATTCGCAGTAACAGGTGGCTTCATTA CTGCCGG (SEQ ID NO: 18) |
| ASP-N24Q-FW | TATCGGATTCGCAGTACAAGGTGGCTTCATTA CTGCCGG (SEQ ID NO: 19) |
| ASP-R35E-FW | CGGTCACTGCGGAGAGACAGGAGCCACTACTG CC (SEQ ID NO:20) |
| ASP-R35D-FW | CGGTCACTGCGGAGACACAGGAGCCACTACTG CC (SEQ ID NO:21) |
| ASP-G54D-FW | AGGTAGCTCGTTTCCGGACAATGATTATGCAT TCGTCCG (SEQ ID NO:21) |
| ASP-A64K-N67L-FW | CCGAACAGGGAAAGGAGTACTGTTGCTTGCCC AAGTCAATAAC (SEQ ID NO:22) |
| ASP-A64K-N67S-FW | CCGAACAGGGAAAGGAGTATCTTTGCTTGCCC AAGTCAATAAC (SEQ ID NO:23) |
| ASP-A64K-N67A-FW | CCGAACAGGGAAAGGAGTAGCTTTGCTTGCCC AAGTCAATAAC (SEQ ID NO:24) |
| ASP-G78D-T86K-FW | TAACTACTCGGGCGACAGAGTCCAAGTAGCAG GACATAAAGCC (SEQ ID NO:25) |

TABLE 3-1-continued

Primers and Sequences

| Primer name | Primer sequences |
|---|---|
| ASP-R123F-R127Q-FW | GTCTTTGGACTTATCCAAACGACGGTTTGTGC CGAACC (SEQ ID NO:26) |
| ASP-R123F-R127K-FW | GTCTTTGGACTTATCAAAACGACGGTTTGTGC CGAACCAG (SEQ ID NO:27) |
| ASP-R123F-R127Y-FW | GTCCGAGGACTTATCTACACGACGGTTTGTGC CGAACC (SEQ ID NO:28) |
| K159F-FW | GGTGGTTCTGGAAATTGTTTCACGGGGGGAAC AACATTC (SEQ ID NO:29) |
| K159E-FW | GGTGGTTCTGGAAATTGTGAGACGGGGGGAAC AACATTC (SEQ ID NO: 30) |
| K159N-FW | GGTGGTTCTGGAAATTGTAACACGGGGGGAAC AACATTC (SEQ ID NO:31) |
| R159K-FW | GGTGGTTCTGGAAATTGTAAGACGGGGGGAAC AACATTC (SEQ ID NO:32) | pUC18-ASP Preparation

The ASP variant containing the substitutions R014I-A064K-T086K-T116E-R123F was cloned from the pHPLT vector into the pUC18 vector (Invitrogen, cat. no 15363013; See, FIG. 1), using the PstI and HindIII restriction sites. Subsequently, the pUC18-ASP plasmid (See, FIG. 2) was electroporated to electrocompetent E. coli cells (Invitrogen, cat. no C4040-52, One Shot® TOP10 Electrocomp™ E. coli, dam+) and selective growth on agar plates containing 100 mg/L ampicillin, resulted in pUC18-ASP plasmid harboring E. coli cells. This method was used to ensure methylated ASP DNA at GATC sites, needed to perform the QCMS protocol, because the plasmid pHPLT-ASP-C1-2 does not grown in E. coli.

Miniprep DNA was prepared from E. coli cells harboring the pUC18-ASP plasmid. Specifically, the strain was grown overnight in 10 mL of 2×TY medium with 100 ppm of ampicillin, after which the cells were spun down. The Qiagen spin miniprep DNA kit (cat. No. 27106) was used for preparing the plasmid DNA by the steps outlined in the Qiagen miniprep kit manual. The miniprep DNA was eluted with 50 uL of Qiagen buffer EB provided in the kit.

Multiple Mutation Library Construction

Sites to be used for multiple mutation library construction were chosen as follows. For each property required in the final molecule, mutations were evaluated as "Up" or "Down," with sites defined as productive. At a minimum, sites to be combined should be productive for each property desired, and at a minimum, for the most important property. To ensure that the libraries had the highest probability for improving or maintaining all important properties, the following criteria were used.

For each property, a cut-off value for $\Delta\Delta G$ was established. For example, for a process taking place at 25° C. $\Delta\Delta G$ values <0.06 Kcal represent those mutations no worse than 90% of the parent proteins activity, while $\Delta\Delta G$ values >1.13 Kcal represent those mutations that are 125% of the parent proteins activity.

The multiple mutation library was constructed as outlined in the Stratagene QCMS kit, with the exception of the primer concentration used in the reactions. Specifically, 1 µL of the methylated, purified pUC18-ASP plasmid (about 70 ng) was mixed with 15 µL of sterile distilled water, 1.5 µL of dNTP, 2.5 µL of 10× buffer, 1 µL of the enzyme blend and 1.0 µL mutant primer mix (for a total of 100 pmol of primers). The primer mix was prepared using 10 µL of each of the eighteen mutant primers (100 pmol/µL); adding 50 ng of each primer for the library as recommended by Stratagene, resulted in fewer mutations in a previous round of mutagenesis. Thus, the protocol was modified in the present round of mutagenesis to include a total of 100 pmol of primers in each reaction. The cycling conditions were 95° C. for 1 min, followed by 30 cycles of 95° C. for 1 min, 55° C. for 1 min, and 65° C. for 12 min, in an MJ Research PTC-200 thermocycler using thin-walled 0.2 mL PCR tubes. The reaction product was digested with 1 µL of DpnI from the QCMS kit by incubating at 37° C. overnight. An additional 0.5 µL of DpnI was added, and the reaction was incubated for 1 hour.

Subsequently, the library DNA (mutagenized single stranded pUC18-ASP product) was electroporated to electrocompetent E. coli cells (Invitrogen, cat. no C4040-52, One Shot® TOP10 Electrocomp™ E. coli, dam+) and selective growth on agar plates containing 100 mg/L ampicillin resulted in the ASP multiple mutation library in E. coli cells. Colonies (tens of thousands) were harvested and the Qiagen spin miniprep DNA kit (cat. No. 27106) was used for preparing the plasmid DNA by the steps outlined in the Qiagen miniprep kit manual. The miniprep DNA was eluted with 50 uL of Qiagen buffer EB provided in the kit.

Miniprep DNA was digested using the PstI and HindIII DNA restriction enzymes. The ASP library fragment mix (PstI×HindIII) was gel purified and cloned in the 4154 base-pair HindIII×PstI pHPLT vector fragment by a ligase reaction using Invitrogen T4 DNA Ligase (Cat. No. 15224-025), utilizing Invitrogen's protocol as recommended for general cloning of cohesive ends). In another approach, synthetic ASP library fragments were produced by GeneArt. These ASP library fragments were also digested with PstI and HindIII, purified and cloned in the 4154 basepair HindIII×PstI pHPLT vector fragment by a ligase reaction.

To transform the ligation reaction mix directly into Bacillus cells, the library DNA (ASP library fragment mix cloned in pHPLT) was amplified using the TempliPhi kit (Amersham cat. #25-6400). For this purpose, 1 µL of the ligation reaction mix was mixed with 5 µL of sample buffer from the TempliPhi kit and heated for 3 minutes at 95° C. to denature the DNA. The reaction was placed on ice to cool for 2 minutes and then spun down briefly. Next, 5 µL of reaction buffer and 0.2 µL of phi29 polymerase from the TempliPhi kit were added, and the reactions were incubated at 30° C. in an MJ Research PCR machine for 4 hours. The phi29 enzyme was heat inactivated in the reactions by incubation at 65° C. for 10 min in the PCR machine.

For transformation of the libraries into Bacillus, 0.1 µL of the TempliPhi amplification reaction product was mixed with 500 µL of competent B. subtilis cells (ΔaprE, ΔnprE, oppA, ΔspoIIE, degUHy32, ΔamyE::(xylR, pxylA-comK) followed by vigorous shaking at 37° C. for 1 hour and 100 and 500 µL was plated on HI-agar plates containing 20 ppm neomycin sulfate (Sigma, Cat. No. N-1876; contains 732 µg neomycin per mg) and 0.5% skim milk. Ninety-five clones from the library were picked for sequencing.

The mutagenesis worked well, in that only 14% of the clones were equal to the backbone sequence (ASP with R014I-A064K-T086K-T116E-R123F), about 3% of clones had extra mutations. The remaining of the sequenced clones (72%) were all mutants, and of these about 94% were unique mutants. The sequencing results for the library are provided below in Table 3-3.

TABLE 3-3

| Variants of ASP with R014I-A064K-T086K-T116E-R123F | | | | | |
|---|---|---|---|---|---|
| G54D | | | | | |
| N24A | | | | | |
| N24Q | | | | | |
| N24T | | | | | |
| N67S | | | | | |
| R127K | | | | | |
| R159F | | | | | |
| R159K | | | | | |
| R159K | | | | | |
| R159N | | | | | |
| R159N | | | | | |
| G78D | R159F | | | | |
| N24Q | R35E | | | | |
| N67S | R159E | | | | |
| R127K | R159E | | | | |
| R127K | R159K | | | | |
| R127K | R159N | | | | |
| R127Q | R159K | | | | |
| R35D | R159E | | | | |
| R35D | R159K | | | | |
| R35E | R159K | | | | |
| G54D | R127K | R159K | | | |
| G78D | R127K | R159K | | | |
| G78D | R127K | R159E | | | |
| G78D | R127Q | R159K | | | |
| N24A | N67A | R159K | | | |
| N24A | N67S | R159K | | | |
| N24E | R35D | G78D | | | |
| N24T | N67S | R159E | | | |
| N67L | G78D | R159K | | | |
| R35D | G78D | R159K | | | |
| N24A | R35E | G78D | R159N | | |
| N24D | R35D | G78D | R159F | | |
| N24E | G54D | G78D | R159K | | |
| N24E | R35D | G78D | R127K | R159N | |
| N24Q | G54D | G78D | R159N | | |
| N24Q | N67L | G78D | R159E | | |
| N24Q | R35D | R127K | R159K | | |
| N24T | R35D | G78D | R159K | | |
| N24T | R35D | G78D | R159K | | |
| N67S | G78D | R127K | R159K | | |
| R35D | G78D | R127K | R159E | | |
| R35D | G78D | R127K | R159N | | |
| R35D | G78D | R127Q | R159K | | |
| R35E | G54D | N67A | R159F | | |
| R35E | N67S | G78D | R127Q | | |
| N24A | G54D | N67S | G78D | R159F | |
| N24A | R35D | N67A | G78D | R159F | |
| N24Q | R35D | N67L | G78D | R159K | |
| N24Q | R35D | N67L | G78D | R159N | |
| N24Q | R35D | N67S | R127K | R159E | |
| N24Q | R35E | N67A | R127K | R159E | |
| N24Q | R35E | N67A | G78D | R159E | |
| N24T | N67A | G78D | R127Q | R159N | |
| N24T | R35E | N67A | G78D | R127Q | |
| R35E | G54D | N67S | G78D | R159K | |
| N24A | G54D | N67S | G78D | R127K | R159K |
| N24A | R35E | N67S | G78D | R127K | R159K |
| N24E | R35E | G54D | N67S | R127K | R159N |
| N24Q | R35D | N67S | G78D | R127K | R159F |
| N24T | G54D | N67S | G78D | R127Y | R159E |
| N24E | R35E | G54D | N67S | G78D | R127K | R159K |

Example 4

Preparation of ASP Variant Crude Enzyme Samples

The Asp variant proteins were produced by growing the B. subtilis transformants (described above and in U.S. patent application Ser. No. 10/576,331) in 96 well MTP at 37° C. for 68 hours in MBD medium (a MOPS based defined medium). MBD medium was made essentially as known in the art (See, Neidhardt et al., J. Bacteriol., 119: 736-747 [1974]), except that $NH_4Cl_2$, $FeSO_4$, and $CaCl_2$ were left out of the base medium, 3 mM $K_2HPO_4$ was used, and the base medium was supplemented with 60 mM urea, 75 g/L glucose, and 1% soytone. Also, the micronutrients were made up as a 100× stock containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1M $CaCl_2$, and 10 ml of 0.5 M sodium citrate.

In the following Examples, tests conducted on various mutants of ASP are described. The methods described above in Example 1 were used. In the following Tables, "Variant Code" provides the wild-type amino acid, the position in the amino acid sequence, and the replacement amino acid (i.e., "F001A" indicates that the phenylalanine at position 1 in the amino acid sequence has been replaced by alanine in this particular variant).

Example 5

Caseinolysis Activity of Multiply-Substituted Variants

In this Example, experiments conducted to determine the caseinolytic activity of various multiply-substituted ASP variants are described. In these experiments, the protocol used is described in Example 1, above. The following table provides the variants, including the mutations in each variant, as well as the casein activity for those with activity greater than that of wild-type ASP plus 1 standard deviation (>1.13 activity units).

TABLE 5-1

Caseinolytic Activity

| Variants | Casein Activity |
|---|---|
| R14L-R79T | 1.61 |
| G12D-R35H-R159E | 1.27 |
| G12D-R35H-R123Q | 1.30 |
| G12D-R35H-R123F-R159E | 1.45 |
| G12D-R35H | 1.69 |
| G12D-R35E-R159E | 1.22 |
| G12D-R35E-R123Q-R159E | 1.16 |
| G12D-R35E-R123Q | 1.14 |
| G12D-R35E | 1.43 |
| G12D-R35D-R159E | 1.18 |
| G12D-R35D-R123Q-R159E | 1.27 |
| G12D-R35D | 1.64 |
| G12D-R159E | 1.49 |
| G12D-R14Q-R35H | 1.39 |
| G12D-R14I-R35H | 1.41 |
| N024E-G049A-A093H--R127K-A143N-R159K-I181Q | 1.15 |
| N24M-S76V-A93H-R127K-R159K | 1.13 |
| R14I-N24E-R35D-A64K-N67A-G78D-R123F-R159K-D184T | 1.13 |

The following table provides the variants, including the mutations in each variant, as well as the casein activity for those with activity greater than that of wild-type ASP plus 1 standard deviation (>0.85 activity units).

TABLE 5-2

Caseinolytic Activity

| Variant | Casein Activity |
|---|---|
| R127A-R159K | 0.86 |
| R14I-G65Q | 1.04 |
| R14I-G65Q-R159K | 0.99 |
| R14I-S76V | 1.43 |

As indicated by these results, numerous multiply-substituted variants performed better than the wild-type ASP in this assay system.

Example 6

Keratin Hydrolysis Activity of Multiply-Substituted Variants

In this Example, experiments conducted to determine the keratinolytic activity of various multiply-substituted ASP variants are described. In these experiments, the protocol used is described in Example 1, above. The following table provides the variants, including the mutations in each variant, as well as the keratin hydrolysis activity for those with activity greater than that of wild-type ASP plus 1 standard deviation ($\geqq 1.1$ performance index).

TABLE 6-1

Keratin Hydrolysis Activity Assay Results

| Variants | Keratin Hydrolysis [Perf. Ind.] |
|---|---|
| N024E-G049A-A093H--R127K-A143N-R159K-I181Q | 1.32 |
| N024E-G049A-A093H-S099A-R127K-A143N-R159K-I181T-V090I | 1.37 |
| N024E-G049A-A093S-S099D-R127K-A143N-R159K-I181Q | 1.28 |
| N024Q-G049A-A093S-S099A-R127K-A143N-R159K-I181Q | 1.17 |
| N024Q-G049A-A093S-S099A-R127K-A143N-R159K-I181T | 1.19 |
| N024Q-G049A-A093S-S099N-R127K-A143N-R159K-I181Q | 1.13 |
| N024T-G049A-A093S-S099A-R127K-A143N-R159K-I181T | 1.12 |
| N024W-G049A-A093S-S099A-R127K-A143N-R159K-I181Q | 1.13 |
| N24A-G54E-S76D-A93G-R127K-R159K | 1.53 |
| N24E-A93G-R127K-R159K | 1.33 |
| N24E-G54L-S76E-A93G-R127K-R159K | 1.21 |
| N24E-G54Q-A93S-R127K-R159K | 1.37 |
| N24E-S76D-A93T-R127K-R159K | 1.64 |
| N24M-G54E-A93H-R127K-R159K | 1.24 |
| N24M-G54E-S76N-A93S-R127K-R159K | 1.24 |

TABLE 6-1-continued

Keratin Hydrolysis Activity Assay Results

| Variants | Keratin Hydrolysis [Perf. Ind.] |
|---|---|
| N24Q-A93G-R127K-R159K | 1.17 |
| N24Q-G54D-S76L-A93G-R127K-R159K | 1.15 |
| N24Q-G54I-S76E-A93H-R127K-R159K | 1.12 |
| N24T-G54D-S76V-A93G-R127K-R159K | 1.11 |
| N24T-G54E-S76V-A93H-R127K-R159K | 1.28 |
| N24W-G54D-A93H-R127K-R159K | 1.20 |
| N24W-S76E-A93G-R127K-R159K | 1.13 |
| R014I-S076A-A093G-R127K-R159K-I181T | 1.27 |
| R014I-S076A-A093H-R127K-R159K-I181Q | 1.22 |
| R014I-S076D-A093H-R127K-R159K-I181Q | 1.40 |
| R014I-S076D-A093H-R127K-R159K-I181T | 1.46 |
| R014I-S076D-A093S-R127K-R159K-I181T | 1.49 |
| R014I-S076E-A093S-R127K-R159K-I181Q | 1.54 |
| R014I-S076E-A093T-R127K-R159K-I181K | 1.34 |
| R014I-S076I-A093S-R127K-R159K-I181Q | 1.27 |
| R014I-S076N-A093H-R127K-R159K-I181Q | 1.18 |
| R014I-S076T-A093G-R127K-R159K-I181Q | 1.22 |
| R014I-S076V-A093H-R127K-R159K-I181Q | 1.23 |
| R014K-S076A-A093S-R127K-R159K-I181T | 1.15 |
| R014K-S076E-A093H-R127K-R159K-I181T | 1.14 |
| R014K-S076E-A093S-R127K-R159K-I181T | 1.19 |
| R014K-S076T-A093H-R127K-R159K-I181Q | 1.11 |
| R014L-S076A-A093H-R127K-R159K | 1.36 |
| R014L-S076A-A093H-R127K-R159K-I181Q | 1.24 |
| R014L-S076D-A093H-R127K-R159K-I181T | 1.32 |
| R014L-S076E-A093H-R127K-R159K-I181K | 1.30 |
| R014M-S076A-A093G-R127K-R159K-I181T | 1.26 |
| R014M-S076A-A093H-R127K-R159K-I181T | 1.15 |
| R014M-S076A-A093S-R127K-R159K-I181K | 1.22 |
| R014M-S076A-A093S-R127K-R159K-I181T | 1.24 |
| R014M-S076A-A093T-R127K-R159K-I181Q | 1.13 |
| R014M-S076D-A093S-R127K-R159K-I181T | 1.36 |
| R014M-S076E-A093G-R127K-R159K-I181T | 1.25 |
| R014M-S076E-A093H-R127K-R159K-I181T | 1.42 |
| R014M-S076E-A093S-R127K-R159K-I181T | 1.46 |
| R014M-S076N-A093G-R127K-R159K-I181K | 1.11 |
| R014M-S076N-A093G-R127K-R159K-I181T | 1.21 |

TABLE 6-1-continued

Keratin Hydrolysis Activity Assay Results

| Variants | Keratin Hydrolysis [Perf. Ind.] |
|---|---|
| R014M-S076N-A093H-R127K-R159K-I181T | 1.23 |
| R014M-S076N-A093S-R127K-R159K-I181T | 1.25 |
| R014M-S076V-A093G-R127K-R159K-I181Q | 1.21 |
| R14I-N24Q-A64K-G78D-R123F-R159K-D184T | 1.11 |
| R14I-N24A-A64K-N67S-G78D-R123F-R159K-D184T | 1.34 |
| R14I-N24Q-R35D-A64K-N67S-R123F-R159K-D184T | 1.21 |
| R14I-N24E-A64K-R123F-R127K-R159K-D184T | 1.31 |
| R14I-N24Q-A64K-R123F-R127Q-R159K-D184T | 1.28 |
| R14I-N24Q-A64K-G78D-R123F-R127Q-R159N-D184T | 1.21 |
| R14I-N24E-A64K-N67L-G78D-R123F-R159K-D184T | 1.49 |
| R14I-N24Q-R35D-A64K-N67S-R123F-R159K-D184T | 1.26 |
| R127Q-R159K | 1.14 |
| G78D-R127K-R159K | 1.24 |
| N67S-G78D-R127K-R159K | 1.39 |
| R35D-R159K | 1.17 |
| G78D-R127Q-R159K | 1.26 |
| N24A-N67A-R159K | 1.17 |
| T36S-R127Q-R159E | 1.77 |
| S15E-T121E-R123Q | 1.32 |
| S15E-R35H-R159E | 1.23 |
| S15E-R35E | 1.33 |
| S15E-R159E | 1.12 |
| S15E-R123Q | 1.54 |
| S15E-R123E | 1.92 |
| R79T R127Q R179Q | 1.55 |
| R35H-R159E | 1.12 |
| R35H-R127Q-R159E | 1.23 |
| R35F R61S R159Q | 1.24 |
| R35F R159Q | 1.39 |
| R35E-R159E | 1.52 |
| R35E-R127Q | 1.21 |
| R35D-R159E | 1.52 |
| R35D-R127Q | 1.29 |
| R16Q R79T R159Q R179Q | 1.36 |
| R16Q R79T R127Q | 1.68 |
| R16Q R79T R123L | 1.35 |
| R16Q R79T | 1.24 |
| R16Q R35F R123L R159Q | 1.20 |
| R16Q R159Q R179Q | 1.14 |
| R16Q R127Q R159Q | 1.35 |
| R16Q R123L R159Q | 1.32 |
| R14Q-T121E | 1.44 |
| R14Q-R35E-T121E | 1.11 |
| R14Q-R35E-R159E | 1.20 |
| R14Q-R35E | 1.49 |
| R14Q-R35D-R127Q | 1.39 |
| R14Q-R35D | 1.46 |
| R14L R79T R127Q R159Q | 1.30 |
| R14L R61S R79T R123L | 1.30 |
| R14L R35F R61S | 1.27 |
| R14L R127Q R159Q R179Q | 1.47 |
| R14L R123L R159Q | 1.34 |
| R14I-R35E-R127Q | 1.74 |
| R14I-R35E-R123E | 1.19 |
| R14I-R35D-R159E | 1.20 |
| R14E-R35H-R127Q | 1.60 |

TABLE 6-1-continued

Keratin Hydrolysis Activity Assay Results

| Variants | Keratin Hydrolysis [Perf. Ind.] |
|---|---|
| R127Q-R159E | 2.44 |
| R127Q R159Q | 1.37 |
| R123Q-R159E | 1.64 |
| R123Q-R127Q-R159E | 1.34 |
| R123L R159Q | 1.51 |
| R123L R127Q R159Q | 1.11 |
| R123F-R159E | 1.64 |
| R123E-R127Q-R159E | 1.15 |
| R123E-R127Q | 1.65 |
| G12D-S15E-R35H-R159E | 1.40 |
| G12D-S15E-R35D | 1.59 |
| G12D-S15E-R159E | 1.34 |
| G12D-S15E | 1.81 |
| G12D-R35H-T121E-R123Q | 1.96 |
| G12D-R35H-R159E | 1.98 |
| G12D-R35H-R127Q-R159E | 1.73 |
| G12D-R35H-R123Q | 2.43 |
| G12D-R35H-R123F-R159E | 1.44 |
| G12D-R35H | 2.02 |
| G12D-R35E-R159E | 1.47 |
| G12D-R35E-R123Q-R159E | 1.29 |
| G12D-R35E-R123Q | 2.28 |
| G12D-R35E | 1.98 |
| G12D-R35D-R159E | 1.23 |
| G12D-R35D-R127Q | 1.59 |
| G12D-R35D | 2.23 |
| G12D-R159E | 2.46 |
| G12D-R14Q-R35H | 2.20 |
| G12D-R14Q-R35D-R123H | 1.20 |
| G12D-R14Q-R159E | 1.55 |
| G12D-R14I-R35H | 2.82 |
| G12D-R14E | 2.00 |
| G12D-R127Q-R159E | 1.83 |
| G12D-R123E-R159E | 1.26 |

The following table provides the variants, including the mutations in each variant, as well as the keratinolytic activity for those with activity greater than that of wild-type ASP plus 1 standard deviation (>1.2 Performance Index).

TABLE 6-2

Kertain Hydrolysis Assay Results

| Variant | Keratin Hydrolysis [Perf. Ind.] |
|---|---|
| R127A-R159K | 1.84 |
| R14I-G65Q | 1.96 |
| R14I-G65Q-R127A-R159K | 1.42 |
| R14I-G65Q-R159K | 1.78 |
| R14I-R127A | 1.23 |
| R14I-R127A-R159K | 1.45 |
| R14I-R159K | 2.69 |
| R14I-R35F | 1.32 |
| R14I-R35F-G65Q | 1.50 |
| R14I-R35F-G65Q-R127A-R159K | 1.66 |
| R14I-R35F-R159K | 1.71 |
| R14I-S76V | 2.39 |
| R14I-T36S-G65Q-R127A-R159K | 1.90 |
| R35F-R127A-R159K | 1.75 |

As indicated by these results, numerous multiply-substituted variants performed better than the wild-type ASP in this assay system.

Example 7

Thermostability of Multiply-Substituted Variants

In this Example, experiments conducted to determine the thermostability of various multiply-substituted ASP variants are described. In these experiments, the protocol used is described in Example 1, above. The following table provides the variants, including the mutations in each variant, as well as the residual casein activity for those with activity greater than that of wild-type ASP plus 1 standard deviation ($\geq 48\%$ residual activity).

TABLE 7-1

Thermostability Assay Results

| Variants | Thermostability [% Res. Act] |
|---|---|
| T121E-R123F-R159E | 61 |
| R79T-R127Q-R179Q | 55 |
| R16Q-R79T-R127Q | 55 |
| R16Q-R79T-R123L-R159Q-R179Q | 61 |
| R16Q-R79T-R123L | 65 |
| R16Q-R79T | 64 |
| R16Q-R123L-R159Q | 49 |
| R14Q-T121E | 59 |
| R14L-R79T | 71 |
| R123L-R159Q | 54 |
| R123L-R127Q-R159Q | 69 |
| G12D-S15E-R35D-R123F-R159E | 59 |
| G12D-S15E-R159E | 54 |
| G12D-S15E | 64 |
| G12D-R35H-T121E-R123Q | 57 |
| G12D-R35H-R123Q | 59 |
| G12D-R35H-R123F-R159E | 60 |
| G12D-R35H | 57 |
| G12D-R35E-R123Q | 51 |
| G12D-R35E | 52 |
| G12D-R159E | 53 |
| G12D-R14Q-S15E-R35D | 52 |
| G12D-R14Q-R35H | 51 |
| G12D-R14Q-R159E | 49 |
| G12D-R14E | 84 |
| G12D-R127Q-R159E | 63 |
| G12D-R123E-R159E | 58 |

As indicated by these results, numerous multiply-substituted variants performed better than the wild-type ASP in this assay system.

Example 8

LAS Stability of Multiply-Substituted Variants

In this Example, experiments conducted to determine the LAS stability of various multiply-substituted ASP variants are described. In these experiments, the protocol used is described in Example 1, above, with a temperature of 25° C. used. The following table provides the variants, including the mutations in each variant, as well as the residual AAPF activity for those with residual activity greater than that of wild-type ASP plus 1 standard deviation ($\geq 10\%$ residual activity).

TABLE 8-1

LAS Stability Assay Results

| Variants | LAS Stability [%] |
|---|---|
| T121E-R123F-R159E | 73 |
| S15E-T121E-R123Q | 87 |
| S15E-R35H-R159E | 88 |
| S15E-R35E-R159E | 93 |
| S15E-R35E-R127Q-R159E | 102 |
| S15E-R35E | 82 |
| S15E-R35D-T121E-R123Q | 100 |
| S15E-R35D-R123Q | 90 |
| S15E-R35D-R123F-R159E | 97 |
| S15E-R35D | 81 |
| S15E-R159E | 62 |
| S15E-R127Q | 67 |
| S15E-R123Q | 66 |
| S15E-R123E | 81 |
| R79T R127Q R179Q | 53 |
| R35H-R159E | 82 |
| R35H-R127Q-R159E | 89 |
| R35H-R123D-R159E | 82 |
| R35F R61S R159Q | 78 |
| R35F R159Q | 44 |
| R35E-T121E-R123E | 92 |
| R35E-R159E | 93 |
| R35E-R127Q | 84 |
| R35D-R159E | 88 |
| R35D-R127Q-R159E | 95 |
| R35D-R127Q | 89 |
| R35D-R123Q-R159E | 94 |
| R16Q R79T R159Q R179Q | 93 |
| R16Q R79T R127Q | 92 |
| R16Q R79T R123L R159Q R179Q | 96 |
| R16Q R79T R123L R159Q | 89 |
| R16Q R79T R123L | 74 |
| R16Q R79T | 38 |
| R16Q R61S R159Q R179Q | 95 |
| R16Q R61S R123L R159Q | 96 |
| R16Q R35F R61S R159Q | 97 |
| R16Q R35F R159Q | 82 |
| R16Q R35F R123L R159Q | 91 |
| R16Q R35F | 54 |
| R16Q R159Q R179Q | 83 |
| R16Q R159Q | 69 |
| R16Q R127Q R179Q | 88 |
| R16Q R127Q R159Q | 76 |
| R16Q R123L R159Q | 85 |
| R14Q-T121E | 88 |
| R14Q-R35E-T121E | 96 |
| R14Q-R35E-R159E | 91 |
| R14Q-R35E | 94 |
| R14Q-R35D-R127Q | 88 |
| R14Q-R35D-R123E-R159E | 93 |
| R14Q-R35D-R123D-R159E | 99 |
| R14Q-R35D | 85 |
| R14Q-R123Q | 87 |
| R14L R79T R127Q R159Q | 90 |
| R14L R79T | 32 |
| R14L R61S R79T R123L | 97 |
| R14L R61S R123L | 85 |
| R14L R35F R79T R123L R159Q | 90 |
| R14L R35F R61S | 80 |
| R14L R127Q R159Q R179Q | 86 |
| R14L R123L R159Q | 91 |

TABLE 8-1-continued

LAS Stability Assay Results

| Variants | LAS Stability [%] |
|---|---|
| R14I-R35E-T121E-R159E | 100 |
| R14I-R35E-R127Q | 97 |
| R14I-R35E-R123E | 95 |
| R14I-R35D-R159E | 98 |
| R14I-R35D-R127Q-R159E | 99 |
| R14E-S15E-R35H | 92 |
| R14E-R35H-R127Q | 91 |
| R14D-S15E-R35E-R159E | 98 |
| R14D-R35H-R123Q-R159E | 98 |
| R127Q-R159E | 40 |
| R127Q R159Q | 39 |
| R123Q-R159E | 42 |
| R123Q-R127Q-R159E | 51 |
| R123L R159Q | 36 |
| R123L R127Q R159Q | 56 |
| R123F-R159E | 67 |
| R123E-R127Q-R159E | 65 |
| R123E-R127Q | 49 |
| G12D-S15E-R35H-R159E | 100 |
| G12D-S15E-R35H-R123F-R127Q-R159E | 100 |
| G12D-S15E-R35E-R159E | 103 |
| G12D-S15E-R35D-R127Q | 99 |
| G12D-S15E-R35D-R123F-R159E | 101 |
| G12D-S15E-R35D-R123E | 100 |
| G12D-S15E-R35D | 97 |
| G12D-S15E-R159E | 96 |
| G12D-S15E | 76 |
| G12D-R35H-T121E-R123Q | 98 |
| G12D-R35H-R159E | 96 |
| G12D-R35H-R123Q-R159E | 97 |
| G12D-R35H-R123Q | 89 |
| G12D-R35H-R123F-R159E | 98 |
| G12D-R35H | 79 |
| G12D-R35E-R159E | 101 |
| G12D-R35E-R123Q-R159E | 96 |
| G12D-R35E-R123Q | 92 |
| G12D-R35E | 97 |
| G12D-R35D-R159E | 95 |
| G12D-R35D-R127Q | 98 |
| G12D-R35D-R123Q-R159E | 103 |
| G12D-R35D | 94 |
| G12D-R159E | 97 |
| G12D-R14Q-S15E-R35D | 101 |
| G12D-R14Q-R35H | 88 |
| G12D-R14Q-R35E-R127Q-R159E | 100 |
| G12D-R14Q-R35D-R123H | 100 |
| G12D-R14Q-R159E | 96 |
| G12D-R14I-R35H | 94 |
| G12D-R14E | 85 |
| G12D-R14D-R35H-R123D-R127Q | 100 |
| G12D-R127Q-R159E | 93 |
| G12D-R123E-R159E | 99 |
| R127A-R159K | 24 |
| R14I-G65Q | 13 |
| R14I-G65Q-N67L-R159K | 11 |
| R14I-G65Q-N67L-Y75G-R127A-R159K | 11 |
| R14I-G65Q-R159K | 33 |
| R14I-G65Q-S76V-R127A-R159K | 11 |
| R14I-R127A | 71 |
| R14I-R127A-R159K | 77 |
| R14I-R159K | 58 |
| R14I-R35F | 64 |
| R14I-R35F-G65Q | 47 |
| R14I-R35F-G65Q-R127A-R159K | 76 |
| R14I-R35F-N67L-R127A-R159K | 61 |
| R14I-R35F-R127A-R159K | 81 |
| R14I-R35F-R159K | 70 |
| R14I-S76V | 14 |
| R14I-T36S-G65Q-R127A-R159K | 32 |
| R35F-R127A-R159K | 57 |
| R35F-S76A-R127A | 58 |

In additional experiments, the LAS stability of variants having multiple substitutions were tested. In the first set of experiments, the test conditions described in Example 1 were used at a temperature of 25° C. In the following Table, the variants with activity greater than wild-type, plus one standard deviation (>20% residual activity) are presented.

TABLE 8-2

Results of LAS Stability Assays at 25° C.

| Variant | LAS-25° C. Stability [%] |
|---|---|
| N024A-G049A-A093H-S099N-R127K-A143N-R159K-I181Q | 25 |
| N024A-S076A-A093H-S099G-R127K-R159K | 47 |
| N024A-S076T-A093S-S099G-R127K-R159K | 41 |
| N024E-G049A-A093G-S099G-R127K-A143N-R159K-I181T | 31 |
| N024E-G049A-A093H--R127K-A143N-R159K-I181Q | 53 |
| N024E-G049A-A093H-S099A-R127K-A143N-R159K-I181T-V090I | 75 |
| N024E-G049A-A093S-S099D-R127K-A143N-R159K-I181Q | 27 |
| N024H-G049A-A093T-S099A-R127K-A143N-R159K-I181Q | 41 |
| N024H-S076A-A093G-S099G-R127K-R159K | 53 |
| N024H-S076A-A093H-S099G-R127K-R159K | 78 |
| N024H-S076A-A093S-S099A-R127K-R159K-G054H-L069H | 26 |
| N024H-S076A-A093T-S099G-R127K-R159K | 46 |
| N024H-S076N-A093Q-S099W-R127K-R159K | 33 |
| N024H-S076V-A093Q-S099G-R127K-R159K | 29 |
| N024L-G049A-A093H-S099A-R127K-A143N-R159K-I181Q | 31 |
| N024L-G049A-A093S-S099A-R127K-A143N-R159K-I181Q | 23 |

TABLE 8-2-continued

Results of LAS Stability Assays at 25° C.

| Variant | LAS-25° C. Stability [%] |
|---|---|
| N024L-S076V-A093H-S099G-R127K | 30 |
| N024L-S076V-A093S-S099A-R127K-R159K | 29 |
| N024M-G049A-A093G-S099A-R127K-A143N-R159K-I181Q | 39 |
| N024M-G049A-A093H-S099D-R127K-A143N-R159K-I181Q | 26 |
| N024M-G049A-A093S-S099A-R127K-A143N-R159K-I181Q | 35 |
| N024M-G049A-A093S-S099W-R127K-A143N-R159K-I181Q | 23 |
| N024Q-G049A-A093H-S099A-R127K-A143N-R159K-I181T | 40 |
| N024Q-G049A-A093S-S099A-R127K-A143N-R159K-I181Q | 50 |
| N024Q-G049A-A093S-S099A-R127K-A143N-R159K-I181T | 28 |
| N024Q-S076A-A093H-S099A-R127K-R159K-T039N | 58 |
| N024Q-S076A-A093H-S099W-R127K-R159K | 38 |
| N024Q-S076I-A093T-S099G-R159K | 25 |
| N024Q-S076T-A093S-R127K-R159K | 48 |
| N024S-S076A-A093G-S099G-R127K-R159K-G054A | 46 |
| N024S-S076A-A093H-S099T-R127K-R159K | 41 |
| N024S-S076A-A093S-S099W-R127K-R159K | 47 |
| N024S-S076A-A093T-S099W-R127K | 21 |
| N024S-S076T-A093Q-S099W-R127K-R159K | 37 |
| N024S-S076Y-A093T-S099A-R127K-R159K | 50 |
| N024T-G049A-A093G-S099A-R127K-A143N-R159K-I181Q | 48 |
| N024T-G049A-A093H-S099A-R127K-A143N-R159K-I181Q | 60 |
| N024T-G049A-A093H-S099A-R127K-A143N-R159K-I181T | 58 |
| N024T-G049A-A093H-S099D-R127K-A143N-R159K-I181Q | 21 |
| N024T-G049A-A093S-S099A-R127K-A143N-R159K-I181T | 41 |
| N024T-G049A-A093T-S099A-R127K-A143N-R159K-I181T | 27 |
| N024T-S076N-A093Q-S099T-R127K-R159K | 26 |
| N024T-S076T-A093T-S099N-R127K-R159K | 37 |
| N024V-S076A-R127K-R159K | 60 |
| N024V-S076V-A093Q-S099G-R127K-R159K | 33 |

TABLE 8-2-continued

Results of LAS Stability Assays at 25° C.

| Variant | LAS-25° C. Stability [%] |
|---|---|
| N024W-A093G-S099W-R127K-R159K | 33 |
| N024W-G049A-A093H-S099A-R127K-A143N-R159K-I181Q | 35 |
| N024W-G049A-A093S-S099A-R127K-A143N-R159K-I181K | 22 |
| N024W-G049A-A093S-S099A-R127K-A143N-R159K-I181Q | 25 |
| N024W-S076A-A093T-S099A-R127K-R159K | 60 |
| N024W-S076I-A093Q-S099G-R127K-R159K | 26 |
| N024W-S076N-A093T-S099G-R159K | 30 |
| N024W-S076T-A093H-S099A-R127K-R159K | 44 |
| N024W-S076T-A093H-S099W-R127K-R159K | 34 |
| N024W-S076V-A093H-S099A-R127K-R159K | 26 |
| N024W-S099W-R127K-R159K | 32 |
| N24A-G54E-S76D-A93G-R127K-R159K | 50 |
| N24E-A93G-R127K-R159K | 53 |
| N24E-G54L-S76E-A93G-R127K-R159K | 22 |
| N24E-G54Q-A93S-R127K-R159K | 50 |
| N24E-S76D-A93T-R127K-R159K | 40 |
| N24H-A93H-R127K-R159K | 41 |
| N24H-G54E-A93G-R127K-R159K | 46 |
| N24H-S76D-A93H-R127K-R159K | 35 |
| N24L-A93G-R127K-R159K | 32 |
| N24L-G54E-A93G-R127K-R159K | 46 |
| N24L-G54L-A93G-R127K-R159K | 21 |
| N24L-G54Q-S76A-A93H-R127K-R159K | 37 |
| N24L-S76T-A93G-R127K-R159K | 24 |
| N24L-S76T-A93H-R127K-R159K | 30 |
| N24M-A93G-R127K-R159K | 33 |
| N24M-A93H-R127K-R159K | 41 |
| N24M-A93S-R127K-R159K | 36 |
| N24M-A93T-R127K-R159K | 29 |
| N24M-G54E-A93H-R127K-R159K | 54 |
| N24M-G54E-S76N-A93S-R127K-R159K | 46 |
| N24M-G54I-A93H-R127K-R159K-S187I | 31 |
| N24Q-A93G-R127K-R159K | 37 |
| N24Q-G54D-A93H-R127K-R159K | 43 |
| N24Q-G54I-A93G-R127K-R159K | 25 |

TABLE 8-2-continued

Results of LAS Stability Assays at 25° C.

| Variant | LAS-25° C. Stability [%] |
|---|---|
| N24Q-G54I-S76E-A93H-R127K-R159K | 22 |
| N24Q-G54Q-A93G-R127K-R159K | 32 |
| N24Q-G54Q-S76T-A93H-R127K-R159K | 30 |
| N24Q-S76A-A93G-R127K-R159K | 37 |
| N24T-G54D-S76V-A93G-R127K-R159K | 26 |
| N24T-G54E-S76V-A93H-R127K-R159K | 38 |
| N24T-G54I-A93G-R127K-R159K | 38 |
| N24T-G54N-A93H-R127K-R159K | 27 |
| N24T-G54Q-S76N-A93G-R127K-R159K | 40 |
| N24T-G54Q-S76V-R127K-R159K | 26 |
| N24T-S76I-R127K-R159K | 25 |
| N24T-S76L-A93G-R127K-R159K | 20 |
| N24W-A93G-R127K-R159K | 35 |
| N24W-G54D-A93H-R127K-R159K | 35 |
| N24W-G54I-S76A-A93H-R127K-R159K | 26 |
| N24W-S76A-A93H-R127K-R159K | 36 |
| N24W-S76E-A93G-R127K-R159K | 21 |
| R014I-S076A-A093G-R127K-R159K-I181T | 44 |
| R014I-S076A-A093H-R127K-R159K-I181K | 54 |
| R014I-S076A-A093H-R127K-R159K-I181Q | 71 |
| R014I-S076A-A093H-R127K-R159K-I181T | 38 |
| R014I-S076D-A093H-R127K-R159K-I181Q | 75 |
| R014I-S076D-A093S-R127K-R159K-I181T | 41 |
| R014I-S076E-A093S-R127K-R159K-I181Q | 64 |
| R014I-S076E-A093T-R127K-R159K-I181K | 30 |
| R014I-S076I-A093S-R127K-R159K-I181Q | 23 |
| R014I-S076N-A093H-R127K-R159K-I181Q | 68 |
| R014I-S076T-A093G-R127K-R159K-I181Q | 57 |
| R014K-S076A-A093G-R127K-R159K-I181K | 20 |
| R014K-S076E-A093H-R127K-R159K-I181K | 20 |
| R014K-S076T-A093H-R127K-R159K-I181Q | 24 |
| R014L-S076A-A093H-R127K-R159K | 69 |
| R014L-S076A-A093H-R127K-R159K-I181Q | 66 |
| R014L-S076D-A093H-R127K-R159K-I181T | 39 |
| R014L-S076E-A093H-R127K-R159K-I181K | 36 |
| R014M-S076A-A093G-R127K-R159K-I181K | 45 |
| R014M-S076A-A093G-R127K-R159K-I181T | 37 |
| R014M-S076A-A093H-R127K-R159K-I181T | 36 |
| R014M-S076A-A093S-R127K-R159K-I181K | 49 |
| R014M-S076A-A093S-R127K-R159K-I181T | 40 |
| R014M-S076A-A093T-R127K-R159K-I181Q | 57 |
| R014M-S076D-A093S-R127K-R159K-I181T | 35 |
| R014M-S076E-A093G-R127K-R159K-I181T | 32 |
| R014M-S076E-A093H-R127K-R159K-I181T | 32 |
| R014M-S076E-A093S-R127K-R159K-I181T | 39 |
| R014M-S076N-A093G-R127K-R159K-I181K | 42 |
| R014M-S076N-A093G-R127K-R159K-I181T | 36 |
| R014M-S076N-A093H-R127K-R159K-I181Q | 75 |
| R014M-S076N-A093H-R127K-R159K-I181T | 42 |
| R014M-S076N-A093S-R127K-R159K-I181T | 37 |
| R014M-S076N-A093T-R127K-R159K-I181T | 33 |
| R014M-S076T-A093H-R127K-R159K-I181K | 37 |
| R014M-S076V-A093G-R127K-R159K-I181Q | 25 |
| R014M-S076V-A093H-R127K-R159K-I181Q | 22 |

In further experiments, yet other test conditions were used. In one set of experiments, the LAS stability was tested at a higher temperature (35° C.), using the protocol described in Example 1. In the following table, the percent residual activity for variants that exhibited activity greater than wild-type plus one standard deviation (>5% residual activity) is presented.

TABLE 8-3

Results of LAS Stability Assay at 35° C.

| Variant | LAS Stability (35° C.) [%] |
|---|---|
| G54E-R14L | 32 |
| G54L-R127S | 6 |
| N24D-G54F-R127C | 6 |
| N24E-R127S | 7 |
| N24E-R159C | 7 |
| N24G-G54I-R127S | 10 |
| N24H-R159Y-T46I | 52 |
| N24I-R127V-R14V | 18 |
| N24T-R127Q-R179F | 11 |
| R127A-R159V-R179F | 12 |
| R127C-R14W | 7 |
| R127S-R159N-R123L | 50 |
| R14A-N24F-R159L | 25 |
| R14A-R127L | 28 |

TABLE 8-3-continued

Results of LAS Stability Assay at 35° C.

| Variant | LAS Stability (35° C.) [%] |
|---|---|
| R14A-R127Y-R159W | 28 |
| R14A-R159W | 9 |
| R14C-S114F-R159G | 25 |
| R14F-R127L-R159F | 19 |
| R14F-R127Q-R159W | 37 |
| R14F-R127S-R159V | 32 |
| R14F-R127V-R159F | 16 |
| R14G-N24L-R159G | 13 |
| R14G-N24S-R127C | 47 |
| R14G-R127C-G63E | 58 |
| R14G-R127G | 19 |
| R14G-R127P | 9 |
| R14L-N24S-R159F | 20 |
| R14L-N24V-R127S-R159I | 31 |
| R14L-R123L | 25 |
| R14L-R127C-R159G | 32 |
| R14L-R127S | 22 |
| R14L-R127S-R159G | 31 |
| R14L-R127V | 17 |
| R14L-R127V-R159F | 27 |
| R14L-R127W-R123Y | 47 |
| R14L-R127Y | 10 |
| R14L-R127Y-R159F | 30 |
| R14L-R159G | 23 |
| R14L-R159L | 30 |
| R14L-R159S | 43 |
| R14L-R159V | 40 |
| R14L-R159W | 5 |
| R14M-N24L-R159S-R123V | 39 |
| R14M-R159F | 17 |
| R14Q-R123F | 56 |
| R14S-N24E-R127W | 13 |
| R14S-N24L-R159G | 17 |
| R14S-R127L-R159F | 41 |
| R14S-R127V | 33 |
| R14T-R14P-R159F | 33 |
| R14T-N24A | 6 |
| R14T-N24T-R127Q | 69 |
| R14T-N24T-R127Y-R159W | 42 |
| R14T-R127Y | 29 |
| R14V-N24A-R127I-R159A | 26 |
| R14V-N24D-R127C | 69 |
| R14V-N24G-P189S | 7 |
| R14V-N24S | 9 |
| R14V-N24Y-R127S-R159G | 37 |
| R14V-R127A | 48 |
| R14V-R127C-R159S | 62 |
| R14V-R127M-R159V | 63 |
| R14V-R127S-R159G | 47 |
| R14V-R127T-R159Y | 49 |
| R14V-R127V | 27 |
| R14V-R159F | 33 |
| R14V-R159V | 53 |
| R14V-R159W | 12 |
| R14W-N24T-R123E | 48 |
| R14W-R123L | 6 |
| R14W-R123V | 19 |
| R14W-R127Q-R159W | 13 |
| R14W-R159V | 13 |
| R159V-G49D | 6 |

In additional experiments, variants were tested at 35° C., using the protocol described in Example 1. In the following Table, results for variants with G12D and R35E, and >70% residual activity are presented.

TABLE 8-4

Results of LAS Stability Assay at 35° C.

| Variant | LAS-35° C. G12D-R35E Stability [%] |
|---|---|
| G012D-R035E-G065E | 73 |
| G012D-R035E-G065E | 73 |
| G012D-R035E-Q081P | 79 |
| G012D-R035E-R016S-A064T | 77 |
| G012D-R035E-R159W | 74 |
| G012D-R035E-R179I | 82 |
| G012D-R035E-S092T-I181V | 71 |

In additional experiments, yet other conditions were used. In one set of experiments, the performance indices for numerous multiple substituted variants were determined using the protocol in Example 1 and tested at 25° C. In the following table, the performance index results (PI) for variants with residual activity greater than wild-type plus 1 standard deviation (>1.1 performance index) are presented.

TABLE 8-5

LAS Assay Stability Results

| Variant | LAS (25° C.) [Perf. Ind.] |
|---|---|
| R14I-N24A-A64K-R123F-R159E-D184T | 2.97 |
| R14I-A64K-R123F-R159F-D184T | 3.99 |
| R14I-A64K-R123F-R159E-D184T | 3.82 |
| R14I-N24Q-R35E-A64K-R123F-D184T | 3.89 |
| R14I-N24Q-A64K-N67S-R123F-R159F-D184T | 1.24 |

TABLE 8-5-continued

LAS Assay Stability Results

| Variant | LAS (25° C.) [Perf. Ind.] |
|---|---|
| R14I-N24A-R35E-A64K-N67S-R123F-R159E-D184T | 1.20 |
| R14I-N24A-R35E-A64K-N67S-G78D-R123F-D184T | 1.20 |
| R14I-N24A-R35D-A64K-G78D-R123F-R127K-R159E-D184T | 1.72 |
| R14I-N24A-R35D-A64K-R123F-R127K-R159F-D184T | 2.88 |
| R14I-N24T-R35D-A64K-G78D-R123F-R127Q-R159F-D184T | 3.75 |
| R14I-A64K-R123F-D184T | 3.99 |
| R14I-N24A-A64K-R123F-R159N-D184T | 2.94 |
| R14I-N24Q-R35D-A64K-N67S-R123F-R159K-D184T | 1.31 |
| R14I-N24E-R35E-A64K-G78D-R123F-R127Q-R159F-D184T | 9.51 |
| R14I-N24E-A64K-R123F-R127K-R159K-D184T | 6.64 |
| R14I-N24A-A64K-R123F-D184T | 2.80 |
| R14I-A64K-R123F-R127K-R159F-D184T | 4.25 |
| R14I-A64K-R123F-R159E-D184T | 4.22 |
| R14I-A64K-R123F-R159N-D184T | 3.93 |
| R14I-A64K-R123F-R159K-D184T | 3.83 |
| R14I-A64K-R123F-R127Y-R159E-D184T | 4.32 |
| R14I-N24A-R35E-A64K-N67A-G78D-R123F-D184T | 2.40 |
| R14I-A64K-R123F-R127Y-R159K-D184T | 4.08 |
| R14I-N24Q-A64K-R123F-R127Q-R159K-D184T | 3.92 |
| R14I-A64K-R123F-R159K-D184T | 4.29 |
| R14I-N24Q-A64K-G78D-R123F-R127Q-R159N-D184T | 1.87 |
| R14I-N24E-A64K-N67L-G78D-R123F-R159K-D184T | 1.33 |
| R14I-N24A-R35E-A64K-G78D-R123F-R127K-R159E-D184T | 1.91 |
| R14I-N24Q-R35D-A64K-N67S-R123F-R159K-D184T | 1.33 |
| R14I-N24A-R35D-A64K-N67A-R123F-R159F-D184T | 1.22 |
| R14I-N24E-R35E-G54D-A64K-N67L-G78D-R123F-R127K-D184T | 2.64 |
| R14I-A64K-G78D-R123F-R127Q-R159N-D184T | 1.60 |
| R14I-N24A-R35E-A64K-G78D-R123F-R159N-D184T | 1.74 |
| R14I-A64K-R123F-R127K-R159E-D184T | 4.27 |
| R14I-N24A-R35E-A64K-N67S-G78D-R123F-R127K-R159F-D184T | 1.20 |
| R14I-A64K-G78D-R123F-R159E-D184T | 1.71 |
| R14I-N24E-R35D-A64K-N67A-G78D-R123F-R159K-D184T | 4.23 |
| N24T-R35D-G78D-R159K | 6.53 |
| N24T-R35E-N67A-G78D-R127Q | 1.36 |
| N24Q-R35E | 6.60 |
| R127K-R159N | 6.02 |
| R35D-R159E | 7.25 |
| R35E-G54D-N67S-G78D-R159K | 1.58 |
| N24Q-G54D-G78D-R159N | 2.84 |
| R127K-R159E | 6.58 |
| R127Q-R159E | 5.76 |
| N24E-R35E-G54D-N67S-R127K-R159N | 9.73 |
| R35D-G78D-R159K | 5.17 |
| N67S-R159E | 2.05 |
| G54D-R127K-R159K | 6.11 |
| G78D-R127K-R159K | 2.76 |
| G78D-R127K-R159E | 2.63 |
| N24E-R35D-G78D-R127K-R159N | 11.02 |
| R35D-G78D-R127K-R159N | 5.38 |
| N24A-R35E-G78D-R159N | 4.03 |
| N24Q-R35D-N67S-R127K-R159E | 2.13 |
| N24T-R35D-G78D-R159K | 6.73 |
| N67S-G78D-R127K-R159K | 1.12 |
| N24Q-R35D-R127K-R159K | 7.33 |
| N24E-G54D-G78D-R159K | 8.72 |
| R35D-R159K | 6.89 |
| R35E-R159K | 7.66 |
| R127K-R159K | 5.82 |
| R35E-N67S-G78D-R127Q | 2.67 |
| N24E-R35D-G78D | 11.21 |
| R35D-G78D-R127K-R159E | 5.44 |
| N24E-R35E-G54D-N67S-G78D-R127K-R159K | 7.87 |
| N24T-N67S-R159E | 3.10 |
| N24D-R35D-G78D-R159F | 9.11 |
| N24Q-R35D-N67S-G78D-R127K-R159F | 1.50 |
| R35D-G78D-R127Q-R159K | 4.41 |
| G78D-R159F | 2.48 |
| N24A-N67S-R159K | 1.14 |
| G78D-R127Q-R159K | 2.63 |
| N24T-G54D-N67S-G78D-R127Y-R159E | 2.42 |

In additional experiments, the LAS stability of numerous variants was tested at 25° C., using the protocol set forth in Example 1. As above, the selection criterion was residual activity greater than WT+1 standard deviation (>1.1 Performance Index).

TABLE 8-6

LAS Stability Assay Results

| Variant | LAS Stab-25° [Perf. Ind] |
|---|---|
| R14I-A63K-G78D-R123F-D184T | 2.66 |
| R14I-A63K-R123F-R159E-D184T | 3.53 |
| R14I-A63K-R123F-R159F-D184T | 3.48 |
| R14I-A63K-R123F-R159K-D184T | 3.33 |
| R14I-A63K-R123F-R159N-D184T | 3.83 |
| R14I-A63K-R123K-D184T | 3.38 |
| R14I-A63K-R123Q-D184T | 3.58 |
| R14I-A63K-R123Y-D184T | 3.62 |
| R14I-A64K-G78D-T86K-T116E-R123F | 1.47 |
| R14I-A64K-T86K-T116E-R123F-R159E | 5.21 |
| R14I-A64K-T86K-T116E-R123F-R159K | 5.11 |
| R14I-A64K-T86K-T116E-R123K | 4.21 |
| R14I-A64K-T86K-T116E-R123Q | 4.74 |
| R14I-A64K-T86K-T116E-R123Y | 4.34 |
| R14I-G54D-A63K-R123F-D184T | 2.74 |
| R14I-G54D-A64K-T86K-T116E-R123F | 4.12 |
| R14I-G54D-S76N-A93H-R127K-R159K-I181Q | 8.53 |
| R14I-G54D-S76V-A93S-R127K-R159K-I181K | 3.53 |
| R14I-N24A-A63K-R123F-D184T | 2.59 |
| R14I-N24A-A64K-T86K-T116E-R123F | 3.11 |
| R14I-N24E-A63K-R123F-D184T | 7.31 |
| R14I-N24E-A64K-T86K-T116E-R123F | 9.39 |
| R14I-N24Q-A63K-R123F-D184T | 4.13 |
| R14I-N24Q-A64K-T86K-T116E-R123F | 4.51 |
| R14I-N24T-A63K-R123F-D184T | 4.35 |
| R14I-N24T-A64K-T86K-T116E-R123F | 6.54 |
| R14I-N24TS76N-A93H-R127K-R159K-I181Q | 7.43 |
| R14I-N24TS76V-A93S-R127K-R159K-I181K | 1.78 |
| R14I-N67AS76N-A93H-R127K-R159K-I181Q | 4.59 |
| R14I-N67LS76N-A93H-R127K-R159K-I181Q | 2.71 |
| R14I-N67SS76N-A93H-R127K-R159K-I181Q | 4.32 |
| R14I-R35D-A64K-T86K-T116E-R123F | 5.72 |
| R14I-R35D-S76N-A93H-R127K-R159K-I181Q | 9.45 |
| R14I-R35E-A63K-R123F-D184T | 3.50 |
| R14I-R35E-A64K-T86K-T116E-R123F | 6.08 |
| R14I-R35E-S76N-A93H-R127K-R159K-I181Q | 9.00 |
| R14I-R35E-S76V-A93S-R127K-R159K-I181K | 5.22 |
| R14I-R35K-A63K-R123F-D184T | 3.10 |
| R14I-S76N-A93H-R127K-R159E-I181Q | 8.54 |
| R14I-S76N-A93H-R127K-R159F-I181Q | 7.56 |
| R14I-S76N-A93H-R127K-R159N-I181Q | 9.01 |
| R14I-S76N-A93H-R127Q-R159K-I181Q | 9.11 |
| R14I-S76N-A93H-R127Y-R159K-I181Q | 6.88 |
| R14I-S76N-G78D-A93H-R127K-R159K-I181Q | 5.55 |
| R14I-S76V-A93S-R127K-R159F-I181K | 1.82 |
| R14I-S76V-A93S-R127K-R159N-I181K | 2.00 |
| R14I-S76V-A93S-R127Q-R159K-I181K | 2.59 |
| R14I-S76V-A93S-R127Y-R159K-I181K | 1.63 |
| R14M-G54D-S76N-A93G-R127K-R159K-I181K | 7.52 |
| R14M-N24A-S76N-A93G-R127K-R159K-I181K | 1.38 |
| R14M-N24E-S76N-A93G-R127K-R159K-I181K | 7.17 |
| R14M-N24Q-S76N-A93G-R127K-R159K-I181K | 3.58 |
| R14M-N24T-S76N-A93G-R127K-R159K-I181K | 5.57 |
| R14M-N67S-S76N-A93G-R127K-R159K-I181K | 1.53 |
| R14M-R35D-S76N-A93G-R127K-R159K-I181K | 8.65 |
| R14M-R35E-S76N-A93G-R127K-R159K-I181K | 9.25 |
| R14M-S76N-A93G-R127K-R159E-I181K | 6.89 |
| R14M-S76N-A93G-R127K-R159F-I181K | 5.14 |
| R14M-S76N-A93G-R127K-R159N-I181K | 6.71 |
| R14M-S76N-A93G-R127Q-R159K-I181K | 5.85 |
| R14M-S76N-A93G-R127Y-R159K-I181K | 4.75 |
| R14M-S76N-G78D-A93G-R127K-R159K-I181K | 2.13 |

As indicated by these results, numerous multiply-substituted variants performed better than the wild-type ASP in this assay system.

Example 9

Stain Removal Performance of Multiply-Substituted Mutants

In these experiments, the protocol used is described in Example 1, above. The following table provides the variants, including the mutations in each variant for those with activity greater than wild-type plus one standard deviation (>1.1 Performance Index [PI]). As indicated by these results, numerous multiply-substituted variants performed better than the wild-type ASP in this assay system.

TABLE 9-1

Wash Performance Results

| Variant | BMI LVJ1 Detergent [Perf. Ind] |
|---|---|
| N24F-R159G | 1.24 |
| N24F-R159L-R123V | 1.22 |
| N24I-R127S | 1.15 |
| N24L-R159S | 1.14 |
| N24S-R159A | 1.41 |
| N24V-R159L | 1.34 |
| N24Y-R159F | 1.14 |
| R14A-N24K-R127S | 1.32 |
| R14A-R159W | 1.12 |
| R14L-N24Y | 1.32 |
| R14L-R159G | 1.22 |
| R14L-R159S | 1.11 |
| R14L-T109M | 1.14 |
| R14L-T39P | 1.26 |
| R14M-R159W | 1.18 |
| R14S-N24V | 1.34 |
| R14S-N24Y | 1.32 |
| R14T-N24A | 1.16 |
| R14V-N24G-P189S | 1.23 |
| R14V-R159W | 1.17 |
| R127A-R159K | 1.23 |
| R14I-G65Q | 1.32 |
| R14I-S76V | 1.27 |
| R14I-G65Q-N67L-R159K | 1.11 |
| R14I-G65Q-R159K | 1.32 |
| R14I-S76V | 1.48 |

In additional experiments using liquid detergent, the following results were obtained. The variants indicated in the following table exhibited activity greater than wild-type plus one standard deviation (>1.1 Performance Index), as shown in the following Tables.

TABLE 9-2

Wash Performance Results for LVJ-1

| Variants | BMI LVJ-1 Detergent [Perf.Ind.] |
|---|---|
| R35F R159Q | 1.13 |
| R16Q R79T | 1.31 |
| R16Q R35F | 1.10 |
| R16Q R159Q | 1.17 |
| R14L R79T | 1.45 |
| R123L R159Q | 1.16 |
| G12D-S15E | 1.23 |
| G12D-R35H | 1.46 |
| G12D-R35D | 1.13 |

TABLE 9-3

Wash Performance Results for TIDE ® 2005

| Variant | BMI Tide2005 Detergent [Perf. Ind] |
|---|---|
| N024E-G049A-A093H--R127K-A143N-R159K-I181Q | 1.23 |
| N024H-S076A-A093S-S099A-R127K-R159K-G054H-L069H | 1.11 |
| N024H-S076A-A093T-S099G-R127K-R159K | 1.16 |
| N024L-S076V-A093S-S099A-R127K-R159K | 1.11 |
| N024Q-G049A-A093S-S099A-R127K-A143N-R159K-I181T | 1.13 |
| N024T-G049A-A093S-S099A-R127K-A143N-R159K-I181T | 1.13 |
| N24E-G54Q-A93S-R127K-R159K | 1.17 |
| N24H-A93H-R127K-R159K | 1.14 |
| N24H-G54L-S76V-A93H-R127K-R159K | 1.28 |
| N24L-G54Q-S76A-A93H-R127K-R159K | 1.13 |
| N24M-A93G-R127K-R159K | 1.10 |
| N24M-G54E-A93H-R127K-R159K | 1.15 |
| N24M-S76V-A93H-R127K-R159K | 1.29 |
| N24Q-G54Q-S76T-A93H-R127K-R159K | 1.11 |
| N24Q-S76A-A93G-R127K-R159K | 1.13 |
| N24T-G54Q-S76N-A93G-R127K-R159K | 1.14 |
| N24T-S76I-R127K-R159K | 1.12 |
| N24W-G54D-A93H-R127K-R159K | 1.20 |
| N24W-S76A-A93H-R127K-R159K | 1.14 |
| N24W-S76T-A93G-R127K-R159K | 1.12 |
| N24W-S76V-A93G-R127K-R159K | 1.12 |
| N24W-S76Y-A93G-R127K-R159K | 1.22 |
| R014I-S076A-A093G-R127K-R159K-I181T | 1.22 |
| R014I-S076A-A093H-R127K-R159K-I181K | 1.23 |
| R014I-S076A-A093H-R127K-R159K-I181Q | 1.14 |
| R014I-S076A-A093H-R127K-R159K-I181T | 1.15 |
| R014I-S076D-A093S-R127K-R159K-I181T | 1.10 |
| R014I-S076E-A093T-R127K-R159K-I181K | 1.28 |
| R014I-S076N-A093H-R127K-R159K-I181Q | 1.26 |
| R014I-S076V-A093H-R127K-R159K-I181Q | 1.22 |
| R014I-S076V-A093S-R127K-R159K-I181K | 1.27 |

TABLE 9-3-continued

Wash Performance Results for TIDE ® 2005

| Variant | BMI Tide2005 Detergent [Perf. Ind] |
|---|---|
| R014K-S076A-A093S-R127K-R159K-I181T | 1.21 |
| R014K-S076E-A093H-R127K-R159K-I181K | 1.19 |
| R014K-S076I-A093S-R127K-R159K-I181T | 1.14 |
| R014K-S076T-A093H-R127K-R159K-I181K | 1.11 |
| R014K-S076T-A093H-R127K-R159K-I181T | 1.23 |
| R014K-S076V-A093H-R127K-R159K-I181K | 1.11 |
| R014L-S076A-A093H-R127K-R159K | 1.34 |
| R014L-S076A-A093H-R127K-R159K-I181Q | 1.13 |
| R014L-S076D-A093H-R127K-R159K-I181T | 1.17 |
| R014L-S076E-A093H-R127K-R159K-I181K | 1.23 |
| R014M-S076A-A093G-R127K-R159K-I181K | 1.25 |
| R014M-S076A-A093G-R127K-R159K-I181T | 1.12 |
| R014M-S076A-A093H-R127K-R159K-I181T | 1.18 |
| R014M-S076A-A093S-R127K-R159K-I181K | 1.46 |
| R014M-S076A-A093S-R127K-R159K-I181T | 1.17 |
| R014M-S076A-A093T-R127K-R159K-I181Q | 1.11 |
| R014M-S076I-A093H-R127K-R159K-I181T | 1.30 |
| R014M-S076I-A093S-R127K-R159K-I181T | 1.23 |
| R014M-S076N-A093G-R127K-R159K-I181K | 1.23 |
| R014M-S076N-A093G-R127K-R159K-I181T | 1.24 |
| R014M-S076N-A093H-R127K-R159K-I181T | 1.39 |
| R014M-S076N-A093S-R127K-R159K-I181T | 1.28 |
| R014M-S076T-A093H-R127K-R159K-I181K | 1.28 |
| R014M-S076V-A093G-R127K-R159K-I181Q | 1.17 |
| R014M-S076W-A093H-R127K-R159K-I181K | 1.14 |
| R014M-S076Y-A093H-R127K-R159K-I181K | 1.29 |
| R014M-S076Y-A093H-R127K-R159K-I181T | 1.14 |
| G012D-R035E-D184N | 1.13 |
| G012D-R035E-N067K | 1.24 |

In further experiments, the following results were obtained. In these experiments, the variants were compared to 0.5 ppm wild-type ASP as a reference. The results in the following table are provided for variants that had activities greater than wild-type plus one standard deviation (>1.1 Performance Index).

TABLE 9-4

Wash Performance Results for TIDE ® SNOW A Detergent

| Variant | BMI TIDE-SNOWA Detergent [Perf. ind] |
|---|---|
| R14I-A64K-R123F-R159F-D184T | 1.27 |
| R14I-A64K-R123F-R159F-D184T | 1.45 |
| R14I-N24Q-A64K-G78D-R123F-R159K-D184T | 1.38 |
| R14I-N24Q-A64K-N67S-R123F-R159F-D184T | 1.34 |
| R14I-N24Q-A64K-N67A-R123F-R159K-D184T | 1.40 |
| R14I-N24A-A64K-N67S-G78D-R123F-R159K-D184T | 1.31 |
| R14I-A64K-R123F-D184T | 1.45 |
| R14I-N24A-A64K-R123F-R159N-D184T | 1.47 |
| R14I-N24Q-R35D-A64K-N67S-R123F-R159K-D184T | 1.23 |
| R14I-N24Q-A64K-N67A-R123F-R159K-D184T | 1.45 |
| R14I-N24E-A64K-R123F-R127K-R159K-D184T | 1.23 |
| R14I-N24A-A64K-R123F-D184T | 1.65 |
| R14I-A64K-R123F-R127K-R159F-D184T | 1.48 |
| R14I-A64K-R123F-R159N-D184T | 1.38 |
| R14I-A64K-R123F-R159K-D184T | 1.66 |
| R14I-A64K-R123F-R127Y-R159K-D184T | 1.11 |

TABLE 9-4-continued

Wash Performance Results for TIDE ® SNOW A Detergent

| Variant | BMI TIDE-SNOWA Detergent [Perf. ind] |
|---|---|
| R14I-N24Q-A64K-R123F-R127Q-R159K-D184T | 1.25 |
| R14I-A64K-R123F-R159K-D184T | 1.55 |
| R14I-N24Q-R35D-A64K-N67S-R123F-R159K-D184T | 1.22 |
| R14I-A64K-N67S-G78D-R123F-R127K-R159K-D184T | 1.48 |
| R14I-N24Q-A64K-N67A-R123F-R127K-R159K-D184T | 1.67 |
| R127K-R159K | 1.53 |
| N24A-N67S-R159K | 1.55 |
| N24A-N67A-R159K | 1.58 |

In additional experiments, the following results were obtained. The variants indicated in the following table exhibited activity greater than wild-type plus one standard deviation (>1.1 Performance Index).

TABLE 9-5

Wash Performance Results for TIDE ®-SNOW

| Variant | BMI TIDE-SNOW Detergent [Perf. Ind] |
|---|---|
| R14I-A63K-G78D-R123F-D184T | 1.39 |
| R14I-A63K-N67A-R123F-D184T | 1.50 |
| R14I-A63K-N67L-R123F-D184T | 1.23 |
| R14I-A63K-N67S-R123F-D184T | 1.48 |
| R14I-A63K-R123F-R159F-D184T | 1.75 |
| R14I-A63K-R123F-R159K-D184T | 1.70 |
| R14I-A63K-R123F-R159N-D184T | 1.67 |
| R14I-A63K-R123K-D184T | 1.40 |
| R14I-A63K-R123Q-D184T | 1.44 |
| R14I-A63K-R123Y-D184T | 1.25 |
| R14I-A64K-G78D-T86K-T116E-R123F | 1.26 |
| R14I-A64K-N67A-T86K-T116E-R123F | 1.66 |
| R14I-A64K-N67L-T86K-T116E-R123F | 1.19 |
| R14I-A64K-T86K-T116E-R123F-R159K | 1.54 |
| R14I-A64K-T86K-T116E-R123K | 1.70 |
| R14I-G54D-A63K-R123F-D184T | 1.13 |
| R14I-G54D-A64K-T86K-T116E-R123F | 1.11 |
| R14I-N24A-A63K-R123F-D184T | 1.47 |
| R14I-N24A-A64K-T86K-T116E-R123F | 1.56 |
| R14I-N24A-S76V-A93S-R127K-R159K-I181K | 1.15 |
| R14I-N24E-A63K-R123F-D184T | 1.36 |
| R14I-N24E-A64K-T86K-T116E-R123F | 1.26 |
| R14I-N24Q-A63K-R123F-D184T | 1.47 |
| R14I-N24Q-A64K-T86K-T116E-R123F | 1.57 |
| R14I-N24Q-S76V-A93S-R127K-R159K-I181K | 1.43 |
| R14I-N24T-A63K-R123F-D184T | 1.57 |
| R14I-N24T-A64K-T86K-T116E-R123F | 1.38 |
| R14I-N24TS76V-A93S-R127K-R159K-I181K | 1.13 |
| R14I-N67SS76N-A93H-R127K-R159K-I181Q | 1.17 |
| R14I-R35E-A63K-R123F-D184T | 1.55 |
| R14I-R35K-A63K-R123F-D184T | 1.20 |
| R14I-S76V-A93S-R127K-R159F-I181K | 1.12 |
| R14I-S76V-A93S-R127K-R159N-I181K | 1.31 |
| R14I-S76V-A93S-R127Y-R159K-I181K | 1.30 |
| R14M-N24T-S76N-A93G-R127K-R159K-I181K | 1.11 |
| R14M-N67S-S76N-A93G-R127K-R159K-I181K | 1.22 |
| R14M-S76N-A93G-R127K-R159F-I181K | 1.41 |
| R14M-S76N-G78D-A93G-R127K-R159K-I181K | 1.20 |

Example 10

Stain Removal Performance of Multiply-Substituted Mutants

In this Example, experiments conducted to determine the stain removal ability of various multiply-substituted ASP variants are described. In these experiments, the following protocols and materials were used.

First, 105 ppm water (~6 gpg) was prepared by first preparing a 10,000 ppm stock solution (3/1 $Ca^{+2}/Mg^{+2}$) by dissolving 11.020 g/L calcium chloride dehydrate ($CaCl_2.2H_2O$) MW 147.01 g/mol and 5.08 g/L magnesium chloride hexahydrate ($MgCl_2.6H_2O$) MW 203.3 g/mol in 1000 ml deionized water. The 105 ppm solution was prepared by diluting 10.50 ml of the 10,000-ppm stock with 989.50 ml deionized water.

A TIDE®E 2005 detergent solution (1.6 gm/L) was prepared in the 105 ppm water by dissolving 11.2 gm TIDE®-2005 in 7 liters of 105 ppm water.

Blood-Milk-Ink (BMI) soiled swatches EMPA 116 (11×8 cm), EMPA117 (11×8 cm) both from EMPA Testmaterialien AG and grass soiled swatches EMPA164 (10×7.5 cm) from EMPA Testmaterialien AG and Equest grass medium soiled (10×7.5 cm) from Warwick Equest Limited used in these experiments were numbered using a waterproof pen (on the soiled sides). The soiled sides of the swatches were measured using Tristimulus Minolta Meter CR-300 (Minolta), and analyzed using the equation L (L*a*b), D65 Std. Illuminate, on a white background. Three readings were made per swatch. As grass stains are very sensitive to light, grass-soiled swatches were covered and stored in the dark until they were used. Every wash performance test was conducted in duplicate.

During the test, extra ballast (more mechanical action) was used. This ballast comprised 2 pieces of 10×10 cm EMPA 221 (unsoiled cotton, EMPA Testmaterialien AG placed in one beaker. These EMPA 221 swatches were not numbered or measured.

The laundry wash performance test was conducted using a 6 pot, bench model Tergotometer (TOM) Model 7243S (United States Testing). The temperature was adjusted 15° C. or 60° F. Half of the inside of the TOM was filled with ice. The wash time was set for 12 minutes. Test beakers were filled with 1 liter of the detergent solution (made in 105 ppm water, as described above). Once the solutions have reached 15° C. or 60° F., the TOM was started with an agitation of 100 rpm. The variant samples were then added to the mixture as indicated below. As a control, the TIDE® 2005 detergent solution (Procter & Gamble) without any added enzyme sample was In order to obtain a measure for the stain removal of each individual variant the delta percentage of soil removal was then calculated by subtracting the percentage of soil removal obtained by the TIDE® 2005 detergent solution without any variant from the percentage of soil removal in the presence of each variant (delta % SR). The results are shown in Table 10.1

In additional experiments, the stain removal abilities of various multiply-substituted ASP variants were tested. The test conditions as described above were used with the following modifications. In these tests a TIDE®2005 SNOW detergent solution (1.5 gm/L) was prepared in the 105 ppm water by, dissolving 37.5 gm TIDE®2005 SNOW in 25 liters of 105 ppm water. Furthermore, the EMPA 116 BMI soiled swatches were cut into pieces of 10×7.5 cm. The EMPA 117 swatches were replaced by EMPA 116 Fixed swatches (CFT) and also cut into pieces of 10×7.5 cm. No EMPA 164 swatches were used in these experiments. The variants were tested at one concentration of 0.55 ppm. Six swatches (i.e. 6 EMPA 116, or 6 EMPA 116 fixed or 6 Equest) were added to each beaker one at a time. In addition, 2 EMPA 221 swatches were added. As a control, TIDE® 2005 SNOW detergent solution (Procter & Gamble), without any added enzyme sample was used. Every wash performance test was conducted in

TABLE 10.1

| Variants/Dosage | EMPA 116 Δ % S.R. (n = 6) | EMPA 117 Δ % S.R. (n = 6) | Equest Grass Δ % S.R. (n = 6) | EMPA 164 Δ % S.R. (n = 6) |
|---|---|---|---|---|
| ASP/0.55 ppm | 5.2 ± 1.2 | 4.9 ± 2.4 | −4.3 ± 4.3 | 1.5 ± 1.1 |
| ASP/2.75 ppm | 9.7 ± 1.4 | 10.7 ± 2.8 | −1.8 ± 5.4 | 3.1 ± 1.6 |
| R123L-R127Q-R179Q/0.55 ppm | 6.0 ± 1.5 | 8.5 ± 2.1 | 1.7 ± 3.7 | 2.1 ± 1.2 |
| R123L-R127Q-R179Q/2.75 ppm | 11.3 ± 1.5 | 14.0 ± 2.7 | 1.1 ± 5.0 | 5.4 ± 1.4 |
| G12D-R35H/0.55 ppm | 7.0 ± 1.1 | 7.9 ± 1.9 | −2.2 ± 5.0 | 2.5 ± 1.3 |
| G12D-R35H/2.75 ppm | 10.1 ± 1.7 | 14.4 ± 1.9 | 3.2 ± 3.8 | 4.5 ± 1.0 |
| G12D-R35E/0.55 ppm | 8.2 ± 1.2 | 10.0 ± 2.1 | 1.3 ± 5.4 | 2.9 ± 1.4 |
| G12D-R35E/2.75 ppm | 10.6 ± 1.4 | 16.6 ± 2.1 | 4.3 ± 4.2 | 5.4 ± 1.4 |
| R35E-R123L-R127Q-R179Q/0.55 ppm | 6.1 ± 1.2 | 6.8 ± 2.1 | 0.4 ± 4.1 | 1.0 ± 1.4 |
| R35E-R123L-R127Q-R179Q/2.75 ppm | 8.8 ± 2.1 | 12.7 ± 1.8 | 4.7 ± 4.3 | 1.7 ± 1.4 | used. The variants were tested at two different concentrations (i.e., at 0.55 ppm and at 2.75 ppm).

Six swatches (with the same soils) were added to each beaker one at a time. In addition, 2 EMPA 221 swatches were added. For example: for BMI soiled swatches 3 EMPA 116 and 3 EMPA117+2 EMPA 221 (total weight is approximately 13.25 gram), or, for grass soiled swatches 3 EMPA 164 and 3 Equest grass medium soiled+2 EMPA 221 (total weight is approximately 13.22 gram). The wash time was then reset on 12 minutes. After 12 minutes of washing, all of the EMPA 116 and EMPA 117 swatches were rinsed in a bucket and all the grass swatches were rinsed a separate bucket for 3 minutes under cold running tap water. The EMPA 221 swatches were then discarded. The swatches were placed in a spin-dryer for 2 minutes (the EMPA 116 and the EMPA 117 swatches were dried separately from the grass stained-swatches). Subsequently, the grass-stained swatches were dried in the air, without light or ironing., whereas the EMPA 116 and EMPA 117 swatches were dried by ironing.

After drying, the soiled sides of the swatches were evaluated using the Tristimulus Minolta Meter CR-300 with equation L (L*a*b), D65 Std. Illuminate, on a white background, 3 readings per swatch. The percent soil removal was calculated using the equation:

% Soil Removal=($L$ value after washing–$L$ value before washing)/($L_{0\ white\ cotton}$–$L$ value before washing)×100% quadruplicate. The results (average delta % SR, Standard deviation (STD) and number of replicates (n)) are shown in FIG. 6.

In another set of experiments, the stain removal ability of numerous multiply-substituted ASP variants, were tested. The test conditions as described above were used with the following modifications. In these tests, a TIDE®2005 SNOW detergent solution (1.5 gm/L) containing HEPES buffer was prepared in the 105 ppm water by dissolving 37.5 gm TIDE® 2005 SNOW in 25 liters of 105 ppm water. Then, 30 g Hepes (=5 mM; $C_8H_{18}N_2O_4S$), was added, the solution was stirred, and the pH adjusted to 7.8 with ±19 ml 4N NaOH. It was noted that this solution can be stored for 36 hours at room temperature. In these tests, only EMPA 116 BMI soiled swatches of 10×7.5 cm and Equest grass medium soiled swatches of 10×7.5 cm were used. The variants were tested at one concentration of 0.55 ppm. Six swatches (either 6 EMPA 116, or 6 Equest grass medium soiled) were added to each beaker one at a time. In addition, 2 EMPA 221 swatches were added. As a control, TIDE® 2005 SNOW detergent solution (Procter & Gamble) with HEPES buffer, without any added enzyme sample was used. Every wash performance test was conducted in quadruplicate. The results (average D % SR, Standard deviation (STD) and number of replicates (n)) are shown in FIG. 7.

As indicated by these results, numerous multiply-substituted variants performed better than the wild-type ASP in this assay system.

Example 11

Stain Removal Performance of Multiply-Substituted Mutants Tested at Low pH

In this Example, experiments conducted to determine the stain removal performance of various multiply-substituted ASP variants are described. In these experiments, the protocol used is described in Example 1, above. The following table provides the variants, including the mutations in each variant for those with activity greater than that of wild-type ASP plus 1 standard deviation (1.1 Performance Index).

TABLE 11-1

| Stain Removal Performance at Low pH | |
|---|---|
| Variant | BMI Low pH [Perf. ind] |
| G54E-R14L | 1.40 |
| N24D-R127Y-R159V | 1.61 |
| N24E-R127S | 1.43 |
| N24E-R159C | 1.14 |
| N24F-R159G | 1.42 |
| N24F-R159G-G54E | 1.98 |
| N24F-R159L-R123V | 1.61 |
| N24G-R127Y | 1.34 |
| N24H-R159Y-T46I | 1.34 |
| N24I-R127S | 1.21 |
| N24I-R127V-R14V | 1.12 |
| N24L-R159S | 1.37 |
| N24S-R159A | 2.48 |
| N24V-R127M-R159V | 1.33 |
| N24V-R127S-R159H | 1.60 |
| N24V-R159L | 1.41 |
| N24Y-G54A | 1.11 |
| N24Y-R127L | 1.37 |
| N24Y-R127S | 1.14 |
| N24Y-R127V | 1.22 |
| N24Y-R159F | 1.29 |
| R127A-R159F | 1.12 |
| R127H-R159Q | 1.78 |
| R127H-R159T-S185F | 1.66 |
| R127M-R159V | 1.70 |
| R127S-R159G | 1.21 |
| R127S-R159L | 1.27 |
| R127T-R159F | 1.28 |
| R127V-R159G | 1.36 |
| R127Y-R159L | 2.14 |
| R14A-N24K-R127S | 1.41 |
| R14A-R127Y-R159W | 1.17 |
| R14G-N24S-R127C | 1.10 |
| R14G-R127G | 1.17 |
| R14L-N24D | 1.73 |
| R14L-N24Y | 1.19 |
| R14L-R123L | 2.11 |
| R14L-R127S | 1.47 |
| R14L-R127V | 1.18 |
| R14L-R127Y | 1.78 |
| R14L-R159G | 1.51 |
| R14L-R159S | 1.52 |
| R14L-T39P | 1.50 |
| R14M-N24L-R159S-R123V | 1.15 |
| R14M-R159F | 1.18 |
| R14M-R159W | 1.36 |
| R14Q-R123F | 1.58 |
| R14S-N24E-R127W | 1.31 |

TABLE 11-1-continued

| Stain Removal Performance at Low pH | |
|---|---|
| Variant | BMI Low pH [Perf. ind] |
| R14S-N24V | 1.11 |
| R14S-N24Y | 1.12 |
| R14T-N24T-R127Q | 1.38 |
| R14T-R127Y | 1.98 |
| R14V-N24D-R127C | 1.28 |
| R14V-N24G-P189S | 1.14 |
| R14V-N24L-R127F | 1.14 |
| R14V-R127A | 1.55 |
| R14V-R159F | 1.43 |
| R14V-R159W | 1.24 |
| R14W-N24A | 1.10 |
| R14W-R123L | 1.19 |
| R14W-R123V | 1.40 |
| R14W-R159V | 1.15 |
| R159V-G49D | 1.67 |
| R159V-R123G | 1.20 |
| N024E-G049A-A093H-R127K-A143N-R159K-I181Q | 1.29 |
| N024E-G049A-A093S-S099D-R127K-A143N-R159K-I181Q | 1.11 |
| N024Q-G049A-A093S-S099A-R127K-A143N-R159K-I181T | 1.12 |
| N24A-G54E-S76D-A93G-R127K-R159K | 1.41 |
| N24E-A93G-R127K-R159K | 1.32 |
| N24E-G54L-S76E-A93G-R127K-R159K | 1.15 |
| N24E-G54Q-A93S-R127K-R159K | 1.46 |
| N24E-S76D-A93T-R127K-R159K | 1.35 |
| N24H-G54E-A93G-R127K-R159K | 1.10 |
| N24L-S76T-A93G-R127K-R159K | 1.24 |
| N24M-A93S-R127K-R159K | 1.23 |
| N24M-A93T-R127K-R159K | 1.18 |
| N24M-G54E-A93H-R127K-R159K | 1.35 |
| N24M-G54E-S76N-A93S-R127K-R159K | 1.36 |
| N24M-S76V-A93H-R127K-R159K | 1.16 |
| N24Q-A93G-R127K-R159K | 1.10 |
| N24Q-G54D-S76L-A93G-R127K-R159K | 1.11 |
| N24Q-G54I-S76T-A93G-R127K-R159K | 1.10 |
| N24Q-G54Q-A93G-R127K-R159K | 1.10 |
| N24Q-S76A-A93G-R127K-R159K | 1.12 |
| N24T-G54Q-S76N-A93G-R127K-R159K | 1.19 |
| N24T-G54Q-S76V-R127K-R159K | 1.20 |
| N24T-S76I-R127K-R159K | 1.14 |

TABLE 11-1-continued

Stain Removal Performance at Low pH

| Variant | BMI Low pH [Perf. ind] |
|---|---|
| N24W-A93G-R127K-R159K | 1.20 |
| N24W-G54D-A93H-R127K-R159K | 1.21 |
| R014I-S076A-A093G-R127K-R159K-I181T | 1.21 |
| R014I-S076A-A093H-R127K-R159K-I181Q | 1.16 |
| R014I-S076D-A093H-R127K-R159K-I181Q | 1.10 |
| R014I-S076D-A093H-R127K-R159K-I181T | 1.27 |
| R014I-S076D-A093S-R127K-R159K-I181T | 1.31 |
| R014I-S076E-A093S-R127K-R159K-I181Q | 1.46 |
| R014I-S076E-A093T-R127K-R159K-I181K | 1.20 |
| R014I-S076N-A093H-R127K-R159K-I181Q | 1.13 |
| R014L-S076A-A093H-R127K-R159K | 1.21 |
| R014L-S076A-A093H-R127K-R159K-I181Q | 1.15 |
| R014L-S076D-A093H-R127K-R159K-I181T | 1.16 |
| R014M-S076A-A093G-R127K-R159K-I181T | 1.30 |
| R014M-S076A-A093S-R127K-R159K-I181K | 1.35 |
| R014M-S076A-A093S-R127K-R159K-I181T | 1.15 |
| R014M-S076A-A093T-R127K-R159K-I181Q | 1.28 |
| R014M-S076D-A093S-R127K-R159K-I181T | 1.31 |
| R014M-S076E-A093H-R127K-R159K-I181T | 1.12 |
| R014M-S076E-A093S-R127K-R159K-I181T | 1.16 |
| R014M-S076N-A093G-R127K-R159K-I181K | 1.12 |
| R014M-S076N-A093G-R127K-R159K-I181T | 1.19 |
| R014M-S076N-A093H-R127K-R159K-I181T | 1.15 |
| R014M-S076N-A093S-R127K-R159K-I181T | 1.32 |

In additional experiments using liquid detergent, the following results were obtained. The variants indicated in the following table exhibited activity greater than wild-type plus one standard deviation (>1.1 Performance Index).

TABLE 11-2

Wash Performance at Low pH

| Variant | BMI Low pH Detergent [Perf.Ind.] |
|---|---|
| T36S-R127Q-R159E | 1.24 |
| S15E-R35E | 1.15 |
| S15E-R35D | 1.20 |
| S15E-R159E | 1.24 |
| S15E-R127Q | 1.39 |
| S15E-R123Q | 1.22 |
| S15E-R123E | 1.38 |
| R79T R127Q R179Q | 1.23 |
| R35H-R159E | 1.37 |
| R35F R61S R159Q | 1.39 |
| R35F R159Q | 1.49 |
| R35D-R127Q | 1.56 |
| R16Q R79T R159Q R179Q | 1.42 |
| R16Q R79T R123L | 1.62 |
| R16Q R79T | 1.59 |
| R16Q R35F | 1.29 |
| R16Q R159Q R179Q | 1.31 |
| R16Q R159Q | 1.26 |
| R14Q-T121E | 1.37 |
| R14Q-R35E | 1.36 |
| R14Q-R35D | 1.27 |
| R14Q-R123Q | 1.33 |
| R14L R79T | 1.59 |
| R127Q-R159E | 1.34 |
| R127Q R159Q | 1.45 |
| R123Q-R159E | 1.51 |
| R123L R159Q | 1.58 |
| R123F-R159E | 1.77 |
| G12D-S15E | 1.71 |
| G12D-R35H-R159E | 1.74 |
| G12D-R35H-R123Q | 1.89 |
| G12D-R35H | 2.38 |
| G12D-R35E | 1.85 |
| G12D-R35D | 1.68 |
| G12D-R159E | 1.32 |
| G12D-R14Q-R35H | 1.44 |
| G12D-R14I-R35H | 1.54 |
| G65Q-R127A-R159K | 1.10 |
| R127A-R159K | 1.35 |
| R14I-G65Q | 1.38 |
| R14I-G65Q-N67L-R159K | 1.14 |
| R14I-G65Q-R127A- | 1.43 |
| R14I-G65Q-R127A-R159K | 1.27 |
| R14I-G65Q-R159K | 1.38 |
| R14I-R127A | 1.33 |
| R14I-R127A-R159K | 1.44 |
| R14I-R159K | 1.32 |
| R14I-R35F | 1.13 |
| R14I-R35F-G65Q | 1.16 |
| R14I-R35F-R159K | 1.28 |
| R14I-S76V | 1.40 |
| R35F-R127A-R159K | 1.17 |

As indicated by these results, numerous multiply-substituted variants performed better than the wild-type ASP in this assay system.

Example 12

Cleaning Performance of ASP Variants in Automatic Dishwashing

In this Example, experiments conducted to determine the cleaning performance of ASP variants in Automatic Dish Washing (ADW) TABLET ACTION PACK® detergent in comparison with a benchmark serine protease ("Protease B")

on protease-sensitive stains described. As shown in the Table below, ASP variants removes stains much better than protease B.

A micro-washing test with 24 well plates was performed. Stainless steel disks were punched out using a hammer and punch. The disks were cleaned and weighed, in order to obtain initial weights. Egg stains were prepared as described below ("Scrambled Egg Preparation" and "Egg Yolk Preparation"). Then, 50 uL of prepared egg were dispensed onto each disk. The preparations were allowed to dry at room temperature for 30 minutes, then were baked in an oven at 80° C. for 2 hours. The disks were cooled to room temperature. After soiling, the disks were weighed in order to obtain the soiled weights of the disks. The soiled disks were inserted into NUNCLON® 24 well polystyrene plate. Auto dish washing product solution was prepared by thoroughly mixing the appropriate amount of ADW without enzyme product (e.g., Powder 4500 ppm) into 1L of 11 gpg water at 40° C. Hardness solution was prepared by mixing 188.57 g $CaCl_2.2H_2O$ and 86.92 g $MgCl_2.6H_2O$ into 1 L DI water. In the test, 2 mL of pre-warmed ADW solution were added at 55° C. to each well. The appropriate amount of enzyme was then to each well. In some embodiments, the tests were run using six across, with four duplicates, while in other embodiments, the test were run four across with six duplicates. The plates were then sealed with film. The plates were placed in a pre-warmed incubator/shaker and secured with flask clamps. Plates were washed for 30 minutes at an appropriate temperature (e.g., 55° C. for European wash conditions), at 180 RPM. After washing, the plates were carefully rinsed by dipping them in a warm water bath three times. The disks were removed from the plates and dried in an oven for 1 hour at 80° C. Once dry, the disks were weighed, in order to obtain the washed disk weights. The gravimetric evaluation resulting in approximate percent removal was calculated as follows:

% Removal=(soiled weight−washed weight)/(soiled weight−clean weight)×100

Removal Index=% Removal/% Removal by Benchmark Protease(Protease B)

Scrambled Egg Preparation

Eggs for use in the testing of the protease and/or detergent compositions comprising test enzyme(s) were prepared as follows. First, 100 mls of 10% fat milk were mixed with 3 whole eggs. This mixture was cooked with continuous stirring until the mixture was slightly runny. Then, an additional 40 ml milk were added and the mixture was blended with a hand mixture or blender on high until smooth, with no signs of lumps. The egg mixture was allowed to cool to room temperature before soiling.

Egg Yolk Preparation

A water bath was heated by setting the temperature probe on the hot plate to 60° C. A pulp strainer was placed over a beaker. To prepare the egg yolks, 6-9 yolks were cracked and the yolks separated from the whites. The yolk sacs were not broken, although any residue present on the yolks was removed. The yolks were gently rinsed in cold water. The yolks were gently broken over the strainer and beaker. Once all of the yolks have been strained, the beaker containing the strained yolks was placed in the water bath. The yolks were stirred for 30 minutes, at 60° C. The yolks were removed from the water bath and placed in a cool water bath for 30 minutes. Any skin that formed on the surface was gently removed.

Preparation of Egg Stains Using Stainless Steel Slides (1×3 Inch)

Each metal slide was dipped into the scrambled egg or egg yolk preparation (prepared as described above) and tapped once, ensuring that there was approximately the same amount of egg on each slide. The backs of the slides were wiped on a tissue to clean them. The slides were then placed on two oven racks in numerical order. The slides were left to dry for 30 minutes at room temperature. The slides were then cooked for 2 hours at 80° C. (+/−1° C.), with the upper and lower shelves being exchanged and rotated by 180° (+/−1° C.) after 1 hour. The cooled, soiled slides were weighed in order 1-96.

For washing, eight stained slides were placed both in top rack and bottom rack of the washing machine. Pre-wash and main wash was based on Whirlpool 840 cup capacity of 40 mls for pre-wash and 60 mls for main wash. Typically in one test, four products were run using four GE 500 machines. For the test cycle, soiled slides were loaded into the machines and test product placed in the pre-wash and main wash cups. The water temperature was set to 120° F. and the machines turned on the normal wash cycle. The slides were removed from the machines for weighting at the end of the final rinse cycle. The slides did not go through the dry cycle. By the end of the fourth repetition, each product was run once in each machine. All four repetitions were run in one day. The next day, this same procedure was repeated using new soiled substrates, to provide a total of 8 repetitions per product, which were then averaged for the final results. The gravimetric evaluation resulting in approximated percent removal was calculated as follows:

% Removal=(soiled weight−washed weight)/(soiled weight−clean weight)×100

Removal Index=% Removal/% Removal by Benchmark Protease(Protease B)

The results of these performance tests are provided below in Table 12-1:

TABLE 12-1

Stain Removal Index vs. Protease B in 24 Well Screening

| Enzyme | On Scrambled Egg | On Egg Yolk |
|---|---|---|
| WT ASP | 101 | 100 |
| R14N-R127K-R159L | 134 | 120 |
| R14I-A64K-T86K-N112E-R123F-D184T | 126 | 124 |
| G12D-R35E-G63R-R79K-T109M | 124 | 113 |
| R14L | 128 | 123 |
| G12D-R35E | 120 | 138 |
| R14M-S76D-A93H-R127K-R159K-I181K | 123 | 103 |

Example 13

Cleaning Performance of ASP Variants in Powder Laundry Detergent

In this Example, experiments conducted to determine the cleaning performance of ASP variants in laundry powder detergent ARIEL® are described. In these experiments, the performance of the variants was compared with a benchmark serine protease (e.g., "Protease C") on Real Item Cleaning (RIC).

The tests are conducted using Meile washing machines using the following conditions: temperature 40-C, hardness 21 gpg, detergent 7300 ppm, protease 0.88 ppm, R10.75 kg, total ballast and RI 2.5 kg, water 13 L, wash time of 20 minutes, rinse time of 3×5 minutes.

In these experiments, king and queen size sheets, and clean socks (J&R Coordinating Service) are quartered for clean ballast. In addition, Consumer Real Items (R1) are tested, including socks, t-shirts, pillowcases, towels, and tea towels. Soils comprising yeast and AS1 (Artificial Soil 1; Equest) are used in these experiments. The composition of AS1 is provided below in Table 13-1.

TABLE 13-1

Composition of AS1

| Component | % |
|---|---|
| Artificial Sebum | 14.5 |
| Tea (PG Tips) | 6.5 |
| Coffee (Nescafe) | 4.0 |
| Orange Juice | 12.0 |
| Tomato Sauce (Heinz) | 13.0 |
| Grass | 4.5 |
| Chocolate (Heinz Baby) | 7.5 |
| Burnt Butter | 2.5 |
| Cooking Oil | 14.0 |
| ETC Clay | 5.0 |
| NTC Clay | 5.0 |
| Hoover Dust | 4.0 |
| Make up | 7.5 |

The garments are cut so as to ensure equal garment size for testing, with garments selected for uniform soil level. The two halves are coded in paneling pair order (e.g., left/right of garment).

| Garment 1 | Garment 2 | Garment 3 | Garment 4 | Garment 5 | Garment 6 | Garment 7 | Garment 8 |
|---|---|---|---|---|---|---|---|
| A B | B A | B A | A B | B A | A B | A B | B A |

Garments labeled "A" are washed with ASP variant, while Garments labeled "B" are washed with Protease C. The tests were conducted 4×4×2 (each treatment is repeated in four machines with two internal replicates of R1).

Test Procedure

Ballast of clean quartered bed sheets and R1 are combined to make a total load weight of 2.5 kg and readied to be loaded into a manual Meile washing machine, with the "21gpg" spout on the front panel turned on. The washer is then turned on. The temperature is set to 40° C. and for the short wash cycle. Next, the ballast and R1 are added to the washing machine. In addition, 20 g AS1 and clean socks stained with 17 g Bakers yeast are added to each replicate. Then, detergent (95 g) is added to detergent tray in the machine and the cycle started. Once the detergent is flushed from the tray, any liquids to be added are added. The machine then runs through its cycles. When the washing cycle is completed, the contents are transferred to a dryer and dried for 30 minutes. The items are then visually graded to provide PSU results and preference numbers in the LSG program.

Test Grading

The whole tests are graded in a single session within 72 hrs of washing and drying the test items. The split item garments are laid out in the panel room and graded by at least 3 judges using the Scheffé scale. Additionally, the stains A vs B are graded by at least 2 judges.

Results Handling

Grades are entered into a hand-held Psion set up with the wash test software. When grading of all split items has been completed, the data are transferred into a personal computer where the average PSU grade, % preference between A and B treatments, and LSD for each garment are calculated. Significant differences between products are calculated to a confidence limit of 90%.

The PSU grading systems are used to compare two products (formulae). The two formulae are tested on performance (e.g., post wash stain residuals). In these experiments several fabrics, washed with both products (e.g., product A and product B), are compared. Two or more judges perform the grading, in which the following Schelle scale is used:

0: No preference
1: I think this product is a little better (unsure)
2: I know this product is a little better
3: This product is better
4: This product is much better Example 14

Storage Stability of ASP Variants

In this Example, experiments conducted to determine the storage stability of various ASP variants tested in liquid TIDE® detergent in comparison with WT ASP are described. The protease activity of the variants and WT ASP were tested using a Hitachi 911 Automatic Analyzer. In these tests succinyl-L-Ala-L-Pro-L-Phe-p-nitroanilide's (pNA) was used to as the substrate to assess protease activity. In this test, the terminal carboxylamide bond is cleaved by active protease yielding p-nitroaniline. The intensity of the resultant yellow color, read at 415 nm/450 nm, is proportional to the activity of the protease in the sample which is calibrated with SAVINASE® protease standard.

As indicated in the following Table, there were significant improvements in storage stability of the engineered variants as compared to WT ASP. In this Table, the "Retained Activity %" was determined using the following formula: Retained Activity %=Activity/Initial Activity×100%

TABLE 14-1

Retained Activity in 28 Days Storage in Liquid TIDE ® at 90° F.

| | Initial | 1 Day | 4 Days | 7 Days | 14 Days | 21 Days | 28 Days |
|---|---|---|---|---|---|---|---|
| WT ASP | 100% | 91% | 32% | 0 | 0 | 0 | 0 |
| R18 | 100% | 99% | 41% | 0 | 0 | 0 | 0 |
| G12D-R35H | 100% | 100% | 100% | 100% | 97% | 92% | 87% |
| G12D-R35E | 100% | 100% | 100% | 100% | 100% | 97% | 94% |
| R35E | 100% | 100% | 100% | 96% | 87% | 79% | 72% |
| R35E-R18 | 100% | 100% | 100% | 94% | 82% | 70% | 61% |
| R35D | 100% | 100% | 100% | 86% | 71% | 56% | 45% |

Example 15

Determination of ASP Cleaning Activity

In this Example, experiments conducted to determine the cleaning activity of ASP under various conditions, as well as the properties of the various wash conditions are described. There is a wide variety of wash conditions including varying detergent formulations, wash water volume, wash water temperature, and length of wash time. Thus, detergent components such as proteases must be able to tolerate and function under adverse environmental conditions. For example, detergent formulations used in different areas have different concentrations of their relevant components present in the wash water. For example, a European detergent typically has about 3000-8000 ppm of detergent components in the wash water, while a Japanese detergent typically has less than 800 (e.g., 667 ppm) of detergent components in the wash water. In North America, particularly the United States, detergent typically have about 800 to 2000 (e.g., 975 ppm) of detergent components present in the wash water.

Latin American detergents are generally high suds phosphate builder detergents and the range of detergents used in Latin America can fall in both the medium and high detergent concentrations, as they range from 1500 ppm to 6000 ppm of detergent components in the wash water. Brazilian detergents typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 3000 ppm to about 8000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution, about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan can be between 10 and 30° C. (e.g., about 20° C.), whereas the temperature of wash water in Europe is typically between 30 and 50° C. (e.g., about 40° C.).

As a further example, different geographies may have different water hardness. Water hardness is typically described as grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies from area to area. Moderately hard (60-120 ppm) to hard (121-181 ppm) water has 60 to 181 parts per million (i.e., parts per million converted to grains per U.S. gallon is ppm # divided by 17.1 equals grains per gallon) of hardness minerals. Table 15-1 provides ranges of water hardness.

TABLE 15-1

| Water Hardness Ranges | | |
|---|---|---|
| Water | Grains per Gallon | Parts per Million |
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

TABLE 15-1-continued

European water hardness is typically greater than 10.5 (e.g., 10.5-20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between 3 to 10 grains, 3-8 grains or about 6 grains. Japanese water hardness is typically lower than North American water hardness, typically less than 4, for example 3 grains per gallon mixed $Ca^{2+}/Mg^{2+}$.

The present invention provides protease variants that provide improved wash performance in at least one set of wash conditions and typically in multiple wash conditions.

As described herein, the protease variants are tested for performance in different types of detergent and wash conditions using a microswatch assay (See above, and U.S. patent application Ser. No. 09/554,992; and WO 99/34011, both of which are incorporated by reference herein). Protease variants are tested for other soil substrates also in a similar fashion.

Example 16

Liquid Fabric Cleaning Compositions

This Example provides liquid fabric cleaning compositions that find use in conjunction with the present invention. These compositions are contemplated to find particular utility under Japanese machine wash conditions, as well as for applications involving cleaning of fine and/or delicate fabrics. Table 13-1 provides a suitable composition. However, it is not intended that the present invention be limited to this specific formulation, as many other formulations find use with the present invention.

TABLE 16-1

| Liquid Fabric Cleaning Composition | |
|---|---|
| Component | Amount (%) |
| AE2.5S | 2.16 |
| AS | 3.30 |
| N-Cocoyl N-methyl glucamine | 1.10 |
| Nonionic surfactant | 10.00 |
| Citric acid | 0.40 |
| Fatty acid | 0.70 |
| Base | 0.85 |
| Monoethanolamine | 1.01 |
| 1,2-Propanediol | 1.92 |
| EtOH | 0.24 |
| HXS | 2.09 |
| Protease[1] | 0.01 |
| Amylase | 0.06 |
| Minors/inerts to 100% | |

TABLE 16-2

Liquid Laundry Detergent Compositions

| Component | I | II | III | IV | V |
|---|---|---|---|---|---|
| LAS | 18.0 | — | 6.0 | — | — |
| $C_{12}$-$C_{15}$ $AE_{1.8}S$ | — | 2.0 | 8.0 | 11.0 | 5.0 |
| $C_8$-$C_{10}$ propyl dimethyl amine | 2.0 | 2.0 | 2.0 | 2.0 | 1.0 |
| $C_{12}$-$C_{14}$ alkyl dimethyl amine oxide | — | — | — | — | 2.0 |
| $C_{12}$-$C_{15}$ AS | — | 17.0 | — | 7.0 | 8.0 |
| CFAA | — | 5.0 | 4.0 | 4.0 | 3.0 |
| $C_{12}$-$C_{14}$ Fatty alcohol ethoxylate | 12.0 | 6.0 | 1.0 | 1.0 | 1.0 |
| $C_{12}$-$C_{18}$ Fatty acid | 11.0 | 11.0 | 4.0 | 4.0 | 3.0 |
| Citric acid (anhydrous) | 5.0 | 1.0 | 3.0 | 3.0 | 2.0 |
| DETPMP | 1.0 | 1.0 | 1.0 | 1.0 | 0.5 |
| Monoethanolamine | 11.0 | 8.0 | 5.0 | 5.0 | 2.0 |
| Sodium hydroxide | 1.0 | 1.0 | 2.5 | 1.0 | 1.5 |
| Percarbonate | — | 3.5 | — | 2.5 | — |
| Propanediol | 12.7 | 14.5 | 13.1 | 10. | 8.0 |
| Ethanol | 1.8 | 1.8 | 4.7 | 5.4 | 1.0 |
| Pectin Lyase | — | — | — | 0.005 | — |
| Amylase | — | 0.002 | — | — | — |
| Cellulase | — | — | 0.0002 | — | 0.0001 |
| Lipase | 0.1 | — | 0.1 | — | 0.1 |
| Protease A | 0.05 | 0.3 | 0.055 | 0.5 | 0.2 |
| DETBCHD | — | — | 0.02 | 0.01 | — |
| SRP1 | 0.5 | 0.5 | — | 0.3 | 0.3 |
| Boric acid | 2.4 | 2.4 | 2.8 | 2.8 | 2.4 |
| Sodium xylene sulfonate | — | — | 3.0 | — | — |
| DC 3225C | 1.0 | 1.0 | 1.0 | 1.0 | 1.0 |
| 2-butyl-octanol | 0.03 | 0.04 | 0.04 | 0.03 | 0.03 |
| DTPA | 0.5 | 0.4 | 0.35 | 0.28 | 0.4 |
| Brightener 1 | 0.18 | 0.10 | 0.11 | — | — |
| ASP Variant | 0.05 | 0.3 | 0.08 | 0.5 | 0.2 |

Balance to 100% perfume/dye and/or water

TABLE 16-3

Liquid Laundry Detergent Compositions

| Component | I | I | II | III | IV | V |
|---|---|---|---|---|---|---|
| LAS | 11.5 | 11.5 | 9.0 | — | 4.0 | — |
| $C_{12}$-$C_{15}AE_{2.85}S$ | — | — | 3.0 | 18.0 | — | 16.0 |
| $C_{14}$-$C_{15}E_{2.5}$ S | 11.5 | 11.5 | 3.0 | — | 16.0 | — |
| $C_{12}$-$C_{13}E_9$ | — | — | 3.0 | 2.0 | 2.0 | 1.0 |
| $C_{12}$-$C_{13}E_7$ | 3.2 | 3.2 | — | — | — | — |
| CFAA | — | — | — | 5.0 | — | 3.0 |
| TPKFA | 2.0 | 2.0 | — | 2.0 | 0.5 | 2.0 |
| Citric Acid (Anhydrous) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| Na Culmene Sulfonate | 4.0 | 4.0 | 1.0 | 3.0 | 1.2 | — |
| Borate | 0.6 | 0.6 | — | 3.0 | 2.0 | 3.0 |
| Na hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Mono-ethanolamine | 3.0 | 3.0 | 1.5 | 1.0 | 2.5 | 1.0 |
| TEPAE | 2.0 | 2.0 | — | 1.0 | 1.0 | 1.0 |
| PB1 | — | — | 4.5 | — | 2.8 | — |
| Protease A | 0.03 | 0.03 | 0.01 | 0.03 | 0.02 | 0.02 |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | — | — | — |
| ASP Variant | 0.03 | 0.05 | 0.01 | 0.03 | 0.08 | 0.02 |
| SRP 1 | 0.2 | 0.2 | — | 0.1 | 0.2 | — |
| DTPA | — | — | — | 0.3 | — | — |
| PVNO | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |

Balance to 100% perfume/dye, and/or water

TABLE 16-4

Liquid Laundry Detergent Compositions

| Component | I | II | III | IV | V |
|---|---|---|---|---|---|
| LAS | 24.0 | 32.0 | 6.0 | 8.0 | 6.0 |
| $C_{12}$-$C_{15}AE_{1.8}S$ | — | — | 8.0 | 11.0 | 5.0 |
| $C_8$-$C_{10}$ propyl dimethyl amine | 2.0 | 2.0 | 2.0 | 2.0 | 1.0 |
| $C_{12}$-$C_{14}$ alkyl dimethyl amine oxide | — | — | — | — | 2.0 |
| $C_{12}$-$C_{15}$ AS | — | — | 17.0 | 7.0 | 8.0 |
| CFAA | — | 5.0 | 4.0 | 4.0 | 3.0 |
| $C_{12}$-$C_{14}$ Fatty alcohol ethoxylate | 12.0 | 6.0 | 1.0 | 1.0 | 1.0 |
| $C_{12}$-$C_{18}$ Fatty acid | 3.0 | — | 4.0 | 4.0 | 3.0 |
| Citric acid (anhydrous) | 6.0 | 5.0 | 3.0 | 3.0 | 2.0 |
| DETPMP | — | — | 1.0 | 1.0 | 0.5 |
| Monoethanolamine | 5.0 | 5.0 | 5.0 | 5.0 | 2.0 |
| Sodium hydroxide | — | — | 2.5 | 1.0 | 1.5 |
| 1 N HCl aqueous solution | #1 | #1 | — | — | — |
| Propanediol | 12.7 | 14.5 | 13.1 | 10. | 8.0 |
| Ethanol | 1.8 | 2.4 | 4.7 | 5.4 | 1.0 |
| DTPA | 0.5 | 0.4 | 0.3 | 0.4 | 0.5 |
| Pectin Lyase | — | — | — | 0.005 | — |
| Amylase | 0.001 | 0.002 | — | — | — |
| Cellulase | — | — | 0.0002 | — | 0.0001 |
| Lipase | 0.1 | — | 0.1 | — | 0.1 |
| ASP Variant | 0.05 | 0.3 | 0.08 | 0.5 | 0.2 |
| Protease A | — | — | — | — | 0.1 |
| SRP1 | 0.5 | 0.5 | — | 0.3 | 0.3 |
| Boric acid | 2.4 | 2.4 | 2.8 | 2.8 | 2.4 |
| Sodium xylene sulfonate | — | — | 3.0 | — | — |
| DC 3225C | 1.0 | 1.0 | 1.0 | 1.0 | 1.0 |
| 2-butyl-octanol | 0.03 | 0.04 | 0.04 | 0.03 | 0.03 |
| Brightener 1 | 0.12 | 0.10 | 0.18 | 0.08 | 0.10 |

Balance to 100% perfume/dye and/or water

The pH of Examples 16-4. compositions (I)-(II) is about 5 to about 7, and of 1(III)-(V) is about 7.5 to about 8.5. #1: add 1N HCl aq. soln to adjust the neat pH of the formula in the range from about 3 to about 5.

Example 17

Liquid Dishwashing Compositions

This Example provides liquid dishwashing compositions that find use in conjunction with the present invention. These compositions are contemplated to find particular utility under Japanese dishwashing conditions. However, it is not intended that the present invention be limited to this specific formulation, as many other formulations find use with the present invention.

The following compact high density dishwashing detergent compositions are provided by the present invention.

TABLE 17-1

Compact High Density Dishwashing Detergent Compositions

| Component | I | II | III | IV | V | VI |
|---|---|---|---|---|---|---|
| STPP | — | 45.0 | 45.0 | — | — | 40.0 |
| 3Na Citrate 2H$_2$O | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |
| PB1 | — | — | 4.5 | — | — | — |
| PB4 | — | — | — | 5.0 | — | — |
| Percarbonate | — | — | — | — | — | 4.8 |
| PAAC | 0.02 | 0.05 | 0.03 | 0.04 | 0.03 | 0.05 |
| BB1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| Paraffin | 0.5 | 0.4 | 0.4 | 0.6 | — | — |
| Protease B | 0.072 | 0.053 | 0.053 | 0.026 | 0.059 | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| ASP Variant | 0.072 | 0.053 | 0.053 | 0.026 | 0.059 | 0.01 |
| BTA | 0.3 | 0.2 | 0.2 | 0.3 | 0.3 | 0.3 |
| Poly-carboxylate | 6.0 | — | — | — | 4.0 | 0.9 |
| Perfume | 0.2 | 0.1 | 0.1 | 0.2 | 0.2 | 0.2 |

Balance to 100% Moisture and/or Minors*
*Brightener/Dye/SRP1/Na Carboxymethylcellulose/Photobleach/MgSO$_4$/PVPVI/Suds suppressor/High Molecular PEG/Clay.
The pH of Examples 17-1 compositions (I) through (VI) is from about 9.6 to about 11.3.

The following hand dish liquid detergent compositions are provided by the present invention.

TABLE 17-2

Hand Dish Liquid Detergent Compositions

| Component | I | II | III | IV | V | VI |
|---|---|---|---|---|---|---|
| C$_{12}$-C$_{15}$AE$_{1.8}$S | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| C$_{10}$-C$_{18}$ Alkyl Dimethyl Amine Oxide | 5.0 | 3.0 | 7.0 | — | — | — |
| Betaine | 3.0 | — | 1.0 | 3.0 | 1.0 | — |
| C$_{12}$ poly-OH fatty acid amide | — | — | — | 3.0 | — | 1.0 |
| C$_{14}$ poly-OH fatty acid amide | — | 1.5 | — | — | — | — |
| C$_{11}$E$_9$ | 2.0 | — | 4.0 | — | — | 20.0 |
| DTPA | — | — | — | — | 0.2 | — |
| Tri-sodium Citrate dihydrate | 0.25 | — | — | 0.7 | — | — |
| Diamine | 1.0 | 5.0 | 7.0 | 1.0 | 5.0 | 7.0 |
| MgCl$_2$ | 0.25 | — | — | 1.0 | — | — |
| Protease A | 0.02 | 0.01 | 0.02 | 0.01 | 0.02 | 0.05 |
| Amylase | 0.001 | — | — | 0.002 | — | 0.001 |
| Sodium Cumene Sulphonate | — | — | — | 2.0 | 1.5 | 3.0 |
| DETBCHD | — | — | — | 0.01 | 0.02 | 0.01 |
| PB1 | 1.5 | 2.8 | 1.2 | — | — | — |
| ASP Variant | 0.02 | 0.01 | 0.03 | 0.01 | 0.02 | 0.05 |

Balance to 100% perfume/dye and/or water

The following liquid automatic dishwashing detergents compositions are provided by the present invention.

TABLE 17-3

Liquid Automatic Dishwashing Detergent Compositions

| Component | I | II | III | IV | V |
|---|---|---|---|---|---|
| STPP | 16 | 16 | 18 | 16 | 16 |
| Potassium Sulfate | — | 10 | 8 | — | 10 |
| 1,2 propanediol | 6.0 | 0.5 | 2.0 | 6.0 | 0.5 |
| Boric Acid | 4.0 | 3.0 | 3.0 | 4.0 | 3.0 |
| CaCl$_2$ dihydrate | 0.04 | 0.04 | 0.04 | 0.04 | 0.04 |
| Nonionic | 0.5 | 0.5 | 0.5 | 0.5 | 0.5 |
| Protease B | 0.03 | 0.03 | 0.03 | 0.03 | 0.03 |
| Amylase | 0.02 | — | 0.02 | 0.02 | — |
| ASP Variant | 0.1 | 0.03 | 0.05 | 0.03 | 0.06 |

Balance to 100% perfume/dye and/or water

The following tablet detergent compositions are provided by the present invention. These compositions are prepared by compression of a granular dishwashing detergent composition at a pressure of 13 KN/cm$^2$, using a standard 12 head rotary press.

TABLE 17-4

Tablet Detergent Compositions

| Component | I | II | III | IV | V | VI | VII | VIII |
|---|---|---|---|---|---|---|---|---|
| STPP | — | 48.8 | 44.7 | 38.2 | — | 42.4 | 46.1 | 36.0 |
| 3Na Citrate 2H$_2$O | 20.0 | — | — | — | 35.9 | — | — | — |
| Na Carbonate | 20.0 | 5.0 | 14.0 | 15.4 | 8.0 | 23.0 | 20.0 | 28.0 |
| Silicate | 15.0 | 14.8 | 15.0 | 12.6 | 23.4 | 2.9 | 4.3 | 4.2 |
| Lipase | 0.001 | — | 0.01 | — | 0.02 | — | — | — |
| Protease B | 0.042 | 0.072 | 0.042 | 0.031 | — | — | — | — |
| Protease C | — | — | — | — | 0.052 | 0.023 | 0.023 | 0.029 |
| ASP Variant | 0.01 | 0.08 | 0.05 | 0.04 | 0.052 | 0.023 | 0.023 | 0.029 |
| Amylase | 0.012 | 0.012 | 0.012 | — | 0.015 | — | 0.017 | 0.002 |
| Pectin Lyase | 0.005 | — | — | 0.002 | — | — | — | — |

TABLE 17-4-continued

Tablet Detergent Compositions

| Component | I | II | III | IV | V | VI | VII | VIII |
|---|---|---|---|---|---|---|---|---|
| PB1 | — | — | 3.8 | — | 7.8 | — | — | 8.5 |
| Percarbonate | 6.0 | — | — | 6.0 | — | 5.0 | — | — |
| PAAC | 0.02 | 0.03 | 0.05 | 0.04 | 0.03 | 0.02 | 0.04 | 0.05 |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |
| Glycerol | — | — | — | — | — | 0.4 | — | 0.5 |
| Perfume | — | — | — | 0.05 | 0.2 | 0.2 | 0.2 | 0.2 |
| Balance to 100% Moisture and/or Minors* | | | | | | | | |

*Brightener/Dye/SRP1/Na Carboxymethylcellulose/Photobleach/MgSO$_4$/PVPVI/Suds suppressor/High Molecular PEG/Clay.
The pH of Examples 17-4.(I) through (VIII) is from about 10 to about 11.5.
The tablet weight of Examples 17-4.(I) through 7(VIII) is from about 20 grams to about 30 grams.

The following dishwashing composition finds particular use under Japanese washing conditions.

TABLE 17-5

Liquid Dishwashing Compositions

| Component | A | B |
|---|---|---|
| AE1.4S | 24.69 | 24.69 |
| N-cocoyl N-methyl glucamine | 3.09 | 3.09 |
| Amine oxide | 2.06 | 2.06 |
| Betaine | 2.06 | 2.06 |
| Nonionic surfactant | 4.11 | 4.11 |
| Hydrotrope | 4.47 | 4.47 |
| Magnesium | 0.49 | 0.49 |
| Ethanol | 7.2 | 7.2 |
| LemonEase | 0.45 | 0.45 |
| Geraniol/BHT | — | 0.60/0.02 |
| Amylase | 0.03 | 0.005 |
| Protease | 0.01 | 0.43 |
| Balance to 100% | | |

Example 18

Liquid Fabric Cleaning Compositions

The proteases of the present invention find particular use in cleaning compositions. For example, it is contemplated that liquid fabric cleaning composition of particular utility under Japanese machine wash conditions be prepared in accordance with the invention. In some preferred embodiments, these compositions comprise the following components shown in Table 18-1.

TABLE 18-1

Liquid Fabric Cleaning Composition

| Component | Amount (%) |
|---|---|
| AE2.5S | 15.00 |
| AS | 5.50 |
| N-cocoyl N-methyl glucamine | 5.50 |
| Nonionic surfactant | 4.50 |
| Citric acid | 3.00 |
| Fatty acid | 5.00 |
| Base | 0.97 |
| Monoethanolamine | 5.10 |
| 1,2-Propanediol | 7.44 |
| EtOH | 5.50 |
| HXS | 1.90 |
| Boric acid | 3.50 |
| Ethoxylated tetraethylenepentaimine | 3.00 |
| SRP | 0.30 |
| Protease | 0.069 |
| Amylase | 0.06 |
| Cellulase | 0.08 |
| Lipase | 0.18 |
| Brightener | 0.10 |
| Minors/inerts to 100% | |

Example 19

Granular Fabric Cleaning Compositions

In this Example, various granular fabric cleaning compositions that find use with the present invention are provided. The following Tables provide suitable compositions. However, it is not intended that the present invention be limited to these specific formulations, as many other formulations find use with the present invention.

TABLE 19-1

Granular Fabric Cleaning Compositions

| | Formulations | | | |
|---|---|---|---|---|
| Component | A | B | C | D |
| Protease1 | 0.10 | 0.20 | 0.03 | 0.05 |
| Protease2 | | | 0.2 | 0.15 |

TABLE 19-1-continued

Granular Fabric Cleaning Compositions

| Component | Formulations | | | |
|---|---|---|---|---|
| | A | B | C | D |
| C13 linear alkyl benzene sulfonate | 22.00 | 22.00 | 22.00 | 22.00 |
| Phosphate (as sodium tripolyphosphate) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelan (diethylaenetriamine-petaacetic acid) | 0.40 | 0.40 | 0.40 | 0.40 |
| Sodium sulfate | 5.50 | 5.50 | 5.50 | 5.50 |
| Water | Balance to 100% | | | |

TABLE 19-2

Granular Fabric Cleaning Compositions

| Component | Formulations | | | |
|---|---|---|---|---|
| | A | B | C | D |
| Protease1 | 0.10 | 0.20 | 0.30 | 0.05 |
| Protease2 | | | 0.2 | 0.1 |
| C12 alkyl benzene sulfonate | 12.00 | 12.00 | 12.00 | 12.00 |
| Zeolite A (1-10 micrometer) | 26.00 | 26.00 | 26.00 | 26.00 |
| C12-C14 secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Fillers, water, minors | Balance to 100% | | | |

The following laundry compositions are provided by the present invention. These compositions are suitable for use as granules or tablets.

TABLE 19-3

Granule and Tablet Laundry Detergent Compositions

| Component | Composition | | | | |
|---|---|---|---|---|---|
| | I | II | III | IV | V |
| Base Product | | | | | |
| $C_{14}$-$C_{15}$AS or TAS | 8.0 | 5.0 | 3.0 | 3.0 | 3.0 |
| LAS | 8.0 | — | 8.0 | — | 7.0 |
| $C_{12}$-$C_{15}AE_3S$ | 0.5 | 2.0 | 1.0 | — | — |
| $C_{12}$-$C_{15}E_5$ or $E_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |
| MA/AA | 2.0 | 2.0 | 2.0 | — | — |
| AA | — | — | — | — | 4.0 |
| 3Na Citrate 2H$_2$O | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |
| Percarbonate | — | — | 3.8 | 5.2 | — |
| NOBS | 1.9 | — | — | — | — |
| NACA OBS | — | — | 2.0 | — | — |
| TAED | 0.5 | 2.0 | 2.0 | 5.0 | 1.00 |
| BB1 | 0.06 | — | 0.34 | — | 0.14 |
| BB2 | — | 0.14 | — | 0.20 | — |
| Anhydrous Na Carbonate | 15.0 | 18.0 | 8.0 | 15.0 | 15.0 |
| Sulfate | 5.0 | 12.0 | 2.0 | 17.0 | 3.0 |
| Silicate | — | 1.0 | — | — | 8.0 |
| Protease B | 0.033 | 0.033 | — | — | — |
| Protease C | — | — | 0.033 | 0.046 | 0.033 |
| Lipase | — | 0.008 | — | — | — |
| Amylase | 0.001 | — | — | — | 0.001 |
| Cellulase | — | 0.0014 | — | — | — |
| Pectin Lyase | 0.001 | 0.001 | 0.001 | 0.001 | 0.001 |
| ASP Variant | 0.03 | 0.05 | 1.0 | 0.06 | 0.1 |
| Balance to 100% Moisture and/or Minors* | | | | | |

*Perfume/Dye, Brightener/SRP1/Na Carboxymethylcellulose/Photobleach/MgSO$_4$/PVPVI/Suds suppressor/High Molecular PEG/Clay.

The following laundry detergent compositions are contemplated to provide particular use under European machine wash conditions.

TABLE 19-3

Granular Fabric Cleaning Compositions

| Component | Formulations | | |
|---|---|---|---|
| | A | B | C |
| LAS | 7.0 | 5.61 | 4.76 |
| TAS | | | 1.57 |
| C45AS | 6.0 | 2.24 | 3.89 |
| C25E25 | 1.0 | 0.76 | 1.18 |
| C45E7 | | | 2.0 |
| C25E3 | 4.0 | 5.5 | |
| QAS | 0.8 | 2.0 | 2.0 |
| STPP | | | |
| Zeolite | 25.0 | 19.5 | 19.5 |
| Citric acid | 2.0 | 2.0 | 2.0 |
| NaSKS-6 | 8.0 | 10.6 | 10.6 |
| Carbonate I | 8.0 | 10.0 | 8.6 |
| MA/AA | 1.0 | 2.6 | 1.6 |
| CMC | 0.5 | 0.4 | 0.4 |
| PB4 | | 12.7 | |
| Percarbonate | | | 19.7 |
| TAED | | 3.1 | 5.0 |
| Citrate | 7.0 | | |
| DTPMP | 0.25 | 0.2 | 0.3 |
| HEDP | 0.3 | 0.3 | 0.3 |
| QEA 1 | 0.9 | 1.2 | 1.0 |
| Protease 1 | 0.02 | 0.05 | 0.035 |
| Lipase | 0.15 | 0.25 | 0.15 |
| Cellulase | 0.28 | 0.28 | 0.28 |
| Amylase | 0.4 | 0.7 | 0.3 |
| PVPI/PVNO | 0.4 | | 0.1 |
| Photoactivated bleach (ppm) | 15 ppm | 27 ppm | 27 ppm |
| Brightener 1 | 0.08 | 0.19 | 0.19 |
| Brightener 2 | | 0.04 | 0.04 |
| Perfume | 0.3 | 0.3 | 0.3 |
| Effervescent granules (malic acid 40%, sodium bicarbonate 40%, sodium carbonate 20%) | 15 | 15 | 5 |
| Silicon antifoam | 0.5 | 2.4 | 2.4 |
| Minors/inerts to 100% | Balance to 100% | | |

Example 20

Hard Surface Cleaning Detergent Compositions

The present invention also provides compositions suitable for cleaning of hard surfaces.

TABLE 20

Liquid Hard Surface Cleaning Detergent Compositions

| Component | I | II | III | IV | V | VI | VII |
|---|---|---|---|---|---|---|---|
| $C_9$-$C_{11}E_5$ | 2.4 | 1.9 | 2.5 | 2.5 | 2.5 | 2.4 | 2.5 |
| $C_{12}$-$C_{14}E_5$ | 3.6 | 2.9 | 2.5 | 2.5 | 2.5 | 3.6 | 2.5 |
| $C_7$-$C_9E_6$ | — | — | — | — | 8.0 | — | — |
| $C_{12}$-$C_{14}E_{21}$ | 1.0 | 0.8 | 4.0 | 2.0 | 2.0 | 1.0 | 2.0 |
| LAS | — | — | — | 0.8 | 0.8 | — | 0.8 |
| Sodium culmene sulfonate | 1.5 | 2.6 | — | 1.5 | 1.5 | 1.5 | 1.5 |
| Isachem ® AS | 0.6 | 0.6 | — | — | — | 0.6 | — |
| $Na_2CO_3$ | 0.6 | 0.13 | 0.6 | 0.1 | 0.2 | 0.6 | 0.2 |
| 3Na Citrate $2H_2O$ | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | — | 0.5 | — | — |
| PAAC | — | — | — | 0.03 | 0.03 | 0.03 | — |
| DETBCHD | 0.03 | 0.05 | 0.05 | — | — | — | — |
| Protease B | 0.07 | 0.05 | 0.05 | 0.03 | 0.06 | 0.01 | 0.04 |
| Amylase | 0.12 | 0.01 | 0.01 | — | 0.02 | — | 0.01 |
| Lipase | — | 0.001 | — | 0.005 | — | 0.005 | — |
| ASP Variant | 0.07 | 0.05 | 0.08 | 0.03 | 0.06 | 0.01 | 0.04 |
| MCAEM ($C_8$-$C_{10}E_2$ Acetate) | 3.5 | 5.6 | 4.8 | 5.3 | 3.6 | 8.0 | 4.7 |
| Pectin Lyase | 0.001 | — | 0.001 | — | — | — | 0.002 |
| PB1 | 3.5 | 4.6 | 2.7 | 3.8 | 3.6 | 4.2 | 2.7 |
| Balance to 100% perfume/dye, and/or water | | | | | | | |

The pH of these compositions is from about 7.4 to about 9.5.

Example 21

Animal Feed Comprising ASP

The present invention also provides animal feed compositions comprising ASP variants. In this Example, one such feed, suitable for poultry is provided. However, it is not intended that the present invention be limited to this specific formulation, as the proteases of the present invention find use with numerous other feed formulations. It is further intended that the feeds of the present invention be suitable for administration to any animal, including but not limited to livestock (e.g., cattle, pigs, sheep, etc.), as well as companion animals (e.g., dogs, cats, horses, rodents, etc.). The following Table provides a formulation for a mash, namely a maize-based starter feed suitable for administration to turkey poults up to 3 weeks of age.

TABLE 21-1

Animal Feed Composition

| Ingredient Amount | (wt. %) |
|---|---|
| Maize | 36.65 |
| Soybean meal (45.6% CP) | 55.4 |
| Animal-vegetable fat | 3.2 |
| Dicalcium phosphate | 2.3 |
| Limestone | 1.5 |
| Mineral premix | 0.3 |
| Vitamin premix | 0.3 |
| Sodium chloride | 0.15 |
| DL methionine | 0.2 |

In some embodiments, this feed formulation is supplemented with various concentrations of the protease(s) of the present invention (e.g., 2,000 units/kg, 4,000 units/kg and 6,000 units/kg).

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Having described the preferred embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention.

It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings failing within the generic disclosure also form part of the invention. This includes the generic description of the invention with a proviso or negative limitation removing any subject matter from the genus, regardless of whether or not the excised material is specifically recited herein.

What is claimed is:

1. An isolated serine protease variant of the *Cellulomonas* 69B4 protease set forth by SEQ ID NO: 8, wherein the variant has at least 80% amino acid identity to SEQ ID NO:8, comprises substitutions R141/A64K/R123F/R159K/D184T, and has the serine protease activity of the *Cellulomonas* 69B4 protease set forth by SEQ ID NO: 8.

2. A composition comprising the isolated serine protease variant of claim 1.

3. A composition comprising the isolated serine protease variant of claim 1, wherein said isolated serine protease variant has immunological cross-reactivity with an antibody to the serine *Cellulomonas* 69B4 protease set forth by the amino acid sequence of SEQ ID NO:8.

4. The variant of claim 1, wherein said variant has improved thermostability as compared to the *Cellulomonas* 69B4 protease set forth by the amino acid sequence of SEQ ID NO:8.

5. The variant of claim 1, wherein said variant has improved LAS stability as compared to the *Cellulomonas* 69B4 protease set forth by the amino acid sequence of SEQ ID NO:8.

6. The variant of claim 1, wherein said variant has improved activity, as compared to the *Cellulomonas* 69B4 protease set forth by the amino acid sequence of SEQ ID NO:8.

7. The variant of claim 6, wherein said variant has improved caseinolytic activity as compared to the *Cellulomonas* 69B4 protease set forth by the amino acid sequence of SEQ ID NO:8.

8. The variant of claim 6, wherein said variant has improved keratinolytic activity as compared to the *Cellulomonas* 69B4 protease set forth by the amino acid sequence of SEQ ID NO:8.

9. The variant of claim 6, wherein said variant has improved wash performance activity as compared to the *Cellulomonas* 69B4 protease set forth by the amino acid sequence of SEQ ID NO:8.

10. The variant of claim 6, wherein said variant has improved dishwashing performance activity as compared to the *Cellulomonas* 69B4 protease set forth by the amino acid sequence of SEQ ID NO:8.

11. The variant of claim 6, wherein said variant has improved stain removal activity as compared to the *Cellulomonas* 69B4 protease set forth by the amino acid sequence of SEQ ID NO:8.

12. The isolated serine protease variant of claim 1, wherein said variant exhibits an altered surface property as compared to the *Cellulomonas* 69B4 protease set forth by the amino acid sequence of SEQ ID NO:8.

13. The isolated serine protease variant of claim 1, wherein said protease variant has at least one improved property as compared to the *Cellulomonas* 69B4 protease set forth by the amino acid sequence of SEQ ID NO:8.

14. The protease of claim 13, wherein said at least one improved property is selected from the group consisting of acid stability, thermostability, casein hydrolysis, keratin hydrolysis, cleaning performance, and LAS stability.

15. A cleaning composition comprising the serine protease variant as set forth in claim 1.

16. A cleaning composition comprising the variant serine protease of claim 1, wherein said serine protease variant has immunological cross-reactivity with an antibody to the serine *Cellulomonas* 69B4 protease set forth by the amino acid sequence of SEQ ID NO:8.

17. The cleaning composition of claim 16, further comprising one or more additional enzymes or enzyme derivatives selected from the group consisting of proteases, amylases, lipases, mannanases, pectinases, cutinases, oxidoreductases, hemicellulases, and cellulases.

18. The cleaning composition of claim 15, further comprising at least one stabilizing agent.

19. The composition of claim 18, wherein said stabilizing agent is selected from borax, glycerol, and competitive inhibitors.

20. The composition of claim 19, wherein said competitive inhibitors stabilize said serine protease variant to anionic surfactants.

21. The composition of claim 18, wherein said serine protease variant is an autolytically stable variant.

22. A cleaning composition comprising at least 0.0001 weight percent of the serine protease variant of claim 1, and optionally, an adjunct ingredient.

23. The cleaning composition of claim 22, wherein said composition comprises from about 0.001 to about 0.5 weight percent of said serine protease variant.

24. The cleaning composition of claim 22, wherein said composition comprises from about 0.01 to about 0.1 weight percent of said serine protease variant.

25. The cleaning composition of claim 22, said cleaning composition comprising a surfactant.

26. The cleaning composition of claim 25, wherein said surfactant material comprises a sodium alkyl sulfate surfactant that comprises an ethylene oxide moiety.

27. The cleaning composition of claim 15, wherein said cleaning composition is selected from liquid, powder, granular, and tablet compositions.

28. The cleaning composition of claim 15, wherein said composition further comprises a hydrogen peroxide source.

29. The cleaning composition of claim 28, wherein said hydrogen peroxide source comprises at least one persalt, wherein said persalt is alkalimetal percarbonate, or a mixture of persalts.

30. The cleaning composition of claim 29, wherein said composition further comprises a bleach catalyst, bleach activator and/or mixtures thereof.

* * * * *

UNITED STATES PATENT AND TRADEMARK OFFICE
CERTIFICATE OF CORRECTION

| | | |
|---|---|---|
| PATENT NO. | : 7,985,569 B2 | Page 1 of 1 |
| APPLICATION NO. | : 11/809104 | |
| DATED | : July 26, 2011 | |
| INVENTOR(S) | : Wolfgang Aehle et al. | |

It is certified that error appears in the above-identified patent and that said Letters Patent is hereby corrected as shown below:

Claim 1, column 143, line 31, delete "R141/ A64K/R123F/R159K/D184T," and insert
-- R14I/A64K/R123F/R159K/D184T, --.

Signed and Sealed this
Eighth Day of January, 2013

David J. Kappos
*Director of the United States Patent and Trademark Office*

SEQUENCE LISTING

```
<160> NUMBER OF SEQ ID NOS: 33

<210> SEQ ID NO 1
<211> LENGTH: 1488
<212> TYPE: DNA
<213> ORGANISM: Cellulomonas strain 69B4

<400> SEQUENCE: 1
atgacaccac gcacagtcac gcgggccctg gccgtggcca ccgcagccgc cacactcctg      60
gcaggcggca tggccgccca ggccaacgag cccgcaccac ccgggagcgc gagcgcaccg     120
ccacgcctgg ccgagaagct cgaccccgac ctcctcgagg ccatggagcg cgacctgggc     180
ctcgacgcgg aggaagccgc cgccaccctg gcgttccagc acgacgcagc cgagaccggc     240
gaggccctcg ccgaagagct cgacgaggac ttcgccggca cctgggtcga ggacgacgtc     300
ctgtacgtcg ccaccaccga cgaggacgcc gtcgaggagg tcgagggcga aggcgccacg     360
gccgtcaccg tcgagcactc cctggccgac ctcgaggcct ggaagaccgt cctcgacgcc     420
gccctcgagg gccacgacga cgtgcccacc tggtacgtcg acgtcccgac caacagcgtc     480
gtcgtcgccg tcaaggccgg agcccaggac gtcgccgccg gcctcgtcga aggtgccgac     540
gtcccgtccg acgccgtgac cttcgtcgag accgacgaga ccccgcggac catgttcgac     600
gtgatcggcg gcaacgccta caccatcggg gggcgcagcc gctgctcgat cgggttcgcg     660
gtcaacggcg ggttcatcac cgccggccac tgcggccgca ccggcgccac caccgccaac     720
cccaccggga ccttcgccgg gtccagcttc ccgggcaacg actacgcgtt cgtccgtacc     780
ggggccggcg tgaacctgct ggcccaggtc aacaactact ccggtggccg cgtccaggtc     840
gccgggcaca ccgcggcccc cgtcggctcg gccgtgtgcc ggtccgggtc gaccaccggg     900
tggcactgcg gcaccatcac tgcgctcaac tcctcggtca cctaccccga gggcaccgtc     960
cgcggcctga tccgcaccac cgtctgcgcc gagcccggcg actccggtgg ctcgctgctc    1020
gccggcaacc aggcccaggg cgtcacgtcc ggcggctccg gcaactgccg caccggtggc    1080
accacgttct tccagccggt caaccccatc ctccaggcgt acggcctgag gatgatcacc    1140
acggactcgg gcagcagccc ggcccctgca ccgacctcct gcaccggcta cgcccgcacc    1200
ttcaccggga ccctcgcggc cggccgggcc gccgcccagc ccaacgggtc ctacgtgcag    1260
gtcaaccggt ccgggaccca cagcgtgtgc ctcaacgggc cctccggtgc ggacttcgac    1320
ctctacgtgc agcgctggaa cggcagctcc tgggtgaccg tcgcccagag cacctccccc    1380
ggctccaacg agaccatcac ctaccgcggc aacgccggct actaccgcta cgtggtcaac    1440
gccgcgtccg gctccggtgc ctacaccatg gggctcaccc tccctga                 1488
```

<210> SEQ ID NO 2
<211> LENGTH: 1404
<212> TYPE: DNA
<213> ORGANISM: Cellulomonas strain 69B4

<400> SEQUENCE: 2

| | | |
|---|---|---|
| aacgagcccg caccacccgg gagcgcgagc gcaccgccac gcctggccga gaagctcgac | 60 |
| cccgacctcc tcgaggccat ggagcgcgac ctgggcctcg acgcggagga agccgccgcc | 120 |
| accctggcgt tccagcacga cgcagccgag accggcgagg ccctcgccga agagctcgac | 180 |
| gaggacttcg ccggcacctg gtcgaggac gacgtcctgt acgtcgccac caccgacgag | 240 |
| gacgccgtcg aggaggtcga gggcgaaggc gccacggccg tcaccgtcga gcactccctg | 300 |
| gccgacctcg aggcctggaa gaccgtcctc gacgccgccc tcgagggcca cgacgacgtg | 360 |
| cccacctggt acgtcgacgt cccgaccaac agcgtcgtcg tcgccgtcaa ggccggagcc | 420 |
| caggacgtcg ccgccggcct cgtcgaaggt gccgacgtcc cgtccgacgc cgtgaccttc | 480 |
| gtcgagaccg acgagacccc gcggaccatg ttcgacgtga tcggcggcaa cgcctacacc | 540 |
| atcgggggc gcagccgctg ctcgatcggg ttcgcggtca acggcgggtt catcaccgcc | 600 |
| ggccactgcg gccgcaccgg cgccaccacc gccaacccca ccgggaccttt cgccgggtcc | 660 |
| agcttcccgg gcaacgacta cgcgttcgtc cgtaccgggg ccggcgtgaa cctgctggcc | 720 |
| caggtcaaca actactccgg tggccgcgtc caggtcgccg ggcacaccgc ggcccccgtc | 780 |
| ggctcggccg tgtgccggtc cgggtcgacc accgggtggc actgcggcac catcactgcg | 840 |
| ctcaactcct cggtcaccta ccccgagggc accgtccgcg gcctgatccg caccaccgtc | 900 |
| tgcgccgagc ccggcgactc cggtggctcg ctgctcgccg gcaaccaggc ccagggcgtc | 960 |
| acgtccggcg gctccggcaa ctgccgcacc ggtggcacca cgttcttcca gccggtcaac | 1020 |
| cccatcctcc aggcgtacgg cctgaggatg atcaccacgg actcgggcag cagcccggcc | 1080 |
| cctgcaccga cctcctgcac cggctacgcc cgcaccttca ccgggaccct cgcggccggc | 1140 |
| cggggccgccg cccagcccaa cgggtcctac gtgcaggtca accggtccgg gacccacagc | 1200 |
| gtgtgcctca acgggccctc cggtgcggac ttcgacctct acgtgcagcg ctggaacggc | 1260 |
| agctcctggg tgaccgtcgc ccagagcacc tcccccggct ccaacgagac catcacctac | 1320 |
| cgcggcaacg ccggctacta ccgctacgtg gtcaacgccg cgtccggctc cggtgcctac | 1380 |
| accatggggc tcaccctccc ctga | 1404 |

<210> SEQ ID NO 3
<211> LENGTH: 1404
<212> TYPE: DNA
<213> ORGANISM: Cellulomonas strain 69B4

<400> SEQUENCE: 3

| | | |
|---|---|---|
| aacgagcccg caccacccgg gagcgcgagc gcaccgccac gcctggccga gaagctcgac | 60 |
| cccgacctcc tcgaggccat ggagcgcgac ctgggcctcg acgcggagga agccgccgcc | 120 |
| accctggcgt tccagcacga cgcagccgag accggcgagg ccctcgccga agagctcgac | 180 |
| gaggacttcg ccggcacctg gtcgaggac gacgtcctgt acgtcgccac caccgacgag | 240 |
| gacgccgtcg aggaggtcga gggcgaaggc gccacggccg tcaccgtcga gcactccctg | 300 |
| gccgacctcg aggcctggaa gaccgtcctc gacgccgccc tcgagggcca cgacgacgtg | 360 |
| cccacctggt acgtcgacgt cccgaccaac agcgtcgtcg tcgccgtcaa ggccggagcc | 420 |
| caggacgtcg ccgccggcct cgtcgaaggt gccgacgtcc cgtccgacgc cgtgaccttc | 480 |

```
gtcgagaccg acgagacccc gcggaccatg ttcgacgtga tcggcggcaa cgcctacacc    540 atcgggggc gcagccgctg ctcgatcggg ttcgcggtca acggcgggtt catcaccgcc     600
ggccactgcg gccgcaccgg cgccaccacc gccaacccca ccgggacctt cgccgggtcc    660
agcttcccgg gcaacgacta cgcgttcgtc cgtaccgggg ccggcgtgaa cctgctggcc    720
caggtcaaca actactccgg tggccgcgtc caggtcgccg gcacaccgc ggcccccgtc     780 ggctcggccg tgtgccggtc cgggtcgacc accgggtggc actgcggcac catcactgcg    840
ctcaactcct cggtcaccta ccccgagggc accgtccgcg gcctgatccg caccaccgtc    900
tgcgccgagc ccggcgactc cggtggctcg ctgctcgccg gcaaccaggc ccagggcgtc    960
acgtccggcg gctccggcaa ctgccgcacc ggtggcacca cgttcttcca gccggtcaac   1020
cccatcctcc aggcgtacgg cctgaggatg atcaccacgg actcgggcag cagcccggcc   1080
cctgcaccga cctcctgcac cggctacgcc cgcaccttca ccgggaccct cgcggccggc   1140
cgggccgccg cccagcccaa cggtcctac gtgcaggtca accggccgg acccacagc      1200 gtgtgcctca cgggcctc cggtgcggac ttcgacctct acgtgcagcg ctggaacggc     1260
agctcctggg tgaccgtcgc ccagagcacc tcccccggct ccaacgagac catcacctac   1320
cgcggcaacg ccggctacta ccgctacgtg gtcaacgccg cgtccggctc cggtgcctac   1380
accatggggc tcaccctccc ctga                                          1404

<210> SEQ ID NO 4
<211> LENGTH: 567
<212> TYPE: DNA
<213> ORGANISM: Cellulomonas strain 69B4

<400> SEQUENCE: 4
ttcgacgtga tcggcggcaa cgcctacacc atcgggggc gcagccgctg ctcgatcggg      60
ttcgcggtca acggcgggtt catcaccgcc ggccactgcg gccgcaccgg cgccaccacc   120
gccaacccca ccgggacctt cgccgggtcc agcttcccgg gcaacgacta cgcgttcgtc   180
cgtaccgggg ccggcgtgaa cctgctggcc caggtcaaca actactccgg tggccgcgtc   240
caggtcgccg gcacaccgc ggcccccgtc ggctcggccg tgtgccggtc cgggtcgacc    300
accgggtggc actgcggcac catcactgcg ctcaactcct cggtcaccta ccccgagggc   360
accgtccgcg gcctgatccg caccaccgtc tgcgccgagc ccggcgactc cggtggctcg   420
ctgctcgccg gcaaccaggc ccagggcgtc acgtccggcg gctccggcaa ctgccgcacc   480
ggtggcacca cgttcttcca gccggtcaac cccatcctcc aggcgtacgg cctgaggatg   540
atcaccacgg actcgggcag cagcccg                                      567

<210> SEQ ID NO 5
<211> LENGTH: 83
<212> TYPE: DNA
<213> ORGANISM: Cellulomonas strain 69B4

<400> SEQUENCE: 5
atgacaccac cacagtcacg cgggccctgg ccgtggccac cgcagccgcc acactcctgg    60
caggcggcat ggccgcccag gcc                                           83

<210> SEQ ID NO 6
<211> LENGTH: 495
<212> TYPE: PRT
<213> ORGANISM: Cellulomonas strain 69B4

<400> SEQUENCE: 6
```

-continued

```
Met Thr Pro Arg Thr Val Thr Arg Ala Leu Ala Val Ala Thr Ala Ala
1               5                   10                  15

Ala Thr Leu Leu Ala Gly Gly Met Ala Ala Gln Ala Asn Glu Pro Ala
            20                  25                  30

Pro Pro Gly Ser Ala Ser Ala Pro Pro Arg Leu Ala Glu Lys Leu Asp
            35                  40                  45

Pro Asp Leu Leu Glu Ala Met Glu Arg Asp Leu Gly Leu Asp Ala Glu
50                  55                  60

Glu Ala Ala Ala Thr Leu Ala Phe Gln His Asp Ala Ala Glu Thr Gly
65                  70                  75                  80

Glu Ala Leu Ala Glu Glu Leu Asp Glu Asp Phe Ala Gly Thr Trp Val
                85                  90                  95

Glu Asp Asp Val Leu Tyr Val Ala Thr Thr Asp Glu Asp Ala Val Glu
                100                 105                 110

Glu Val Glu Gly Glu Gly Ala Thr Ala Val Thr Val Glu His Ser Leu
                115                 120                 125

Ala Asp Leu Glu Ala Trp Lys Thr Val Leu Asp Ala Ala Leu Glu Gly
            130                 135                 140

His Asp Asp Val Pro Thr Trp Tyr Val Asp Val Pro Thr Asn Ser Val
145                 150                 155                 160

Val Val Ala Val Lys Ala Gly Ala Gln Asp Val Ala Ala Gly Leu Val
                165                 170                 175

Glu Gly Ala Asp Val Pro Ser Asp Ala Val Thr Phe Val Glu Thr Asp
                180                 185                 190

Glu Thr Pro Arg Thr Met Phe Asp Val Ile Gly Gly Asn Ala Tyr Thr
                195                 200                 205

Ile Gly Gly Arg Ser Arg Cys Ser Ile Gly Phe Ala Val Asn Gly Gly
            210                 215                 220

Phe Ile Thr Ala Gly His Cys Gly Arg Thr Gly Ala Thr Thr Ala Asn
225                 230                 235                 240

Pro Thr Gly Thr Phe Ala Gly Ser Ser Phe Pro Gly Asn Asp Tyr Ala
                245                 250                 255

Phe Val Arg Thr Gly Ala Gly Val Asn Leu Leu Ala Gln Val Asn Asn
                260                 265                 270

Tyr Ser Gly Gly Arg Val Gln Val Ala Gly His Thr Ala Ala Pro Val
            275                 280                 285

Gly Ser Ala Val Cys Arg Ser Gly Ser Thr Thr Gly Trp His Cys Gly
            290                 295                 300

Thr Ile Thr Ala Leu Asn Ser Ser Val Thr Tyr Pro Glu Gly Thr Val
305                 310                 315                 320

Arg Gly Leu Ile Arg Thr Thr Val Cys Ala Glu Pro Gly Asp Ser Gly
                325                 330                 335

Gly Ser Leu Leu Ala Gly Asn Gln Ala Gln Gly Val Thr Ser Gly Gly
            340                 345                 350

Ser Gly Asn Cys Arg Thr Gly Thr Thr Phe Phe Gln Pro Val Asn
            355                 360                 365

Pro Ile Leu Gln Ala Tyr Gly Leu Arg Met Ile Thr Thr Asp Ser Gly
            370                 375                 380

Ser Ser Pro Ala Pro Ala Pro Thr Ser Cys Thr Gly Tyr Ala Arg Thr
385                 390                 395                 400

Phe Thr Gly Thr Leu Ala Ala Gly Arg Ala Ala Gln Pro Asn Gly
                405                 410                 415

Ser Tyr Val Gln Val Asn Arg Ser Gly Thr His Ser Val Cys Leu Asn
            420                 425                 430
```

```
Gly Pro Ser Gly Ala Asp Phe Asp Leu Tyr Val Gln Arg Trp Asn Gly
            435                 440                 445

Ser Ser Trp Val Thr Val Ala Gln Ser Thr Ser Pro Gly Ser Asn Glu
        450                 455                 460

Thr Ile Thr Tyr Arg Gly Asn Ala Gly Tyr Tyr Arg Tyr Val Val Asn
465                 470                 475                 480

Ala Ala Ser Gly Ser Gly Ala Tyr Thr Met Gly Leu Thr Leu Pro
            485                 490                 495

<210> SEQ ID NO 7
<211> LENGTH: 467
<212> TYPE: PRT
<213> ORGANISM: Cellulomonas strain 69B4

<400> SEQUENCE: 7

Asn Glu Pro Ala Pro Pro Gly Ser Ala Ser Ala Pro Pro Arg Leu Ala
1               5                   10                  15

Glu Lys Leu Asp Pro Asp Leu Leu Glu Ala Met Glu Arg Asp Leu Gly
                20                  25                  30

Leu Asp Ala Glu Glu Ala Ala Ala Thr Leu Ala Phe Gln His Asp Ala
            35                  40                  45

Ala Glu Thr Gly Glu Ala Leu Ala Glu Leu Asp Glu Asp Phe Ala
        50                  55                  60

Gly Thr Trp Val Glu Asp Val Leu Tyr Val Ala Thr Thr Asp Glu
65                  70                  75                  80

Asp Ala Val Glu Glu Val Glu Gly Glu Gly Ala Thr Ala Val Thr Val
                85                  90                  95

Glu His Ser Leu Ala Asp Leu Glu Ala Trp Lys Thr Val Leu Asp Ala
            100                 105                 110

Ala Leu Glu Gly His Asp Asp Val Pro Thr Trp Tyr Val Asp Val Pro
        115                 120                 125

Thr Asn Ser Val Val Val Ala Val Lys Ala Gly Ala Gln Asp Val Ala
130                 135                 140

Ala Gly Leu Val Glu Gly Ala Asp Val Pro Ser Asp Ala Val Thr Phe
145                 150                 155                 160

Val Glu Thr Asp Glu Thr Pro Arg Thr Met Phe Asp Val Ile Gly Gly
                165                 170                 175

Asn Ala Tyr Thr Ile Gly Gly Arg Ser Arg Cys Ser Ile Gly Phe Ala
            180                 185                 190

Val Asn Gly Gly Phe Ile Thr Ala Gly His Cys Gly Arg Thr Gly Ala
        195                 200                 205

Thr Thr Ala Asn Pro Thr Gly Thr Phe Ala Gly Ser Ser Phe Pro Gly
210                 215                 220

Asn Asp Tyr Ala Phe Val Arg Thr Gly Ala Gly Val Asn Leu Leu Ala
225                 230                 235                 240

Gln Val Asn Asn Tyr Ser Gly Gly Arg Val Gln Val Ala Gly His Thr
                245                 250                 255

Ala Ala Pro Val Gly Ser Ala Val Cys Arg Ser Gly Ser Thr Thr Gly
            260                 265                 270

Trp His Cys Gly Thr Ile Thr Ala Leu Asn Ser Ser Val Thr Tyr Pro
        275                 280                 285

Glu Gly Thr Val Arg Gly Leu Ile Arg Thr Thr Val Cys Ala Glu Pro
290                 295                 300

Gly Asp Ser Gly Gly Ser Leu Leu Ala Gly Asn Gln Ala Gln Gly Val
305                 310                 315                 320
```

```
Thr Ser Gly Gly Ser Gly Asn Cys Arg Thr Gly Gly Thr Thr Phe Phe
                325                 330                 335

Gln Pro Val Asn Pro Ile Leu Gln Ala Tyr Gly Leu Arg Met Ile Thr
            340                 345                 350

Thr Asp Ser Gly Ser Ser Pro Ala Pro Ala Pro Thr Ser Cys Thr Gly
        355                 360                 365

Tyr Ala Arg Thr Phe Thr Gly Thr Leu Ala Ala Gly Arg Ala Ala Ala
    370                 375                 380

Gln Pro Asn Gly Ser Tyr Val Gln Val Asn Arg Ser Gly Thr His Ser
385                 390                 395                 400

Val Cys Leu Asn Gly Pro Ser Gly Ala Asp Phe Asp Leu Tyr Val Gln
                405                 410                 415

Arg Trp Asn Gly Ser Ser Trp Val Thr Val Ala Gln Ser Thr Ser Pro
            420                 425                 430

Gly Ser Asn Glu Thr Ile Thr Tyr Arg Gly Asn Ala Gly Tyr Tyr Arg
        435                 440                 445

Tyr Val Val Asn Ala Ala Ser Gly Ser Gly Ala Tyr Thr Met Gly Leu
    450                 455                 460

Thr Leu Pro
465

<210> SEQ ID NO 8
<211> LENGTH: 189
<212> TYPE: PRT
<213> ORGANISM: Cellulomonas strain 69B4

<400> SEQUENCE: 8

Phe Asp Val Ile Gly Gly Asn Ala Tyr Thr Ile Gly Gly Arg Ser Arg
1               5                   10                  15

Cys Ser Ile Gly Phe Ala Val Asn Gly Gly Phe Ile Thr Ala Gly His
                20                  25                  30

Cys Gly Arg Thr Gly Ala Thr Thr Ala Asn Pro Thr Gly Thr Phe Ala
            35                  40                  45

Gly Ser Ser Phe Pro Gly Asn Asp Tyr Ala Phe Val Arg Thr Gly Ala
        50                  55                  60

Gly Val Asn Leu Leu Ala Gln Val Asn Asn Tyr Ser Gly Gly Arg Val
65                  70                  75                  80

Gln Val Ala Gly His Thr Ala Ala Pro Val Gly Ser Ala Val Cys Arg
                85                  90                  95

Ser Gly Ser Thr Thr Gly Trp His Cys Gly Thr Ile Thr Ala Leu Asn
                100                 105                 110

Ser Ser Val Thr Tyr Pro Glu Gly Thr Val Arg Gly Leu Ile Arg Thr
            115                 120                 125

Thr Val Cys Ala Glu Pro Gly Asp Ser Gly Gly Ser Leu Leu Ala Gly
        130                 135                 140

Asn Gln Ala Gln Gly Val Thr Ser Gly Gly Ser Gly Asn Cys Arg Thr
145                 150                 155                 160

Gly Gly Thr Thr Phe Phe Gln Pro Val Asn Pro Ile Leu Gln Ala Tyr
                165                 170                 175

Gly Leu Arg Met Ile Thr Thr Asp Ser Gly Ser Ser Pro
            180                 185

<210> SEQ ID NO 9
<211> LENGTH: 28
<212> TYPE: PRT
<213> ORGANISM: Cellulomonas strain 69B4
```

<400> SEQUENCE: 9

Met Thr Pro Arg Thr Val Thr Arg Ala Leu Ala Val Ala Thr Ala Ala
1               5                   10                  15

Ala Thr Leu Leu Ala Gly Gly Met Ala Ala Gln Ala
            20                  25

<210> SEQ ID NO 10
<211> LENGTH: 1488
<212> TYPE: DNA
<213> ORGANISM: Artificial Sequence
<220> FEATURE:
<223> OTHER INFORMATION: synthetic Asp

<400> SEQUENCE: 10

| | |
|---|---:|
| atgacaccac gaactgtcac aagagctctg gctgtggcaa cagcagctgc tacactcttg | 60 |
| gctggggta tggcagcaca agctaacgaa ccggctcctc aggatctgc atcagcccct | 120 |
| ccacgattag ctgaaaaact tgaccctgac ttacttgaag caatggaacg cgatctgggg | 180 |
| ttagatgcag aggaagcagc tgcaacgtta gcttttcagc atgacgcagc tgaaacggga | 240 |
| gaggctcttg ctgaggaact cgacgaagat ttcgcgggca cgtgggttga agatgatgtg | 300 |
| ctgtatgttg caaccactga tgaagatgct gttgaagaag tcgaaggcga aggagcaact | 360 |
| gctgtgactg ttgagcattc tcttgctgat ttagaggcgt ggaagacggt tttggatgct | 420 |
| gcgctggagg gtcatgatga tgtgcctacg tggtacgtcg acgtgcctac gaattcggta | 480 |
| gtcgttgctg taaaggcagg agcgcaggat gtagctgcag acttgtgga aggcgctgat | 540 |
| gtgccatcag atgcggtcac ttttgtagaa acggacgaaa cgcctagaac gatgttcgac | 600 |
| gtaattggag caacgcata tactattggc ggccggtcta gatgttctat cggattcgca | 660 |
| gtaaacggtg gcttcattac tgccggtcac tgcggaagaa caggagccac tactgccaat | 720 |
| ccgactggca catttgcagg tagctcgttt ccgggaaatg attatgcatt cgtccgaaca | 780 |
| ggggcaggag taaatttgct tgcccaagtc aataactact cgggcggcag agtccaagta | 840 |
| gcaggacata cggccgcacc agttggatct gctgtatgcc gctcaggtag cactacaggt | 900 |
| tggcattgcg aactatcac ggcgctgaat tcgtctgtca cgtatccaga gggaacagtc | 960 |
| cgaggactta tccgcacgac ggtttgtgcc gaaccaggtg atagcggagg tagccttta | 1020 |
| gcgggaaatc aagcccaagg tgtcacgtca ggtggttctg gaaattgtcg acgggggga | 1080 |
| acaacattct tcaaccagt caacccgatt ttgcaggctt acggcctgag aatgattacg | 1140 |
| actgactctg gaagttcccc tgctccagca cctacatcat gtacaggcta cgcaagaacg | 1200 |
| ttcacaggaa ccctcgcagc aggaagagca gcagctcaac cgaacggtag ctatgttcag | 1260 |
| gtcaaccgga gcggtacaca ttccgtctgt ctcaatggac ctagcggtgc ggactttgat | 1320 |
| ttgtatgtgc agcgatggaa tggcagtagc tgggtaaccg tcgctcaatc gacatcgccg | 1380 |
| ggaagcaatg aaaccattac gtaccgcgga aatgctggat attatcgcta cgtggttaac | 1440 |
| gctgcgtcag gatcaggagc ttacacaatg ggactcaccc tcccctga | 1488 |

<210> SEQ ID NO 11
<211> LENGTH: 30
<212> TYPE: PRT
<213> ORGANISM: Artificial Sequence
<220> FEATURE:
<223> OTHER INFORMATION: synthetic Asp

<400> SEQUENCE: 11

Met Arg Ser Lys Lys Arg Thr Val Thr Arg Ala Leu Ala Val Ala Thr

```
1               5              10              15
Ala Ala Ala Thr Leu Leu Ala Gly Gly Met Ala Ala Gln Ala
                20              25              30
```

<210> SEQ ID NO 12
<211> LENGTH: 53
<212> TYPE: DNA
<213> ORGANISM: Artificial Sequence
<220> FEATURE:
<223> OTHER INFORMATION: primer

<400> SEQUENCE: 12
tcatgcaggg taccatgaga agcaagaagc gaactgtcac aagagctctg gct           53

<210> SEQ ID NO 13
<211> LENGTH: 37
<212> TYPE: DNA
<213> ORGANISM: Artificial Sequence
<220> FEATURE:
<223> OTHER INFORMATION: primer

<400> SEQUENCE: 13
gtgtgcaagc tttcaagggg aacttccaga gtcagtc                             37

<210> SEQ ID NO 14
<211> LENGTH: 45
<212> TYPE: DNA
<213> ORGANISM: Artificial Sequence
<220> FEATURE:
<223> OTHER INFORMATION: primer

<400> SEQUENCE: 14
tgagctgcta gcaaaaggag agggtaaaga atgagaagca agaag                    45

<210> SEQ ID NO 15
<211> LENGTH: 38
<212> TYPE: DNA
<213> ORGANISM: Artificial Sequence
<220> FEATURE:
<223> OTHER INFORMATION: primer

<400> SEQUENCE: 15
catgcatccc gggttaaggg gaacttccag agtcagtc                            38

<210> SEQ ID NO 16
<211> LENGTH: 39
<212> TYPE: DNA
<213> ORGANISM: Artificial Sequence
<220> FEATURE:
<223> OTHER INFORMATION: primer

<400> SEQUENCE: 16
tatcggattc gcagtagagg gtggcttcat tactgccgg                           39

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17
tatcggattc gcagtagccg gtggcttcat tactgccgg                           39

<210> SEQ ID NO 18
<211> LENGTH: 39

```
<212> TYPE: DNA
<213> ORGANISM: Artificial Sequence
<220> FEATURE:
<223> OTHER INFORMATION: primer

<400> SEQUENCE: 18
tatcggattc gcagtaacag gtggcttcat tactgccgg                              39

<210> SEQ ID NO 19
<211> LENGTH: 39
<212> TYPE: DNA
<213> ORGANISM: Artificial Sequence
<220> FEATURE:
<223> OTHER INFORMATION: primer

<400> SEQUENCE: 19
tatcggattc gcagtacaag gtggcttcat tactgccgg                              39

<210> SEQ ID NO 20
<211> LENGTH: 34
<212> TYPE: DNA
<213> ORGANISM: Artificial Sequence
<220> FEATURE:
<223> OTHER INFORMATION: primer

<400> SEQUENCE: 20
cggtcactgc ggagagacag gagccactac tgcc                                   34

<210> SEQ ID NO 21
<211> LENGTH: 34
<212> TYPE: DNA
<213> ORGANISM: Artificial Sequence
<220> FEATURE:
<223> OTHER INFORMATION: primer

<400> SEQUENCE: 21
cggtcactgc ggagacacag gagccactac tgcc                                   34

<210> SEQ ID NO 22
<211> LENGTH: 43
<212> TYPE: DNA
<213> ORGANISM: Artificial Sequence
<220> FEATURE:
<223> OTHER INFORMATION: primer

<400> SEQUENCE: 22
ccgaacaggg aaaggagtac tgttgcttgc ccaagtcaat aac                         43

<210> SEQ ID NO 23
<211> LENGTH: 43
<212> TYPE: DNA
<213> ORGANISM: Artificial Sequence
<220> FEATURE:
<223> OTHER INFORMATION: primer

<400> SEQUENCE: 23
ccgaacaggg aaaggagtat ctttgcttgc ccaagtcaat aac                         43

<210> SEQ ID NO 24
<211> LENGTH: 43
<212> TYPE: DNA
<213> ORGANISM: Artificial Sequence
<220> FEATURE:
<223> OTHER INFORMATION: primer

<400> SEQUENCE: 24
ccgaacaggg aaaggagtag ctttgcttgc ccaagtcaat aac                         43
```

-continued

<210> SEQ ID NO 25
<211> LENGTH: 43
<212> TYPE: DNA
<213> ORGANISM: Artificial Sequence
<220> FEATURE:
<223> OTHER INFORMATION: primer

<400> SEQUENCE: 25
taactactcg ggcgacagag tccaagtagc aggacataaa gcc         43

<210> SEQ ID NO 26
<211> LENGTH: 38
<212> TYPE: DNA
<213> ORGANISM: Artificial Sequence
<220> FEATURE:
<223> OTHER INFORMATION: primer

<400> SEQUENCE: 26
gtctttggac ttatccaaac gacggtttgt gccgaacc         38

<210> SEQ ID NO 27
<211> LENGTH: 40
<212> TYPE: DNA
<213> ORGANISM: Artificial Sequence
<220> FEATURE:
<223> OTHER INFORMATION: primer

<400> SEQUENCE: 27
gtctttggac ttatcaaaac gacggtttgt gccgaaccag         40

<210> SEQ ID NO 28
<211> LENGTH: 38
<212> TYPE: DNA
<213> ORGANISM: Artificial Sequence
<220> FEATURE:
<223> OTHER INFORMATION: primer

<400> SEQUENCE: 28
gtccgaggac ttatctacac gacggtttgt gccgaacc         38

<210> SEQ ID NO 29
<211> LENGTH: 39
<212> TYPE: DNA
<213> ORGANISM: Artificial Sequence
<220> FEATURE:
<223> OTHER INFORMATION: primer

<400> SEQUENCE: 29
ggtggttctg gaaattgttt cacgggggga acaacattc         39

<210> SEQ ID NO 30
<211> LENGTH: 39
<212> TYPE: DNA
<213> ORGANISM: Artificial Sequence
<220> FEATURE:
<223> OTHER INFORMATION: primer

<400> SEQUENCE: 30
ggtggttctg gaaattgtga gacgggggga acaacattc         39

<210> SEQ ID NO 31
<211> LENGTH: 39
<212> TYPE: DNA
<213> ORGANISM: Artificial Sequence
<220> FEATURE:
<223> OTHER INFORMATION: primer

```
<400> SEQUENCE: 31
ggtggttctg gaaattgtaa cacgggggga acaacattc                              39

<210> SEQ ID NO 32
<211> LENGTH: 39
<212> TYPE: DNA
<213> ORGANISM: Artificial Sequence
<220> FEATURE:
<223> OTHER INFORMATION: primer

<400> SEQUENCE: 32
ggtggttctg gaaattgtaa gacgggggga acaacattc                              39

<210> SEQ ID NO 33
<211> LENGTH: 39
<212> TYPE: DNA
<213> ORGANISM: Artificial Sequence
<220> FEATURE:
<223> OTHER INFORMATION: primer

<400> SEQUENCE: 33
aggtagctcg tttccggaca atgattatgc attcgtccg                              39
```